United States Patent
Walton et al.

(10) Patent No.: US 9,404,136 B2
(45) Date of Patent: Aug. 2, 2016

(54) A-XYLOSIDASE ENHANCED CONVERSION OF PLANT BIOMASS INTO FERMENTABLE SUGARS

(71) Applicant: Board of Trustees of Michigan State University, East Lansing, MI (US)

(72) Inventors: Jonathan D. Walton, East Lansing, MI (US); John S. Scott-Craig, East Lansing, MI (US); Melissa Borrusch, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 13/791,304

(22) Filed: Mar. 8, 2013

(65) Prior Publication Data

US 2014/0004572 A1    Jan. 2, 2014

Related U.S. Application Data

(60) Provisional application No. 61/665,513, filed on Jun. 28, 2012.

(51) Int. Cl.
 *C12P 19/14* (2006.01)
 *C12P 19/02* (2006.01)
 *C12N 9/24* (2006.01)
 *C12N 9/42* (2006.01)

(52) U.S. Cl.
 CPC ............... *C12P 19/14* (2013.01); *C12N 9/248* (2013.01); *C12P 19/02* (2013.01); *C12Y 302/01177* (2013.01); *C12N 9/2434* (2013.01); *Y02P 20/52* (2015.11)

(58) Field of Classification Search
 None
 See application file for complete search history.

(56) References Cited

PUBLICATIONS

Scott-Craig et al., Biochemical and molecular characterization of secreted α-xylosidase from Aspergilllus niger, J. Biol. Chem.. Oct. 2011, 286, 42848-54.*
Banjeree et al., Alkaline peroxide pretreatment of corn stover: effects of biomass, peroxide, and enzyme loading and composition on yields of glucose and xylose, Jun. 9, 2011, Biotech. for Biofuels 4, 16.*
Berlin et al., Optimization of Enzyme Complexes for Lignocellulose Hydrolysis, Biotech. Bioeng., 2007, 97, 287- 296.*
Dien et al., Enhancing alfalfa conversion efficiencies for sugar recovery and ethanol production by altering lignin composition, Bioresource Tech., Mar. 2011, 102, 6479-86.*
Uniprot, Accession No. G3Y866, 2015, www.uniprot.org.*
Larnsbrink et al., Structural and enzymatic characterization of a glycoside hydrolase family 31 _-xylosidase from Cellvibrio japonicas involved in xyloglucan saccharification, Biochem J., Mar. 2011, 436, 567-80.*
Gao et al., Mixture optimization of six core glycosyl hydrolases for maximizing saccharification of ammonia fiber expansion (AFEX) pretreated corn stover, Bioresouce Tech., Nov. 2009, 101, 2770-81.*
Matsushita et al., Purification and properties of an a-D-xylosidase from Aspergillus niger, J. Biochem., 1985, 98, 825-32.*
O'Neill et al., Purification and Characterization of a Xyloglucan Oligosaccharide-specific Xylosidase from Pea Seedlings, J. Biol. Chem., 1989, 264, 20430-37.*

* cited by examiner

*Primary Examiner* — Robert Mondesi
*Assistant Examiner* — Todd M Epstein
(74) *Attorney, Agent, or Firm* — Schwegman Lundberg & Woessner, P.A.

(57) ABSTRACT

The invention relates to increasing the availability of fermentable sugars from plant biomass, such as glucose and xylose. As described herein, α-xylosidases can be employed with cellulases to enhance biomass conversion into free, fermentable sugar residues.

Figure 1A:
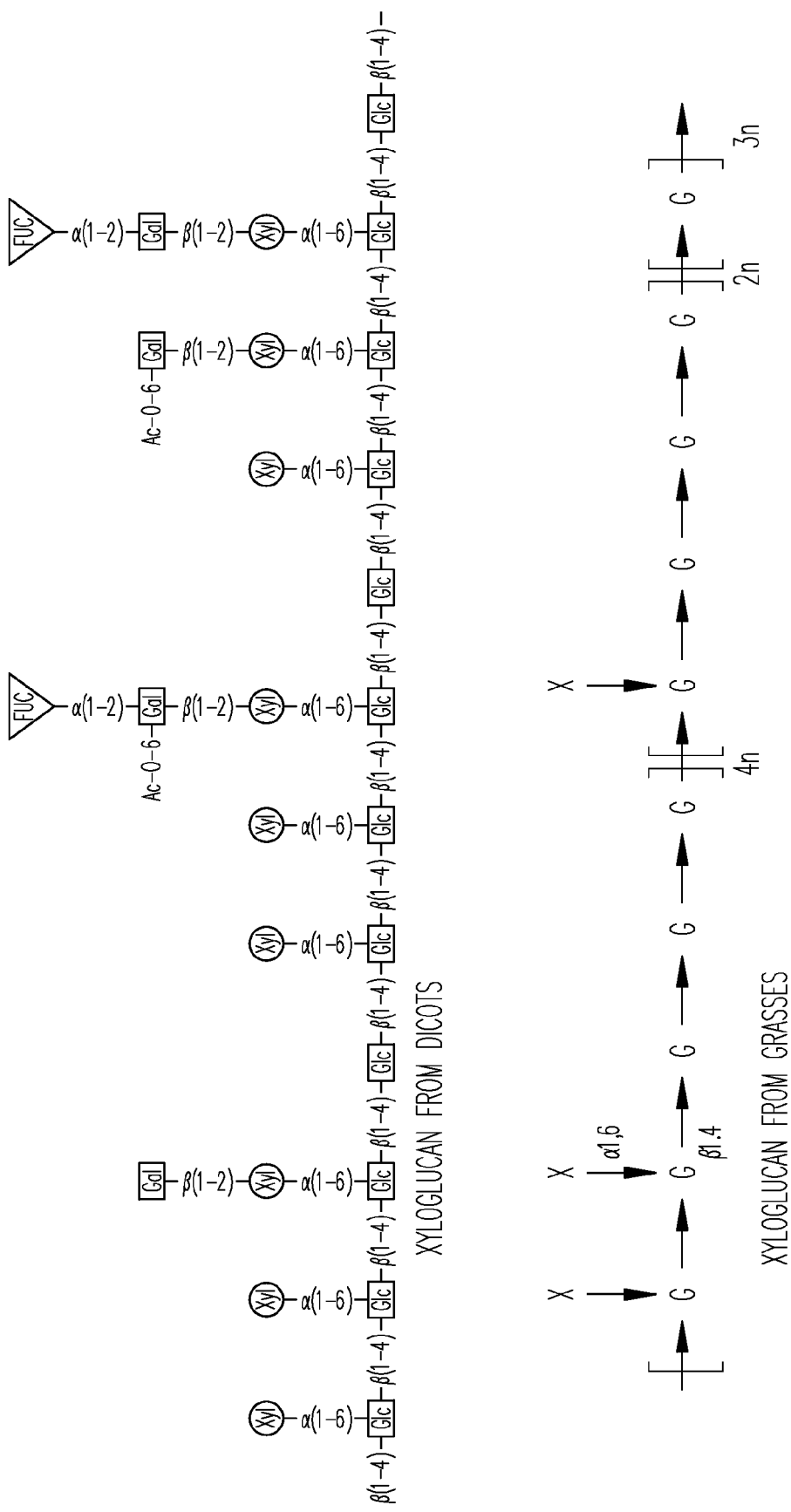

15 Claims, 24 Drawing Sheets ns
α-XYLOSIDASE ENHANCED CONVERSION OF PLANT BIOMASS INTO FERMENTABLE SUGARS

This application claims benefit of the filing date of U.S. Provisional Application Ser. No. 61/665,513, filed Jun. 28, 2012, the contents of which are specifically incorporated herein by reference in their entirety.

STATEMENT OF GOVERNMENTAL SUPPORT

This invention was made with government support under Grant Nos. DE-FG02-91ER200021 and DE-FC02-07ER64494 by the U.S. Department of Energy. The government has certain rights in the invention.

FIELD OF THE INVENTION

This invention is related to the production of biofuels by converting lignocellulosic materials into fermentable sugars. For example, the release of fermentable sugars from a plant biomass may be enhanced using an α-xylosidase enzyme. Such an α-xylosidase enzyme efficiently facilitates degradation of xyloglucan (a major component of biomass from plant cell walls) by cellulase enzymes into xylose and glucose. Without addition of α-xylosidase, commercial cellulase mixtures do not convert xyloglucan to glucose and xylose.

BACKGROUND

Microbial enzymes exist for catalyzing the depolymerization of plant cell wall polysaccharides allowing the carbon in the plant cell walls to be recycled into free sugars that ultimately are metabolized to $CO_2$. An emerging application of microbial enzymes is for conversion (e.g., deconstruction or digestion) of lignocellulosic materials (e.g., corn stover) into fermentable sugars useful for ethanol production. However, while mixtures of microbial enzymes have been isolated from fermentation vats of *Trichoderma*, such mixtures are expensive and do not contain optimal amounts or types of enzymes. The high cost of commercially available enzyme mixtures is currently a significant barrier to the development of a viable lignocellulosic biofuel industry. See, e.g., Banerjee et al., Bioenergy Res. 3:82-92 (2010); and Yang et al., Biofuels 2:421-450 (2011).

What are needed are methods and compositions that make the lignocellulosic conversion enzyme mixtures more efficient, thereby reducing their cost when expressed as dollars per gallon of ethanol.

SUMMARY

This invention is related to the production of biofuels by converting lignocellulosic materials into fermentable sugars. α-Xylosidase can be used to improve currently available enzymatic conversion products, and reduce the expense of such conversion so that fermentable sugars from a plant biomass can be obtained more efficiently and less expensively. For example, addition of α-xylosidase to cellulase mixtures can lead to enhanced degradation of xyloglucans into xylose and glucose. Commercially available enzyme mixtures degrade xyloglucans only partially. The resulting product contains significant amounts of disaccharides of glucose and xylose called isoprimeverose, which most microorganisms (e.g., yeast) cannot ferment to fuels such as ethanol. Fermenting microorganisms typically can ferment only free glucose and other monosaccharides such as xylose. Appropriate pretreatment (such as alkaline hydrogen peroxide or acid) of lignocellulosic materials can also improve the release of fermentable sugars by mixtures of enzymes that include α-xylosidase.

One aspect of the invention is a composition or enzyme mixture comprising an isolated α-xylosidase. In some embodiments, the isolated α-xylosidase is a purified α-xylosidase. The enzyme mixture can include an isolated α-xylosidase with at least one other enzyme (e.g., one or more cellulases). For example, the mixture can include at least one cellulose converting or depolymerizing enzyme, at least one cellulase, and/or at least one other enzyme that can cleave linkages found in the polysaccharides of plant cell walls. Examples of enzymes can, for example, be selected from the group consisting of a cellobiohydrolase, an endoglucanase, a polysaccharide monooxygenase (e.g., cel61, see NCBI accession no. AY094489.1 GI:21694046), an endoxylanase, a β-glucosidase, a β-1,4-glucanase, a β-galactosidase, an α-fucosidase, a β-galactosidase, an endoxylanase, a β-xylosidase, α-arabinosidase, α-glucuronidase, polysaccharide monooxygenase, an esterase and combinations thereof. Such a cellulose enzyme mixture or composition can have at least 5%, or at least 10%, or at least 15% cellulase or at least 20%, or at least 25% cellulase, or at least 30% cellulase, or at least 40% cellulase, or at least 50%, or at least 60% cellulase.

In some embodiments, the mixture can include at least two, or at least three cellulose depolymerizing enzymes or cellulases.

The α-xylosidase can be a secreted enzyme. The α-xylosidase can have substantially no quaternary structure. In one embodiment, the α-xylosidase has a pH optimum of approximately 4.0. In one embodiment, the α-xylosidase has a temperature optimum of approximately 50° C. The α-xylosidase can be obtained or cloned from a fungal, or bacterial species. In one embodiment, the α-xylosidase is derived from a fungal extracellular extract. In one embodiment, the fungal extracellular extract is derived from an *Aspergillus niger* extracellular extract. In one embodiment, the *Aspergillus niger* secreted α-xylosidase is Aspni5|43342 (DOE-JGI database) or has the GenBank accession number DAA35002.1.

Another aspect of the invention is a method that includes:
a) providing;
  i) a plant biomass that includes hemicellulose; and
  ii) an enzyme mixture comprising an isolated α-xylosidase; and
b) incubating the biomass with the enzyme mixture to create a degradation product that comprises fermentable sugars. The enzyme mixture can include other enzymes such as cellulases, depolymerizing enzymes, and/or other enzymes that can cleave linkages found in the polysaccharides of plant cell walls. For example, the enzyme mixture can include a cellobiohydrolase, an endoglucanase, a polysaccharide monooxygenase (e.g., cel61, see NCBI accession no. AY094489.1 GI:21694046), an endoxylanase, a β-glucosidase, a β-1,4-glucanase, an α-fucosidase, a β-galactosidase, and combinations thereof.

In some embodiments, the method can also include c) identifying the percentage of free fermentable xylose and glucose residues in the degradation product; or c) isolating the free fermentable xylose and glucose residues from the degradation product. Such a method can further comprise treating the plant biomass with alkaline hydrogen peroxide or acid, for example, before incubation with the enzyme mixture.

Such a method can release substantial proportions of free fermentable sugars from the plant biomass. For example, such a method can release about 50%, or about 60%, or about 70%, or about 75%, or about 85%, or about 90%, or about 95% of free fermentable sugars contained within the plant biomass. In one embodiment, the degraded hemicellulose material is completely (e.g., 98%-99.9%) degraded by the enzyme mixture into a plurality of free fermentable xylose and glucose residues.

The plant biomass can be derived from a number of sources. For example, the plant biomass can be derived from a dicotyledonous plant. In another embodiment, the plant biomass can be derived from a monocotyledon plant. In one embodiment, plant biomass can be derived from grass or wood. In one embodiment, the plant biomass comprises corn stover.

The conditions employed for the plant biomass into fermentable sugar can vary. In one embodiment, the plant biomass is first exposed to a pretreatment such as alkaline hydrogen peroxide or sulfuric acid or ammonia. Incubation with the enzyme mixture can be performed at a temperature ranging from approximately 40° to approximately 50° C. In one embodiment, the incubation is performed at a pH ranging from approximately 4 to approximately 5.

DEFINITIONS

The term "converting enzyme mixture" as used herein, refers to a mixture that contains an isolated α-xylosidase and at least one, and preferably more than one, enzyme having catalytic activity directed towards cleavage of covalent bonds in plant biomass materials. For example, the at least one enzyme may hydrolyze saccharide linkages of an alpha or beta nature, to release free fermentable sugar residues including, but not limited to, glucose, galactose, mannose, fucose, or xylose.

The term "lignocellulose" as used herein, refers to any of several closely related substances comprising plant cell walls comprising sugar-based backbone polymers including, but not limited to, cellulose and/or hemicellulose.

The term "plant biomass" as used herein, refers to any collection of biological material derived from a plant source.

The term "secreted", "secrete" and/or "secreting" as used herein, refers to the process of segregating, elaborating, and releasing some material (e.g., a protein or enzyme) from a cell or across a cell wall or membrane into the extracellular environment.

The term "extracellular" as used herein, refers to any product, compound or process situated or occurring outside a cell.

The term "degrade", "degrading", or "degraded" as used herein, refers to any process that reduces the complexity of a material (e.g., an organic chemical compound such as a polysaccharide) by splitting off one or more groups or larger components (e.g., free fermentable sugar residues). A material or product that is "degraded" has reduced complexity relative to the original material or product, for example, because polymers in the material or product have been converted (e.g., cleaved) into subunits (e.g., fermentable sugars) and/or oligomers (e.g., oligosaccharides).

The term "free, fermentable sugar residues" as used herein, refers to any hexose or pentose sugar moiety that can be metabolized by a biochemical catabolic pathway. For example, one biochemical catabolic pathway produces ethanol as an end product. In some embodiments, the hexose or pentose is underivatized.

The term "quaternary structure" as used herein, refers to a protein multi-unit complex that includes three dimensionally folded proteins and/or enzymes.

The term "xyloglucan" as used herein, refers to hemicellulose that occurs mainly in the primary cell wall of vascular plants having a backbone of β1→4-linked glucose residues, some of which are substituted with α1→6 linked xylose. About 60-75% (or, in grasses, about 30-40%) of the glucose residues have side-chains attached to position 6, and alpha-linked D-xylopyranosyl is one of the major moieties attached at position 6. The xylose residues are often capped with a galactose residue sometimes followed by a fucose residue. The specific structure of xyloglucan varies among plant families. Other side chains attached to the β-(1→4)-D-glucopyranose backbone include: D-galactopyranosyl-β-(1→2)-D-xylopyranosyl-α-(1→6), L-arabinofuranosyl-(1→2)-D-xylopyranosyl-α-(1→6), and (except in grasses) L-fucopyranosyl-α-(1→2)-D-galactopyranosyl-β-(1→2)-D-xylopyranosyl-α-(1→6).

The term "dicot" as used herein, refers to a group of flowering plants known as dicotyledons, whose seed typically has two embryonic leaves or cotyledons.

The term "monocot" as used herein, refers to a group of flowering plants known as monocotyledons, whose seed typically has one embryonic leaf or cotyledon.

The term "stover" as used herein, refers to the residual leaves, stalks and other above-ground plant materials left in a field after harvest, as well as other plants materials such as weeds and plant-derived waste (e.g., paper, cardboard, etc.). Stover makes up a substantial proportion of a crop (e.g., half or more of a crop such as wheat or maize). Stover may be derived from any plant source including but not limited to, corn, peas, carrots, grasses, recycled paper, recycled cardboard, and the like.

The term "derived from" as used herein, refers to the source of a compound or sequence. In one respect, a compound or sequence can be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, and containing the elements carbon, hydrogen, nitrogen, oxygen, and usually sulfur. A protein is generally larger than a peptide. For example, a protein can comprise more than 100 amino acids.

The term "peptide" as used herein, refers to a short polymer of amino acids where various amino acids are linked by amide bonds formed between the amino group of one acid with the carboxyl group of another. Peptides can be obtained by partial hydrolysis of proteins. For example, a peptide can comprise about 10-100 amino acids.

The term, "purified" as used herein, refers to any molecule or compound (e.g., a proteinaceous enzyme, such as an α-xylosidase) that has been subjected to treatment (for example, fractionation) to remove various components with which it is naturally associated or with which it is naturally secreted. Such a purified molecule or compound substantially retains its expressed biological activity. Where the term "substantially purified" is used, this designation will refer to a composition in which the molecule or compound forms the major component of the composition, such as constituting about 50%, about 60%, about 70%, about 80%, about 90%, about 95% or more of the composition (for example, weight/weight and/or weight/volume). The purified molecule or compound (e.g., an α-xylosidase) can be purified from an *Aspergillus niger* extracellular extract. The term "purified to homogeneity" is used to include a molecule or compound that has been purified to "apparent homogeneity" such that there is single molecule or compound species (for example, based upon SDS-PAGE or HPLC analysis). A purified composition can contain some trace impurities. A purified composition includes the molecule or compound with a carrier.

The terms "amino acid sequence," "protein sequence" and "polypeptide sequence" as used herein, are interchangeable and to refer to a sequence of amino acids.

As used herein the term "portion" when in reference to a protein (as in "a portion of a given protein") refers to fragments of that protein. The fragments can range in size from four amino acid residues to the entire amino acid sequence minus one amino acid.

The term "derivative" as used herein, refers to any chemical modification of a nucleic acid, sugar, polysaccharide or an amino acid. Illustrative of such modifications would be replacement of hydrogen by an alkyl, acyl, or amino group.

The terms "homology" and "homologous" as used herein in reference to nucleic acid and/or amino acid sequences refer to the degree of identity of the primary structure between two sequences. Such a degree of identity may be directed a portion of each sequence, or to the entire length of the sequence. Two or more nucleic acid or two or more amino acid sequences that are "substantially homologous" may have at least 50% identity, preferably at least 75% identity, more preferably at least 85% identity, most preferably at least 95%, or 100% identity.

ABBREVIATIONS

AHP, alkaline hydrogen peroxide; Ara, arabinose; BSA, bovine serum albumin; Fuc, fucose; Gal, galactose; Glc, glucose; IgG, immunoglobulin; IP, isoprimeverose; Man, mannose; pNPαX, p-nitrophenyl-α-xyloside; Xyl, xylose; XG, xyloglucan; xyloglucan heptasaccharide, a chain of four glucose residues linked together by beta 1,4 linkages where three of the glucose residues are linked by alpha 1,6 linkages to a xylose (shorthand notation XXXG).

DETAILED DESCRIPTION OF THE FIGURES

In the figures, "% of maximum" means the Glc or Xyl released as a percentage of the total Glc and Xyl content of the biomass, as determined by the methods cited in Banerjee et al., *Bioresour. Technol.* 101: 9097-9105 (2010).

Figure 1B:
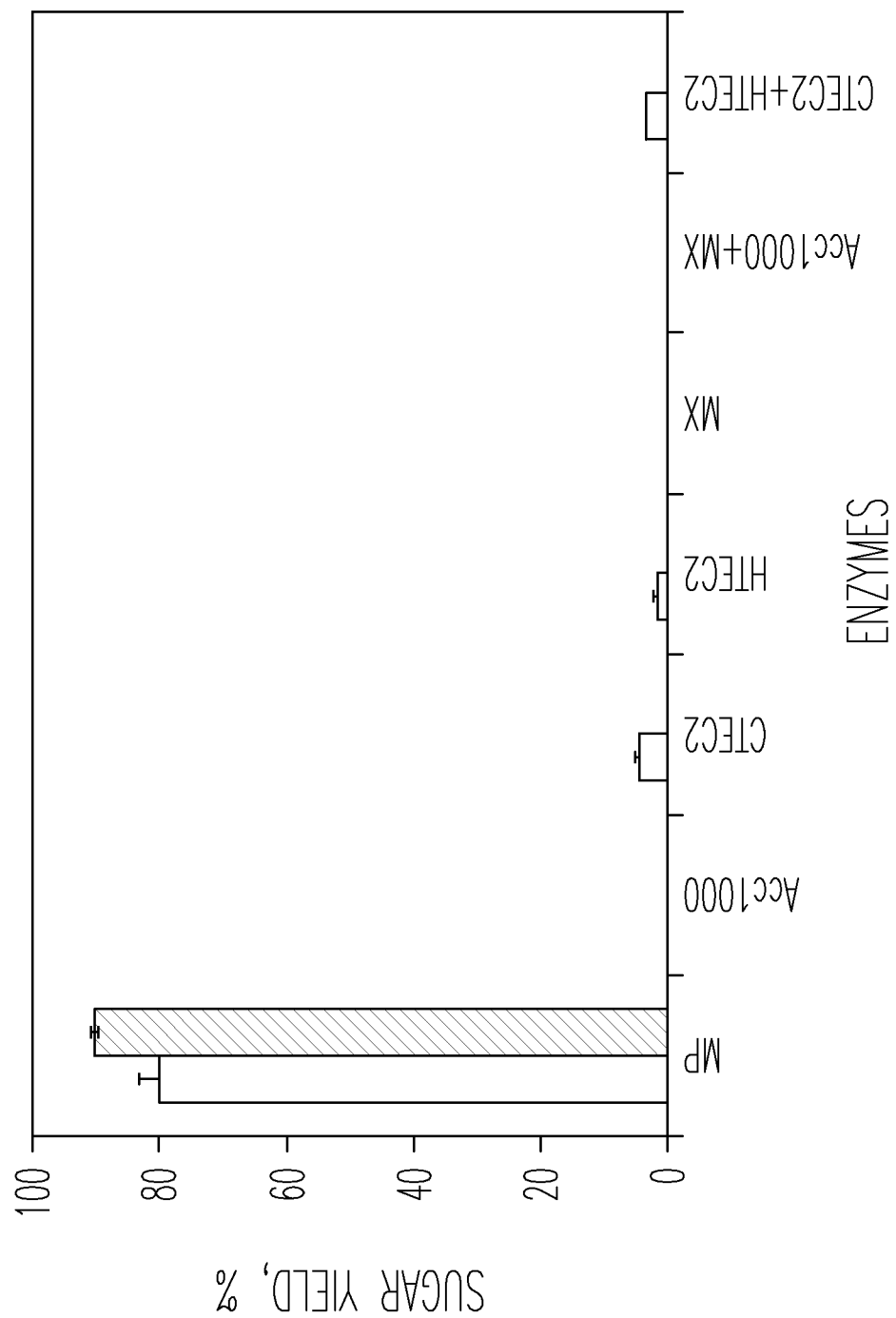

FIG. 1A illustrates exemplary structures of xyloglucan molecules from dicots and grasses. A secreted α-xylosidase (Ax1A) described herein cleaves the α1,6-linked xylose (Xyl) from the glucan backbone. See, Kato et al., Plant Cell Physiol 23: 351 (1982); M. Pauly and K. Keegstra (2008) Cell-wall carbohydrates and their modification as a resource for biofuels. Plant J. 54:559-568. FIG. 1B illustrates release of free glucose and xylose from tamarind xyloglucan by commercial enzyme mixtures as assessed by the percentage of the total glucose and xylose released. MP, Multifect Pectinase; Acc1000, Accellerase 1000; MX, Multifect Xylanase; Acc1000+MX, 50:50 mixture of Accellerase 1000 and Multifect Xylanase; and CTec2+HTec2, 50:50 mixture. CMAX (a product of Dyadic, Inc.) did not release glucose or xylose from tamarind xyloglucan.

Figure 2:
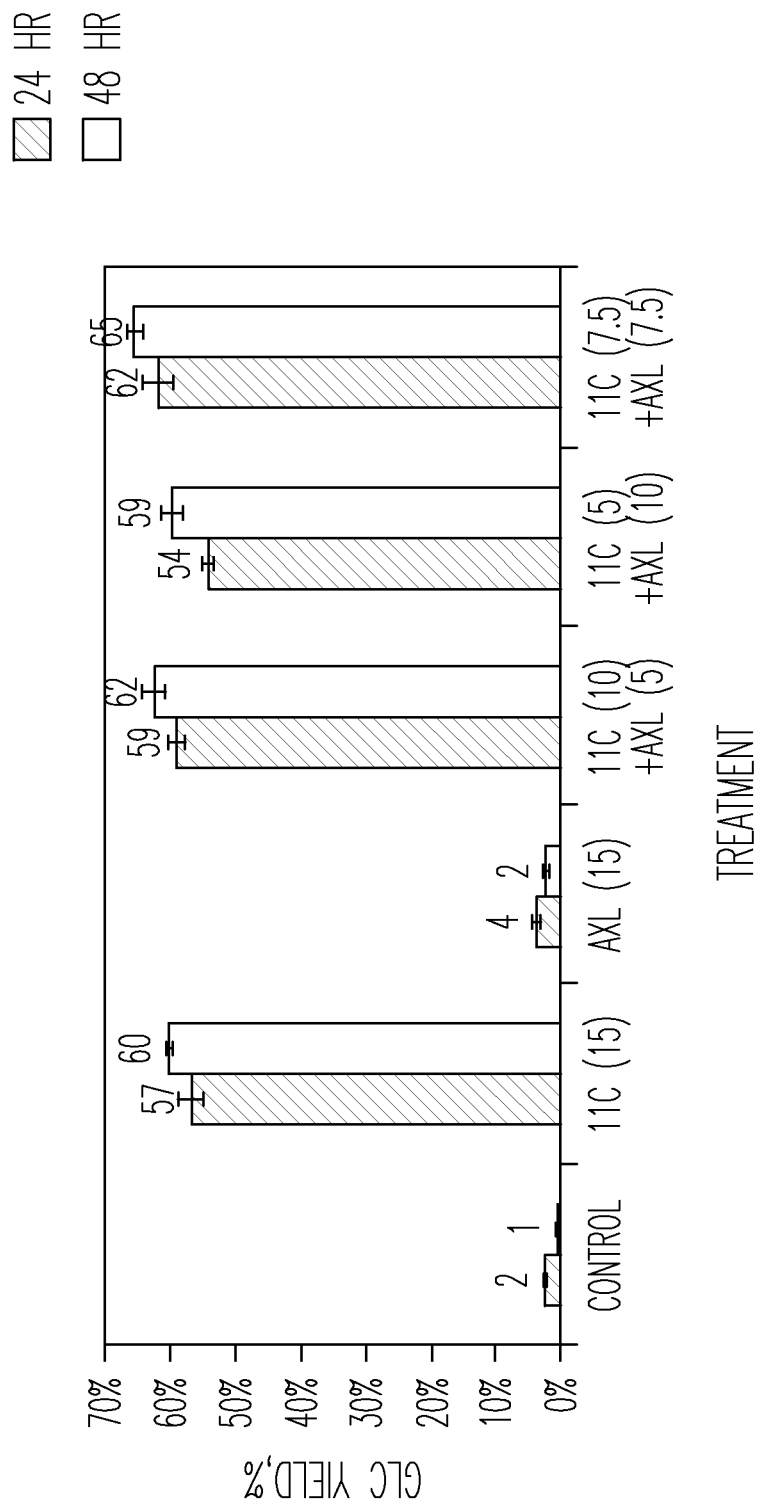

FIG. 2 is a bar graph illustrating that a secreted α-xylosidase described herein increases glucose (Glc) release from corn stover when mixed with an 11-component synthetic enzyme mixture (11C) at equal total protein loading. The 11C enzyme mixture is described by Banerjee et al. *Bioresource Technology* 101:9097-9105 (2010). The numbers in parentheses indicate the mg of protein/gm glucan for each mixture. Corn stover was incubated with the indicated enzyme mixtures for 24 or 48 hr and the released monomeric glucose was measured. The 11-component mixture alone (11C) released 60% of available glucose in 48 hr; a 50:50 mixture of 11C supplemented with secreted α-xylosidase released 65% of the available glucose. Therefore, use of the α-xylosidase allowed 5% more glucose to be obtained with the same total protein loading. Total enzyme concentration was kept constant in all experiments at a total protein loading of 15 mg/g glucan. Numbers in parentheses on the x-axis are the individual loading enzyme concentrations in mg/g glucan for each assay. The numbers above the data bars are the actual glucose values, given as a percentage of the total maximum possible yield. For the composition of the 11-C mixture, see Banerjee et al., *Bioresour Technol* 101:9097-9105 (2010). Control: no enzymes. Abbreviations: 11C: 11-component synthetic enzyme mixture; AXL: α-xylosidase (Aspni5|43342; NCBI accession no. DAA35002.1).

Figure 3:
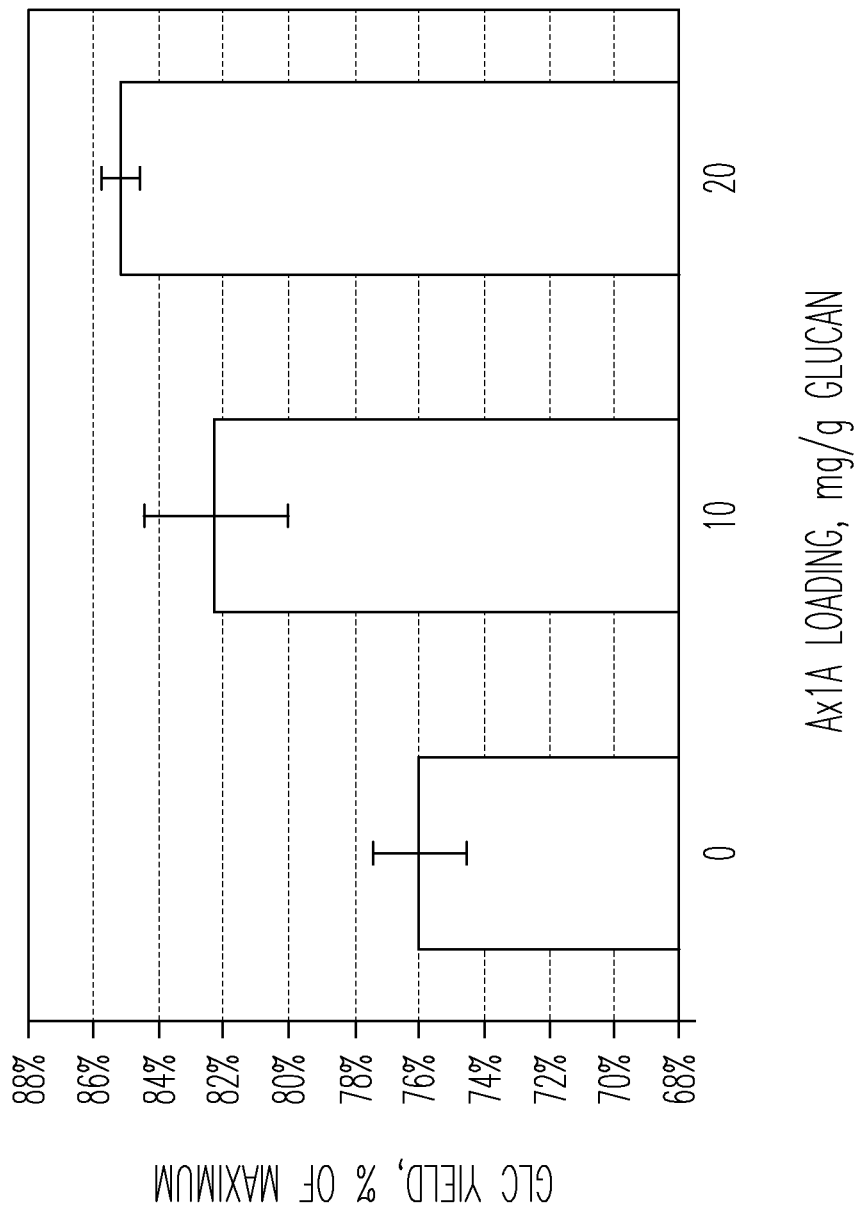

FIG. 3 presents exemplary data showing that the α-xylosidase as described herein increases glucose yield from alkaline hydrogen peroxide (AHP) treated corn stover when added to the commercially available Accellerase® 1000 (Acc1000) enzyme mixture. Acc1000 loading was 10 mg/g glucan. The α-xylosidase (Ax1A) increased the yield of glucose from 76% of maximum possible yield to 85%, an absolute increase of 9%. Ax1A: α-xylosidase (Aspni5|43342; GenBank DAA35002.1).

Figure 4:
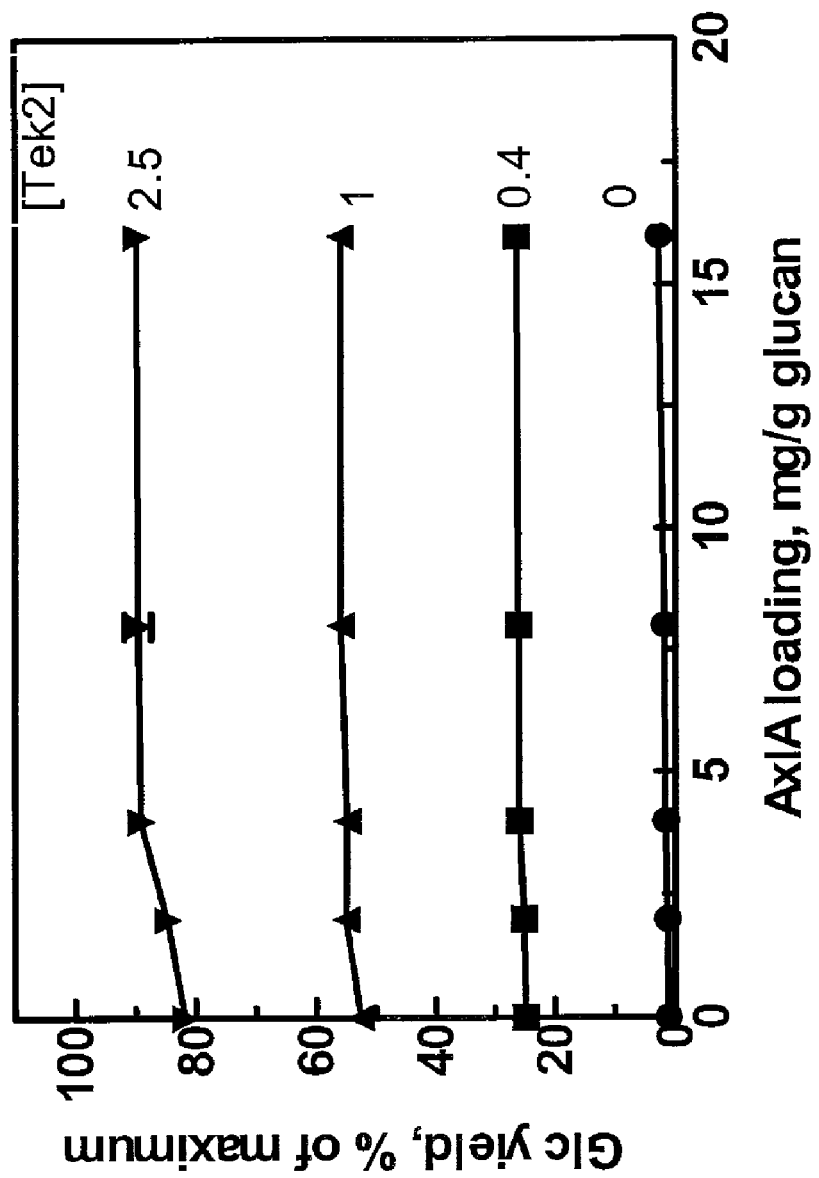

FIG. 4 presents exemplary data showing a dose response effect of the α-xylosidase (Ax1A) described herein on glucose yield in combination with a commercially available enzyme mixture composed of 50:50 Cellic® CTec2 and Cellic® HTec2 ("Tek2" in the figure) at different loadings of 0, 0.4, 1 and 2.5 mg/g glucan. The stimulating effect of α-xylosidase is most pronounced at the 2.5 mg/g CTec2:HTec2 loading.

Figure 5:
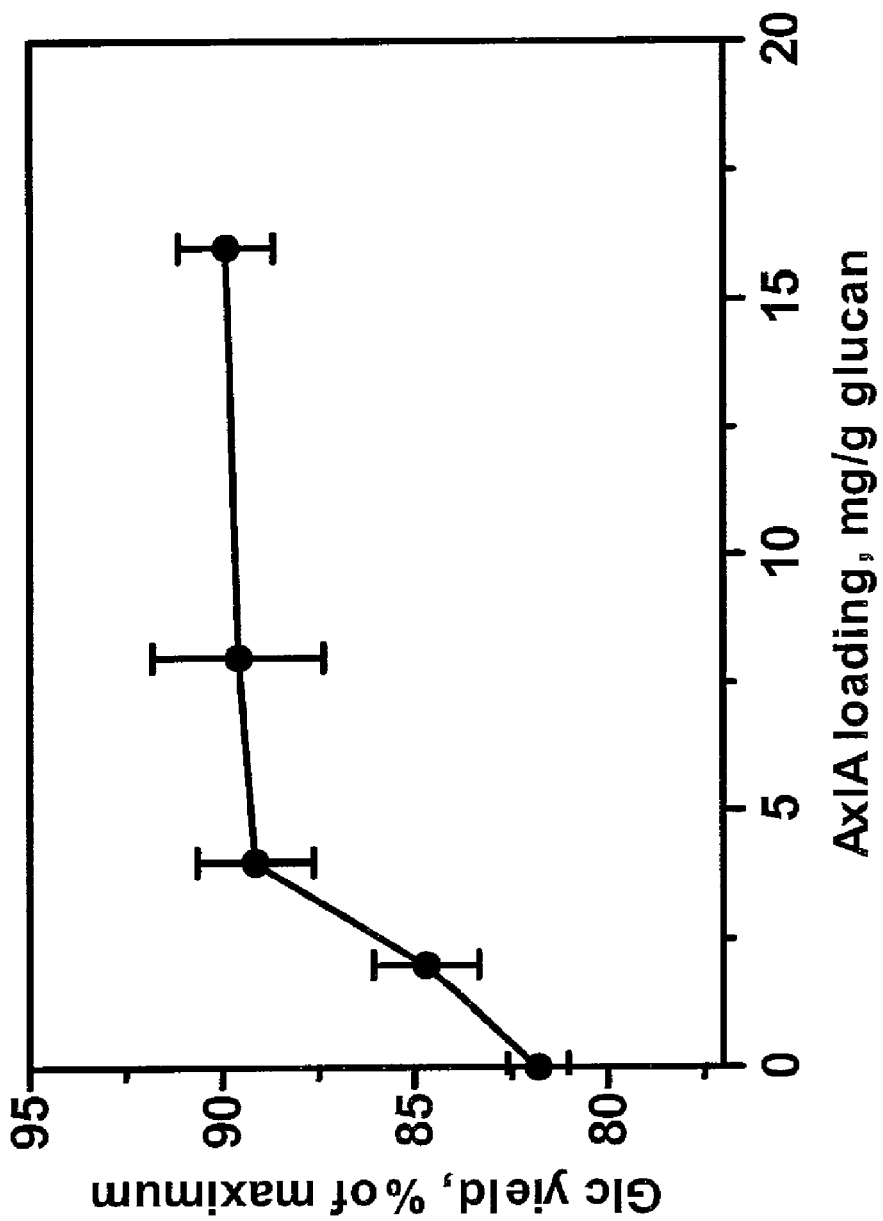

FIG. 5 graphically illustrates an expanded scale of the CTec2:HTec2 2.5 mg/g loading data from FIG. 4.

Figure 6:
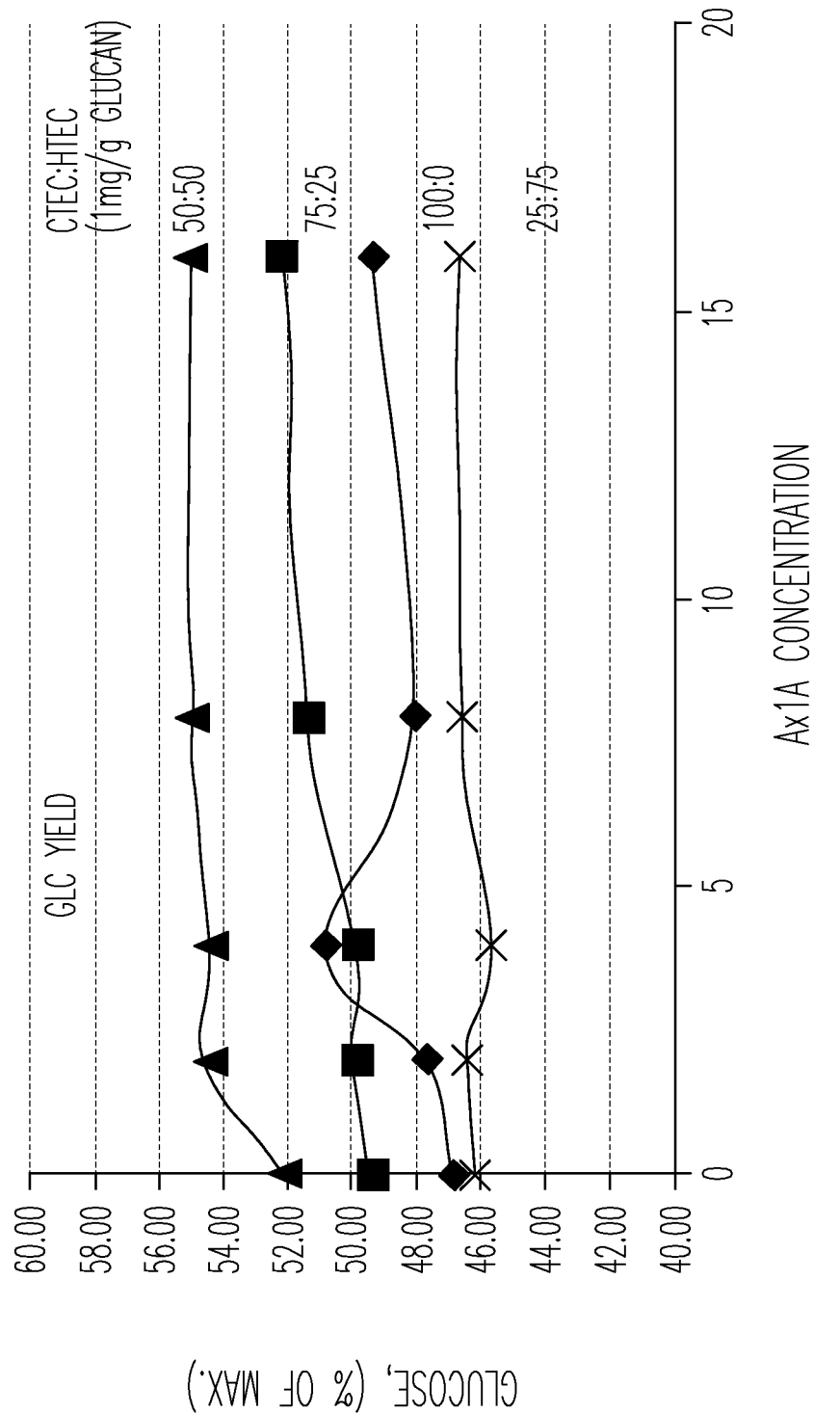

FIG. 6 graphically illustrates a secreted α-xylosidase (Ax1A) dose response curve for glucose release when combined with various proportions of CTec2 and HTec2. Total CTec2+HTec2 loading in every case was 1 mg/g glucan. As the concentration of α-xylosidase was increased, glucose release was enhanced at almost all proportions of CTec2 and HTec2, including 100:0 (diamond symbols), 50:50 (triangle symbols), and 75:25 (square symbols), but not 25:75 (X symbols).

Figure 7:
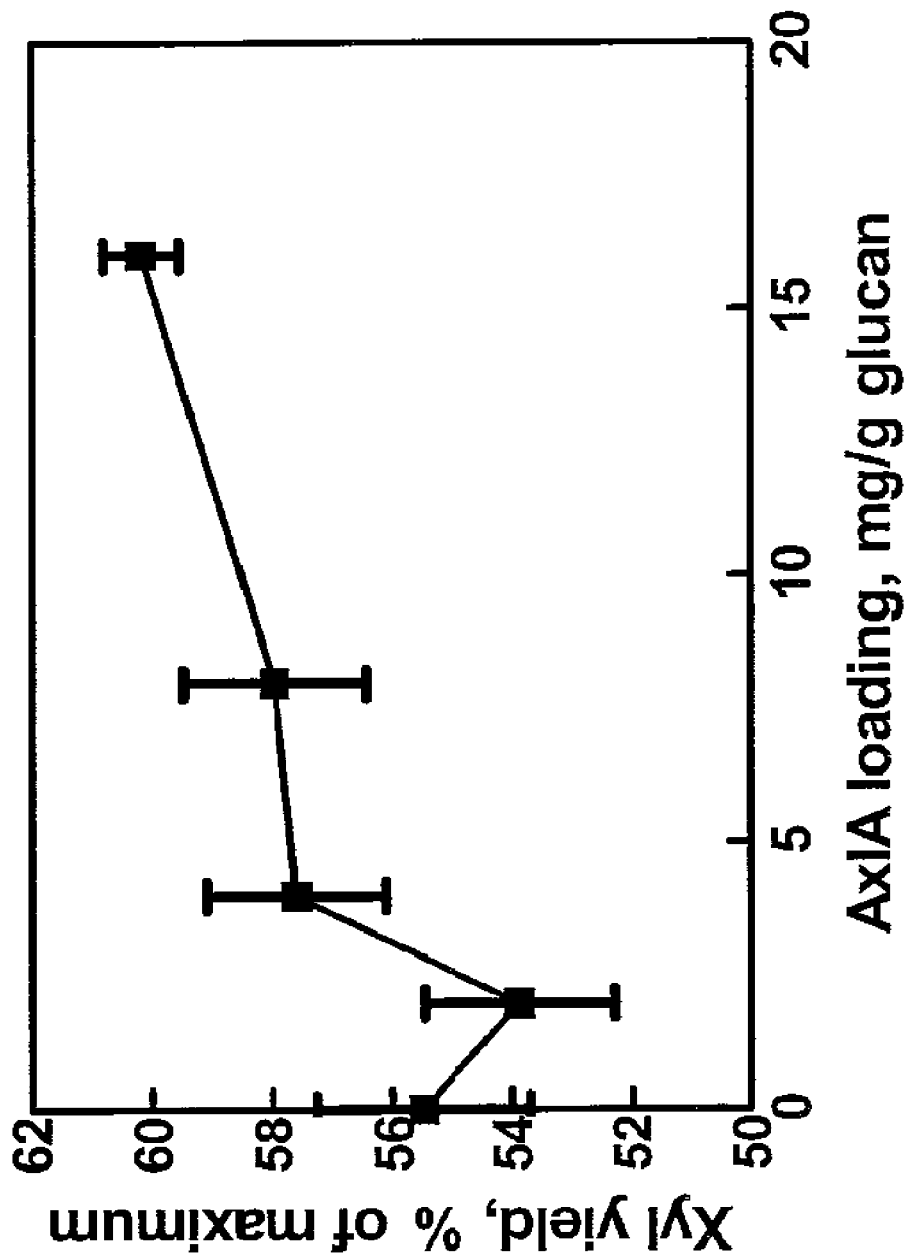
Figure 8:
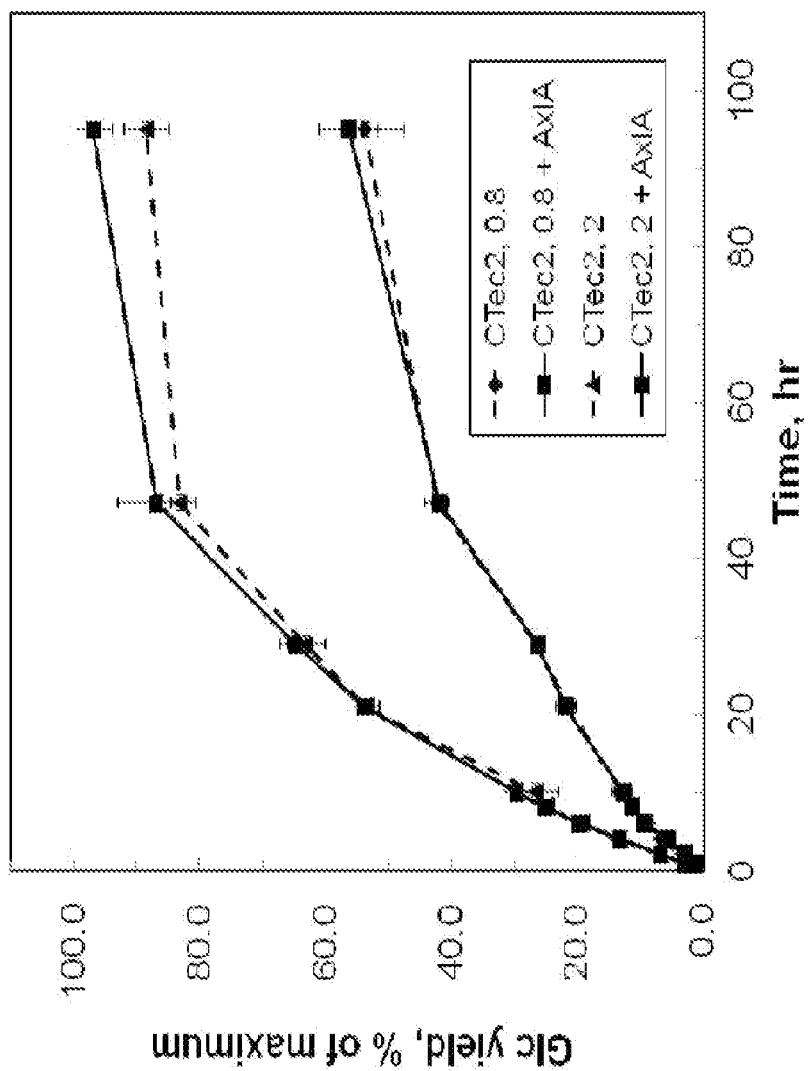

FIG. 7 illustrates enhancement of xylose yields from alkaline hydrogen peroxide-treated corn stover by α-xylosidase (Ax1A) used in combination with a CTec2:HTec2 mixture (75:25) at an enzyme loading of 2.5 mg/g glucan. The data are from the same experiment shown in FIG. 4 at expanded scale FIG. 8 illustrates a time course of enzymatic hydrolysis of alkaline-hydrogen peroxide-pretreated corn stover with or without supplementation with α-xylosidase (Ax1A), as detected by glucose release from the corn stover. The α-xylosidase loading was 0 or 4 mg/g glucan. CTec2 and HTec2 (in the proportion 75:25) loading was 0.8 or 2 mg/g glucan. Addition of the α-xylosidase (+Ax1A) enhanced glucose yield (solid lines) compared to the glucose release without addition of α-xylosidase (−Ax1A; dashed lines).

Figure 9:
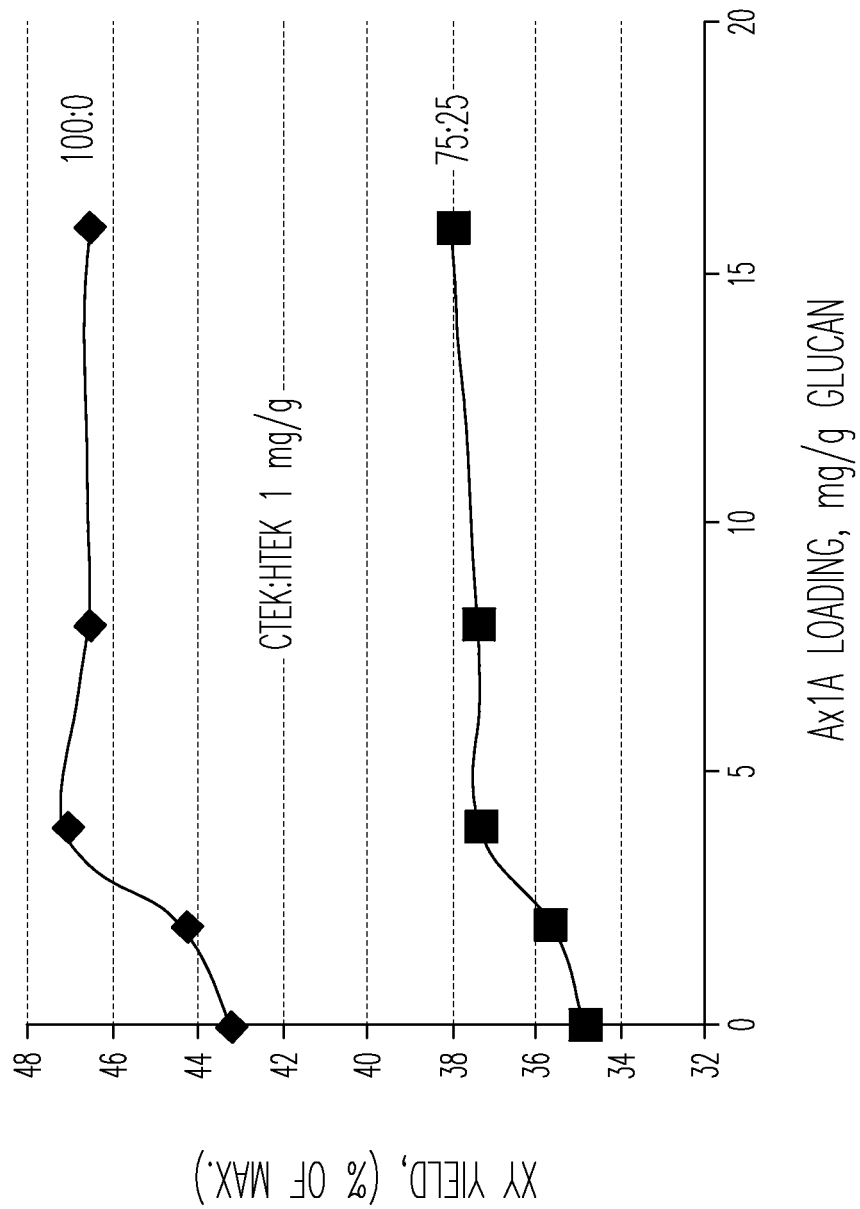

FIG. 9 illustrates enhancement of xylose (XY) yields from alkaline hydrogen peroxide-treated corn stover in response to addition of α-xylosidase (Ax1A) to a CTec2:HTec2 mixture (enzyme loading concentration of 1 mg/g glucan) at the indicated proportions.

Figure 10A:
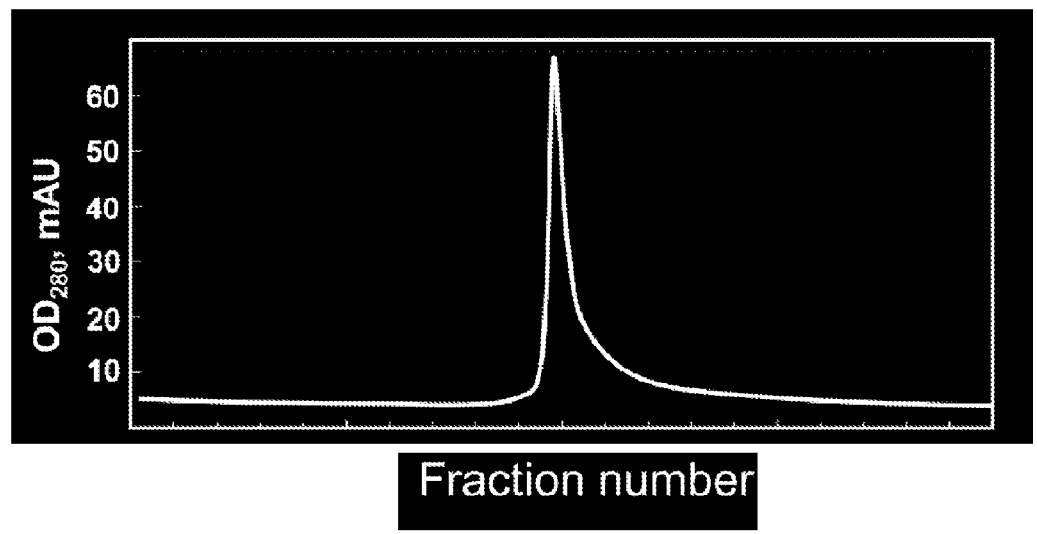
Figure 10B:
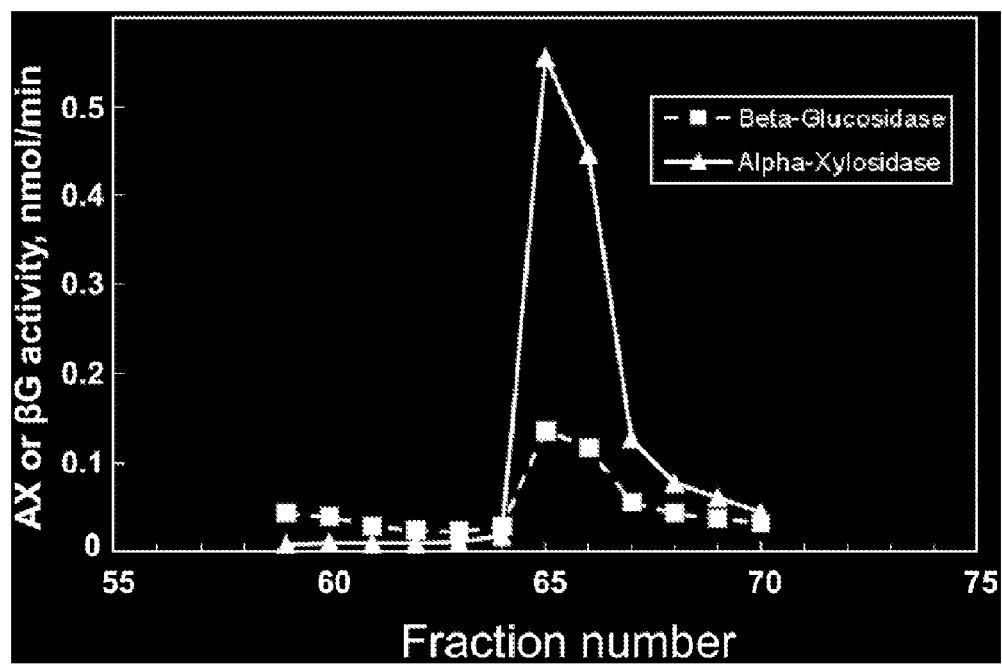

FIG. 10A-B presents exemplary data of a final purification step of α-xylosidase by hydrophobic interaction chromatography. FIG. 10A shows the ultraviolet absorption of proteins eluted. FIG. 10B correlates α-xylosidase and β-glucosidase (βG) activities with the elution fraction number, where the α-xylosidase and β-glucosidase (βG) were determined using pNPαX and p-nitrophenyl-β-D-glucoside (pNPβG), respectively, as substrates. mAU=milliabsorbance units.

Figures 11A, 11B:
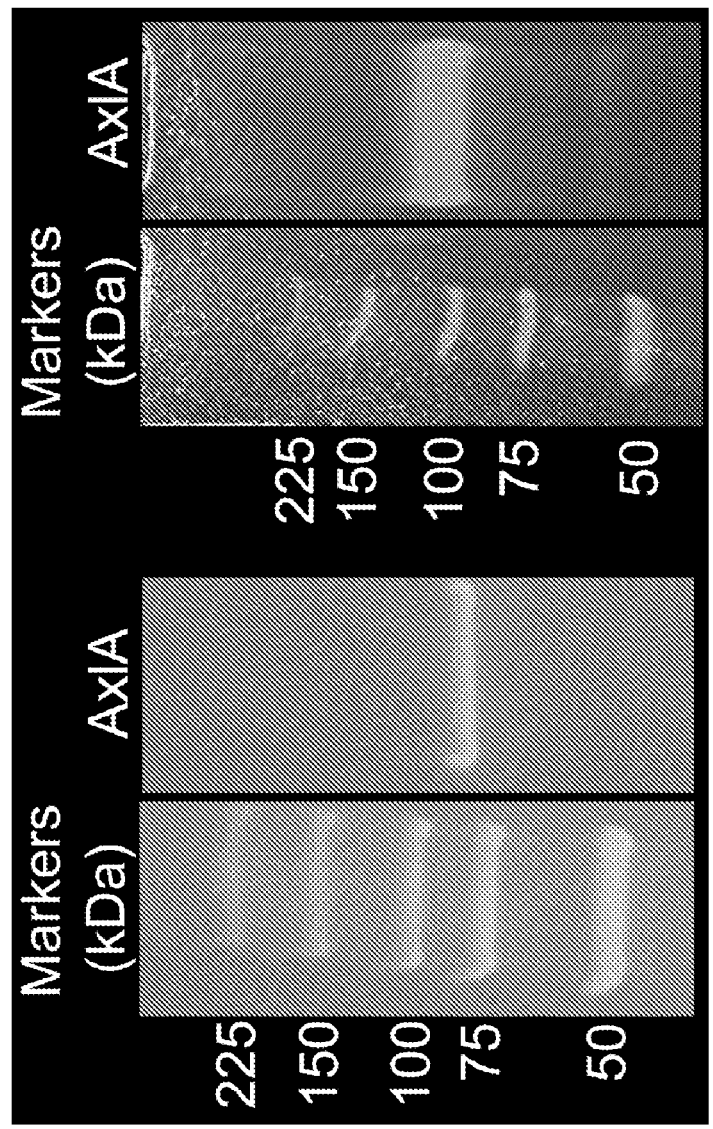

FIG. 11A-B shows proteins separated by SDS-PAGE after isolation and purification of the secreted α-xylosidase enzyme (Ax1A) described herein. The standards and unknowns are from the same gel. The gels were stained with Coomassie Blue. FIG. 11A: Native α-xylosidase enzyme purified from *Aspergillus niger*. FIG. 11B: Recombinant secreted α-xylosidase enzyme expressed in *Pichia pastoris*.

Figure 12A:
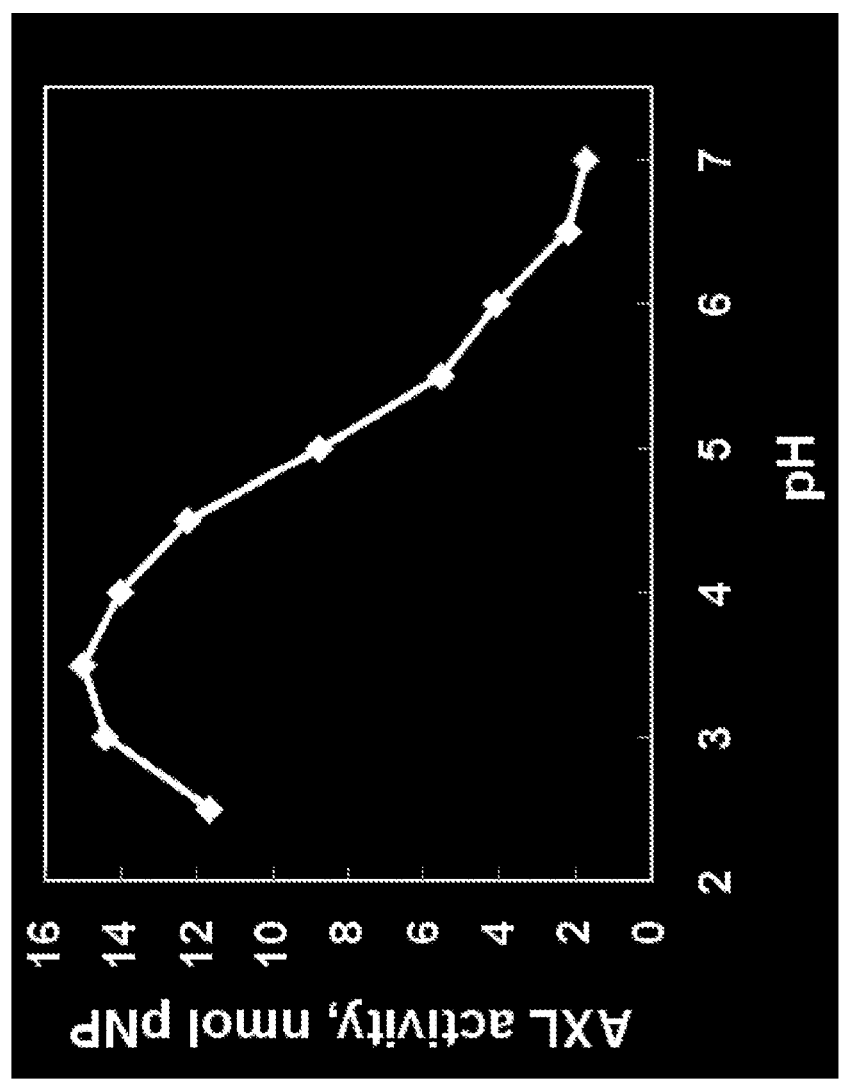
Figure 12B:
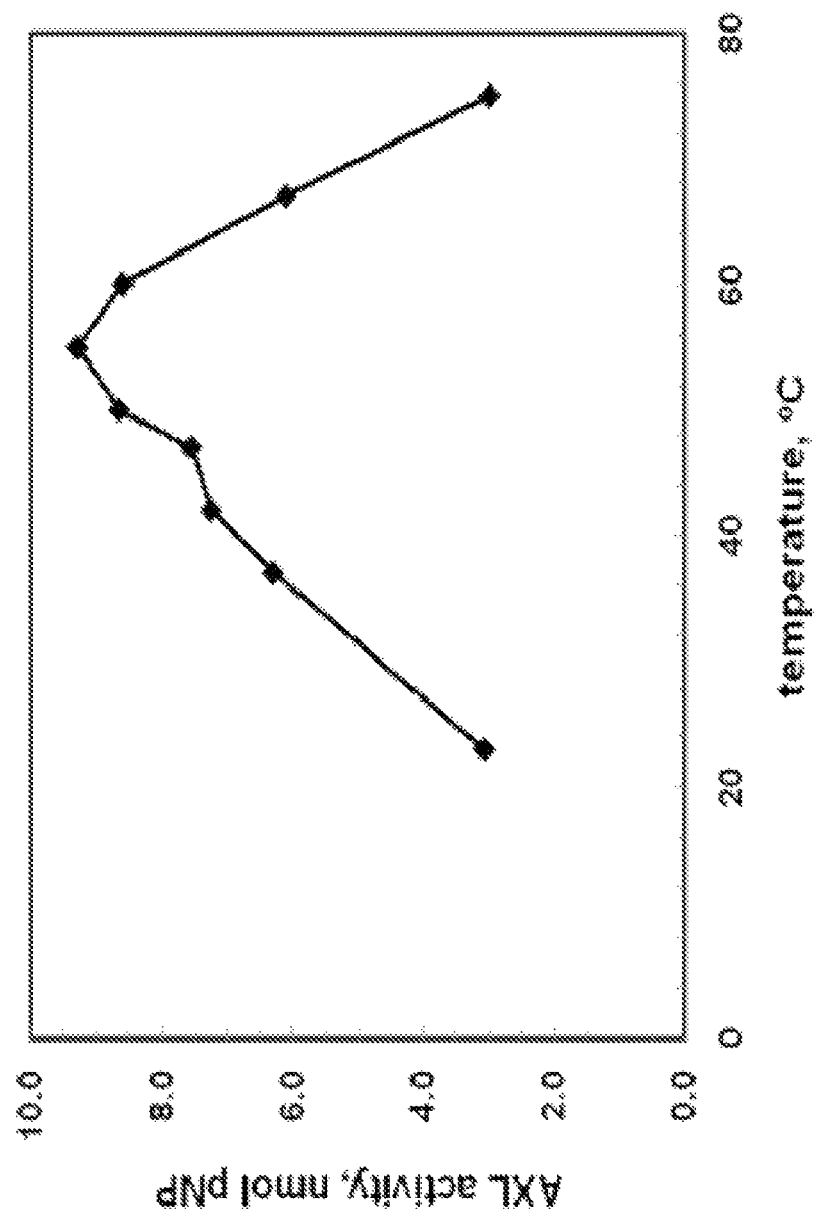

FIG. 12A-B illustrate the pH and temperature optima for α-xylosidase (AXL) enzyme activity. FIG. 12A graphically illustrates the pH dependence of secreted α-xylosidase (Ax1A) enzyme activity. Assays were performed with 10 mM pNPαX at 50° C. for 30 min. FIG. 12B graphically illustrates the response of α-xylosidase (Ax1A) enzyme activity to temperature, where the enzyme concentration was 88 ng/ml, the concentration of pNPαX was 2.5 mM, and the reaction time was 60 min.

Figure 13:
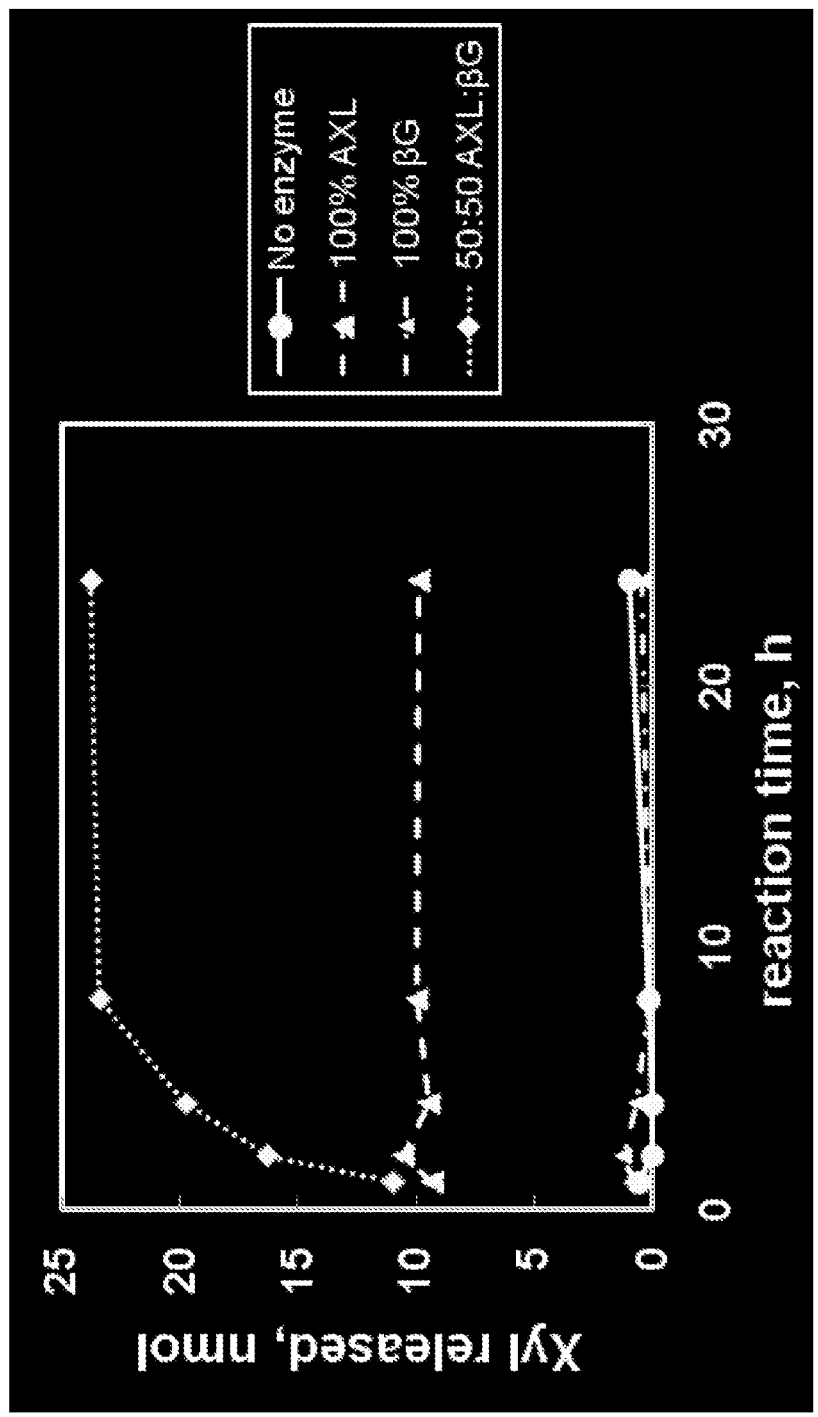

FIG. 13 presents exemplary data showing the digestion of xyloglucan heptasaccharide (a chain of four glucose residues linked together by beta 1,4 linkages where three of the glucose residues are linked by alpha 1,6 linkages to a xylose residue (shorthand notation XXXG)) to free xylose by the α-xylosidase (AXL) described herein (dashed line with large filled triangles), by β-glucosidase (dashed, dotted line with small filled triangles), or by a 50:50 combination of the two (diamond symbols). The concentration of the heptasaccharide was 1 mg/ml. Total protein concentration was 30 μg/ml. The results show that either enzyme alone cannot completely degrade xyloglucan heptasaccharide, but a combination of the two can. The xylose released by the α-xylosidase alone is consistent with the α-xylosidase being able to remove one alpha-linked xylose residue but not the other two without the intervening action of β-glucosidase.

Figure 14:
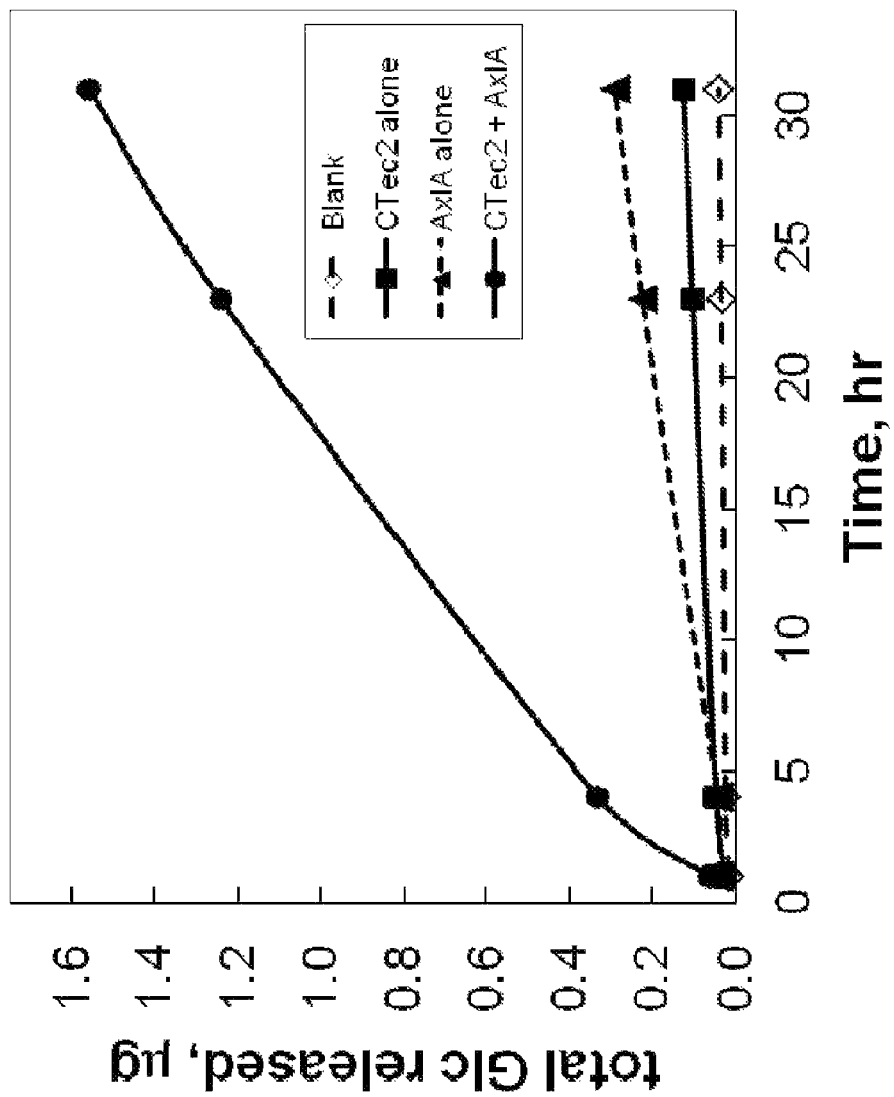

FIG. 14 shows that α-xylosidase (Ax1A) supplementation of a 75:25 mixture of CTec2 and HTec2 strongly enhances release of free glucose from purified pea xyloglucan. Each reaction contained 10 μg xyloglucan, 50 ng of the CTec2:HTec2 mixture, and 80 ng α-xylosidase in a total volume of 50 μl. The free glucose content in 10 μl of the reaction mixture was measured at each time point by an enzyme-linked assay (Banerjee et al., *Bioresour. Technol.* 101: 9097-9105 (2010); Scott-Craig et al. (*J Biol Chem* 286:42848-42854 (2011)).

Figure 15:
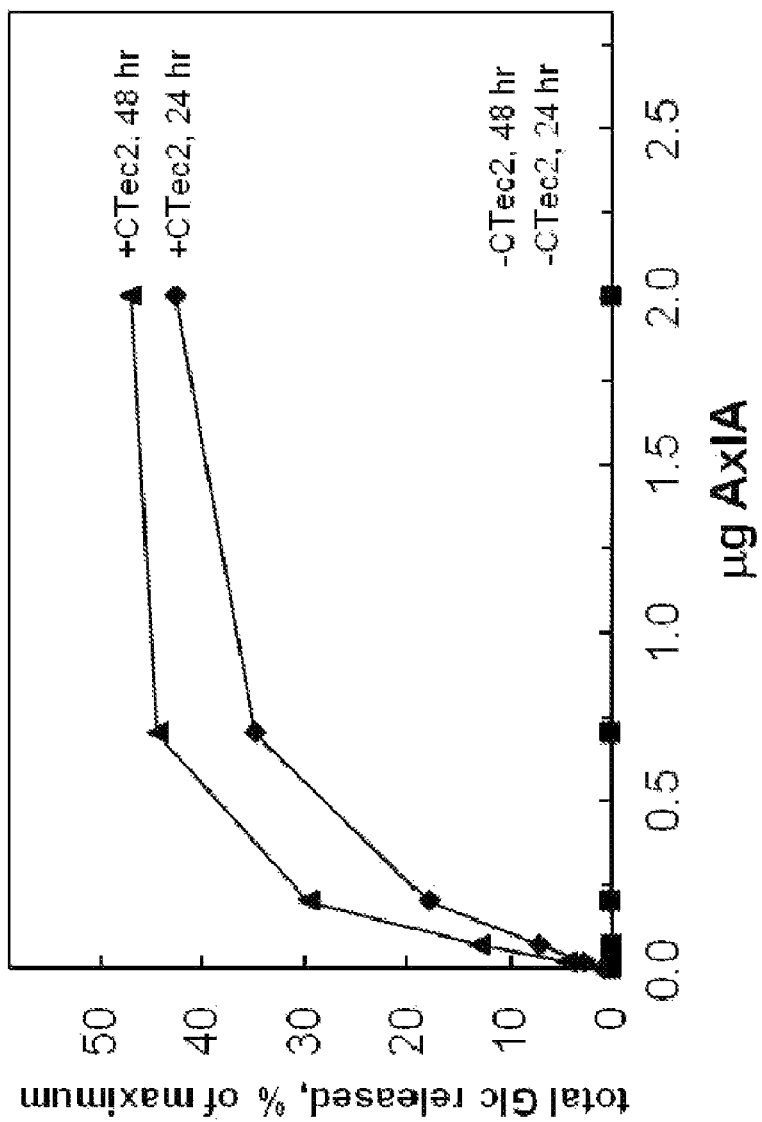

FIG. 15 illustrates glucose release from tamarind xyloglucan as a function of α-xylosidase (Ax1A) concentration. The α-xylosidase was combined with 75:25 CTec2:HTec2 loaded at 2.5 mg/g glucan using a reaction volume of 500 μl. The xyloglucan concentration was 3 mg/ml, giving a maximum possible yield of 1.5 mg glucose/ml.

Figure 16:
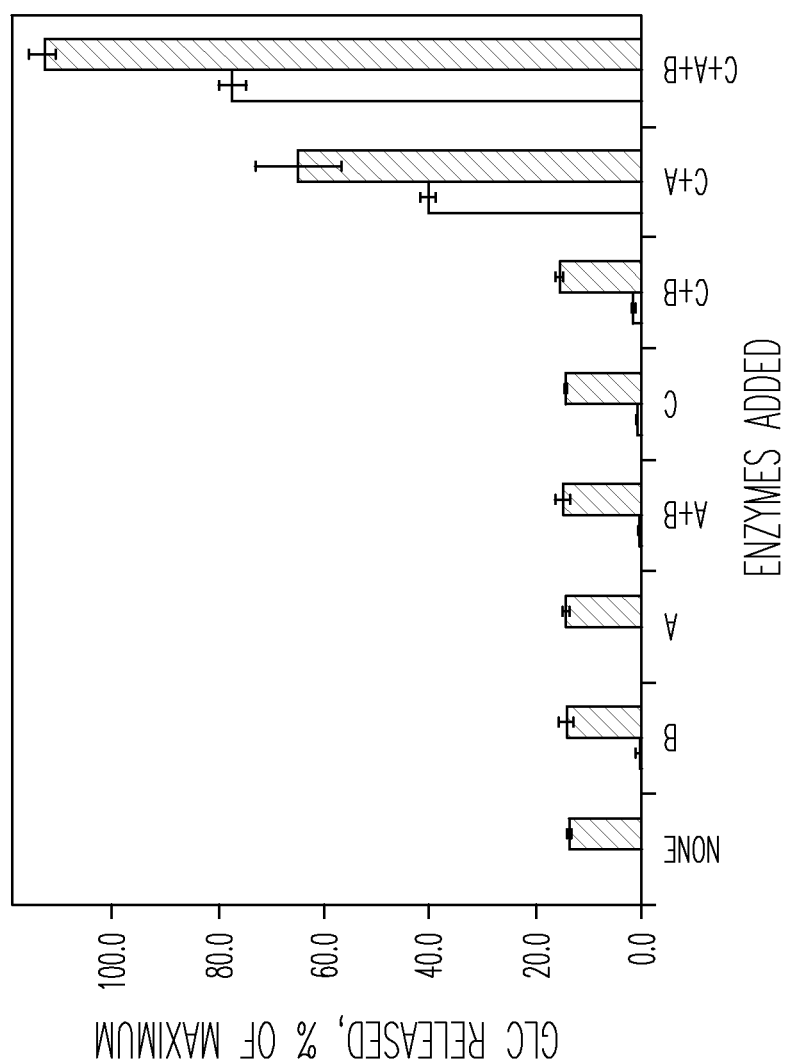

FIG. 16 shows that supplementation of the CTec2:HTec2+α-xylosidase enzyme mixture with β-galactosidase (B) improves yields of glucose from tamarind xyloglucan, compared to α-xylosidase alone (A), and/or a mix of CTec2:HTec2 (C). The tamarind xyloglucan concentration was 3 mg/ml, the CTec2:HTec2 (75:25) loading was 2.5 mg/g glucan, and the α-xylosidase and β-galactosidase loadings were each 8 mg/g glucan. A, α-xylosidase; B, β-galactosidase; C, CTec2:HTec2.

Figure 17:
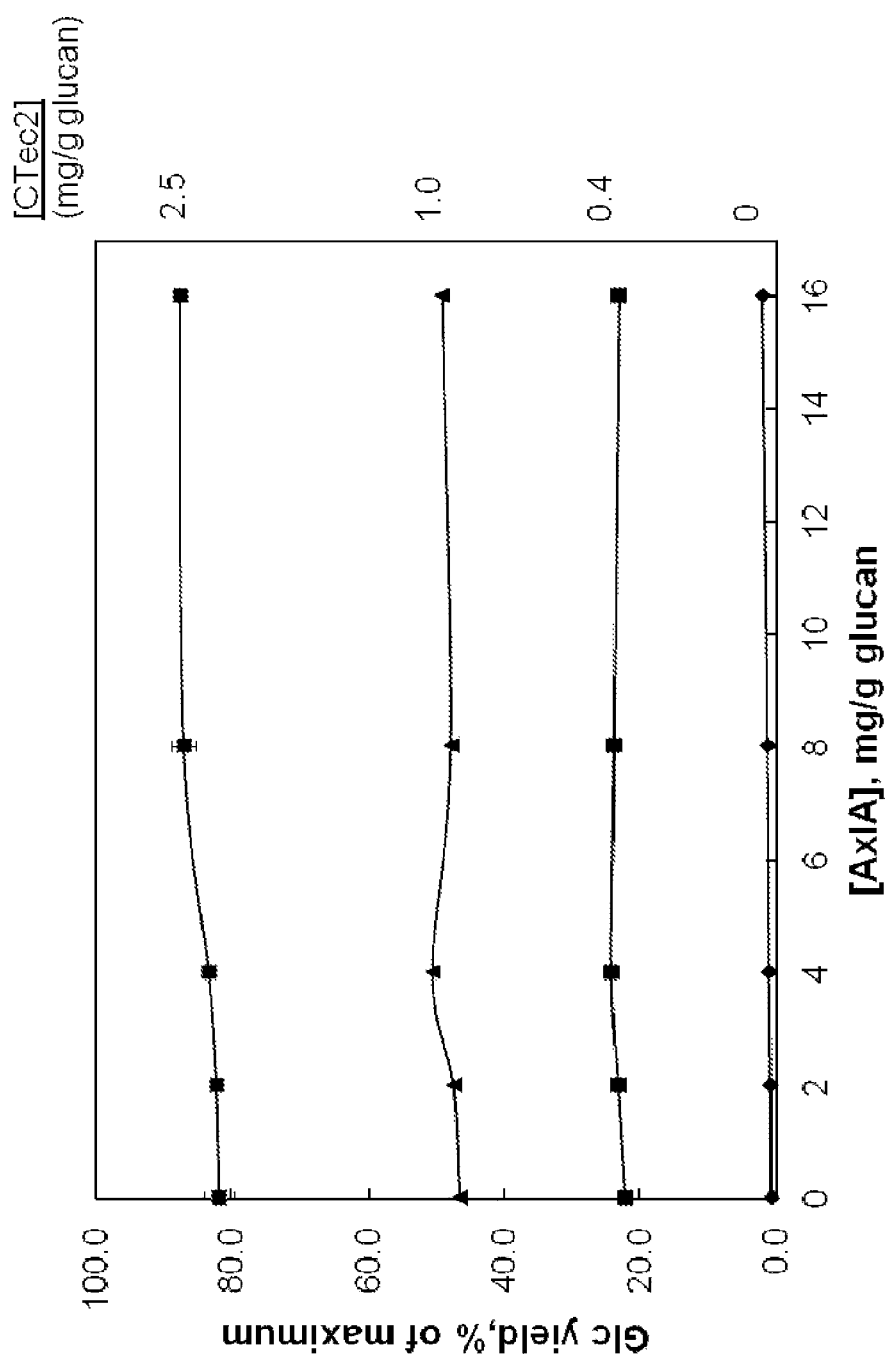

FIG. 17 shows that α-xylosidase (Ax1A) supplementation of CTec2:HTec2 improves glucose yields from alkaline hydrogen peroxide-pretreated corn stover. The CTec2:HTec2 ratio was 100:0. The CTec2:HTec2 loading was 0, 0.4, 1.0, or 2.5 mg/g glucan and the incubation time was 48 hr. Similar results were obtained with a 75:25 ratio of CTec2:HTec2 (data not shown).

Figure 18A:
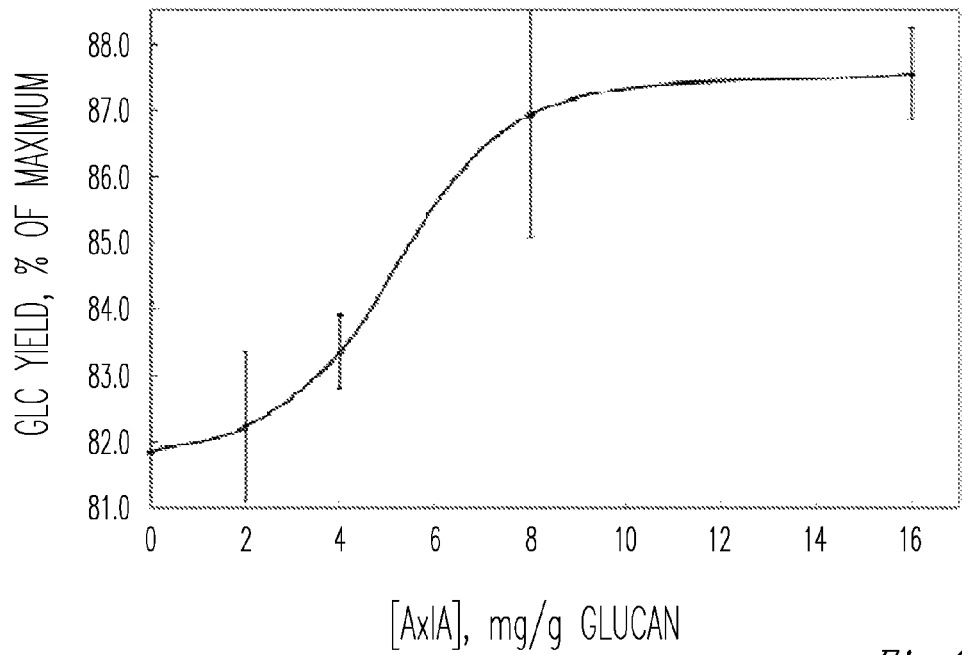
Figure 18B:
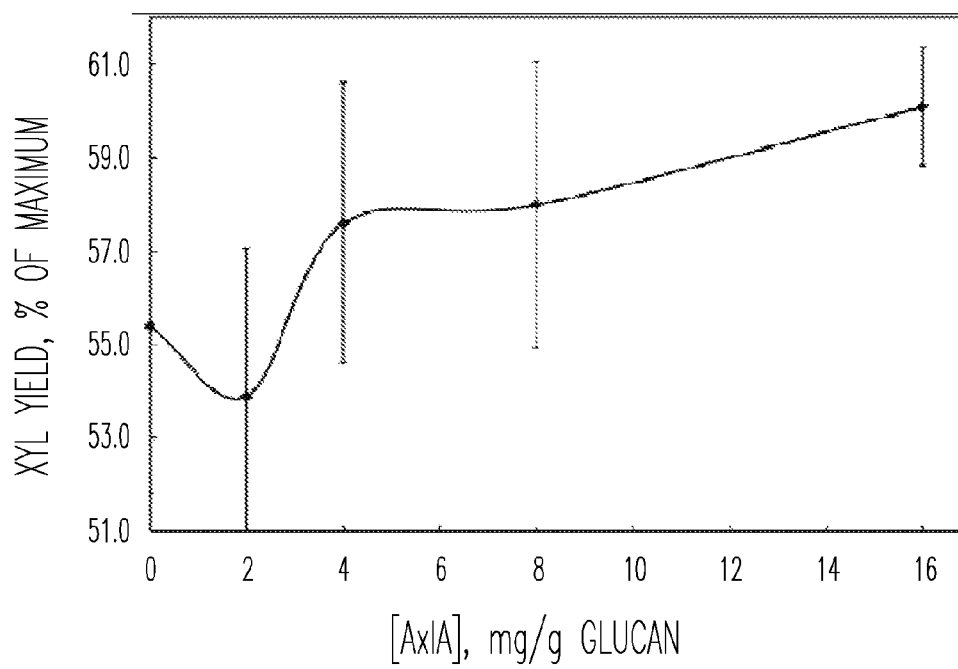

FIG. 18A-18B illustrate the effect of α-xylosidase supplementation on sugar yields, shown in expanded scale. FIG. 18A illustrates glucose release in an expanded scale of the results from FIG. 17 for 2.5 mg/g glucan CTec2:HTec2. FIG. 18B illustrates xylose release from the same experiment shown in expanded scale.

Figure 19A:
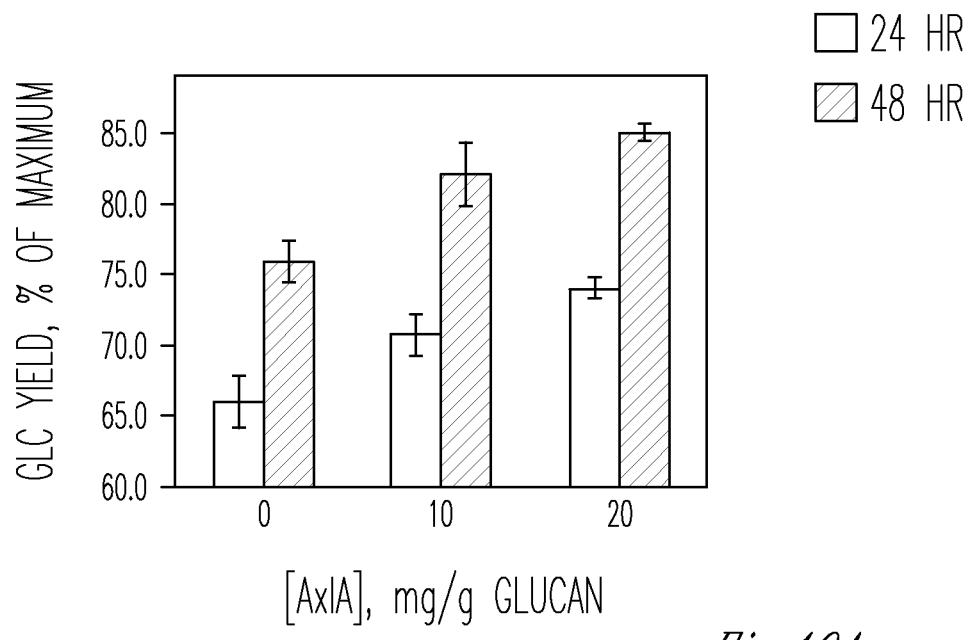
Figure 19B:
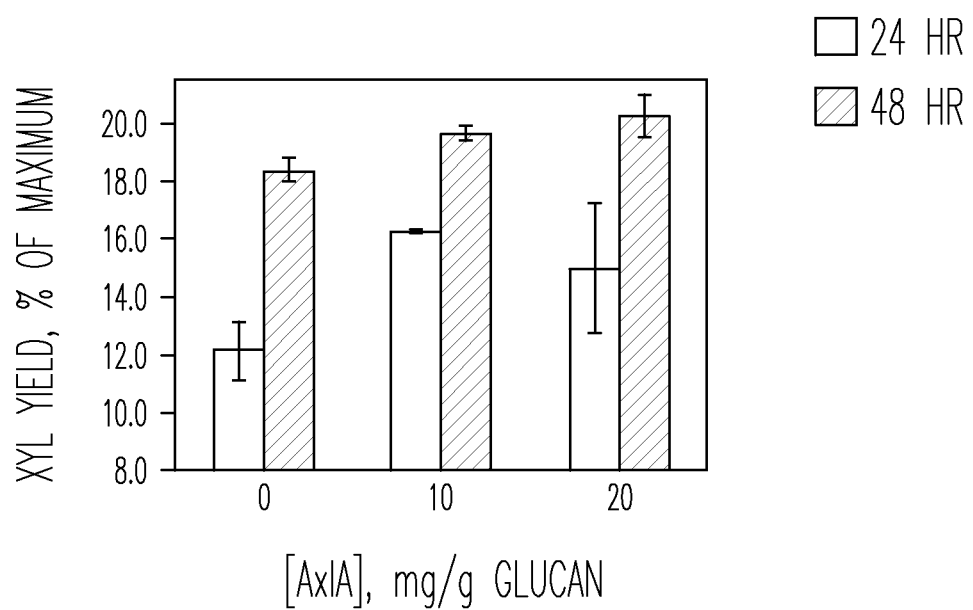

FIG. 19A-19B shows that α-xylosidase (Ax1A) supplementation also enhances the activity of the cellulase enzyme mixture known as Accellerase 1000. FIG. 19A illustrates glucose yield at 24 hr and 48 hr hydrolysis times from AHP-pretreated corn stover in response to 5 mg/g glucan Accellerase 1000 and the indicated concentrations of Ax1A. FIG. 19B shows xylose yields from the same experiment.

Figure 20:
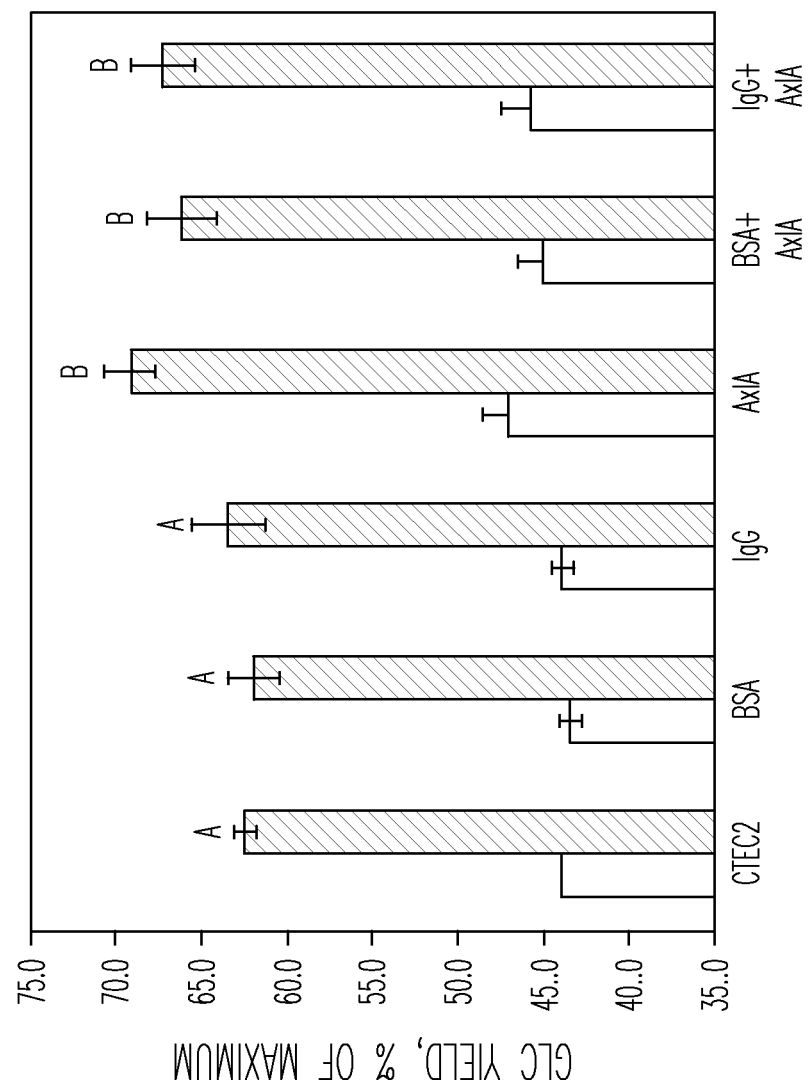

FIG. 20 illustrates that α-xylosidase-enhanced sugar release is not just a general protein effect. "CTec2" indicates a 75:25 mixture of CTec2 and HTec2 at a loading of 2.5 mg/g glucan. Neither BSA nor IgG stimulated glucose yields in response to CTec2:HTec2, nor did either protein affect the enhancement by α-xylosidase. The loadings of α-xylosidase (Ax1A), bovine serum albumin (BSA), and bovine immunoglobulin (IgG) were 8 mg/g glucan. Lowercase letters above the data bars indicate significantly different or not from CTec2:HTec2 alone (P<0.05 in Tukey's multiple comparison test, n=6).

Figure 21:
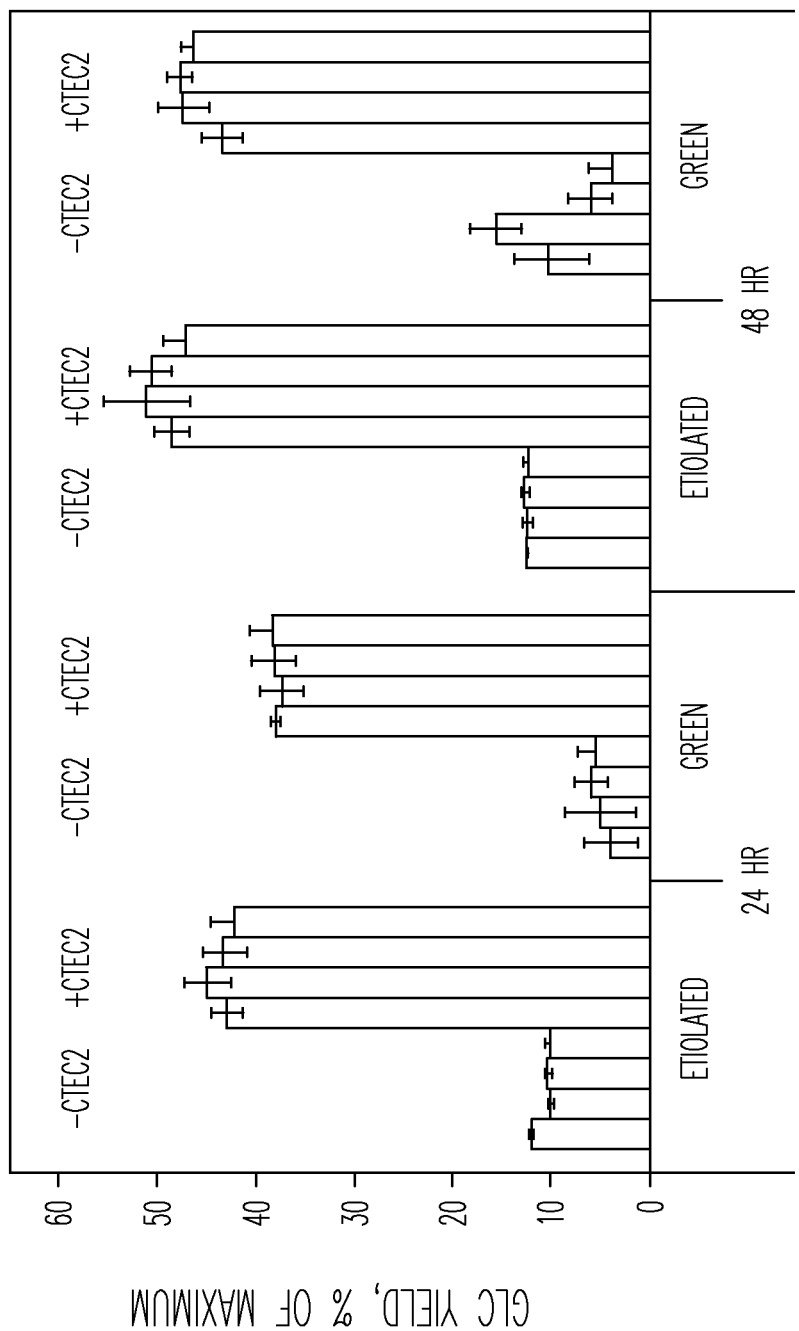

FIG. 21 shows that α-xylosidase supplementation does not enhance glucose yield from pea (*Pisum sativum*) biomass. Etiolated (dark-grown) and green (light-grown) peas (all above-ground parts) were not washed before or after AHP pretreatment. "+CTec2" indicates that 15 mg/g glucan 75:25 CTec2:HTec2 was used; "−CTec2" indicates neither CTec2 nor HTec2 was used. Within each group of four data bars, the mg α-xylosidase/g glucan loadings increased from left to right: 0 mg α-xylosidase/g glucan (first bar), 4 mg α-xylosidase/g glucan (second bar), 8 mg α-xylosidase/g glucan (third bar), and 16 mg α-xylosidase/g glucan (fourth bar).

Figure 22A:
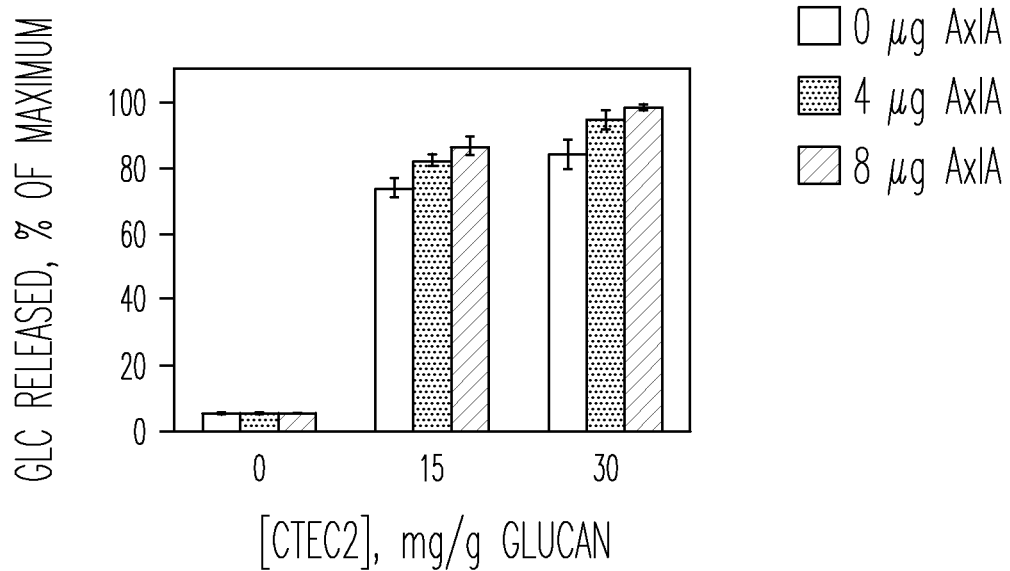
Figure 22B:
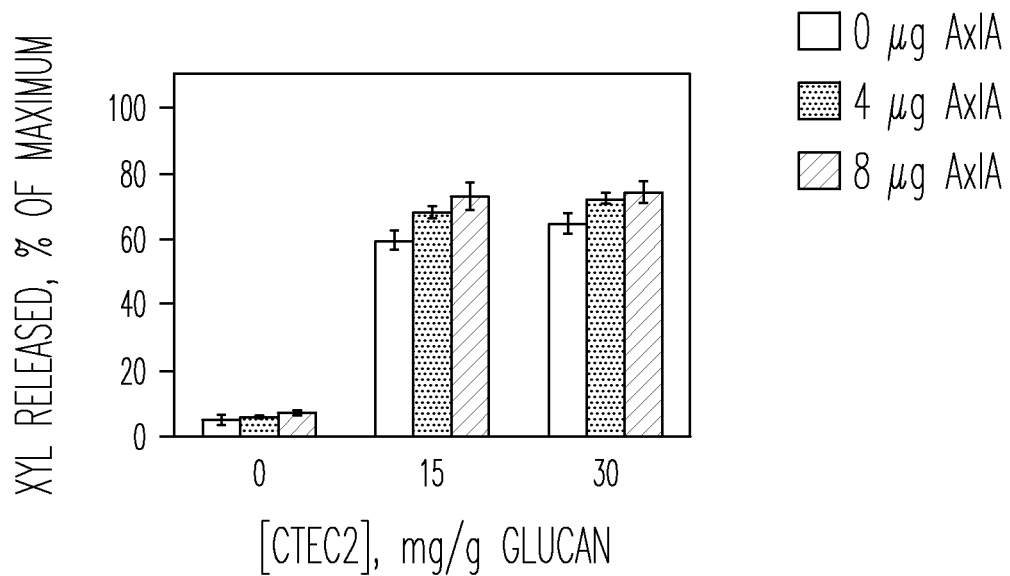

FIG. 22A-22B show that α-xylosidase (Ax1A) supplementation enhances glucose and xylose yields from the herbaceous dicot (forb) lamb's quarters (*Chenopodium album*). FIG. 22A shows glucose yield, while FIG. 22B shows xylose yield. The CTec2:HTec2 ratio was 75:25. Hydrolysis time was 48 hr.

DETAILED DESCRIPTION

This invention is related to the production of biofuels by converting cellulosic materials into fermentable sugars. For example, the release of fermentable sugars from a plant biomass may be enhanced using an extracellular and/or secreted α-xylosidase fungal enzyme. For example, the secreted α-xylosidase fungal enzyme efficiently degrades xyloglucans into xylose and glucose, a compound typically not degraded to xylose and glucose by most commercially available enzyme mixtures. Additionally, chemical and/or heat pretreatment of the plant biomass (e.g., with alkaline hydrogen peroxide), further enhances the release of fermentable sugars from a lignocellulose material by an α-xylosidase and other enzymes.

In one embodiment, the present invention contemplates a composition comprising an α-xylosidase and a plurality of microbial enzymes that can depolymerize plant biomass materials. In one embodiment, the α-xylosidase is a secreted α-xylosidase. For example, the α-xylosidase can be derived from a fungal species. Addition of a secreted α-xylosidase to a plurality of microbial enzymes provides a novel enzymatic activity that is not present in current commercial cellulase mixtures, and increases fermentable sugar release from a plant biomass. Commercially, such an increased sugar release lowers the overall cost of biofuel production (expressed as dollars of enzyme needed per liter of fuel).

One embodiment of the invention is a method for expressing α-xylosidase in vitro (e.g. in a cell culture vat, bioreactor or fermenter) that involves obtaining a host cell that includes an isolated nucleic encoding an α-xylosidase enzyme and culturing the host cell for a time and under conditions for expression of the α-xylosidase enzyme from the isolated nucleic acid. The α-xylosidase enzyme can be a secreted α-xylosidase. Such a secreted α-xylosidase enzyme can be isolated from cell culture medium without destruction of the host cells. For example, the cells can be removed and recycled, or the cell culture medium can be decanted, filtered or otherwise separated from host cells that are retained in the cell culture apparatus. The host cells can include bacterial, fungal, insect or other cell types. For example, the host cells can be yeast or filamentous fungi cells. Examples of suitable host cells include *Trichoderma reesei* cells, *Sporotrichum thermophile* cells, *Pichia pastoris* cells, *Aspergillus niger* cells, and combinations thereof (see FIG. 11). The isolated nucleic acid can also include a promoter operably linked to a nucleic acid segment that encodes the α-xylosidase enzyme. For example, the promoter can include a native secreted α-xylosidase gene promoter, an inducible promoter, a constitutively active promoter, a developmentally regulated promoter, a tissue-specific promoter, or a combination thereof. In one embodiment, the method includes simultaneous production of a plurality of enzymes, for example, in a cell culture that includes a plurality of host cells (of the same of different species) that express a plurality of enzymes.

The results described herein indicate that α-xylosidase can be more effective at the "limit" of glucose and xylose production, i.e., when glucose and xylose yields are highest due to extended hydrolysis time or to high enzyme loadings. For example, the α-xylosidase can catalyze the final step in the release of glucose and xylose from xyloglucan.

I. Conventional Plant Biomass Degradation

Currently, the production of ethanol and/or other biofuels derived from a lignocellulosic material begins with the conversion of the lignocellulosic material into free, fermentable sugar compounds (e.g., glucose, xylose etc.). Usually, this conversion (also referred to as deconstruction) is performed with a mixture of microbial enzymes. Many of these lignocellulosic-depolymerizing microbial enzymes can be obtained from fungi. An example of a fungal species from which these lignocellulosic-depolymerizing enzymes can be obtained includes, but are not limited to *Trichoderma reesei* and *Sporotrichum thermophile*. Pre-made microbial enzyme mixtures, containing more than eighty (80) proteins, are commercially available (i.e., for example, Accellerase 1000 and Spezyme CP) and generally made by expression from *Trichoderma reesei* host cells. However, one technical disadvantage of these commercial mixtures is that their effectiveness is limited to the specific catalytic activity of each individual enzyme. For example, if one wishes to degrade cellulose, the microbial enzyme mixture must contain a β-1,4-glucanase. Similarly, if one wishes to degrade xylan, the microbial enzyme mixture should contain a β-1,4-xylanase. Use of a variety of different enzymes allows release of more fermentable sugars.

Commercial enzyme mixtures generally have high levels of cellulases (for example, cellobiohydrolase, endoglucanase, and β-glucosidase), which degrade cellulose. However, these enzyme mixtures are suboptimal for degrading hemicelluloses.

Hemicelluloses are structurally more complex than cellulose and can have different monosaccharides. Moreover, different plant species and different parts of the same plant can have different types of hemicelluloses.

One of the major types of hemicellulose in the primary walls of herbaceous dicotyledons is xyloglucan. Xyloglucan comprises a backbone of β-1,4-glucose substituted with α-1,6-linked xylose, β-linked galactose, and in some plants, α-linked fucose. Hsieh et al., *Mol. Plant.* 2:943-965 (2009). Another hemicellulose, glucuronoarabinoxylan, is present with xyloglucan in some grasses (e.g., the Poaceae family). Most plants comprise α-linked xylose sugars in polysaccharide xyloglucan complexes. Xyloglucan is comprised of a hemicellulose residing in the primary cell walls of all plants. Furthermore, xyloglucan may or may not be substituted with galactose (Gal) and/or fucose (Fuc). For example, in some grasses, xyloglucan is less substituted, typically lacking galactose or fucose. It has been observed that xyloglucan in some grasses has reduced numbers of xylose, galactose and/or fucose substitutions compared with other plant species. Hayashi T., *Annu. Rev. Plant Physiol. Plant Mol. Biol.* 40:139-168 (1989); see FIG. 1. As described herein, xyloglucan is substituted with xylose, a sugar that cannot be released efficiently with any commercially available cellulase enzyme mixtures. Considering that plant cell-derived xyloglucan comprises metabolizable sugars (e.g., fermentable sugars) an efficient mixture for biomass deconstruction of xyloglucan-containing plant biomass should have the full range and proper proportions of enzymes needed for its degradation. For example, these mixtures should contain enzymes capable of efficiently cleaving xylose residues from the xyloglucan backbone structure.

Although it is not necessary to understand the mechanism of an invention, it is believed that degrading xyloglucan hemicellulose is advantageous for two reasons: i) hemicelluloses inhibit cellulase degradation of cellulose by blocking cellulase access to cellulose; and ii) hemicelluloses comprise fermentable sugars, including but not limited to, glucose, xylose, galactose, fucose, and mannose.

Some commercial enzyme mixtures comprise hemicellulose degrading enzymes, including but not limited to, β-1,4-xylanase, β-xylosidase, α-arabinosidase, mixed-linked glucanase, α-glucuronidase, etc. In contrast, the most common commercial enzyme mixtures (e.g., Spezyme CP, Accellerase® 1000, Multifect Xylanase, Cellic® CTec2, HTec2, CTec3, HTec3, and AlternaFuel® CMAX) do not include an α-xylosidase enzyme that has catalytic activity directed to hydrolyzing α-linked xylose (Xyl) residues from substrates such as isoprimeverose, or xyloglucan (FIG. 1B and data not shown).

A complete deconstruction of xyloglucan can involve use of multiple enzymes including, but not limited to: i) α-fucosidase to remove a terminal fucose residue; ii) β-galactosidase to remove a penultimate galactose; iii) α-xylosidase to remove an α-1,6-linked xylose residue, preferably a secreted α-xylosidase; and iv) a β-1,4-glucanase and/or a β-glucosidase to depolymerize a glucan backbone. Some β-1,4-glucanases have xyloglucanase activity, i.e. they can hydrolyze β-1,4-glucan linkages in substituted glucans such as xyloglucan. However, other β-1,4-glucanases act only on unsubstituted β-1,4-glucans such as cellulose. Grishutin et al., *Biochim. Biophys. Acta* 1674:268-281 (2004). Neither β-1,4-glucanases nor xyloglucanases can release xylose from xyloglucan. This is a property only of an effective α-xylosidase.

Effective enzyme mixtures for biomass degradation and/or deconstruction should have a combined catalytic activity capable of cleaving any saccharide linkage found in plant cell walls to release free, fermentable sugar residues. Many microorganisms that live in lignocellulose-rich environments secrete large numbers and broad ranges of cell wall-active enzymes, including, but not limited to, cellulases, hemicellulases, pectinases, and/or proteases. Most commercially available deconstruction enzyme mixtures contain between approximately twenty-five to one hundred and fifty (25-150) enzymes. Nagendran et al., *Fung. Genet. Biol.* 46: 427-435 (2009); Banerjee et al., *Bioresour. Technol.* 101: 9097-9105 (2010); and Scott-Craig et al., *J Biol Chem* 286:42848-42854 (2011). However, these mixtures are not necessarily ideal with respect to the range of combined catalytic activities or the relative proportions of such catalytic activities. Such suboptimal ranges and proportions of catalytic activity limit the applicability of these commercially available enzyme mixtures. For example, the commercially available enzyme mixtures may work well with certain biomass types that have been subjected to certain pretreatment conditions. But the current commercially available enzyme mixtures are not effective for all types of biomasses. To achieve optimal release of fermentable sugars, diverse types of biomasses subjected to various pretreatment conditions will need an enzyme mixture containing diverse enzymes.

Superior and more efficient enzyme mixtures would ensure that the appropriate enzyme catalytic activity is present for any particular biomass being degraded. For example, although all higher plant cell walls contain cellulose, different plant species and even different tissues within a plant can have quite different hemicellulose compositions and proportions. Pauly et al., *Plant J.* 54:559-568 (2008). Hemicelluloses are present within many plant cell wall components including, but not limited to, xyloglucan, glucuronoarabinoxylan, mannan, galactan, arabinan, mixed-linked glucan, and/or glucuronoarabinoxylan. Carpita, N., and McMann, M. (2000), In: BIOCHEMISTRY AND MOLECULAR BIOLOGY OF PLANTS (Buchanan, B. B., Gruissem, W., and Jones, R. L., eds.) pp. 52-108, American Society of Plant Physiologists, Rockville, Md. Hemicelluloses contain a number of fermentable, or potentially fermentable, monosaccharides including, but not limited to, glucose, xylose, galactose, arabinose, mannose, fucose, rhamnose, and uronic acids. Many of these sugars are also found in pectins and wall proteins such as extensins and arabinogalactan proteins.

II. α-Xylosidase Mediated Plant Biomass Degradation

Amongst the cell wall active depolymerases, α-xylosidase is not a well understood enzyme because relatively few microbial α-xylosidase enzymes have been described in the literature. α-Xylosidase enzymes are classified in glycosyl hydrolase family 31 (as per the CAZy database), which also includes enzymes with a number of other activities, especially α-glucosidases. Henrissat et al, *Curr. Opin. Struct. Biol.* 7:637-644 (1997). α-Xylosidase enzymes have been identified in various biological sources including, but not limited to, fungi, bacteria, and/or plants. Notably, distinguishing α-xylosidase enzymes from α-glucosidases based solely on nucleic acid and/or amino acid sequence information is not possible, so comparative biochemical data should be used for this purpose. Thus, an enzyme should be purified or cloned to permit testing and characterization of its enzymatic activity.

In most bacteria and fungi that can metabolize xyloglucan, extracellular enzymes first break the xyloglucan down to the disaccharide isoprimeverose, the isoprimeverose is imported into the cytoplasm, and then the isoprimeverose is broken down into free xylose and glucose using a cytoplasmic α-xylosidase. For example, the bacterium *Lactobacillus pentosus* has an isoprimeverose (IP) utilization operon, which includes an isoprimeverose transporter and a cytoplasmic α-xylosidase. Chaillou et al., *J Bacterial.* 180:2312-2320 (1998). Other bacteria have been reported to have α-xylosidase enzymes encoded in their genomes, for example: i) *Escherichia coli* (yicI) (Lovering et al., *J Biol Chem* 280:2105-2115 (2005)), ii) *Sulfolobus solfataricus* (xylS) (Moracci et al., *J Biol Chem* 275:22082-22089 (2000); and iii) *Cellvibrio japonicus* (xyl31A); Larsbrink et al., *Biochem J* 436:567-580 (2011); Okuyama et al., Protein Expr. Purif. 37:170-179 (2004). The prokaryotic cytosolic α-xylosidase from the archaean *Sulfolobus solfataricus* has been characterized, and has a preferred temperature of greater than 80° C., with low activity at 50° C. Consequently, one would not expect the α-xylosidase enzyme from *Sulfolobus solfataricus* (xylS) to improve the efficiency of commercially available lignocellulose depolymerizing enzyme mixtures from, for example, *Trichoderma* and/or *Aspergillus*, which optimally degrade biomass between approximately 40-50° C.

In regard to fungi, the only α-xylosidase enzymes that have been studied are cytoplasmic, from *Aspergillus flavus*, *Aspergillus niger*, and *Penicillium wortmanii*, The α-xylosidases characterized from *A. niger* are cytoplasmic, not secreted, and therefore significantly different from the preferred α-xylosidase described herein. They also have quaternary structure and therefore would not be preferred for industrial applications, e.g., biomass deconstruction. Furthermore, the genes encoding any fungal α-xylosidase have not previously been unequivocally identified and/or characterized. Matsuo et al., *Biosci. Biotechnol. Biochem.* 60:341-343 (1996); Matsushita et al., *Agric. Biol. Chem.* 51:2015-2016 (1987); and Yoshikawa et al., *Biosci. Biotechnol. Biochem.* 58:1392-1398 (1994). For example, a gene referred to as AN7505, which purportedly encodes an α-xylosidase from *A. nidulans*, was identified by expression in *Pichia pastoris*. The function of AN7505 was not well characterized because it was tested only against the synthetic α-xylosidase substrate pNPαX, and not against a more complex and demanding substrate such as that found in lignocellulosic biomass. Bauer et al., *Proc. Natl. Acad. Sci. U.S.A.* 103:11417-11422 (2006). Substrates used to characterize α-xylosidase enzyme activity should include activity comparison of the substrates p-nitrophenyl-α-xyloside (pNPαX), isoprimeverose (IP), and xyloglucan oligosaccharides and polysaccharides. Furthermore AN7505 lacks a signal peptide and is therefore probably a cytoplasmic enzyme, and thus not suited to industrial biotechnology applications.

A. α-Xylosidase Enzymes

α-Xylosidase enzymes in plants may be involved in mobilization of seed storage xyloglucan and/or remodeling of cell wall xyloglucan. Nakai et al., *J Biochem.* 142:491-500 (2007); O'Neill et al., *J Biol. Chem.* 264:20430-20437 (1989); and Sampedro et al., *Plant Physiol.* 126:910-920 (2001). These α-xylosidases are not of fungal origin, and would be less suited to industrial-scale conversion of xyloglucan to free glucose and xylose. One salient feature of the microbial α-xylosidase enzymes studied to date is that most (probably all) are intracellular (e.g., cytoplasmic) enzymes and few, if any, have been reported to be secreted free into the medium. Matsushita et al., Agric. Biol. Chem. 51:2015-2016 (1987). Further, it has been reported that Xyl31A (*C. japonicus*) is partially cytoplasmic and partially anchored to the outer cell wall. Larsbrink et al., *Biochem. J.* 436:567-580 (2011). The intracellular location of XylS of *S. solfataricus* has not been reported, but clustering of its encoding gene with a gene for a disaccharide transporter suggests that it is cytoplasmic, like the α-xylosidase of *L. pentosus*. Moracci et al., *J. Biol. Chem.* 275:22082-22089 (2000). Consistent with a cytoplasmic location for most fungal α-xylosidase enzymes, the majority of the fungal proteins in GenBank™ that are annotated as belonging to GH31 lack predicted signal peptides.

Because intracellular fungal α-xylosidases are reported to be labile, comprise a quaternary structure, and lack a signal sequence, it is believed that intracellular fungi α-xylosidases are insufficiently robust to support industrial fermentation applications. Yoshikawa et al. *Biosci Biotechnol Biochem* 57:1275 (1993); and Yoshikawa et al. *Biosci Biotechnol Biochem* 58:1392 (1994).

B. Secreted Extracellular α-Xylosidase Enzymes

Unlike intracellular cytosolic α-xylosidases, the secreted α-xylosidase enzymes are structurally configured to survive in harsh and unstable extracellular environments and are therefore generally preferred over cytoplasmic proteins for the compositions and methods provided herein. In one embodiment, a composition is provided comprising a secreted, extracellular α-xylosidase. In one embodiment, the secreted α-xylosidase enzyme is derived from a fungus. In one embodiment, the fungus is *A. niger*.

Extracellular α-xylosidases can be active at mesophilic temperatures (about 50° C.) and have an optimum pH close to that of other fungal enzymes (about pH 4.8). Furthermore, extracellular α-xylosidases can degrade isoprimeverose and xyloglucan oligosaccharides that are native components of plant cell walls. As a result, an α-xylosidase that is normally secreted as an extracellular fungal enzyme can be more robust than intracellular α-xylosidase enzymes. For an industrial process such as lignocellulose breakdown, which takes places in a potentially harsh environment, an extracellular enzyme is preferable. However, secreted fungal α-xylosidases are believed to be rare and have not previously been documented in the literature.

Even though some plants (i.e., for example, rice, nasturtium, and/or *Arabidopsis*) have secreted α-xylosidases that degrade storage xyloglucan and/or remodel their cell walls during growth, α-xylosidases from such plants would not be a preferred source for biomass degradation because it is more likely that a fungal α-xylosidase would be compatible with other fungal enzymes for biomass degradation applications. Crombie et al., *Planta* 214:406-413 (2002); and Nakai et al. *J Biochem* 142:491-500 (2007).

1. Identification and Purification

The data presented herein evaluate several fungi for secreted α-xylosidase activity on a variety of substrates. These fungi were *Cochliobolus carbonum, Fusarium graminearum, Trichoderma reesei, Aspergillus niger*, and *Phanerochaete chrysosporium*. The fungi were cultured on ground tamarind seed (which contains high levels of xyloglucan), corn stover (*Zea mays*), pea cell walls (*Pisum sativum*), and carrot cell walls (*Daucus carota*) that were either supplemented or not supplemented with lactose or xylose for 5-14 days. No activity against pNPαX was seen in any of the resulting culture filtrates indicating that α-xylosidase was not being secreted under these growth conditions. The following commercial enzyme products were also examined: Accellerase 1000, Accellerase XY, Multifect Xylanase, Multifect Pectinase, Novozyme 188, CTec2, and HTec2. α-Xylosidase activity against pNPαX was not seen in any of the commercially available enzyme mixtures tested except Multifect Pectinase, which had a specific activity of 0.197 μmol/min/mg. Consistent with the presence of α-xylosidase activity in this preparation, and only in this preparation, degradation of tamarind xyloglucan to free xylose and glucose was observed. FIG. 1B. Among all commercial enzyme mixtures tested, Multifect Pectinase was also the only one that exhibited activity against isoprimeverose. However, Multifect Pectinase is no longer available in the market, and it was a complex mixture of previously unidentified proteins. It was used in the food industry (e.g., for processing fruits) and no evidence is available that it has been used for digestion of cellulose-containing plant biomasses. Testing shows that Multifect Pectinase contained 4% or less of the protein as cellulase. Commercially available enzyme mixtures are typically made by growing fungal and/or bacterial cells and collecting the secreted enzymes. Thus, commercially available enzyme mixtures contain hundreds of enzymes. The amount and identity of the enzymes in the mixture is typically unknown.

To evaluate potential sources of α-xylosidases, mixtures were purified by High Performance Liquid Chromatography (HPLC) using three high resolution purification stages. A low level of β-glucosidase (βG) activity was consistently associated with the peak of α-xylosidase activity. FIG. 10. The secreted α-xylosidase activity peak did not contain any α-glucosidase or β-xylosidase activity as measured using pNPαG and p-nitrophenyl-β-D-xyloside, respectively. Other data indicates that the β-glucosidase activity was probably due to co-purification of a separate enzyme (infra). Their co-elution through multiple purification steps suggests that the two enzymes might form a complex in vivo. Although the secreted proteins of aerobic filamentous fungi are generally considered to be "noncomplexed," evidence for the formation of complexes between the secreted enzymes of a filamentous fungus has been reported recently. Gonzalez-Vogel et al., *Appl. Microbial. Biotechnol.* 89:145-155 (2011).

The molecular weight of the secreted α-xylosidase enzyme by SDS-PAGE was about 85 kDa. FIG. 11A. This secreted α-xylosidase enzyme has been identified as Aspni5|43342 (a numerical identification from the Department of Energy Joint Genome Institute) by proteomics. The dominant band was excised and subjected to tryptic digestion and mass spectrometric proteomics based on the whole predicted proteome of *A. niger* ATCC 1015 as the query database. Eight unique peptides amounting to 16% coverage of the Aspni5|43342 amino acid sequence were detected at about 95% probability. The only other protein detected was Aspni5|50997 which is an β-glucosidase in GH family 3. This might account for the residual β-glucosidase (βG) activity co-eluting with secreted α-xylosidase (supra), a conclusion that was supported by heterologous expression data (infra).

Unfractionated Multifect Pectinase enzyme mixture was also analyzed by mass spectrometric proteomics. At high confidence (about 95% probability), 132 proteins were identified (Table 4). More than 90% of the proteins have predicted signal peptides. Both Aspni5|43342 (secreted α-xylosidase) and Aspni5|50997 (βG) were detected (Table 4). However, Aspni5|56782 was the most abundant β-glucosidase (βG) in Multifect Pectinase (Table 4). In the JGI database, Aspni5|43342 is annotated as "Glycoside hydrolase family 31". Before the invention, the precise biochemical function of Aspni5|43342 was not known.

Aspni5|43342 (identified in various databases as XP_001393647, An09g03300, CAK40270, jgi|Aspni5|43342, fgenesh1_pg.C_scaffold_11000279) is a predicted protein in GH family 31, a family which includes predominantly α-glucosidases and known or putative α-xylosidases. Such putative α-xylosidases may not actually have any α-xylosidase activity, and/or may not have adequate α-xylosidase activity. Unless significant sequence identity is present, testing is needed to definitively establish whether a protein has α-xylosidases activity.

The cytosolic protein AN7505 (Genbank DQ490509.1) of *A. nidulans* has minimal amino acid sequence identity with the extracellular Aspni5|43342 enzyme of *A. niger* (also referred to herein as Ax1A). Yuan et al. showed that the gene for Aspni5|43342 is induced by growth on xylose and speculated that Aspni5|43342 may be a secreted α-xylosidase because of its weak homology to AN7505. Yuan et al., *Mol. Genet. Genomics* 279:545-561 (2008). However, Yuan et al. presented no biochemical or enzymatic data to support such a conclusion. For example, a 25% amino acid identity between AN7505 and Ax1A as described herein is weak. Furthermore xylose-induction of α-xylosidase expression is contrary to accepted understandings of biochemical feedback mechanisms. Typically, expression of an enzyme is repressed, not induced, by the products of the enzyme (in this case xylose). This makes biological sense because when free xylose is present, the fungus does not need to make enzymes to produce xylose. This is the biological logic of why, for example, glucose represses the expression of cellulase genes.

Consequently, the data presented herein provide the first experimental evidence that isolated and purified Aspni5|43342 (Ax1A) is, in fact, a true secreted α-xylosidase that has its primary function in the extracellular environment.

The data presented herein identifies an extracellular (i.e., secreted) α-xylosidase with a predicted signal sequence extracted from a filamentous fungus (i.e., for example, *Aspergillus niger*; Aspni5|43342, XP_001393647, GI: 145242002, shown below as SEQ ID NO:1).

```
  1 MYFSSFLALG ALVQAAAATY FAPNSTGLRI QHGFETILIQ
 41 PFGYDGFRVR AWPFRPPSGN EISFIYDPPI EGYEDTAHGM
 81 SYDTATTGTE PRTLRNGNII LRTTGWGGTT AGYRLSFYRV
121 NDDGSETLLT NEYAPLKSLN PRYYYWPGPG AEFSAEFSFS
161 ATPDEQIYGT GTQQDHMINK KGSVIDMVNF NSYIPTPVFM
201 SNKGYAFIWN MPAEGRMEFG TLRTRFTAAS TTLVDYVIVA
241 AQPGDYDTLQ QRISALTGRA PAPPDFSLGY IQSKLRYENQ
281 TEVELLAQNF HDRNIPVSMI VIDYQSWAHQ GDWALDPRLW
321 PNVAQMSARV KNLTGAEMMA SLWPSVADDS VNYAALQANG
361 LLSATRDGPG TTDSWNGSYI RNYDSTNPSA RKFLWSMLKK
401 NYYDKGIKNF WIDQADGGAL GEAYENNGQS TYIESIPFTL
441 PNVNYAAGTQ LSVGKLYPWA HQQAIEEGFR NATDTKEGSA
481 CDHVSLSRSG YIGSQRFCSM IWSGDTTSVW DTLAVQVASG
521 LSAAATGWGW WTVDAGGFEV DSTVWWSGNI DTPEYRELYV
561 RWLAWTTFLP FMRTHGSRTC YFQDAYTCAN EPWSYGASNT
601 PIIVSYIHLR YQLGAYLKSI FNQFHLTGRS IMRPLYMDFE
641 KTDPKISQLV SSNSNYTTQQ YMFGPRLLVS PVTLPNVTEW
681 PVYLPQTGQN NTKPWTYWWT NETYAGGQVV KVPAPLQHIP
721 VFHLGSREEL LSGNVF
```

A cDNA for the SEQ ID NO:1 protein is available from the NCBI database (www.ncbi.nlm.nih.gov) as accession number XM_001393610.1, GI:145242001, and provided below as SEQ ID NO:2.

```
   1 ATGTACTTCT CTTCCTTCTT GGCCCTAGGG GCCTTGGTTC
  41 AGGCTGCAGC AGCAACCTAT TTTGCCCCCA ACTCTACCGG
  81 TCTTCGTATC CAGCATGGTT TTGAGACGAT TCTTATCCAG
 121 CCGTTTGGGT ACGACGGATT CCGTGTGCGC GCATGGCCCT
 161 TCCGTCCGCC TTCGGGTAAC GAGATCAGCT TCATCTACGA
 201 TCCCCCGATC GAAGGCTATG AGGACACTGC GCATGGCATG
 241 AGCTATGACA CCGCAACCAC CGGCACGGAG CCTCGCACCT
 281 TGCGCAACGG CAATATCATC CTGCGCACCA CCGGCTGGGG
 321 TGGTACCACA GCCGGATACC GACTGTCCTT TTATCGCGTC
 361 AATGACGATG GAAGTGAGAC CCTTCTCACA AACGAATATG
 401 CTCCGCTGAA GTCTCTCAAC CCCCGGTACT ATTACTGGCC
 441 GGGACCTGGG GCCGAATTCT CAGCTGAGTT CTCTTTCAGT
 481 GCGCAGCCGG ATGAGCAGAT CTATGGTACG GGCACGCAAC
 521 AGGATCATAT GATCAACAAG AAGGGCTCCG TAATTGACAT
 561 GGTCAACTTC AACTCCTACA TCCCTACCCC GGTCTTCATG
 601 AGCAATAAAG GCTATGCCTT CATCTGGAAC ATGCCAGCTG
 641 AGGGGCGTAT GGAATTTGGC ACCCTCCGGA CCAGATTCAC
 681 CGCCGCGTCC ACGACGCTTG TTGACTATGT AATCGTCGCC
 721 GCGCAGCCGG GCGACTACGA CACCTTGCAG CAGCGGATTT
 761 CGGCCCTCAC AGGACGGGCC CCGGCCCCGC CTGACTTCTC
 801 GCTTGGATAC ATCCAGTCCA AGCTACGATA TGAAAACCAA
 841 ACGGAGGTGG AGCTGCTGGC TCAAAACTTC CATGACCGAA
 881 ACATCCCGGT GTCCATGATC GTTATTGACT ACCAGTCCTG
 921 GGCTCACCAG GGTGATTGGG CGCTCGATCC TCGCCTGTGG
 961 CCCAATGTTG CGCAGATGTC GGCGCGGGTC AAGAACCTCA
1001 CCGGCGCCGA AATGATGGCA TCGCTATGGC CCAGTGTTGC
1041 CGACGACAGC GTCAATTACG CAGCCCTGCA GGCGAACGGC
1081 CTTCTCTCGG CCACGCGCGA TGGACCTGGT ACCACTGACT
1121 CCTGGAACGG ATCATACATC CGGAACTATG ACTCCACCAA
1161 CCCCTCGGCG CGGAAGTTCC TCTGGAGCAT GCTGAAGAAG
1201 AACTACTACG ACAAGGGTAT CAAAAACTTT TGGATTGACC
1241 AAGCCGATGG CGGAGCGCTG GGTGAGGCGT ATGAGAACAA
1281 CGGACAGAGC ACGTATATTG AGTCCATCCC GTTCACCCTG
1321 CCAAACGTGA ACTATGCCGC TGGTACGCAG CTCAGCGTGG
1361 GTAAGCTGTA CCCCTGGGCG CATCAGCAGG CAATTGAGGA
1401 GGGGTTCCGC AATGCAACAG ATACCAAGGA AGGGAGCGCA
1441 TGCGATCATG TCTCCCTGAG TCGGTCTGGA TACATCGGAT
1481 CCCAGCGGTT CTGCAGCATG ATCTGGTCGG AGACACTAC
1521 ATCCGTTTGG GACACCCTGG CAGTGCAAGT AGCCAGTGGA
1561 CTGTCCGCCG CAGCAACAGG CTGGGGTTGG TGGACGGTCG
1601 ATGCCGGTGG CTTCGAAGTC GACTCGACTG TTTGGTGGAG
1641 TGGAAACATT GACACGCCTG AATACCGGGA GTTGTATGTG
1681 CGCTGGCTGG CTTGGACGAC TTTCCTGCCA TTCATGCGCA
```

```
1721 CTCACGGTAG CCGGACCTGC TATTTCCAGG ACGCCTACAC
1761 CTGTGCCAAT GAGCCGTGGT CCTATGGTGC AAGCAACACA
1801 CCCATCATTG TCTCGTACAT TCATCTGCGC TACCAGCTGG
1841 GTGCTTACCT GAAGTCCATC TTCAACCAGT TCCACCTCAC
1881 AGGCCGGAGC ATCATGCGCC CATTGTATAT GGATTTCGAG
1921 AAGACAGACC CGAAGATCTC CCAGCTGGTG TCGTCGAACA
1961 GCAACTACAC GACGCAACAG TACATGTTTG GCCCACGTCT
2001 CCTGGTCTCG CCAGTGACCT TGCCGAACGT GACTGAGTGG
2041 CCCGTGTATC TGCCGCAGAC GGGACAGAAC AACACCAAGC
2081 CTTGGACATA CTGGTGGACG AATGAAACGT ATGCCGGAGG
2121 ACAGGTCGTC AAGGTGCCTG CCCCCTTGCA ACATATCCCC
2161 GTGTTTCATC TGGGATCGCG CGAAGAGCTT CTCTCGGGTA
2201 ATGTTTTCTA G
```

Ax1A fungal orthologs were identified by BLASTP against the GenBank™ nonredundant database. Many of these orthologs are annotated as belonging to GH family 31 and as having β-glucosidase and/or α-xylosidase activity. However, there is no supporting biochemical evidence for any of the α-xylosidase activity annotations in GenBank except perhaps for AN7505 (*A. nidulans*). Bauer et al., *Proc. Natl. Acad. Sci. U.S.A.* 10311417-11422 (2006). However, AN7505 has no predicted signal peptide, and there is no evidence that the native protein is secreted from its native host. AN7505 has been tested on only a single, artificial substrate and never shown to be active on natural α-xylosides such as tamarind xyloglucan or isoprimeverose, which are the substrates of industrial, practical relevance. AN7505 is only weakly related (25% sequence identity) to Ax1A of *A. niger*.

The top BLASTP hits for the Ax1A of *A. niger* (e.g., E-values=0.0 and percent identities ranging from 52 to 81%) were from *Aspergillus* species, *Neosartorya fischeri*, and *Schizophyllum commune* (XP_003031084) and *Serpula lachrymans* (EG001163).

The *Schizophyllum commune* (XP_003031084.1, GI:302682806) amino acid sequence is shown below as SEQ ID NO:3.

```
  1 MLLRSLAALC AALACANLAL AQGSETNSTG IKLQNGFERV
 41 FIQPFGENGF RVRTSLMRDP TGNEWSGLID PPLEGPGGNA
 61 GLTYDTLLPY HGNATIQNGN ILATVDLGVL SFFRLEPNGS
121 TTLLTGEFTD EKAIPARYYT RNFLSDSFAV DLAFSAEKDE
161 QFYGTGQQAC CKDHSVNKKG QVVDLFNFNS NVALPVYMSS
201 KGYLQFFNMP SQGRIEFSPL RTRFHATETT VVDYYITTAQ
241 PGDYDTLQKQ FTSVTGRQPT PPDFLLGYQH SKLRYFEQQQ
281 VLDVAQRFHD EQINVSLLVV DFFAWKYQGD WSFNPEYWPD
321 PEGMAAKVKE LTGAEMMASL WPSVEDNSEN YAALQEQGLL
361 ATTRDGTGVT DSFAGAYTRL IDSTNPAARE FLWKRLNDSY
401 FSKGIYNFWI DQADGGTLGE AFENNGQTIQ NIPYSRAFTQ
441 YYIGTQEGAG KMYPWFHEQA VDEGHRNLTN TARDDPACPY
481 MSLTRSTWVG GQRFCTYLWS GDTRSEWATL SQQVTAGASV
521 AASGISSWTL DIGGFAGLNV DQEEDRELFV RWFGFGTFLP
561 YVSTYTVAGE REPWSFGDDN FVVLKKYISL RYQLVPYVKK
601 LFVDLQASGK TIMRALYYDF SLSDPAVVEG TRTNDPSIVH
641 EYMLGPRLLV APVWATNVTS WEVYLPKLPE AYVDEGWEWT
681 HWWTDEAYGA GGEKVNVSAQ LDEIPVFYLG SKDDIFSGNV
```

A nucleotide sequence for the SEQ ID NO:3 protein is available as accession number XM_003031038.1 (GI: 302682805), provided below as SEQ ID NO:4.

```
   1 ATGCTACTAA GATCACTTGC CGCCCTATGT GCGGCGCTTG
  41 CTTGCGCGAA CCTTGCCCTC GCGCAAGGTT CCGAGACCAA
  61 CTCCACGGGC ATCAAACTTC AGAACGGCTT CGAACGCGTC
 121 TTCATTCAAC CCTTTGGCGA GAATGGCTTC CGCGTCCGGA
 161 CCAGCCTCAT GCGCGATCCC ACCGGGAACG AATGGAGCGG
 201 CCTTATCGAC CCGCCCCTCG AAGGCCCCGG AGGCAATGCG
 241 GGACTCACCT ACGACACCCT CCTCCCCTAC CACGGCAACG
 281 CGACTATCCA GAACGGCAAC ATTCTCGCCA CCGTAGACCT
 321 CGGCGTTCTC TCCTTCTTCC GCCTCGAGCC TAACGGTAGC
 361 ACCACGCTTC TCACCGGCGA GTTTACCGAC GAGAAGGCGA
 401 TCCCGGCGCG ATACTACACG CGCAACTTCC TCTCCGATAG
 441 CTTTGCCGTC GATCTCGCGT TCTCGGCGGA GAAGGACGAG
 481 CAGTTCTATG GCACGGGGCA GCAGGCGTGT GCAAGGACC
 521 ACTCGGTCAA TAAGAAGGGG CAGGTGGTGG ACTTGTTCAA
 561 CTTCAATAGC AATGTGGCAC TTCCGGTGTA TATGTCGAGC
 601 AAGGGGTACC TGCAGTTCTT CAATATGCCT AGTCAAGGGA
 641 GGATAGAGTT CAGCCCATTG AGGACTCGTT CCATGCCAC
 681 GGAAACGACC GTCGTGGATT ACTATATCAC GACCGCACAA
 721 CCCGGCGACT ATGATACCCT GCAGAAACAG TTCACCTCCG
 761 TCACCGGGCG TCAGCCTACG CCGCCCGACT TCCTTCTCGG
 801 CTACCAGCAC TCCAAACTGC GGTACTTTGA GCAGCAACAA
 841 GTCCTCGACG TCGCGCAGCG CTTCCATGAT GAACAGATCA
 881 ACGTCTCGCT GCTGGTCGTA GACTTCTTTG CTTGGAAGTA
 921 CCAGGGTGAC TGGTCTTTCA ACCCAGAGTA TTGGCCCGAC
 961 CCCGAGGGCA TGGCCGCGAA AGTCAAGGAG CTCACTGGCG
1001 CCGAGATGAT GGCCTCGCTC TGGCCCAGCG TCGAAGATAA
1041 CTCCGAGAAC TACGCAGCGC TGCAGGAGCA GGGTCTGTTG
1081 GCGACGACGC GTGATGGCAC GGGCGTGACG GACTCATTTG
1121 CGGGGGCGTA TACGAGGTTG ATCGACTCGA CGAATCCGGC
1161 AGCGCGCGAG TTTTTGTGGA AGCGGCTGAA TGATAGTTAC
1201 TTCTCTAAGG GTATATACAA CTTCTGGATC GATCAGGCAG
```

```
1241 ACGGTGGAAC CCTCGGAGAG GCTTTCGAGA CAACGGTCA
1281 AACCATCCAA AACATCCCCT ACAGCCGCGC CTTCACCCAA
1321 TACTACATCG GCACGCAGGA AGGCGCCGGC AAGATGTACC
1361 CCTGGTTCCA CGAACAAGCC GTCGACGAGG CCACCGCAA
1401 CCTCACCAAC ACCGCGCGCG ACGACCCCGC GTGCCCCTAC
1441 ATGTCCCTCA CGCGCAGCAC GTGGGTCGGC GGGCAGCGCT
1481 TCTGCACGTA CCTCTGGTCG GGCGACACGC GCTCGGAGTG
1521 GGCGACGCTG TCGCAGCAGG TGACGGCGGG CGCGAGCGTC
1561 GCGGCATCGG GCATCTCGTC GTGGACGCTC GATATTGGCG
1601 GGTTTGCGGG GTTGAATGTC GATCAGGAGG AGGATAGGGA
1641 GTTGTTTGTG CGGTGGTTTG GGTTTGGGAC GTTTTTGCCG
1681 TATGTGAGTA CATACACGGT GGCGGGAGAG AGGGAGCCCT
1721 GGTCCTTCGG AGATGACAAC TTCGTTGTTT TGAAGAAGTA
1761 CATCTCTCTG CGCTACCAGC TCGTCCCCTA CGTCAAGAAG
1801 CTCTTCGTCG ACCTCCAGGC CTCGGGCAAG ACGATCATGC
1841 GCGCGCTTTA CTACGACTTC TCGCTCTCGG ACCCAGCAGT
1861 AGTCGAGGGC ACGCGCACCA ACGACCCCGC GATCGTCCAC
1921 GAGTACATGC TGGGCCCGCG GCTGCTTGTT GCGCCGGTGT
1961 GGGCGACAAA CGTGACGAGC TGGGAGGTGT ATCTTCCGAA
2001 GTTGCCGGAG GCTTATGTGG ATGAGGGTTG GGAGTGGACG
2041 CATTGGTGGA CGGACGAGGC TTACGGCGCC GGGGGCGAGA
2081 AGGTGAACGT AAGCGCGCAG CTGGACGAGA TTCCTGTGTT
2121 CTATCTCGGG TCCAAGGACG ATATCTTCTC AGGCAATGTT
2161 TGA
```

Among species of *Aspergillus*, Ax1A orthologs with strong E-values and percent amino acid identity are present in *A. flavus*, *Aspergillus oryzae*, *Aspergillus terreus*, *Aspergillus aculeatus*, and *Aspergillus carbonarius*. Proteins with strong identity to Ax1A were not observed in *A. fumigatus*, *A. clavatus*, or *A. nidulans* (Aspergillus Comparative Database (Broad Institute) and DOE Joint Genome Institute). All of the Ax1A orthologs in *Aspergillus* have strongly predicted signal peptides, like Ax1A as described herein.

Reannotation of protein XP_002378848 from *A. flavus* by reassigning the ATG start codon indicates that it probably also has a signal peptide. The sequence for this *A. flavus* protein is shown below as SEQ ID NO:5.

```
  1 MLILALGAVK FAGVGHHIPW LMVKDPASLR IWAKYLLALS
 41 FLYLGSVNLP KFSILLLYHR LFPTKKMGAI IKLMMVVLCV
 81 ITISTIVGAS LVCRPFSANW DGPIPGNCGN KKVLYIWASF
121 PNIVTDVILL LLPMPVLWSL NVSPRLKVGL TITFAVGSIG
161 LVTSVMRFQI FFRNNAFLDG TWVAVELIIW TQVETGVYLI
201 SACLPTYRPL IEHGFNPKML SKMYRWLVAL TVCATQLVQA
241 TPIQTRESDY FLPNSTGFRM QHGFETILVQ PFGFDGFRVR
281 AWPFRPPTGH EISFIYDPPL EGFENGQAHG LTFDTAFNGN
321 HTVAIRNGNT IVRTSGWGGN PGGYRLAFYR IEQDGSESLL
361 TNEYAPLKSI NPRYYSWNGP GSEFSAEFSF STDPDEQFYG
401 TGTQQDHLVN KKGTVIDLIN FNTHIPTPVF MSNKGYAFIW
441 NMPAQGRMEF GQLRTKLTAE STTVVDYVIV ATTPGDYDTL
481 QKRLSALTGR APTPPDFSLG YIQSKLRYEN QTELELLAQK
521 FKDNNVPVGM FVIDYQSWRN QGDWGLDPAL WPDVAAMAKK
561 VKDLTGAEIM ASLWPSVSDA SDNYLELQAN GYLSATRDGP
601 GTTDSWNGSY IRNVDSTNPG ARKFIWSTLK RNYYDKGIKN
641 FWIDQADGGA LGEAYENNGQ STYIQSVPFA LPNVLYAAGT
681 QQSAGKYYPW AHQLAIEEGF RNVTDSKEGE ACEHISLSRS
721 GYIGSQRFCS MIWSGDTTSA WETLGLQVAS GLSAAATGWG
761 WWTMDAGGFQ PDPTVPWSSN IDTPEYRELY VRWLQWATFV
801 PFMRTHGQRV CDNQDAYTCN NEPWSYGEKN TPIILSYIHL
841 RYQLASYLRA LFDQFHKTGR MIMRPLYMDF EKTDPKVSQW
881 TQANNNVTTQ QYMFGPRLLV SPITTPNVTE WSVYLPQTGQ
921 NGTKPWTYWW TNQTYAGGQT VTVPAPVEHI PVFHLGKRED
961 ILSGNVF
```

A nucleotide sequence for the SEQ ID NO:5 protein is available as XM_002378807.1 (GI:238495223), provided below as SEQ ID NO:6.

```
  1 ATGCTAATTC TTGCTTTAGG TGCTGTAAAG TTCGCTGGCG
 41 TGGGACACCA CATCCCATGG TTAATGGTGA AAGACCCTGC
 81 CAGTCTAAGA ATTTGGGCGA AATATCTCCT GGCTTTGTCA
121 TTTCTCTATT TGGGAAGTGT TAATCTTCCA AAGTTCTCTA
161 TCCTATTACT GTACCATAGG CTCTTCCCCA CAAAGAAAAT
201 GGGCGCGATC ATCAAATTGA TGATGGTGGT CCTGTGTGTC
241 ATCACGATAT CTACGATCGT TGGCGCGAGT CTCGTCTGCC
281 GACCGTTCTC CGCTAACTGG GACGGTCCTA TCCCTGGCAA
321 CTGTGGTAAC AAGAAAGTTC TTTACATCTG GGCCAGTTTT
361 CCTAACATTG TGACCGATGT AATTCTACTG CTCCTTCCAA
401 TGCCAGTGCT GTGGTCACTT AATGTCAGTC CACGACTGAA
441 GGTAGGACTG ACAATCACAT TCGCAGTAGG GAGCATAGGC
481 TTAGTCACTT CCGTTATGCG CTTCCAGATC TTTTTTCGAA
521 ACAACGCCTT CCTCGATGGG ACCTGGGTAG CGGTTGAGCT
561 GATTATATGG ACCCAAGTCG AGACCGGGGT TTACCTGATA
601 TCTGCCTGCC TGCCCACATA TAGACCACTT ATCGAACACG
641 GCTTCAATCC CAAGATGTTG AGCAAAATGT ATCGCTGGCT
681 GGTGGCCCTA ACAGTCTGCG CCACACAGCT GGTGCAGGCG
721 ACCCCAATCC AGACGCGGGA GTCGGACTAC TTCCTGCCCA
761 ACTCGACTGG ATTTCGCATG CAGCATGGCT TCGAGACTAT
```

```
 801 TCTGGTACAG CCCTTTGGCT TCGATGGGTT CCGTGTGCGC
 841 GCCTGGCCCT TCCGGCCGCC TACGGGCCAT GAGATCAGCT
 881 TCATCTACGA TCCACCATTG GAAGGATTCG AGAATGGACA
 921 AGCGCATGGA CTAACCTTTG ACACGGCATT TAATGGCAAT
 961 CACACTGTTG CTATCCGCAA TGGAAACACT ATCGTGCGCA
1001 CCTCTGGCTG GGGTGGAAAT CCCGGAGGAT ATCGGCTGGC
1041 ATTCTACCGC ATCGAGCAAG ATGGTTCTGA GTCACTGTTA
1081 ACAAACGAGT ATGCGCCACT CAAATCGATC AATCCACGAT
1121 ACTACTCGTG AACGGCCCG GGAAGCGAAT TTTCTGCCGA
1161 GTTTTCATTC AGTACGGACC CCGACGAGCA GTTCTATGGC
1201 ACGGGTACGC AACAGGACCA TCTTGTCAAC AAGAAAGGAA
1241 CGGTCATTGA CTTGATCAAC TTCAATACCC ACATCCCCAC
1281 ACCTGTGTTC ATGAGCAACA AGGGCTACGC CTTCATCTGG
1321 AATATGCCAG CTCAGGGTCG CATGGAATTT GGACAGCTAC
1361 GCACCAAGCT CACCGCGGAG TCCACCACGG TCGTCGACTA
1401 TGTCATTGTG GCCACGACAC CAGGCGACTA CGACACATTG
1441 CAGAAACGTC TATCCGCCCT GACGGGTAGA GCACCCACTC
1481 CGCCTGACTT CTCACTCGGA TACATCCAGT CTAAGCTCCG
1521 CTATGAGAAC CAGACTGAAC TAGAACTCCT GGCGAAGAAG
1561 TTCAAGGACA CAACGTCCC CGTTGGAATG TTCGTCATCG
1601 ACTACCAATC CTGGCGGAAT CAAGGCGACT GGGGTCTTGA
1641 CCCAGCGCTA TGGCCGGACG TAGCAGCAAT GGCGAAGAAG
1681 GTAAAGGATC TCACCGGAGC AGAGATCATG GCATCTCTCT
1721 GGCCCAGTGT ATCGGATGCG AGCGACAACT ACTTGGAGCT
1761 TCAAGCCAAC GGATACCTAT CTGCGACTCG CGACGGACCC
1801 GGAACCACCG ATTCATGGAA CGGCTCGTAC ATCCGCAACG
1841 TGGACTCTAC GAACCCAGGC GCACGGAAAT TCATCTGGTC
1881 GACCTTGAAG CGCAACTACT ACGACAAGGG AATCAAGAAC
1921 TTCTGGATCG ACCAAGCTGA CGGTGGTGCC CTGGGCGAAG
1961 CCTACGAAAA CAACGGTCAA AGCACCTACA TTCAGTCTGT
2001 CCCCTTCGCC CTACCCAACG TCCTCTACGC AGCTGGCACC
2041 CAACAGAGCG CCGGAAAATA TTACCCCTGG GCCCACCAGC
2081 TGGCAATCGA AGAGGGCTTC GCAACGTCA CCGACAGCAA
2121 GGAAGGCGAA GCCTGCGAGC ACATCTCGCT CAGTCGGTCT
2161 GGCTACATCG GATCTCAACG ATTCTGCAGC ATGATCTGGT
2201 CAGGAGACAC CACCTCCGCC TGGGAAACAC TAGGCCTCCA
2241 AGTTGCTAGT GGAACCACCG CCGCCGCAAC AGGATGGGGC
2281 TGGTGGACTA TGGACGCAGG CGGTTTCCAA CCTGACCCGA
2321 CAGTACCATG GAGCTCTAAC ATCGACACAC CGGAGTACCG
2361 CGAGTTGTAC GTGCGCTGGC TGCAGTGGGC TACATTCGTC
2401 CCCTTCATGC GTACACACGG TCAGCGAGTC TGCGACAACC
2441 AGGACGCATA CACATGTAAC AACGAGCCGT GGTCGTATGG
2481 CGAGAAGAAC ACCCCCATTA TCCTCTCGTA CATTCACCTC
2521 CGATACCAAT TGGCCTCGTA TCTGCGTGCC CTCTTCGACC
2561 AGTTCCACAA GACCGGTCGC ATGATCATGC GTCCCTTGTA
2601 TATGGATTTC GAGAAGACTG ATCCGAAAGT TTCACAGTGG
2641 ACGCAGGCCA CAACAATGT GACAACGCAG CAGTACATGT
2681 TCGGCCCGAG ATTGCTGGTA TCACCTATTA CCACGCCGAA
2721 TGTCACCGAA TGGTCGGTAT ATCTGCCGCA GACGGGCCAG
2761 AATGGGACGA AGCCTTGGAC GTACTGGTGG ACTAATCAGA
2801 CATATGCTGG TGGTCAGACG GTTACTGTGC CGGCGCCTGT
2841 GGAGCATATT CCTGTGTTCC ATCTTGGGAA GAGAGAGGAT
2881 ATTCTCAGTG GTAATGTCTT CTAG
```

An α-xylosidase from *Aspergillus kawachii* strain IFO 4308 has NCBI accession number GAA91593.1, and has 97% sequence identity to the α-xylosidase described herein with SEQ ID NO:1. This α-xylosidase from *Aspergillus kawachii* strain IFO 4308 has SEQ ID NO:7.

```
  1 MYFSSFLALG ALIQAAAATY LAPNSTGLRI QHGFETILIQ
 41 PFGYDGFRVR AWPFRPPSGN EISFIYDPPI EGYEDTAHGM
 61 SYDTATTGTE PRTLRNGNII LRTTGWGGTT AGYRLSFYRV
121 NDDGSETLLT NEYAPLKSLN PRYYSWPGPG AEFSAEFSFS
161 ATPDEQIYGT GTQQDHMINK KGSVIDLVNF NTHIPTPVFM
201 SNKGYAFIWN MPAEGRMEFG SLRTRFTAAS TTLVDYVIVA
241 AQPGDYDTLQ QRISALTGRA PTPPDFSLGY IQSKLRYENQ
281 TEVELLAQNF HDRDIPVSMI VIDYQSWAHQ GDWALDPRLW
321 PNVAQMSATV KNLTGAEMMA SLWPSVADDS VNYAALQANG
361 LLSATRDGPG TTDSWNGSYI RNYDSTNPSA RKFLWSMLKK
401 NYYDKGIKNF WIDQADGGAL GEAYENNGQS TYIQSIPYTL
441 PNVNYAAGTQ LGVGKLYPWA HQQAIEEGFR NATDTKEGSA
481 CDHVSLSRSG YIGSQRFCSM IWSGDTTSVW DTLAVQVASG
521 LSAAATGWGW WTVDAGGFEV DSTVWWSGNI DTPEFRELYV
561 RWLACTTFLP FMRTHGSRAC YYQDAYTCAN EPWSYGASNT
601 PIIVSYIHLR YQLGAYLKSI FNQFHLTGRS IMRPLYMDFE
641 KTDPKISQLV SSNSNYTTQQ YMFGPRLLVS PVTLPNVTEW
681 PVYLPQTGDN STKPWTYWWT NETYAGGQVV KVPAPVQHIP
721 VFHLGSREEL LSGDVF
```

An α-xylosidase from *Aspergillus terreus* strain NIH2624 has NCBI accession number XP_001217011.1, and has 81% sequence identity to the α-xylosidase described herein with SEQ ID NO:1. This α-xylosidase from *Aspergillus terreus* strain NIH2624 has SEQ ID NO:8.

```
  1 MYRWLVALAA CAGQLALANP VHPRDTDYFK PNSTGFRMRH
 41 GFETVLVQPF GYDGFRVRAW PFRPPTGQEL SFVYDPPLEG
 81 FEDGQAHGMD YDTAFTGNES LAIRNGNMIV RTTGWGGNPG
121 GYRLAFYRVE EDGSETLLTN EYAPLKSVNP RYYSWNGPGA
161 EFSAEFTFST TPDEQFYGTG TQQDHLVNKK GTVIDLINFN
201 THIPTPVFMS NKGYGFVWNM ASEGRMEFGQ LRNKFTAASA
241 TLVDYVIVAS PAGDYDTLQQ RLSALTGRAP TPPDFALGYI
281 QSKLRYENQT EVELLAQNFK DHNIPVGMIV IDYQSWADQG
321 DWALDPRLWP DVAAMARKVK ELTGAEMMAS LWPSVSDDSV
361 NYEALQMNGW LTATRDGPGT TDSWNGSYIR NIDSTNPDAR
401 RFLWDTLKRN YYDKGIRNFW IDQADGGALG EAYENNGQSL
441 YIQSIPYALP NVLYAAGTQL GVGKMYPWTH QMAIDEGFRN
481 ATDSKPGSAC EHISLSRSGY IGSQRFCSMI WSGDITSVWE
521 TLGLQVASGL SAAATGWGWW TVDAGGFQPD PTVPWSANID
561 TPEYRELYVR WLQWTTFLPF MRTHGSRECD SQNAYTCNNE
601 PWSYGEENTP VIVSYIHLRY QLGAYLRAIF KKFHETGRSI
641 MRPLYMDFEK TDPRIRTMTQ ANTNVTTQQY MFGPRLLVSP
681 VTTPNTTEWP VYLPQTGQNG TKPWTYWWTN ETYAGGQTVK
721 VPAPVEHIPV FHLGTREEIL SGDVF
```

An α-xylosidase from *Neosartorya fischeri* NRRL 181 has NCBI accession number EAW23703.1, and has 79% sequence identity to the α-xylosidase described herein with SEQ ID NO:1. This α-xylosidase from *Neosartorya fischeri* strain NRRL 181 has SEQ ID NO:9.

```
  1 MVSIKRWLLG LCAVSTVWAN PIQTREADYV MPNSTGFRMQ
 41 HGFETVLVQP FGYDGFRVRA WPYRPPTGNE VSFIYDPPLE
 81 GFEDGMAHGL GFDTAFNGNR TVAIRNGKIV VRTSGWGGNP
121 GGYRLAFYRV EKDGSETLLT NEYAPLKSVN PRYYFWRGPG
161 SEFSAEFSFS STPDEQIYGT GTQQDHMVNK KGSVIDLINF
201 NTHIPTPVIV SNKGYGFVWN MASEGRMELG ALRTKFTAES
241 ATVVDYAIVA AEQGDYDTLQ RRLSALTGRA PTPPEASLGY
281 IQSKLRYENQ TEVELLAQQF KDHNIPVSMI VIDYQSWAHQ
301 GDWALDPRLW PDVASMAKKV KDLTGAEMMA SLWPSVADNS
361 ENYLELIANG LLSATRSGPG TTDSWNGSYI RNIDSTNPAA
401 RAFLWKTLKR NYYDKGIKNF WIDQADGGAL GEAYENNGQS
441 SYIESIPFSL PNVLYAAGTQ LSAGKLYPWA HQQAIEEGYR
481 NATGTKMGEA CDHISLSRSG YIGSQRFCSM IWSGDTTSVW
521 DTLAVQVASG LSAAATGWGW WTMDAGGFQA DPTVPWSSNI
541 DTPEYRELYV RWFQWAAFLP FMRTHGSRKC NVQNAYTCNN
601 EPWSYGEENT PIIVSYIQLR YQLKAYLQAV FEQFHHTGRA
641 LMRPLYMDFE RTDPQIAKMT RENVNATTQQ YMLGPRLLVT
681 PVTLPNATEW EVYLPLTAQN ETKPWTYWWT NETYAGGQTV
721 TVPAPIEHIP LFYLGKREDI LSGSVF
```

An α-xylosidase from *Aspergillus flavus* NRRL3357 has NCBI accession number XP_002378848.1, and has 79% sequence identity to the α-xylosidase described herein with SEQ ID NO:1. This α-xylosidase from *Aspergillus flavus* strain NRRL3357 has SEQ ID NO:10.

```
  1 MLILALGAVK FAGVGHHIPW LMVKDPASLR IWAKYLLALS
 41 FLYLGSVNLP KFSILLLYHR LFPTKKMGAI IKLMMVVLCV
 81 ITISTIVGAS LVCRPFSANW DGPIPGNCGN KKVLYIWASF
121 PNIVTDVILL LLPMPVLWSL NVSPRLKVGL TITFAVGSIG
161 LVTSVMRFQI FFRNNAFLDG TWVAVELIIW TQVETGVYLI
201 SACLPTYRPL IEHGFNPKML SKMYRWLVAL TVCATQLVQA
241 TPIQTRESDY FLPNSTGFRM QHGFETILVQ PFGFDGFRVR
281 AWPFRPPTGH EISFIYDPPL EGFENGQAHG LTFDTAFNGN
321 HTVAIRNGNT IVRTSGWGGN PGGYRLAFYR IEQDGSESLL
361 TNEYAPLKSI NPRYYSWNGP GSEFSAEFSF STDPDEQFYG
401 TGTQQDHLVN KKGTVIDLIN FNTHIPTPVF MSNKGYAFIW
441 NMPAQGRMEF GQLRTKLTAE STTVVDYVIV ATTPGDYDTL
481 QKRLSALTGR APTPPDFSLG YIQSKLRYEN QTELELLAQK
521 FKDNNVPVGM FVIDYQSWRN QGDWGLDPAL WPDVAAMAKK
561 VKDLTGAEIM ASLWPSVSDA SDNYLELQAN GYLSATRDGP
601 GTTDSWNGSY IRNVDSTNPG ARKFIWSTLK RNYYDKGIKN
641 FWIDQADGGA LGEAYENNGQ STYIQSVPFA LPNVLYAAGT
681 QQSAGKYYPW AHQLAIEEGF RNVTDSKEGE ACEHISLSRS
721 GYIGSQRFCS MIWSGDTTSA WETLGLQVAS GLSAAATGWG
761 WWTMDAGGFQ PDPTVPWSSN IDTPEYRELY VRWLQWATFV
781 PFMRTHGQRV CDNQDAYTCN NEPWSYGEKN TPIILSYIHL
841 RYQLASYLRA LFDQFHKTGR MIMRPLYMDF EKTDPKVSQW
881 TQANNNVTTQ QYMFGPRLLV SPITTPNVTE WSVYLPQTGQ
921 NGTKPWTYWW TNQTYAGGQT VTVPAPVEHI PVFHLGKRED
961 ILSGNVF
```

An α-xylosidase from *Aspergillus oryzae* has NCBI accession number XP_001823456.1, and has 78% sequence identity to the α-xylosidase described herein with SEQ ID NO:1. This α-xylosidase from *Aspergillus oryzae* has SEQ ID NO:11.

```
  1 MLSKMYRWLV ALTVCATQLV QATPIQTRES DYFLPNSTGF
 41 RMQHGFETIL VQPFGFDGFR VRAWPFRPPT GHEISFIYDP
 81 PLEGFENGQA HGLTFDTAFN GNHTVAIRNG NTIVRTSGWG
121 GNPGGYRLAF YRIEQDGSES LLTNEYAPLK SINPRYYSWN
161 GPGSEFSAEF SFSTTPDEQF YGTGTQQDHL VNKKGTVIDL
```

```
201 INFNTHIPTP VFMSNKGYAF IWNMPAQGRM EFGQLRTKLT
241 AESTTVVDYV IVATTPGDYD TLQKRLSALT GRAPTPPDFS
281 LGYIQSKLRY ENQTELELLA QKFKDNNVPV GMIVIDYQSW
321 RNQGDWGLDP ALWPDVAAMA KKVKDLTGAE IMASLWPSVS
361 DASDNYLELQ ANGYLSATRD GPGTTDSWNG SYIRNVDSTN
401 PGARKFIWST LKRNYYEKGI KNFWIDQADG GALGEAYENN
441 GQSTYIQSVP FALPNVLYAA GTQQSAGKYY PWAHQLAIEE
481 GFRNVTDSKE GEACEHISLS RSGYIGSQRF CSMIWSGDTT
521 SAWETLGLQI ASRLSAAATG WGWWTMDAGG FQPDPTVPWS
561 SNIDTPEYRE LYVRWLQWAT FVPFMRTHGQ RVCDNQDAYT
601 CNNEPWSYGE KNTPIILSYI HLRYQLASYL RALFDQFHKT
641 GRMIMRPLYM DFEKTDPKVS QWTQANNNVT TQQYMFGPRL
681 LVSPITTPNV TEWSVYLPQT GQNGTKPWTY WWTNQTYAGG
721 QTVTVPAPVE HIPVFHLGKR EDILSGNVF
```

An α-xylosidase from *Macrophomina phaseolina* strain MS6 has NCBI accession number EKG20540.1, and has 70% sequence identity to the α-xylosidase described herein with SEQ ID NO:1. This α-xylosidase from *Macrophomina phaseolina* strain MS6 has a signal sequence and amino acid sequence SEQ ID NO:12.

```
  1 MHLLYSLVSL PLLTVSAQNI TSEYFAPNST GFRMTHGFET
 41 ILVQPYGYDG FRVRAWPFRP PNGNEISFLY DPPLEGPENG
 81 EARAMSYDFT TNGNQSAIIR NGNTVVKTYG LEGAHYRLAF
121 YRIEPDGTET LLTNEFNPVK ALNPRYYSWT STGYEFSASF
161 SFTTTPDEQI FGTGTQQDFL LNKKGSVIDM INFNSYIPTP
201 VFMSSKGYGF VWNSAAQGRM EFGPRRNKFT SDSTTLVDYA
241 IVSAPEGDYD SLQQKLTAIT GRAPTPPDFS LGYLHSKLRY
281 ENQTEVVLLA QGFRDRNIPV SMIVIDYESW AQNGDWGLDP
321 ALWPDVASMA AQVKNLTGAE MMASLWPAVE DDSLNYAEMQ
361 QLGLLAATMS GPGTTDSWNG SYIRNYDSTN PRAREFLWNT
401 LKRNYYDKGI KNFWIDQADG GALGEAWENN GQTAYVQSIP
441 YPLPQVLYHA GTQASVGKLY PWAHQQAIEE GTRNATGTEQ
481 GTACDYISLS RSGYIGSQRF CSMIWSGDTE ASWEVLGNQI
521 PNALSAAATG WSWYTVDAGG FQPDPAIEWS NNIDRPEYRE
561 LYVRWLQWTT FLPFMRNHGS RACDVQHAFT CDNEPWTYGA
601 QNTPTIVSYI NLRYRLAPYV RALFEQLSRT GRQILRPLFM
641 DFGKSDANVV AWTRENKNIT TQQYMFGPRL LVAPVVLPNV
681 TTWPVYLPKT AGEGSGQRPW TYWWTNETFA GGQTVNVSAP
721 VEHIPLFYLG DRDDIFSGNV F
```

An α-xylosidase from *Serpula lacrymans* var. *lacrymans* S7.3 has NCBI accession number EKG20540.1, and has 52% sequence identity to the α-xylosidase described herein with SEQ ID NO:1. This α-xylosidase from *Serpula lacrymans* var. *lacrymans* S7.3 has a signal sequence if it is reannotated to remove the first 20 amino acids, and has amino acid sequence SEQ ID NO:13.

```
  1 MPYKPSRNIV RLCVPSRTCK MLGILSIVAV ITTAYAANTS
 41 IPSSTGIKLQ NGFERVYIQP FGNNGIRVRA SLLRDPTGNE
 61 LSALLDPPLE GPGGNQGLAY DQLVGFQGNA NLTNGNIAAE
121 IATGYLSFYR IESNGSRTLL TSEFTDDKAL YPRYYIQEYK
161 SPSFSAEFSF TAEPDEQIYG VGQQACCKDN SVNKKGQSID
201 LINFNSFVPL PVYMSNKGYL QFFNMPSQGR MEFSPIRTRF
241 VSSEATVVDY WITTAEPGDY DTLQEQYTAV TGRQPTPPTF
281 THGYQQSKLR YFNQTQVEDL AQEFHDRQIN VSLIVIDFFN
321 WKYQGDWSFD PEYWPDPAAM TAKVKELTGA EMMVSLWPSV
361 EDLSVNYLTL QEQGLLATTR DGTGISDSFA GVYTRLIDST
401 NPASREFLWK RLNESYFSNG IHNFWIDQAD GGTLGEAFEN
441 NGQTIETIPY ARAFSQYFIG TQEGAGKMYP WLHQQAINEG
481 LHNLTDTPAT ATSCEYMSLT RSTFAGGQRY CSYLWSGDTM
521 AEFPVLLQQI TSAVSVAASG ISSWTLDLGG FTGLDIDTAY
561 GKELYVRWFA MGVFLPYMRT HGDRICDIPP PTTPSNANYC
601 PNEPWSYGEE NYPILKMYIE LRYKLVPYVT QLFAMLQNNG
641 RTIMRALYFD FSLSDPFVAS ATAANDPLVS HQFMFGPRIL
681 VSPVGVQNAT SKEVYLPRLT QAMLDQNYTW THWWTNTSYG
721 QGGASVNVSA PLDQIPVFYL GSMADILSGN I
```

An α-xylosidase from *Agaricus bisporus* has NCBI accession number EKM78298.1, and has 49% sequence identity to the α-xylosidase described herein with SEQ ID NO:1. This α-xylosidase from *Agaricus bisporus* has a signal sequence, and has amino acid sequence SEQ ID NO:14.

```
  1 MVLQSLILCY LVLPISLSLA ADYFNPNATG IKLQNGFERI
 41 HIQPFGNHGF RVRASLLRDP TGREPSALID PPLEGPSSKG
 81 LEHSITIPFR GNATVRNGNL VVDVSFGVTS FSRVEPNGTL
121 TLLTSEYADT KVLPARYYVQ DIHGQSFQAQ FGFSADPDEM
161 FFGTGQHACC KDHTVNKKGQ IVDLINYNSH VTLPIWMSNK
201 GYLMFFNYPG QGRIEFDRLR TRFVADEATV VDYWITTAPP
241 EDYDALQQQF TGVTGRQPTP PDFSLGFQQS KLRYYNQTQI
281 IDLAQRFHDE QVPISLIVID FFAWKFQGDW SLDVDVWPDP
321 TAMAAEVKRL TGAELMVSLW PSVEDLSENY LTLQEEGLLA
361 ITRDGTGIQD SFEGVYTRLI DSTNPDAREF LWKRLNDSYF
401 SKGIHNFWID QADGGTLGEP FENNGQSISS IPYSRSFTQY
441 FLGSQEGFGK MYPWLHQQAI QEGFQNLTGT DSSQESCEYM
481 SLTRSTFIGG QRFCSYLWSG DTDSKFDVLL QQITAGVSVA
521 ASGISSWTLD IGGFAGLDID TDEGKELFVR WFSMGVFLPY
561 TRVHGTRSCN IPRTSTLPHA NPCPNEPWSY GEDNFVILKK
```

-continued

```
601 YIALRYQLIP YVKTLFQMLH TSGKVILRPL YFDFSKSDEF

641 VRKGTKTNDP VVVHQFMFGP RLLVAPVGEF GVKTWDVYLP

681 KLDTQTWKHW QVTTNQIPRW TDHDFGKGGM SITIDAPLDQ

721 IPVFYLGDKD DILNGNI
```

An α-xylosidase from *Penicillium chrysogenum* has NCBI accession number XP_002566456.1, and has 35% sequence identity to the α-xylosidase described herein with SEQ ID NO:1. This α-xylosidase from *Penicillium chrysogenum* has no predicted signal sequence, and has amino acid sequence SEQ ID NO:15.

```
  1 MLYAEDDKLV FRFDDHILWV QPWGENAFRV RATKQASIPT

41 EDWALPSKPS SPSPSIEISA DQEATITNGK IKATVSRRGK

81 IIIYDSKGNK LLEEYARHRQ DPMDPKCSAL TVEARELRPI

121 LGGDYHLTMR FESLDHKEKI FGMGQYQQPY LNLKGADLEL

161 AHRNSQASVP FAVSSLGYGF LWNNPGIGRA VLGTNVMSFE

201 AYSTKALDYW VVAGDTPAEI EEAYAKVTGY VPMMPEYGLG

241 FWQCKLRYTN QEQLLNIARE YRRREVPLDL IVIDFFHWKH

281 QGEWSFDPEF WPDPEAMVKE LKELKVELMV SIWPTVENAS

321 ENFPEMLEQG LLIRHDRGMR VAMQCDGDIT HFDATNPAAR

361 KFIWSKAKQN YYDIGIKTFW LDEAEPEYSI YDFDIYRYHA

401 GSNLQIGNTY PKEYARGFYE GMTAEGQTNI VNLLRCAWAG

441 SQKYGALVWS GDIASSWSSF RNQLAAGLNM GLAGIPWWTT

481 DIGGFHGGNP DDPLFRELFT RWFQWGTFCP VMRLHGDREP

521 KPEGQPTASG ADNEIWSYGD EVYEICKRYI GIREKLREYT

561 RGLMREAHEK GTPVMRTLFY EFPSDERAWE VETQYMFGSK

601 YLVVPVLEPG QRTVKVYLPA GASWKLWDEK DVLHEGGRNV

641 EIECPIENMP VFCRQ
```

Another α-xylosidase from *Penicillium chrysogenum* has a Joint Genome Institute (JGI; see jgi.doe.gov) accession number JGI 85065 and has a signal peptide and amino acid sequence SEQ ID NO:16.

```
  1 MRLALIALGA IWASSSVASP VQQTTYHKPT SKGFRMQHGF

41 ETVLVQPFGY DGFRVRAWPF RAPTGHEIGF VYDPPLEGPE

81 NGEAHGMTFD TAFNGNRSEE LRNGNMIVRT SGWGGSPGGY

121 RLAFYRVEAN GSETLLTNEY APLKSLNPRY YSWTGPGSEF

161 AAEFSFSTTP EEQIYGTGTQ QDHLVNKKGL TIDLINFNTH

201 IPTPVFMSNK GYGFIWNMAS TGRMEFGPLR NRFTADAASV

241 VDYVIVSSDP SDYDTLQQRL SALVGRAPTP PDWSLGYLQS

281 KLRYENQSEV IQLAQQFHDR KIPVSMIVID YQSWAHQGDW

321 GLDPALWPDV AEMARQVKDL TNAEMMASLW PSVADDSVNY

361 LEMMAQGFLS ATRSGPGTTD SWNGSYIRNY DSTNPGARRF

401 LWNTLKRNYF DKGIKNFWID QADGGSLGEA YENNGQSDYI

441 QSLPFPMPDV LYAAGTQRNV GKLYPWAHQQ AIEEGFRNAT

481 STDMGSPCNY LSLSRSGYIG SQRFCSMIWS GDITSVWETL

521 SAQVASGLSA AATGWGWWTL DAGGFQADPT VPWSGNIDSP

561 EYRELYVRWF QWSTFLPFMR THGSRTCDFQ DAYTCANEPW

601 SYGSENTPIL VSYINLRYQL SAYLRAVFAQ LHKSGRMIMR

641 PLYMDFEKSD PHVARWTSAN TNITTQQYMF GPRLLVSPVT

681 IPNVTEWSVY LPQTAGDDSK PWTYWWSNQT YSGGQTVTVP

721 APKEHIPLFH LGTRADIVDG RVFA
```

An α-xylosidase from *Aspergillus carbonarius* has JGI accession number jgi|Aspca3|209950, has a signal peptide sequence, and has amino acid sequence SEQ ID NO:17.

```
  1 MYFPSLLALG ALVQAAAATY IAPNSTGLRL QHGFETILIQ

41 PFGYDGFRVR AWPFRPPSGN EISFIYDPPL EGFEDSAHGM

81 SYDTATTGSE PRTLRNGNMI LRTTGWGGET GGYRLSFSRV

121 NEDGSETLLT NEYAPLKSLN PRYYHWPGPG PEFSAEFSFS

161 ATPDEQIYGT GTQQDHMINK KGQVIDMVNF NTHIPTPVFM

201 SNKGYAFIWN MPAEGRMEFG PLRTRFTAAT TTLVDYVIVA

241 SAPGDYDTLQ RRISALTGRA PVPPDFALGY IQSKLRYENE

281 TEVELLAQNF HDRGIPVAMI VIDYQSWAHQ GDWALDPRLW

321 PNVGQMSARV KNLTGAEMMA SLWPSVADNS VNYAALQANG

361 LLSATRDGPG TTDSWNGSYI RNYDSTNPSA RQFLWSMLKK

401 NYYDKGIKNF WIDQADGGAL GEAYENNGQS TYIESIPFAL

441 PNVLYAAGTQ LSVGKLYPWA HQQAIDEGFR NATDTEEGSA

481 CDHVSLSRSG YIGSQRFCSM IWSGDTTSVW DTLAVQVASG

521 LSAAATGWGW WTVDAGGFQA DPTVWWSGNI DTPEFRELYV

561 RWLSWTTFLP FMRTHGSRAC YFQDAYTCAN EPWSYGEANT

601 PIIVSYIHLR YQLGAYLRSI FKQFHLTGRS IMRPLYMDFE

641 KTDPKISTLT ASNSNYTTQQ YMFGPRLLVS PVTLPNVTEW

681 PVYLPQTGGN STKPWTYWWT NETYAGGQVV TVSAPVQHIP

721 VFHLGSREEL LTGNVF
```

An α-xylosidase from *Aspergillus brasiliensis* has JGI accession number jgi|Aspbr1|131273, has a signal peptide sequence, and has amino acid sequence SEQ ID NO:18.

```
  1 MYFSSFFALG ALVQAAAATY FAPNSTGLRI QHGFETILVQ

41 PFGYDGFRVR AWPFRPPSGN EISFIYDPPI EGYEDTAHGM

81 SYDTATTGAE PRTLRNGNII LRTTGWGGDT AGYRLSFYRV

121 NEDGSETLLT NEYAPLKSLN PRYYSWPGPG AEFSAEFSFS

161 ATPDEQIYGT GTQQDHMINK KGSVIDMVNF NTHIPTPVFM

201 SNKGYAFIWN MPAEGRMEFG TLRTRFTAAS TTLVDYVIVA

241 AQPGDYDTLQ QRISALTGRA PTPPDFSLGY IQSKLRYENQ
```

```
281  TEVELLAQNF HDRNIPVSMI VIDYQSWAHQ GDWALDPRLW
321  PNVAQMSARV KNLTGAEMMA SLWPSVEDNS VNYATLQANG
361  LLSATRDGPG TTDSWNGSYI RNIDSTNPAA RKFLWSTLKK
401  NYYDKGIKNF WIDQADGGAL GEAYENNGQS TYIQSIPYTL
441  PNVNYAAGTQ LGVGKLYPWA HQQAIEEGFR NATDTKEGSA
481  CDHVSLSRSG YIGSQRFCSM IWSGDTTSVW DTLAVQVASG
521  LSAAATGWGW WTVDAGGFEV DSTVWWSGNI DTPEFRELYV
561  RWLAWTTFLP FMRTHGSRTC YYQDAYTCAN EPWSYGASNT
601  PIIVSYIHLR YQLGAYLKSI FNQFHLTGRS IMRPLYMDFE
641  KTDPKISQLV SSNSNYTTQQ YMFGPRLLVS PVTLPNVTEW
681  PVYLPQTGEN NTKPWTYWWT NETYAGGQVV KVPAPVQHIP
721  VFHLGSREEL LSGDVF
```

An α-xylosidase from *Aspergillus acidus* has JGI accession number jgi|Aspfo1|143652, has a signal peptide sequence, and has amino acid sequence SEQ ID NO:19.

```
  1  MYFSSFLALG ALIQAAAATY LAPNSTGLRI QHGFETILIQ
 41  PFGYDGFRVR AWPFRPPSGN EISFIYDPPI EGYEDTAHGM
 81  SYDTATTGTE PRTLRNGNII LRTTGWGGTT AGYRLSFYRV
121  NDDGSETLLT NEYAPLKSLN PRYFSWPGPG AEFSAEFSFS
161  ATPDEQIYGT GTQQDHMINK KGSVIDLVNF NTHIPTPVFM
201  SNKGYAFIWN MPAEGRMEFG SLRTRFTAAS TTLVDYVIVA
241  AQPGDYDTLQ QRISALTGRA PTPPDFSLGY IQSKLRYENQ
281  TEVELLAQNF HDRDIPVSMI VIDYQSWAHQ GDWALDPRLW
321  PNVAQMSATV KNLTGAEMMA SLWPSVADDS VNYAALQANG
361  LLSATRDGPG TTDSWNGSYI RNYDSTNPSA RKFLWSMLKK
401  NYYDKGIKNF WIDQADGGAL GEAYENNGQS TYIQSIPYTL
441  PNVNYAAGTQ LGVGKLYPWA HQQAIEEGFR NATDTKEGSA
481  CDHVSLSRSG YIGSQRFCSM IWSGDTTSVW DTLAVQVASG
521  LSAAATGWGW WTVDAGGFEVDSTVWWSGNIDTPEFRELYV
561  RWLAWTTFLP FMRTHGSRAC YYQDAYTCAN EPWSYGASNT
601  PIIVSYIHLR YQLGAYLKSI FNQFHLTGRS IMRPLYMDFE
641  KTDPKISQLV SSNSNYTTQQ YMFGPRLLVS PVTLPNVTEW
681  PVYLPQTGDN STKPWTYWWT NETYAGGQVV KVPAPVQHIP
721  VFHLGSREEL LSGDVF
```

A cDNA encoding the *Aspergillus acidus* α-xylosidase has SEQ ID NO:20.

```
   1  ATGTATTTTT CTTCCTTTTT GGCCCTAGGG GCCCTGATTC
  41  AGGCAGCAGC AGCAACCTAT CTCGCCCCCA ACTCTACCGG
 121  TCTCCGTATC CAGCATGGCT TCGAGACCAT CCTCATCCAG
 161  CCGTTTGGGT ACGACGGATT CCGCGTGCGC GCATGGCCCT
 201  TCCGTCCGCC TTCGGGCAAC GAGATTAGCT TCATCTATGA
 241  TCCCCCGATT GAAGGTTATG AGGACACCGC ACATGGCATG
 281  AGCTATGACA CCGCAACAAC CGGCACGGAG CCTCGCACCT
 321  TGCGCAACGG CAATATCATC CTGCGCACCA CTGGCTGGGG
 361  TGGCACCACC GCCGGATACC GCCTGTCCTT CTACCGCGTC
 401  AATGATGATG GGAGTGAGAC CCTGCTCACA AACGAATATG
 441  CTCCGCTGAA GTCTCTCAAC CCCCGATACT TTCCTGGCC
 481  GGGACCTGGG GCCGAATTCT CTGCCGAGTT CTCCTTCAGT
 521  GCGACTCCGG ATGAGCAGAT TTATGGCACG GGCACGCAAC
 561  AAGACCATAT GATCAACAAG AAGGGTTCCG TTATCGACTT
 601  GGTCAACTTC AACACCCACA TCCCTACCCC AGTCTTCATG
 641  AGCAACAAAG GCTATGCCTT TATCTGGAAC ATGCCGGCCG
 681  AGGGGCGTAT GGAGTTTGGC AGCCTGCGCA CCAGGTTCAC
 721  CGCGGCGTCC ACGACGCTTG TCGACTATGT AATCGTCGCC
 761  GCTCAGCCAG GTGATTACGA CACCCTCCAG CAGCGGATTT
 801  CGGCCCTGAC AGGACGGGCA CCGACCCCGC CGACTTTTC
 841  TCTCGGGTAC ATCCAGTCCA AGCTACGATA TGAGAACCAA
 881  ACGGAGGTGG AGCTGCTGGC TCAGAACTTC CATGATAGAG
 921  ACATCCCGGT GTCCATGATC GTTATTGACT ACCAGTCGTG
 961  GGCTCATCAG GGTGACTGGG CGCTCGATCC GCGCCTGTGG
1001  CCCAATGTCG CGCAGATGTC GGCGACAGTC AAGAATCTGA
1041  CCGGAGCCGA AATGATGGCG TCTCTATGGC CCAGTGTTGC
1081  CGATGACAGT GTCAACTACG CAGCCCTGCA GGCGAACGGT
1121  CTGCTCTCAG CCACCCGCGA CGGCCCTGGT ACCACTGACT
1161  CCTGGAACGG ATCATACATC CGGAACTATG ACTCCACCAA
1201  CCCCTCGGCG CGGAAATTCC TCTGGAGCAT GCTGAAGAAA
1241  AACTACTACG ACAAGGGTAT TAAGAACTTT TGGATTGATC
1281  AGGCCGATGG CGGAGCATTG GGCGAGGCTT ATGAGAACAA
1321  CGGCCAGAGC ACATACATTC AGTCCATTCC GTATACCCTG
1361  CCGAACGTGA ACTACGCCGC TGGCACGCAG CTCGGCGTGG
1401  GTAAGTTGTA CCCCTGGGCG CAGCAACAGG CAATCGAAGA
1441  AGGCTTCCGC AATGCGACAG ACACCAAGGA AGGAAGCGCT
1481  TGCGATCACG TCTCCCTGAG TCGGTCCGGA TACATCGGAT
1521  CTCAGCGGTT CTGCAGCATG ATCTGGTCTG GAGACACCAC
1561  CTCTGTTTGG GACACACTGG CAGTGCAGGT CGCCAGTGGT
1601  CTGTCCGCCG CAGCAACAGG CTGGGGTTGG TGGACCGTCG
1641  ATGCTGGCGG CTTCGAAGTC GACTCGACAG TTTGGTGGAG
1681  TGGAAACATT GACACGCCCG AATTCCGGGA GTTGTATGTG
1721  CGCTGGCTGG CCTGGACGAC CTTCCTGCCA TTCATGCGCA
1761  CTCATGGTAG TCGGGCCTGC TACTACCAGG ACGCCTACAC
1801  TTGTGCCAAT GAGCCATGGT CCTATGGTGC AAGCAACACC
```

```
1841 CCCATTATTG TCTCGTATAT CCACCTGCGT TACCAATTGG

1881 GTGCTTATCT GAAGTCGATT TTCAACCAGT TCCACCTCAC

1921 GGGTCGCAGT ATCATGCGCC CGTTGTACAT GGATTTCGAG

1961 AAGACCGACC CGAAGATCTC TCAGCTGGTG TCGTCGAACA

2001 GAGACACCAC AACTCAACAG TACATGTTTG GTCCACGTCT

2041 CCTAGTCTCT CCAGTGACCT TGCCAAACGT CACTGAGTGG

2081 CCTGTGTATC TTCCGCAGAC GGGAGATAAT AGCACTAAGC

2121 CTTGGACGTA CTGGTGGACG AATGAGACGT ATGCGGGAGG

2161 ACAGGTCGTC AAGGTTCCTG CGCCCGTGCA GCATATCCCG

2201 GTATTCCATC TGGGATCGCG CGAGGAGCTT CTGTCGGGTG

2241 ATGTATTCTA G
```

An α-xylosidase from *Aspergillus tubingensis* has JGI accession number jgi|Asptu1|396136, has a signal peptide sequence, and has amino acid sequence SEQ ID NO:21.

```
  1 MYFSSLLALG ALVQAAAATY FAPNSTGLRI QHGFETILIQ

41 PFGYDGFRVR AWPFRPPSGN EISFIYDPPI EGYEDTAHGM

121 SYDTATTGTE PRTLRNGNII LRTTGWGGTT AGYRLSFYRV

161 NDDGSETLLT NEYAPLKSLN PRYYYWPGPG AEFSAEFSFS

201 ATPDEQIYGT GTQQDHMINK KGSVIDLVNF NTHIPTPVFM

241 SNKGYAFIWN MPAEGRMEFG SLRTRFTAAS TTLVDYVIVA

281 AQPGDYDTLQ QRISALTGRA PTPPDFSLGY IQSKLRYENQ

321 TEVELLAQNF HDRDIPVSMI VIDYQSWAHQ GDWALDPRLW

361 PNVAQMSATV KNLTGAEMMA SLWPSVADDS VNYAALQANG

401 LLSATRDGPG TTDSWNGSYI RNYDSTNPSA RKFLWSMLKK

441 NYYDKGIKNF WIDQADGGAL GEAYENNGQS TYIQSIPYTL

481 PNVNYAAGTQ LGVGKLYPWA HQQAIEEGFR NATDTKKGSA

521 CDHVSLSRSG YIGSQRFCSM IWSGDTTSVW DTLAVQVASG

561 LSAAATGWGW WTVDAGGFEV DSTVWWSGNI DTPEFRELYV

601 RWLAWTTFLP FMRTHGSRTC YYQDAYTCAN EPWSYGASNT

641 PIIVSYIHLR YQLGAYLKSI FNQFHLTGRS IMRPLYMDFE

681 KTDPKISQLV SSNSNYTTQQ YMFGPRLLVS PVTLPNVTEW

721 PVYLPQTGDN STKPWTYWWT NETYAGGQVV KVPAPVQHIP

761 VFHLGSREEL LSGDVF
```

The following AN7505 (GenBank XP 680774 or, DQ490509.1, or ABF50885.1 with SEQ ID NO:22) polypeptide sequence from *Aspergillus nidulans* has about 25% amino acid identity to Ax1A, lacks a predicted signal peptide, and is thereby most likely an intracellular, cytosolic α-xylosidase enzyme. See, also, Bauer et al, *Proc. Natl. Acad. Sci. U.S.A.* 103:11417-11422 (2006).

```
  1 MKFTEGMWLL REGIRIDWMS NVERLNVDKD TVNLLLNKFQ

41 RHRGDTLNSS TVSARVTSPL EGIIGVKLVH WAGGLDNGPH

81 YELNTSAGHT EITHEKGKNL KYTSGRLELD INIAPNELAF

121 TFTTGADGQD KRKKLTGHSF RSIGYVGDST TPKSQLSDGI

161 FYERQGYTLA ELDLSVGEKL YGLGERFGPF VKNGQSVNIW

201 NEDGGTSSEL AYKNIPFYIS SNGYGVFVNH PGKVSLELQS

241 ERTTRVNVSV EGEELEYFVI EGKNPKEILK RWTDLTGKPA

281 LVPAWSYGLW LTTSFTTNYS ERTVTGFLDG FKDRNLPLSV

321 FHFDCFWMKS YQWCDFEFDA DMFPDAAGYL ARLKERGLKL

361 SIWINPYVGQ ASPLFEIGKR EGYFIKRIDG SVWQWDLWQA

401 GMAVVDFTNP AACSWYTGHL KRLMDLGIDT FKTDFAERIP

441 FKNITYHDGS DPARMHNYYA LLYNKVVYET MTSISGKSNS

481 LLFARSTSVG GQKYPVHWGG DCESTYEAMA ESLRGGLSLG

521 LAGYIFWASD IGGFEGTPPP ALYKRWVQFG LLSSHSRLHG

561 SSSFRVPWIY GEDCSDVLRD CVKRKISLTP YLLAEALNGH

601 RSGTPLMRPM FMEFPEDLNT YPLDTQYMFG SNLLVAPVFS

641 DEGIVTFYVP RTPEEEGRKQ WISWFDHGKK YEGGRWYTET

681 HGFDTLPILI RPGSVTPINY KLEKPEGNPL DGLEILVNGS

721 IDKEVEIEIV DPETTHKVLK VMTVSERETE NGVEVIARLD

761 GVDGNENSVK VNWVGHGVTK
```

Therefore, even if native AN7505 is an α-xylosidase, the data highly suggest that the enzyme is localized within the intracellular cytoplasmic space.

The α-xylosidase described herein with SEQ ID NO:1 is also referred to as Ax1A. The Ax1A is present in both sequenced strains of *A. niger*, ATCC1015 and CBS 513.88, with 100% amino acid identity and 99% nucleotide identity in the coding region. Pel et al., *Nat. Biotechnol.* 25: 221-231 (2007); and Andersen et al., *Genome Res.* 21:885-897 (2011). *A. nidulans* has 10 predicted GH31 genes, five of which have signal peptides. Of these, AN7120 (XP_664724) has the best amino acid identity to Ax1A (30%), but no signal peptide. *A. niger* ATCC 1015 and CBS 513.88 both have seven predicted GH31 genes, the best of which (after Ax1A itself) being ANI_1_620014 (also known as Aspni5|55419), with 32% identity.

The Ax1A mRNA and protein expression have been reported to be induced by *A. niger* growth on xylose as compared with maltose. Gonzalez-Vogel et al., *Appl. Microbial. Biotechnol.* 89:145-155 (2011); Jørgensen et al., *BMC Genomics* 10:44 (2009); and de Oliveira et al., *PLoS ONE* 6:e20865 (2011). Ax1A was not included in a genome-wide microarray expression study comparing *A. nidulans, A. oryzae*, and *A. niger*, presumably because it is not common to all three species. Andersen et al., *Proc. Natl. Acad. Sci. U.S.A.* 105, 4387-4392 (2008).

After the first tier Ax1A orthologs were identified in species of *Aspergillus*, approximately the next best 20 hits to Ax1A in GenBank™, have E-values ranging from e-97 to e-23 and percent identities ranging from 22% to 52%, encompassing a much wider variety of fungi. All of these proteins are hypothetical, and it is not known whether they have α-xylosidase, β-glucosidase, or any other catalytic activities. However, the majority of these second tier orthologs lack predicted signal peptides. This is a strong indication that they are not extracellularly secreted and are probably functional orthologs of the cytoplasmic α-xylosidase enzymes of *A. flavus, A. niger*, and *P. wortmanii*.

*T. reesei* has only two poor (E-value>e-10 and <25% amino acid identity) BLASTP hits to Ax1A (Trire2|121351 and Trir2|69944 [JGI numbering]), and neither of these has a predicted signal peptide. It appears that *T. reesei* does not have the genetic potential to biosynthesize a secreted α-xylosidase related to Ax1A, which is consistent with the observed lack of this enzymatic activity in commercial enzyme mixtures derived from *T. reesei*. FIG. 1B.

Taken together, the evidence indicates that only a small subset of fungi have the genetic potential to biosynthesize secreted enzymes with α-xylosidase activity.

Proteins and nucleic acids related to those specifically described herein can be isolated and identified by a variety of methods. For example, any of SEQ ID NO:1-6 can be mutated and/or can be isolated by hybridization to DNA and/or RNA isolated from other species (e.g., other fungal species) using any of the SEQ ID NO:2, 4 or 6 nucleic acids as probes. The sequence of the α-xylosidase enzyme (e.g., SEQ ID NO:1, 3, 5, 7-19, 19, 21 and/or 22) can also be examined and used as a basis for designing alternative α-xylosidase nucleic acids that encode related α-xylosidase polypeptides.

In one embodiment, the α-xylosidase nucleic acids of the invention include any nucleic acid that can selectively hybridize to SEQ ID NO:2, 4, 6 and/or 20.

The term "selectively hybridize" includes hybridization, under stringent hybridization conditions, of a nucleic acid sequence to a specified nucleic acid target sequence (e.g., SEQ ID NO:2, 4, 6 and/or 20) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, at least 50% sequence identity, at least 60% sequence identity, at least 70% sequence identity, at least 80% sequence identity, at least 90% sequence identity, at least 95% sequence identity, or 60-90% sequence identity, or 90-95% sequence identity, or 90-99% sequence identity, or 95-97% sequence identity, or 98-99% sequence identity, or 100% sequence identity (or complementarity) with each other. In some embodiments, a selectively hybridizing sequence has about at least about 90% sequence identity or complementarity with SEQ ID NO:2, 4, 6 and/or 20.

Thus, the nucleic acids of the invention include those with about 500 of the same nucleotides as SEQ ID NO:2, 4, 6 and/or 20, or about 700 of the same nucleotides as SEQ ID NO:2, 4, 6 and/or 20, or about 900 of the same nucleotides as SEQ ID NO:2, 4, 6 and/or 20, or about 1000 of the same nucleotides as SEQ ID NO:2, 4, 6 and/or 20, or about 1200 of the same nucleotides as SEQ ID NO:2, 4, 6 and/or 20, or about 1400 of the same nucleotides as SEQ ID NO:2, 4, 6 and/or 20, or about 1600 of the same nucleotides as SEQ ID NO:2, 4, 6 and/or 20, or about 1800 of the same nucleotides as SEQ ID NO:2, 4, 6 and/or 20, or about 2000 of the same nucleotides as SEQ ID NO:2, 4, 6 and/or 20, or about 2100 of the same nucleotides as SEQ ID NO:2, 4, 6 and/or 20, or about 2150 of the same nucleotides as SEQ ID NO:2, 4, 6 and/or 20, or about 700-2150 of the same nucleotides as SEQ ID NO:2, 4, 6 and/or 20. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., or 90-99% sequence identity, what is meant is that the value can be any integer between 90 and 99 inclusive, i.e., 90, 91, 92, 93, 94, 95, 96, 97, 98 or 99.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5° C. + 16.6(\log M) + 0.41(\% \, GC) - 0.61(\% \, \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C.

lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to SEQ ID NO:2, 4, 6 and/or 20.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison (e.g., any of SEQ ID NO:1-6). The reference sequence can be a nucleic acid sequence (e.g., SEQ ID NO:2, 4, 6 and/or 20) or an amino acid sequence (e.g., SEQ ID NO:1, 3, 5, 7-19, 21 and/or 22). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, preferably 60%, preferably 70%, preferably 80%, more preferably at least 90% or at least 95% sequence identity to the reference sequence over a specified comparison window. Optimal alignment may be ascertained or conducted using the homology alignment algorithm of Needleman and Wunsch, supra.

An indication that two polypeptide sequences are substantially identical is that both polypeptides have α-xylosidase activity, meaning that both polypeptides can hydrolyze α-1, 6-linked xylose residues. The polypeptide that is substantially identical to an α-xylosidase with any of SEQ ID NO:1, 3, 5, 7-19, 21 and/or 22 sequence (especially one substantially identical to the SEQ ID NO:1 sequence), may not have exactly the same level of activity as an α-xylosidase with any of SEQ ID NO:1, 3, 5, 7-19, 21 and/or 22. Instead, the substantially identical polypeptide may exhibit greater or lesser levels of α-xylosidase activity than the α-xylosidase with SEQ ID NO:1, 3, 5, 7-19, 21 and/or 22 (especially SEQ ID NO:1), as measured by assays available in the art or described herein (see, e.g., Example II). For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the an α-xylosidase with the SEQ ID NO:1, 3, 5, 7-19, 21 and/or 22 sequences (especially the SEQ ID NO:1 sequence) when measured by similar assay procedures.

Alternatively, substantial identity is present when second polypeptide is immunologically reactive with antibodies raised against the first polypeptide (e.g., any of polypeptides with SEQ ID NO:1, 3, 5, 7-19, 19, 21 and/or 22). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The α-xylosidase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of any of the SEQ ID NO:1, 3, 5, 7-19, 21 and/or 22 sequences. Alternatively, the α-xylosidase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:1, 3, 5, 7-19, 21 and/or 22 sequences.

2. Properties of Secreted Ax1A

The pH optimum of secreted α-xylosidase (Ax1A) on pNPαX was between 3 and 4. FIG. 12A. The temperature optimum was 55° C. The activity was about 50% of maximum at 65° (FIG. 12B). The native protein was approximately as active on isoprimeverose (IP) as on the synthetic substrate pNPαX. See, Table 1.

TABLE 1

Ax1A enzyme kinetics

| Enzyme source | Substrate | $K_m$ μm | $K_m$ 95% confidence interval | $k_{cat}$ min$^{-1}$ | $k_{cat}$ 95% confidence interval |
| --- | --- | --- | --- | --- | --- |
| Native | pNPαX | 3.68 | 1.83-5.53 | 1393 | 1130-1656 |
| Native | IP | 9.78 | 7.73-11.84 | 917 | 834-999 |
| Pichia-expressed | pNPαX | 6.91 | 4.25-9.56 | 1234 | 1047-1420 |
| Pichia-expressed | IP | 4.03 | 3.36-4.71 | 1337 | 1265-1409 |

Nonlinear curve-fitting software (GraphPad Prism) was used to calculate the parameters and confidence intervals.

3. Heterologous Expression of Secreted Ax1A

When expressed in *P. pastoris*, recombinant secreted Ax1A had an apparent molecular weight of about 110,000, larger than the native protein. Recombinant secreted Ax1A also ran as a more diffuse band than the native protein. FIG. 11B. Both of these observations suggest that recombinant secreted Ax1A is hyperglycosylated when expressed in *P. pastoris*. Secreted Ax1A has at least ten predicted N-glycosylation sites. Nonetheless, the heterologously expressed protein showed kinetic properties similar to the native protein on both pNPαX and isoprimeverose. See, Table 1. The recombinant secreted Ax1A expressed in *P. pastoris* had no detectable β-glucosidase, β-xylosidase, or α-glucosidase activity when assayed with p-nitrophenyl-β-D-glucoside, p-nitrophenyl-β-D-xyloside, or pNPβG, respectively (data not shown). This supports the conclusion that the β-glucosidase activity seen in the "purified" α-xylosidase is due to contamination with another protein. FIG. 10.

4. Activity of Secreted Ax1A on Xyloglucan Heptasaccharide

HPLC-purified native Ax1A (supra) degraded the heptasaccharide XXXG into free glucose and xylose sugar residues (data not shown). However, the above data suggested that this preparation contained residual β-glucosidase (βG) activity. FIG. 10. Recombinant secreted Ax1A released about 10 nmol of xylose, a quantity that did not increase with time. FIG. 13. This proportion of xylose corresponds to approximately one-third of the total xylose present in the xyloglucan heptasaccharide sample (i.e., for example, about 34 nmol in a 12 μl of a reaction volume of 500 μl). This result is consistent with secreted Ax1A removing a single xylose residue from the heptasaccharide to produce WOW and is further evidence that secreted Ax1A does not have intrinsic β-glucosidase activity. Digestion of the xyloglucan heptasaccharide with no enzyme or β-glucosidase alone released no to little xylose. FIG. 13. Digestion with a combination of secreted Ax1A and β-glucosidase released 83.4% of the theoretical maximum of xylose in 10 h. FIG. 13. Thus, β-glucosidase and α-xylosidase together are capable of substantially depolymerizing the heptasaccharide, which is the repeating unit of native xyloglucan (FIG. 1).

5. Activity of Secreted Ax1A on Tamarind Xyloglucan

Because xyloglucan contains β-linked galactose and β-linked glucose in addition to α-linked xylose, four enzymes were included in the experiment: xyloglucanase, β-glucosidase, and β-galactosidase, all from *T. reesei*, in addition to secreted Ax1A as described herein. See, Table 2.

TABLE 2

Optimal proportions of four hemicellulases for release of glucose and xylose from tamarind xyloglucan.
Total protein loading was 15 mg/g glucan
βG is β-glucosidase

| Product | Optimal enzyme proportions (%) | | | | Sugar Yield % |
|---|---|---|---|---|---|
| | Ax1A | Xyloglucanase | βG | β-Galactosidase | |
| glucose | 51 | 19 | 5 | 25 | 99 |
| xylose | 59 | 11 | 5 | 25 | 100 |

An optimized mixture of the four enzymes was developed using GENPLAT at fixed total protein loading. In the first experiment, the lower limit of each enzyme was set to 0%. However, because many combinations failed to yield about 5% of xylose or glucose, a statistically valid model could not be determined. In subsequent experiment, the lower limit of each enzyme was set to 5%, which gave a statistically valid model for both glucose and xylose and a complete digestion of tamarind xyloglucan was achieved (data not shown). The optimized proportions of the four enzymes for glucose and xylose release are shown in Table 2. Of these four enzymes, secreted Ax1A was present in the highest proportion (e.g., 51% for glucose and 59% for xylose).

6. Summary

A secreted α-xylosidase from *A. niger* was isolated, purified and characterized. Evidence that it is secreted include, but is not limited to: 1) presence of a predicted signal peptide in secreted Ax1A itself; and 2) secretion of Ax1A from *P. pastoris* under the control of its native signal peptide.

Previously reported α-xylosidase enzymes from filamentous fungi are usually intracellular. Consistent with this, the large majority of proteins (all of which are hypothetical) annotated as being in glycosyl hydrolase family 31, lack predicted signal peptides. For example, a putative *A. nidulans* cytosolic α-xylosidase (AN7505, GenBank DQ490509.1 or ABF50885) has minimal sequence identity (about 25%) to the secreted Ax1A α-xylosidase described herein. In the report showing that α-xylosidase AN7505 is secreted from *Pichia pastoris*, a yeast signal peptide was fused to the amino terminus of the protein. Therefore, secretion under such conditions does not indicate whether the native protein is secreted or not. Bauer et al., *Proc. Natl. Acad. Sci. U.S.A.* 103:11417-11422 (2006). Like most other known and presumed fungal α-xylosidase enzymes, the native cellular location of AN7505 is most likely the cytoplasm.

Despite the abundance of α-linked xylose in plant cell wall polysaccharides, there has been relatively little previous work on α-xylosidase enzymes. van den Brink, J. et al., *Appl. Microbial. Biotechnol.* 91:1477-1492 (2011). The investigations described herein indicate that this may be because secreted microbial α-xylosidase enzymes are rare. The available data from both bacteria and fungi suggest that even though most lignocellulolytic microorganisms secrete enzymes that can degrade xyloglucan to isoprimeverose, they transport and degrade isoprimeverose intracellularly. That is, although α-xylosidases are made by many micro-organisms, as a general rule they do not secrete the enzyme. The rarity of secreted α-xylosidase enzymes in fungi is illustrated by the example of the commercial enzyme product known as Driselase®, which comes from the basidiomycete *Irpex lacteus*. Although Driselase® contains dozens of cell wall-active enzymes, it lacks α-xylosidase activity. This has made it a useful diagnostic tool for studying xyloglucan because treatment of plant cell walls with Driselase® completely degrades xyloglucan into isoprimeverose molecules, which can be quantitated by several methods including chromatography. Lorences et al., *Carbohydr. Res.* 263:285-293 (1994).

The hypothesis that secreted α-xylosidase enzymes are rare among microorganisms is consistent with the preponderance of predicted GH31 proteins without signal peptides in the genomes of sequenced filamentous fungi and with the existence of isoprimeverose utilization operons in bacteria such as *L. pentosus*. Chaillou et al., *J. Bacterial.* 180:2312-2320 (1998). The best BLASTP hits of Ax1A to the GenBank™ database are to α-xylosidase enzymes that have signal peptides, but this is only a small subset of all of the putative fungal GH31 proteins. Orthologs of secreted Ax1A with signal peptides are from species of *Aspergillus* and several basidiomycetes. *Aspergillus* species have many additional predicted GH31 proteins without signal peptides.

Secreted Ax1A has activity against pNPαX, isoprimeverose, xyloglucan heptasaccharide, and tamarind xyloglucan. As a naturally secreted protein, it should be able to tolerate a variety of environmental conditions. Secreted Ax1A is therefore predicted to be a versatile α-xylosidase enzyme that should find utility in biotechnological applications such as deconstruction of lignocellulosic materials into free, fermentable sugar residues (e.g., xylose, glucose) to support biofuel production. Because herbaceous dicotyledonous plants contain higher amounts of xyloglucan than grasses, Ax1A may be particularly useful for processing biomass from dicot species. Ax1A has a pH optimum of about 4.0, whereas most cellulase mixtures perform better at pH 4.5-5.0.

III. Secreted α-Xylosidase Enhanced Plant Biomass Degradation

Xylose (Xyl) is usually present in an isoprimeverose (IP) disaccharide molecule linked by an α-1,6 bond with a glucose (Glc) molecule. α-Xylosidases, either cytosolic or secreted, can cleave the xylose-glucose isoprimeverose molecule and/or xyloglucan oligosaccharides (i.e., for example, the heptasaccharide, XXXG). Fry et al. *Plant Physiol* 89:1-3 (1993); and FIG. 1. Some embodiments of the present invention are commercially applicable because: i) xyloglucan is a major component of plant cell walls; ii) complete breakdown of xyloglucan is enhanced by α-xylosidase, preferably a secreted α-xylosidase; iii) in the absence of a secreted α-xylosidase, xyloglucan may remain in a non-fermentable form of isoprimeverose, thereby reducing the efficiency of the plant biomass degradation process into fermentable sugars; and iv) most, if not all, commercial enzyme preparations lack secreted α-xylosidase enzymes. Although it is not necessary to understand the mechanism of an invention, it is believed that both glucose and xylose are desirable for fermentation, and a secreted α-xylosidase is useful for improving the effectiveness of any enzyme mixture for biomass degradation.

Conventionally used enzyme mixtures for biomass deconstruction (supra) do not contain α-xylosidase enzymes because the α-xylosidase gene is not naturally present in most fungal genomes that are usually the source of commercial enzyme mixtures (i.e., for example, *Trichoderma reesei*). The data presented herein demonstrates that the efficiency of most commercially available enzyme mixtures is increased when a secreted α-xylosidase is added. This increased efficiency results in the production of higher sugar yields. For example, use of a secreted α-xylosidase enhances glucose (Glc) and xylose (Xyl) yields when mixed with a commercially available cellulase enzyme mixtures (CTec2, Novozyme; Accellerase 1000, Genencor). Use of a secreted α-xylosidase also enhances glucose and xylose yields from corn stover that has been pretreated with alkaline hydrogen peroxide (infra).

The secreted Ax1A described herein is a true extracellular fungal α-xylosidase, which can be expressed by *Picha pastoris* and which exhibits degradation activity on isoprimeverose molecules. The data presented herein demonstrates that secreted Ax1A is an α-xylosidase active on a range of substrates including natural substrates such as isoprimeverose and tamarind xyloglucan. Specifically, Ax1A enhances the release of glucose and xylose from natural lignocellulosic materials, especially when combined with commercial mixtures of cellulase enzymes. The biomass used in these experiments was AHP (alkaline-hydrogen peroxide) pretreated corn stover. Hydrolysis conditions were 0.2% glucan loading, 48 hr, 50° C., unless otherwise indicated.

Secreted Ax1A increased glucose release from this alkaline-hydrogen peroxide treated biomass by 9%, from 76% to 85% when combined with Accellerase 1000 (a Genencor product). See, FIG. 3. Similarly, secreted Ax1A enhanced glucose release from 83% to 90% when combined with a CTec2:HTec2 enzyme mixture (Novozymes product). See, FIGS. 4 and 5B. When using CTec2 alone, a secreted Ax1A dose response curve enhanced glucose release from AHP by 7%, from 82 to 89%. See, FIG. 5. When CTec2 and HTec2 were combined in various proportions, a secreted Ax1A dose response curve showed enhanced glucose release of about 0.5-7% in all combinations, except the 25:75 mixture of CTec2 and HTec2. See, FIG. 6. A time course at two different Ctec2:Htec2 loading concentrations showed enhanced glucose release of about 2-10% in the presence of secreted Ax1A as compared to the absence of Ax1A. See, FIG. 8.

Secreted Ax1A enhanced xylose release from 56% to 60% in a dose response fashion when in combination with CTec2 and HTec2 (75:25) at a 2.5 mg/g glucan loading dose. See, FIG. 7. Similar enhancement of xylose release was seen in a dose response fashion with either CTec2, alone, or a CTec2:Htec2 combination (75:25) at a 1.0 mg/g glucan loading dose. See, FIG. 9. These data indicate that secreted Ax1A increases the ultimate yields of glucose and xylose when used in sufficient concentration and over time. Although it is not necessary to understand the mechanism of an invention, it is believed that these data suggest that the secreted Ax1A acts on the final step(s) of xyloglucan degradation.

IV. Compositions

Compositions of the α-xylosidase(s) described herein are also provided. Such compositions are also referred to as converting enzyme mixtures, or simply enzyme mixtures. Such compositions can include any of the α-xylosidase(s) described herein. For example, the compositions can include a carrier, α-xylosidase(s), and at least 5% weight percentage cellulase(s).

The carrier can include a convenient solvent such as an aqueous medium. The carrier can also include agents such as protease inhibitors, chelation agents, sugars, oligosaccharides, polyols, osmolytes, protein stabilizers, buffers, salts, and the like. In some instances, the carrier is a microbial fermentation or growth medium that has been employed to grow the microbial host cells that express the α-xylosidase(s). After fermentation and/or growth of the microbial host cells, the host cells are removed, and a microbial fermentation medium can be filtered, diluted, proteins in the medium can be concentrated, and/or agents such as those listed above can be added.

The α-xylosidase(s) in the compositions and enzyme mixtures can include any of those described herein For example, the α-xylosidase(s) in the compositions and enzyme mixtures can include polypeptides with sequences having at least 40% sequence identity with any of SEQ ID NO:1, 3, 5, 7-19, or 21. The α-xylosidase(s) in the compositions and enzyme mixtures can also include polypeptides with sequences having other percentages of sequence identity with any of SEQ ID NO:1, 3, 5, 7-19, or 21. Such percentages of sequence identity can be any of the percentages described herein (e.g., at least 50%, at least 60%, at least 70%, at least 80%, at least 90%, and/or at least 95% sequence identity with any of SEQ ID NO:1, 3, 5, 7-19, or 21). In some embodiments, the compositions, enzyme mixtures and converting enzyme mixtures do not include a polypeptide having SEQ ID NO:22.

The α-xylosidase(s) can be present in the compositions and enzyme mixtures in varying amounts. For example, the compositions and enzyme mixtures can include about 0.1%, about 0.25%, about 0.5%, about 1%, about 2%, about 3%, about 5%, about 7%, about 10%, about 15%, or about 20% by weight α-xylosidase(s). In some instances, the compositions and enzyme mixtures can include about 0.1% to about 20% by weight α-xylosidase(s), or about 0.2% to about 10% by weight α-xylosidase(s), or about 0.5% to about 5% by weight α-xylosidase(s), or about 0.5% to about 3% by weight α-xylosidase(s).

The cellulases included in the compositions and enzyme mixtures can include any cellulase or lignocellulosic depolymerizing enzyme available to those of skill in the art. For example, the compositions and enzyme mixtures can include a cellobiohydrolase, a polysaccharide oxidase (e.g., cel61, see NCBI accession no. AY094489.1 GI:21694046), an endoxylanase, a β-glucosidase, a β-1,4-glucanase, a β-galactosidase, an α-fucosidase, a β-galactosidase, an endoxylanase, a β-xylosidase, α-arabinosidase, α-glucuronidase, an esterase and combinations thereof.

The cellulase or cellulase mixture is present in the compositions and enzyme mixtures at weight percentages of at least 5%, or at least 10%, or at least 15% cellulase or at least 20%, or at least 25% cellulase, or at least 30% cellulase, or at least 40% cellulase, or at least 50%.

The following non-limiting Examples illustrate aspects of the invention.

EXPERIMENTAL

Example I

Fungal Strains, Enzymes, and Substrates

*Aspergillus niger* strain FGSC A1144 (ATCC 1015) was obtained from the Fungal Genetics Stock Center (Kansas City, Mo.), *Trichoderma reesei* (also known as *Hypocrea jecorina*) strain QM9414 was obtained from the United States Department of Agriculture National Center for Agricultural Utilization Research (Peoria, Ill.), *Fusarium graminearum* (*Gibberella zeae*) strain PH-1 was obtained from Dr. L. P. Hart (Department of Plant Pathology, Michigan State University), and *Phanerochaete chrysosporium* strain RP-78 was obtained from Dr. D. Cullen (United States Department of Agriculture Forest Products Laboratory, Madison, Wis.). *P. pastoris* strain X-33 and plasmid pPicZB were obtained from Invitrogen.

Commercial enzyme preparations (Multifect Pectinase, Multifect Xylanase, Accellerase XY, Accellerase 1000, Accellerase 1500, and Stargen) were obtained from Dupont/Danisco, Inc. (Genencor Division (Rochester, N.Y.)). CTec2 and HTec2 were obtained from Novozymes, Inc. (Franklinton, N.C.). Isoprimeverose (catalog no. 0-IPRM), xyloglucan from tamarind (catalog no. P-XYGLN), and borohydride-reduced xyloglucan-derived heptasaccharide (catalog no. O-X3G4R) were purchased from Megazyme Intl. (Wicklow, Ireland). The monosaccharide composition of the xyloglucan heptasaccharide and the tamarind xyloglucan were reanalyzed by the alditol acetate method. Foster et al., *J. Vis. Exp.* doi:10.3791/1837 (2010). For the xyloglucan heptasaccharide assay, total recovery of sugars was 101±2% of the mass and the molar percent composition was 0.2% arabinose, 43.2% xylose, 0.8% galactose, and 55.8% glucose. This is very close to a 4:3 ratio of xylose:glucose, which is consistent with the manufacturer's stated structure of XXXG. Fry et al., *Physiol. Plant.* 89:1-3 (1993). Reanalysis of the tamarind xyloglucan indicated that it contains 2.3% arabinose, 35.1% xylose, 15.5% galactose, and 47.1% glucose, on a molar basis. This is in good agreement with the manufacturer's stated composition of 4% arabinose, 38% xylose, 16% galactose, and 42% glucose.

Example II

Enzyme Assays p-Nitrophenyl-α-D-glucoside (pNP α G), p-nitrophenyl-α-D-xyloside (pNP α X), p-nitrophenyl-α-D-xyloside, and p-nitrophenyl-α-D-glucoside were purchased from Sigma. Enzyme reactions were performed in 96-well microtiter plates in a total volume of 0.2 ml and the absorbance of reaction mixtures were read on a SpectraMax Plus microplate reader (Molecular Devices, Sunnyvale, Calif.). The influence of pH on α-xylosidase activity was measured at 37° C. in McIlvaine buffers adjusted to pH values from 2.5 to 7.5. McIlvaine T. C., *J. Biol. Chem.* 49:183-186 (1921). Free glucose and xylose were measured colorimetrically using enzyme-linked assays in 96-well plates. Banerjee et al., *Biotechnol. Bioengineer.* 106:707-720 (2010). Enzyme kinetics were analyzed by nonlinear curve fitting using GraphPad Prism™ software (La Jolla, Calif.).

Example III

Purification of α-Xylosidase

A column of DEAE-cellulose (Sigma D0909), 3-ml bed volume in a 5-ml syringe, was equilibrated with 25 mM sodium acetate, pH 4.0, and 1 ml of Multifect Pectinase applied and eluted with 25 mM sodium acetate, pH 4.0. Active fractions were combined and loaded onto a cation exchange HPLC column (TSK-Gel SP-5PW, Tosoh Bioscience, Montgomeryville, Pa.), equilibrated in the same buffer, and eluted with a gradient of 0-0.6 M NaCl in 30 min at a flow rate of 1 ml/min. Fractions containing α-xylosidase activity were combined, and dry $NH_4SO_4$ was added to 1.7 M. This material was applied to a hydrophobic interaction column (TSK-gel Phenyl-5PW, Tosoh BioScience) equilibrated in 25 mM sodium acetate, pH 4.0+1.7 M $NH_4SO_4$. Proteins were eluted with a 30 min linear gradient to 100% water followed by 20 min of water at a flow rate of 1 ml/min. In some experiments, an additional fractionation step on hydroxyapatite CHT5-1 (10×64 mm, Bio-Rad) was included between the cation exchange and hydrophobic interaction steps. Elution conditions were 10 to 500 mM $Na_2HPO_4$, pH 7.0, in 30 min at 1 ml/min.

HPLC fractions were analyzed by SDS-PAGE (4-20% acrylamide, Tris-HCl, Bio-Rad). Proteins were visualized with ProtoBlueSafe (National Diagnostics, Atlanta, Ga.). Proteins were quantitated using Bio-Rad protein assay reagent and bovine IgG as standard. Bradford, M. M., *Anal. Biochem.* 72:248-254 (1976).

For mass spectrometric proteomics, proteins were excised from SDS-PAGE gels, digested with trypsin, and analyzed at the Michigan State University Proteomics Facility. For the proteomics analysis of Multifect Pectinase, 100 g of protein were separated by SDS-PAGE, the gel was divided into four equal portions, and each was processed individually as described Nagendran et al., *Fung. Genet. Biol.* 46:427-435 (2009). The mass spectral data were analyzed using Scaffold software and the *A. niger* proteome as the query database (version 3.0, Department of Energy Joint Genome Institute, Walnut Creek, Calif.). Signal peptides were predicted using the SignalP server (version 4.0).

Example IV

α-Xylosidase Gene Expression in *P. pastoris*

A cDNA corresponding to Aspni5|43342 from *A. niger* (Department of Energy Joint Genome Institute numbering) was synthesized by GeneArt (Invitrogen) with the addition of restriction sites for PmlI (5' end) and XbaI (3' end) and cloned into pPICZB (Invitrogen). The amino acid sequence of the encoded α-xylosidase is provided below (SEQ ID NO:1).

```
  1  MYFSSFLALG ALVQAAAATY FAPNSTGLRI QHGFETILIQ

41  PFGYDGFRVR AWPFRPPSGN EISFIYDPPI EGYEDTAHGM

81  SYDTATTGTE PRTLRNGNII LRTTGWGGTT AGYRLSFYRV

121  NDDGSETLLT NEYAPLKSLN PRYYYWPGPG AEFSAEFSFS

161  ATPDEQIYGT GTQQDHMINK KGSVIDMVNF NSYIPTPVFM

201  SNKGYAFIWN MPAEGRMEFG TLRTRFTAAS TTLVDYVIVA

241  AQPGDYDTLQ QRISALTGRA PAPPDFSLGY IQSKLRYENQ

281  TEVELLAQNF HDRNIPVSMI VIDYQSWAHQ GDWALDPRLW

321  PNVAQMSARV KNLTGAEMMA SLWPSVADDS VNYAALQANG

361  LLSATRDGPG TTDSWNGSYI RNYDSTNPSA RKFLWSMLKK

401  NYYDKGIKNF WIDQADGGAL GEAYENNGQS TYIESIPFTL

441  PNVNYAAGTQ LSVGKLYPWA HQQAIEEGFR NATDTKEGSA

481  CDHVSLSRSG YIGSQRFCSM IWSGDTTSVW DTLAVQVASG

521  LSAAATGWGW WTVDAGGFEV DSTVWWSGNI DTPEYRELYV

561  RWLAWTTFLP FMRTHGSRTC YFQDAYTCAN EPWSYGASNT

601  PIIVSYIHLR YQLGAYLKSI FNQFHLTGRS IMRPLYMDFE

641  KTDPKISQLV SSNSNYTTQQ YMFGPRLLVS PVTLPNVTEW

681  PVYLPQTGQN NTKPWTYWWT NETYAGGQVV KVPAPLQHIP

721  VFHLGSREEL LSGNVF
```

P. pastoris was grown and induced as previously described, except with the addition of 1% Casamino acids (Difco Laboratories), which enhanced yield and stability of Ax1A. Banerjee et al., *Bioresour. Technol.* 101:9097-9105 (2010). Secretion was driven by the native signal peptide of Ax1A.

Twenty independent *P. pastoris* transformants were confirmed by colony PCR, purified by single colony isolation, and grown in 10-ml cultures. The three isolates exhibiting the highest activity on pNPαX were grown in 500-ml cultures and then concentrated and desalted. Banerjee et al., *Bioresour. Technol.* 101:9097-9105 (2010). In some cases, Ax1A was further purified by cation exchange HPLC as described above.

Xyloglucanase (also known as Cel74A; Trire2|49081 [JGI numbering]) and β-galactosidase (Trire2|80240) from *T. reesei* were expressed as previously reported for the expression of β-glucosidase (βG) from *T. reesei* (Trire2|76672) in *P. pastoris*. Banerjee et al., *Biotechnol. Bioengineer.* 106:707-720 (2010).

Example V

Digestion of Xyloglucan Heptasaccharide

Each reaction contained 0.5 mg xyloglucan-derived heptasaccharide (Megazyme) in a reaction volume of 0.5 ml of sodium acetate (50 mM, pH 5.0). The Ax1A and β-glucosidase were produced in *P. pastoris*. The final total enzyme concentration was 30 μg/ml, and the reactions were run at 50° C. FIG. 13 illustrates the amount (nmol) of xylose released as a function of time.

Example VI

Digestion of Tamarind Xyloglucan and Optimization with GENPLAT®

For digestion of tamarind xyloglucan with commercial enzymes, the reaction volume was 0.5 ml, the total protein loading in each assay was 15 μg/g glucan, the reaction time was 24 h, and the reaction temperature was 50° C.

The mixture optimization experiments with enzymes active on xyloglucan used Design Expert™ software (State-Ease, Inc., Minneapolis, Minn.) and robotic handling of biomass and enzymes in an integrated platform called GENPLAT. A four component quadratic model was used, which involved 15 reactions performed in duplicate. The four components were α-xylosidase, β-glucosidase, xyloglucanase, and β-galactosidase. The stock solution of tamarind xyloglucan was 2.5 mg/ml in 50 mM citrate buffer, pH 4.8, and the final concentration was 1 mg/ml in a volume of 500 μl. The total protein loading in each reaction was fixed at 15 μg. The reaction plates were incubated at 50° C. for 48 h with end-over-end mixing at 10 rpm, after which 200 μl was transferred to a fresh 96-well plate. Glucose and xylose were measured by enzyme-linked colorimetric assays. Banerjee et al., *Bioresour. Technol.* 101:9097-9105 (2010); and Banerjee et al., *Biotechnol. Bioengineer.* 106:707-720 (2010).

Example VII

Identification and Purification of α-Xylosidase

Several fungi grown on a variety of substrates were tested for α-xylosidase activity. These included *Cochliobolus carbonum, F. graminearum, T. reesei, A. niger*, and *P. chrysosporium*. The fungi were grown on ground tamarind seed, corn (*Zea mays*) stover, pea (*Pisum sativum*) cell walls, carrot (*Daucus carona*) cell walls, lactose, or xylose for 5-14 days in still culture. No activity against pNPαX was seen in any of the resulting culture filtrates. An assortment of commercial enzyme products was also examined, including Accellerase 1000, Accellerase XY, Multifect Xylanase, Multifect Pectinase, Novozyme 188, CTec2, and HTec2. Activity against pNPαX was not seen in any of them except Multifect Pectinase, which had a specific activity of 0.197 μmol/min/mg. Consistent with the presence of α-xylosidase activity this preparation, and only in this preparation, could degrade tamarind xyloglucan to free xylose and glucose (FIG. 1B). Among all of the commercial enzyme mixtures tested, Multifect Pectinase was also the only one that showed activity against IP.

The protein responsible for α-xylosidase activity was purified by HPLC, the final step of which is shown in FIG. 10. Through three high resolution purification stages, a low level of βG activity was consistently associated with the peak of α-xylosidase activity (FIG. 10). The peak of α-xylosidase activity did not contain any α-glucosidase or β-xylosidase activity as measured using pNPαG and p-nitrophenyl-β-D-xyloside, respectively. Later experiments indicated that the β-glucosidase activity was probably due to co-purification of a separate enzyme. Their co-elution through multiple purification steps suggests that the two enzymes might form a complex in vivo. Although the secreted proteins of aerobic filamentous fungi are generally considered to be "noncomplexed," evidence for the formation of complexes between the secreted enzymes of a filamentous fungus has been reported recently (Gonzalez-Vogel et al., *Appl. Microbiol. Biotechnol.* 89, 145-155 (2011).

The molecular weight of α-xylosidase by SDS-PAGE was about 85 kDa (FIG. 11A). The dominant band was excised and subjected to tryptic digestion and mass spectrometric proteomics based on the whole predicted proteome of *A. niger* ATCC 1015 as the query database. (Multifect Pectinase is produced by fermentation of *A. niger*.) Eight unique peptides amounting to 16% coverage of Aspni5|43342 were detected at greater than 95% probability. The only other protein detected, at a lower level, was Aspni5|50997 (two unique peptides, 6% coverage), which is a β-glucosidase in GH family 3. This might account for the residual βG activity co-eluting with α-xylosidase (FIG. 10), a conclusion that was supported by heterologous expression (described below).

Unfractionated Multifect Pectinase was also analyzed by mass spectrometric proteomics. At high confidence (95% probability according to Scaffold, and at least two peptides), 132 proteins were identified. More than 90% of the proteins have predicted signal peptides. Both Aspni5|43342 and Aspni5|50997 were detected. Aspni5|56782, not Aspni5|50997, is the most abundant βG in Multifect Pectinase. See Table 4.

Aspni5|43342 is a predicted protein in GH family 31, which includes known α-xylosidases. Alternate designations for this gene and its product are XP_001393647, An09g03300, and CAK40270. On the basis of its weak amino acid similarity to AN7055 of *A. nidulans* and its induction by growth on xylose, Yuan et al. (Mol. Genet. Genomics 279, 545-561 (2008)) hypothesized that this protein is an α-xylosidase and named it Ax1A. The results provided herein are the first experimental evidence that Aspni5|43342 is, in fact, an α-xylosidase. The name Ax1A is used herein.

By BLASTP against the GenBank™ nonredundant database, Ax1A has many orthologs throughout the higher fungi (both ascomycetes and basidiomycetes). Many of these orthologs are annotated as belonging to GH family 31 and as having α-glucosidase or α-xylosidase activity, but with the exception of AN7505 of *A. nidulans*, there is no supporting biochemical evidence for any of these annotations (Bauer et al., *Proc. Natl. Acad. Sci. U.S.A.* 103, 11417-11422 (2006)). The top BLASTP hits (all with E-values of 0.0 and percent identities ranging from 52 to 81%) are from several species of *Aspergillus*, the closely related species *Neosartorya fischeri*, and two basidiomycetes (*Schizophyllum commune* XP_003031084 and *Serpula lachrymans* EG001163) (see Table 3).

TABLE 3

Best BLASTP hits of Ax1A against GenBank nr and against GenBank "fungi". All are annotated as putative GH31 proteins.

| Accession | Species | score | E value | % identity | SP? |
|---|---|---|---|---|---|
| XP_001217011.1 | Aspergillus terreus | 1259 | 0.0 | 81 | yes |
| XP_001265600.1 | Neosartorya fischeri | 1234 | 0.0 | 79 | yes |
| XP_002378848.1 | Aspergillus flavus | 1232 | 0.0 | 79 | yes* |
| XP_001823456.1 | Aspergillus oryzae | 1230 | 0.0 | 78 | yes |
| gb|EGO01163.1 | Serpula lacrymans | 751 | 0.0 | 52 | no |
| XP_003031084.1 | Schizophyllum commune | 708 | 0.0 | 51 | yes |
| ZP_07294496.1 | Streptomyces hygroscopicus | 376 | 8e-118 | 35 | no |
| gb|EGP91994.1 | Mycosphaerella graminicola | 374 | 3e-117 | 33 | no |
| ZP_08605161.1 | Lachnospiraceae bacterium | 369 | 3e-115 | 34 | no |
| YP_003842451.1 | Clostridium cellulovorans | 369 | 5e-115 | 32 | no |
| gb|ADI06537.1 | Streptomyces bingchenggensis | 368 | 1e-114 | 34 | no |
| ZP_06576342.1 | Streptomyces ghanaensis | 366 | 2e-114 | 33 | no |
| Against fungi only: | | | | | |
| XP_001217011.1 | Aspergillus terreus | 1259 | 0.0 | 81 | yes |
| XP_001265600.1 | Neosartorya fischeri | 1234 | 0.0 | 79 | yes |
| XP_002378848.1 | Aspergillus flavus | 1232 | 0.0 | 79 | yes* |
| XP_001823456.1 | Aspergillus oryzae | 1230 | 0.0 | 78 | yes |
| gb|EGO01163.1 | Serpula lacrymans | 751 | 0.0 | 52 | Yes* |
| XP_003031084.1 | Schizophyllum commune | 708 | 0.0 | 51 | yes |
| gb|EGP91994.1 | Mycosphaerella graminicola | 374 | 3e-121 | 33 | no |
| XP_003048593.1 | Nectria haematococca | 359 | 1e-115 | 33 | no |
| XP_388973.1 | Gibberella zeae | 358 | 4e-115 | 32 | no |
| XP_003047209.1 | Nectria haematococca | 355 | 5e-114 | 33 | no |

TABLE 3-continued

Best BLASTP hits of Ax1A against GenBank nr and against GenBank "fungi". All are annotated as putative GH31 proteins.

| Accession | Species | score | E value | % identity | SP? |
|---|---|---|---|---|---|
| gb|AEO58673.1 | Myceliophthora thermophila | 354 | 1e-113 | 33 | No |
| XP_364756.1 | Magnaporthe grisea | 352 | 1e-112 | 32 | no |

*reannotation to use a different ATG translational start site reveals a signal peptide Among species of *Aspergillus*, orthologs with strong E-values and percent amino acid identity to Ax1A are present in *A. flavus*, *Aspergillus oryzae*, *Aspergillus terreus*, *Aspergillus aculeatus*, and *Aspergillus carbonarius*, but not *A. fumigatus*, *A. clavatus*, or *A. nidulans* (*Aspergillus* Comparative Database (Broad Institute) and DOE Joint Genome Institute) (Table 3). All of the orthologs in *Aspergillus* have strongly predicted signal peptides, like Ax1A itself (Reannotation of protein XP_002378848 from *A. flavus* by reassigning the ATG start codon indicates that it probably also has a signal peptide). Ax1A is present in both sequenced strains of *A. niger*, ATCC1015 and CBS 513.88, with 100% amino acid identity and 99% nucleotide identity in the coding region. *A. nidulans* has 10 predicted GH31 genes, five of which have signal peptides. Of these, AN7120 (XP 664724) has the best amino acid identity to Ax1A (30%) but no signal peptide. *A. niger* ATCC 1015 and CBS 513.88 both have seven predicted GH31 genes, the best of which (after Ax1A itself) being ANI_1_620014 (also known as Aspni5|55419), with 32% identity.

The Ax1A mRNA and protein are induced by growth of *A. niger* on xylose compared with maltose. Ax1A was not included in a genome-wide microarray expression study comparing *A. nidulans*, *A. oryzae*, and *A. niger*, presumably because it is not common to all three species (Andersen et al., *Proc. Natl. Acad. Sci. U.S.A.* 105, 4387-4392 (2008)).

After the orthologs in species of *Aspergillus*, the next best approximate 20 hits to Ax1A in GenBank™, with E-values ranging from e-97 to e-23 and percent identities ranging from 22% to 52%, are to a much wider variety of fungi. All of these proteins are hypothetical, and it is not known whether they have α-xylosidase, α-glucosidase, or other catalytic activities. However, the majority lack predicted signal peptides. This is a strong indication that they are not secreted and are probably functional orthologs of the cytoplasmic α-xylosidase enzymes of *A. flavus*, *A. niger*, and *P. wortmanii* (Matsuo et al., Biosci. Biotechnol. Biochem. 60, 341-343 (1996); Matsushita et al., Agric. Biol. Chem. 51: 2015-2016 (1987); Yoshikawa et al. Biosci. Biotechnol. Biochem. 58, 1392-1398 (1994)). Note that greater than 90% of the proteins in Multifect Pectinase have predicted signal peptides (Table 4). To the best of our knowledge, the encoding genes of the cytoplasmic α-xylosidase fungal enzymes have not been identified.

TABLE 4

Proteins identified in Multifect Pectinase by proteomics

| Protein # | Protein ID (JGI A. niger ATCC 1015 v. 3) | Molecular Weight (kDa) | Protein Name | CAZy Family (GH unless otherwise indicated) | CBM? | Signal Peptide? (cleavage site) | Total Spectral Counts |
|---|---|---|---|---|---|---|---|
| 1 | 51764 | 110 | β-galactosidase, lacA, | 2 or 35 | No | 18/19 | 318 |
| 2 | 200605 | 53 | α-L-arabinofuranosidase B, abfB | 54 | No | 18/19 | 256 |
| 3 | 56782 | 93 | β-glucosidase, bglA | 3 | No | 19/20 | 250 |
| 4 | 205670 | 87 | β-xylosidase, xlnD | 3 | No | 26/27 | 182 |
| 5 | 43342 | 83 | GH31 glucoside hydrolase | 31 | No | 18/19 | 124 |
| 6 | 57436 | 35 | xylanase | 10 | No | 19/20 | 123 |
| 7 | 213597 | 68 | glucoamylase (amyloglucosidase), glaA | 15 | No | 18/19 | 106 |
| 8 | 55136 | 36 | α-L-arabinofuranosidase, axhA | 62 | No | 26/27 | 101 |
| 9 | 46065 | 42 | exo-polygalacturonase | 28 | No | 18/19 | 100 |
| 10 | 44585 | 36 | Pectin methylesterase | CE8 | No | 17/18 | 91 |
| 11 | 177434 | 106 | β-galactosidase | 35 | No | 19/20 | 81 |
| 12 | 55604 | 50 | aldose 1-epimerase |  | No | No | 80 |
| 13 | 41815 | 40 | pectin lyase | PL1 | No | 20/21 | 72 |
| 14 | 138876 | 104 | β-mannosidase; Mannanase | 2 | No | 21/21 | 70 |
| 15 | 56619 | 94 | α-glucuronidase, aguA | 67 | No | 20/21 | 63 |
| 16 | 203143 | 34 | endo-1,5-α-L-arabinosidase A | 43 | No | 19/20 | 62 |
| 17 | 205517 | 56 | α-mannosidase | 47 | No | 21/22 | 54 |
| 18 | 206387 | 68 | α-N-arabinofuranosidase A, ABF A | 51 | No | 25/26 | 49 |
| 19 | 50997 | 86 | β-glucosidase | 3 | No | 22/23 | 47 |
| 20 | 209376 | 37 | endoglucanase B | 5 | No | 18/19 | 46 |
| 21 | 42917 | 46 | exo-rhamnogalacturonase C | 28 | No | 20/21 | 44 |
| 22 | 214233 | 109 | Alpha-glucosidase, Maltase | 31 | No | 19/20 | 44 |
| 23 | 46429 | 112 | β-galactosidase | 35 | No | 20/21 | 43 |
| 24 | 206333 | 90 | endoglucanase C, EglC (xyloglucanase) | 74 | C-term | 19/20 | 41 |
| 25 | 174365 | 43 | Pectin methylesterase |  | No | 19/20 | 38 |
| 26 | 187227 | 39 | β-1,4-endogalactanase A | 53 | No | 17/18 | 36 |
| 27 | 214608 | 52 | endo-1,4-β-glucanase | 5 | C-term | 18/19 | 35 |
| 28 | 212716 | 57 | 1,3-β-glucanosyltransferase, membrane anchor |  | No | 19/20 | 31 |
| 29 | 42916 | 74 | α-L-rhamnosidase | 78 | No | 19/20 | 30 |
| 30 | 194447 | 46 | Glycoside hydrolase | 5 | No | 19/20 | 30 |
| 31 | 54830 | 72 | hypothetical protein |  | No | 20/21 | 29 |
| 32 | 53702 | 91 | AMP dependent synthetase/ligase |  | No | No | 29 |
| 33 | 46255 | 40 | Polygalacturonase-4 | 28 | No | 19/20 | 25 |
| 34 | 41596 | 48 | hypothetical protein |  | No | No | 24 |
| 35 | 41606 | 72 | α-D-galactosidase | 27 | No | 17/18 | 24 |
| 36 | 54398 | 59 | β-N-acetylhexosaminidase | 20 | No | No | 24 |
| 37 | 52011 | 25 | xyloglucanase 2 | 2 | No | 15/16 | 24 |

TABLE 4-continued

Proteins identified in Multifect Pectinase by proteomics

| Protein # | Protein ID (JGI *A. niger* ATCC 1015 v. 3) | Molecular Weight (kDa) | Protein Name | CAZy Family (GH unless otherwise indicated) | CBM? | Signal Peptide? (cleavage site) | Total Spectral Counts |
|---|---|---|---|---|---|---|---|
| 38 | 214460 | 61 | carboxypeptidase C(cathepsin A) | | No | 18/19 | 24 |
| 39 | 52418 | 61 | sugar transporter | | No | 20/21 | 24 |
| 40 | 45030 | 23 | hypothetcial protein | | No | 21/22 | 4 |
| 41 | 47911 | 64 | 1,4-α-D-glucan glucanohydrolase | 13 | starch | 24/25 | 23 |
| 42 | 213462 | 36 | Cel 45/expansin | | No | 22/23 | 22 |
| 43 | 50161 | 51 | endo-polygalacturonase D | 28 | No | 17/18 | 21 |
| 44 | 214857 | 35 | pectinmethylesterase | | No | 22/23 | 21 |
| 45 | 197446 | 44 | endochitinase | 18 | No | No | 21 |
| 46 | 43957 | 41 | endopolygalacturonase C | 28 | No | 19/20 | 20 |
| 47 | 50979 | 68 | α-L-arabinofuranosidase | | No | 20/21 | 20 |
| 48 | 55270 | 99 | exo-β-1,3-glucanase | 55 | No | 20/21 | 19 |
| 49 | 189722 | 47 | rhamnogalacturonase | 28 | No | 18/19 | 19 |
| 50 | 214598 | 39 | endo-polygalacturonase A | 28 | No | 19/20 | 19 |
| 51 | 211032 | 66 | tripeptidyl peptidase | | No | 26/27 | 18 |
| 52 | 52219 | 38 | endo-polygalacturonase B | 28 | No | 20/21 | 18 |
| 53 | 53361 | 45 | secretory lipase | | No | 19/20 | 17 |
| 54 | 172944 | 48 | exo-polygalacturonase | 28 | No | 19/20 | 17 |
| 55 | 44517 | 47 | Glycoside hydrolase | 17 | No | 22/23 | 17 |
| 56 | 184037 | 83 | α-fucosidase | 65 or 95 | No | 20/21 | 17 |
| 57 | 206342 | 81 | Catalase R | | No | 16/17 | 17 |
| 58 | 196122 | 31 | Glycoside hydrolase | 16 | No | 19/20 | 17 |
| 59 | 45801 | 48 | Glycoside hydrolase | 30 | No | 18/19 | 17 |
| 60 | 53159 | 48 | 1,4-β-D-glucan cellobiohydrolase A | 7 | No | 17/18 | 16 |
| 61 | 119858 | 93 | α-glucosidase | 31 | No | 14/15 | 16 |
| 62 | 49710 | 59 | hypothetical carboxylesterase (type B) | | No | 21/22 | 16 |
| 63 | 201655 | 41 | extracellular aspartic protease, pepA | | No | 20/21 | 16 |
| 64 | 51773 | 52 | 1,4-β-D-glucan cellobiohydrolase B | 7 | C-term | 21/22 | 15 |
| 65 | 51478 | 57 | Feruloyl esterase B | | No | 17/18 | 14 |
| 66 | 205580 | 43 | endo-β-1,4-glucanase | 5 | C-term | 19/20 | 14 |
| 67 | 122978 | 47 | glycosyl hydrolase | 43 | No | 17/18 | 14 |
| 68 | 44858 | 58 | hypothetical protein | | No | 23/24 | 14 |
| 69 | 191158 | 48 | exo-polygalacturonase B | 28 | No | 15/16 | 13 |
| 70 | 54860 | 44 | purine nucleoside permease | | No | 24/25 | 13 |
| 71 | 209408 | 55 | glycoside hydrolase | 71 | No | 21/22 | 13 |
| 72 | 179265 | 82 | glycoside hydrolase | 3 | No | 19/20 | 13 |
| 73 | 173481 | 81 | hypothetical protein | | No | 17/18 | 13 |
| 74 | 182100 | 35 | Glycoside hydrolase | 43 | No | 21/22 | 13 |
| 75 | 185301 | 65 | extracellular carboxylesterase | | No | 17/18 | 12 |
| 76 | 50148 | 24 | hypothetical protein | | No | 18/19 | 12 |
| 77 | 202490 | 46 | exo-β-1,3 glucanase | 5 | No | 22/23 | 11 |
| 78 | 57027 | 51 | inositol polyphosphate phosphatase, phyA | | No | 21/22 | 11 |
| 79 | 141677 | 37 | polygalacturonase | 28 | No | 18/19 | 10 |
| 80 | 198063 | 64 | beta fructofuranosidase, invertase | 32 | No | 15/16 | 10 |
| 81 | 42184 | 47 | glycoside hydrolase, polygalacturonase | 28 | No | 22/23 | 10 |
| 82 | 214786 | 57 | hypothetical protein | | No | 21/22 | 10 |

TABLE 4-continued

Proteins identified in Multifect Pectinase by proteomics

| Protein # | Protein ID (JGI A. niger ATCC 1015 v. 3) | Molecular Weight (kDa) | Protein Name | CAZy Family (GH unless otherwise indicated) | CBM? | Signal Peptide? (cleavage site) | Total Spectral Counts |
|---|---|---|---|---|---|---|---|
| 83 | 51662 | 31 | feruloyl esterase A; cinnamoyl esterase, faeA | | No | 21/22 | 10 |
| 84 | 173684 | 62 | extracellular carboxylesterase, type B | | No | 17/18 | 10 |
| 85 | 51794 | 29 | Ribonuclease T2 | | No | 23/24 | 10 |
| 86 | 52688 | 37 | glycoside hydrolase | 61 | No | 25/26 | 10 |
| 87 | 38973 | 61 | FAD/FMN-containing dehydrogenase | | No | 20/21 | 10 |
| 88 | 199085 | 37 | glycoside hydrolase | 16 | No | 21/22 | 10 |
| 89 | 50378 | 41 | β-mannanase | 5 | No | 16/17 | 9 |
| 90 | 135787 | 27 | Lipolytic enzyme, G-D-S-L | | No | No | 9 |
| 91 | 56161 | 60 | Peptidase S10, serine carboxypeptidase | | No | 23/24 | 9 |
| 92 | 35378 | 50 | Phosphoesterase | | No | 18/19 | 9 |
| 93 | 54734 | 63 | Peptidase S10, serine carboxypeptidase | | No | 19/20 | 9 |
| 94 | 209830 | 54 | FAD/FMN-containing dehydrogenase | | No | 20/21 | 9 |
| 95 | 170172 | 70 | α-rhamnosidase | | No | 17/18 | 8 |
| 96 | 41679 | 26 | necrosis-inducing proteins | | No | 19/20 | 8 |
| 97 | 182156 | 38 | Endopolygalacturonase-2 | 28 | No | 21/22 | 8 |
| 98 | 46876 | 56 | hypothetical protein | | No | No | 8 |
| 99 | 50599 | 41 | hypothetical protein | | No | 19/20 | 8 |
| 100 | 206560 | 156 | possible dynactin | | No | No | 7 |
| 101 | 209490 | 65 | glycosyl hydrolase | 76 | No | 22/23 | 7 |
| 102 | 172825 | 42 | hypothetical protein | | No | No | 7 |
| 103 | 207264 | 49 | α-galactosidase | 27 | No | 16/17 | 7 |
| 104 | 55665 | 65 | Peptidase S8 and S53, subtilisin, kexin | | No | 20/21 | 7 |
| 105 | 47780 | 73 | rhamnogalacturonan lyase | PL4 | No | 19/20 | 7 |
| 106 | 52703 | 59 | Peptidase S28 | | No | 22/23 | 6 |
| 107 | 177169 | 45 | lactonohydrolase | | No | 18/19 | 6 |
| 108 | 197735 | 34 | arabinanase | 43 | No | 15/16 | 6 |
| 109 | 48594 | 200 | Cytokinesis protein sepA | | No | No | 6 |
| 110 | 42242 | 63 | saponin hydrolase | | No | 26/27 | 6 |
| 111 | 124618 | 38 | predicted protein | | No | 16/17 | 6 |
| 112 | 37735 | 17 | predicted protein | | No | 17/18 | 6 |
| 113 | 133986 | 43 | Cellobiohydrolase | 6 | No | 28/29 | 5 |
| 114 | 207829 | 87 | α-1,2-mannosidase | 92 | No | 25/26 | 5 |
| 115 | 57215 | 67 | Metallophosphoesterase | | No | 20/21 | 5 |
| 116 | 52849 | 12 | predicted protein | | No | 19/20 | 5 |
| 117 | 189254 | 28 | rhamnogalacturonan acetylesterase | | No | 17/18 | 4 |
| 118 | 210947 | 57 | rhamnogalacturonan lyase A | PL4 | No | 20/21 | 4 |
| 119 | 46979 | 58 | extracellular serine carboxypeptidase S10 | | No | 18/19 | 4 |
| 120 | 52460 | 76 | glutaminase A | | No | 19/20 | 4 |
| 121 | 131668 | 52 | hypothetical protein | | No | No | 4 |
| 122 | 208679 | 109 | hypothetical protein | | No | 19/20 | 4 |
| 123 | 40102 | 74 | extracellular carboxylesterase (type B) | | No | 21/22 | 4 |
| 124 | 45021 | 34 | pectate lyase A | | No | 20/21 | 4 |
| 125 | 52700 | 62 | Peptidase S8 and S53, subtilisin, kexin, sedolisin | | No | 19/20 | 4 |
| 126 | 171242 | 41 | predicted protein | | No | No | 4 |
| 127 | 37736 | 60 | α-galactosidase | 27 | No | 31/32 | 3 |
| 128 | 53620 | 54 | Phosphoesterase | | No | 17/18 | 3 |
| 129 | 56664 | 59 | Glycoside hydrolase, exo-inulinase | 32 | No | 19/20 | 3 |
| 130 | 56689 | 63 | Peptidase S28 | | No | 17/18 | 3 |
| 131 | 128537 | 11 | Allergen Asp F7 | | No | No | 2 |
| 132 | 50333 | 55 | Histidine acid phosphatase | | No | 20/21 | 2 |

T. reesei has only two poor (E-value greater than e-10 and less than 25% amino acid identity) BLASTP hits to Ax1A (Trire2|121351 and Trir2|69944), and neither of these has a predicted signal peptide. Therefore, T. reesei does not have the genetic potential to biosynthesize a secreted α-xylosidase-related to Ax1A, which explains the lack of this enzymatic activity in commercial enzyme mixtures derived from T. reesei (FIG. 1B).

AN7505 (XP_680774) of A. nidulans has less than 25% amino acid identity to Ax1A and lacks a predicted signal peptide. When expressed in P. pastoris fused to a yeast signal peptide, AN7505 was secreted and showed activity against pNPαX but was not further characterized (Bauer et al., Proc. Natl. Acad. Sci. U.S.A. 103, 11417-11422 (2006)). Therefore AN7505 is not an extracellular α-xylosidase.

Properties of Ax1A—

The pH optimum of AX on pNPX was between 3 and 4 (FIG. 12A). The temperature optimum was 55° C. (FIG. 12B). The activity was about 50% of maximum at 65°. The native protein was approximately as active on IP as on the synthetic substrate pNPαX (Table 1).

Heterologous Expression of Ax1A—

When expressed in P. pastoris, Ax1A had an apparent molecular weight of about 110,000, larger than the native protein. It also ran as a more diffuse band than the native protein (FIG. 11B). Both of these observations suggest that recombinant Ax1A is hyperglycosylated when expressed in *P. pastoris*. (Ax1A has 10 predicted N-glycosylation sites.) Nonetheless, the heterologously expressed protein showed kinetic properties similar to the native protein on both pNPαX and IP (Table 1). The protein expressed in *P. pastoris* had no detectable βG, β-xylosidase, or α-glucosidase activity when assayed with p-nitrophenyl-β-D-glucoside, p-nitrophenyl-β-D-xyloside, or pNPαG, respectively (data not shown).

This supports the conclusion that the βG activity seen in the α-xylosidase assay shown in FIG. 10 was due to impurities.

Activity of Ax1A on Xyloglucan Heptasaccharide—

Ax1A purified by HPLC (FIG. 11), without addition or other enzymes, was able to degrade the heptasaccharide XXXG to free glucose and xylose (data not shown). However, this preparation contained residual β-glucosidase activity (FIG. 10). Recombinant Ax1A released about 10 nmol of xylose, and the quantity did not increase with time (FIG. 13). This proportion of xylose corresponds to approximately one-third of the total xylose present in the xyloglucan heptasaccharide sample (34 nmol in 12 µl of a reaction volume of 500 µl). This result is consistent with Ax1A removing a single xylose residue from the heptasaccharide to produce WOW and is further evidence that Ax1A does not have intrinsic β-glucosidase activity. Digestion of the xyloglucan heptasaccharide with no enzyme or β-glucosidase alone released no to little xylose (FIG. 13). Digestion with a combination of Ax1A and β-glucosidase released 83.4% of the theoretical maximum of xylose in 10 h (FIG. 13). Thus, β-glucosidase and Ax1A together are capable of substantially depolymerizing this heptasaccharide repeating unit of native xyloglucan.

Activity of Ax1A on Tamarind Xyloglucan—

Because xyloglucan contains β-linked galactose and β-linked glucose in addition to α-linked xylose, four enzymes were included in the experiment: xyloglucanase, β-glucosidase, and β-galactosidase, all from *T. reesei*, in addition to Ax1A (Table 2). An optimized mixture of the four enzymes was developed using GENPLAT at fixed total protein loading (Banerjee et al. *Bioresour. Technol.* 101, 9097-9105 (2010); Banerjee et al. Biotechnol. Bioengineer. 106, 707-720 (2010)). In the first experiment (Table 5) the lower limit of each enzyme was set to 0%.

TABLE 5

First experimental design and experimental results for optimization of a cocktail of four enzymes for deconstruction of tamarind XG. The lower proportion of each enzyme was set to 0%. This gave a statistically invalid model (see Table 7). Glucose (Glc) yields are expressed as a percentage of total glucose in the biomass, ±1 SD of the mean (n = 8).

| β-glucosidase | β-galactosidase | xyloglucanase | Ax1A | Glc yield, % |
|---|---|---|---|---|
| 1.00 | 0.00 | 0.00 | 0.00 | 3.1 ± 0.6 |
| 0.00 | 1.00 | 0.00 | 0.00 | 3.2 ± 0.7 |
| 0.00 | 0.00 | 1.00 | 0.00 | 4.2 ± 0.5 |
| 0.00 | 0.00 | 0.00 | 1.00 | 3.1 ± 0.6 |
| 0.50 | 0.50 | 0.00 | 0.00 | 3.8 ± 0.5 |
| 0.50 | 0.00 | 0.50 | 0.00 | 4.5 ± 0.2 |
| 0.50 | 0.00 | 0.00 | 0.50 | 11.8 ± 0.1 |
| 0.00 | 0.50 | 0.50 | 0.00 | 4.3 ± 0.7 |
| 0.00 | 0.50 | 0.00 | 0.50 | 3.1 ± 0.8 |
| 0.00 | 0.00 | 0.50 | 0.50 | 4.1 ± 0.8 |
| 0.63 | 0.13 | 0.13 | 0.13 | 93.3 ± 0.0 |
| 0.13 | 0.63 | 0.13 | 0.13 | 97.1 ± 0.0 |
| 0.13 | 0.13 | 0.63 | 0.13 | 99.4 ± 0.0 |
| 0.13 | 0.13 | 0.13 | 0.63 | 100.0 ± 0.0 |
| 0.25 | 0.25 | 0.25 | 0.25 | 100.0 ± 0.0 |

However, many combinations failed to yield greater than 5% of xylose or glucose. In the second experiment (Table 6), the lower limit of each enzyme was set to 5%, which gave a statistically valid model for both glucose and xylose.

TABLE 6

Second experimental design and experimental results for optimization of a cocktail of four enzymes for deconstruction of tamarind XG. The lower limit of each enzyme was set to 5% (mandating the upper limit of each enzyme at 85%). This experiment gave a valid model (see Table 7). Glucose (Glc) and xylose (Xyl) yields are expressed as a percentage of total glucose or xylose in the biomass, ±1 SD of the mean (n = 8).

| β-glucosidase | β-galactosidase | xyloglucanase | Ax1A | Glc yield, % | Xyl yield, % |
|---|---|---|---|---|---|
| 0.85 | 0.05 | 0.05 | 0.05 | 78.9 ± 2.0 | 80.8 ± 0.8 |
| 0.05 | 0.85 | 0.05 | 0.05 | 65.6 ± 0.5 | 63.1 ± 1.2 |
| 0.05 | 0.05 | 0.85 | 0.05 | 80.9 ± 1.3 | 71.7 ± 0.8 |
| 0.05 | 0.05 | 0.05 | 0.85 | 97.1 ± 0.4 | 97.7 ± 0.1 |
| 0.45 | 0.45 | 0.05 | 0.05 | 73.2 ± 0.6 | 70.6 ± 0.1 |
| 0.45 | 0.05 | 0.45 | 0.05 | 80.6 ± 0.5 | 76.8 ± 0.7 |
| 0.45 | 0.05 | 0.05 | 0.45 | 95.5 ± 0.7 | 100.6 ± 2.2 |
| 0.05 | 0.45 | 0.45 | 0.05 | 75.2 ± 1.3 | 71.4 ± 2.1 |
| 0.05 | 0.45 | 0.05 | 0.45 | 98.4 ± 0.0 | 100.4 ± 0.3 |
| 0.05 | 0.05 | 0.45 | 0.45 | 99.1 ± 0.6 | 100.5 ± 0.1 |

TABLE 6-continued

Second experimental design and experimental results for optimization of a cocktail of four enzymes for deconstruction of tamarind XG. The lower limit of each enzyme was set to 5% (mandating the upper limit of each enzyme at 85%). This experiment gave a valid model (see Table 7). Glucose (Glc) and xylose (Xyl) yields are expressed as a percentage of total glucose or xylose in the biomass, ±1 SD of the mean (n = 8).

| β-glucosidase | β-galactosidase | xyloglucanase | Ax1A | Glc yield, % | Xyl yield, % |
|---|---|---|---|---|---|
| 0.55 | 0.15 | 0.15 | 0.15 | 98.4 ± 2.6 | 94.5 ± 0.9 |
| 0.15 | 0.55 | 0.15 | 0.15 | 97.4 ± 1.2 | 88.1 ± 1.7 |
| 0.15 | 0.15 | 0.55 | 0.15 | 97.7 ± 0.0 | 89.1 ± 0.3 |
| 0.15 | 0.15 | 0.15 | 0.55 | 96.3 ± 2.0 | 85.7 ± 0.0 |
| 0.25 | 0.25 | 0.25 | 0.25 | 96.9 ± 0.5 | 87.4 ± 0.2 |

Complete digestion of tamarind xyloglucan was achieved (Table 7).

TABLE 7

Statistical values for the models shown in Tables 5 and 6.

| | Sugar | p-value | F-value | $R^2$ | Pred $R^2$ | Adj $R^2$ | Adeq Precision |
|---|---|---|---|---|---|---|---|
| Table 5 | Glc | 0.4 | 1.1 | 0.34 | 0.04 | −0.6 | 2.9 |
| Table 6 | Glc | <0.0001 | 7.1 | 0.77 | 0.66 | 0.53 | 9.0 |
| Table 6 | Xyl | <0.0001 | 8.2 | 0.80 | 0.70 | 0.64 | 9.0 |

The optimized proportions of the four enzymes for glucose and xylose release are shown in Table 2. Of the four enzymes, Ax1A was needed in the highest proportions (51% for glucose and 59% for xylose). The need for a high proportion of Ax1A might reflect a lower specific activity, steric hindrance, or the fact that the reactions were run at a suboptimal pH for Ax1A (see FIG. 12B).

Example VIII

Enhancement of Fermentable Sugar Yields by α-Xylosidase Supplementation

This Example illustrates that α-xylosidase supplementation improves glucose yields from real biomass substrates.

Methods

Plant Materials and Pretreatments

Stover of corn (*Zea mays* L.) was ground to 0.5 mm particle size with a Wiley mill before pretreating with alkaline hydrogen peroxide (AHP) as described by Banerjee et al., *Biotechnol Biofuels* 2011, 4:16. AHP conditions were 10% biomass loading, 0.5 g $H_2O_2$/g biomass, and shaking at 90 rpm and 24° C. for 24 hr. Peas (*Pisum sativum* L. "Little Marvel") were soaked in water for 24 hr with bubbling air and grown in vermiculite in either total darkness for 5-7 days ("etiolated peas") or for 9-14 days in a greenhouse ("green peas"). After freeze-drying, the etiolated plants were ground in liquid nitrogen. The green peas were freeze-dried and then ground in a Wiley mill to pass a 0.5-mm screen. Both were then pretreated by the same AHP conditions used for corn stover. *Chenopodium album* L. (lamb's quarters) was collected from local abandoned fields in mid-August. Plants were dried at 50° C. and ground in a Wiley mill to pass a 0.5 mm screen and pretreated by AHP.

Pea xyloglucan was prepared as described by Paper et al. (*Appl Microbiol Biotechnol* 2012, in press) and Zablackis et al. (*Plant Physiol* 1995, 107:1129-1138). After such preparation, the pea xyloglucan composition was analyzed by the alditol acetate method (Foster et al. *J Vis Exp* 2010). It was judged to be partially pure by its atypical content of arabinose and because the sum of the neutral sugars did not add up to 100% (Table 8). Tamarind xyloglucan was purchased from Megazyme, Inc. (Wicklow, Ireland), and its composition is reported in Scott-Craig et al. (*J Biol Chem* 2011, 286:42848-42854).

TABLE 8

Monomer sugar composition of plant materials used in this study. All values (±1 SD, n = 3) are mg/g dry weight. Materials were dried but otherwise not processed by washing or other fractionation before acid hydrolysis. "Total" indicates the percentage of the original dry weight accounted for by the indicated neutral sugars.

| Plant Material | Glc | xylose | Ara[a] | Man[a] | Gal | Total |
|---|---|---|---|---|---|---|
| pea xyloglucan | 226 ± 19.0 | 287 ± 25.2 | 127 ± 8.1 | 8.5 ± 0.6 | 75 ± 6.0 | 72.4% |
| tamarind xyloglucan[b] | 471 ± 8.3 | 351 ± 9.2 | 23 ± 2.1 | 0.0 | 155 ± 5.3 | 100% |
| etiolated peas | 281.6 ± 12.0 | 49.4 ± 4.4 | 55.8 ± 4.8 | | 48.3 ± 2.2 | 43.5% |
| green peas | 106.7 ± 12.0 | 19.6 ± 0.7 | 30.8 ± 2.0 | | 23.7 ± 2.7 | 18.1% |
| corn stover | 391.5 ± 0.35 | 194.7 ± 10.9 | 33.3 ± 5.3 | | 9.4 ± 2.3 | 62.9% |

TABLE 8-continued

Monomer sugar composition of plant materials used in this study. All values (±1 SD, n = 3) are mg/g dry weight. Materials were dried but otherwise not processed by washing or other fractionation before acid hydrolysis. "Total" indicates the percentage of the original dry weight accounted for by the indicated neutral sugars.

| Plant Material | Glc | xylose | Ara[a] | Man[a] | Gal | Total |
|---|---|---|---|---|---|---|
| lamb's quarters | 170.1 ± 1.7 | 30.2 ± 0.03 | 24.6 ± 0.64 | | 14.4 ± 0.14 | 23.9% |

[a]The HPLC protocol could not resolve arabinose and mannose. Pea and tamarind xyloglucans (XGs) were analyzed by gas chromatography of alditol acetates after hydrolysis with trifluoroacetic acid (Foster et al. *J Vis Exp* 2010).
[b]From Scott-Craig et al. (*J Biol Chem* 2011, 286: 42848-42854).

Cell Wall Analysis

Cell wall sugar composition (of materials other than pea xyloglucan) was determined by two-stage hydrolysis with sulfuric acid without prior removal of extractives (Sluiter et al., U.S. Department of Energy National Renewable Energy Laboratory, 2011). Sugars were separated by HPLC using a Bio-Rad (Hercules, Calif.) Aminex HPX-87P column at 80° C. with 1 ml/min water as mobile phase and detection by refractive index. Each run took about 20 min. Under these conditions, arabinose and mannose could not be resolved and are reported together. Because the biomass was not washed to remove extractives prior to acid hydrolysis, the compositional analysis includes any contributions from starch, sucrose, free monomeric sugars, or acid-labile conjugated glucose and xylose. Recovery from the acid hydrolysis step was calculated to be 95% for glucose, arabinose, and galactose, and 85% for xylose.

Enzymes

Cellic CTec2 (lot number VCPI0004) and HTec2 (lot number VHN00002) were obtained from Novozymes, Inc. (Davis, Calif.) and typically used at a ratio of 3:1 on a protein mass basis. The protein concentrations of CTec2 and HTec2 were determined to be 130 mg/ml and 101 mg/ml, respectively, by the dye-binding assay of Bradford (*Anal Biochem* 1976, 72:248-254) using bovine IgG as standard. The CTec2:HTec2 enzyme mixture was typically diluted 500-fold with 50 mM sodium citrate, pH 4.8, on the day of use and used at a final protein concentration of 2.5 mg/g glucan. Accellerase 1000 (lot number 1600844643; 69 mg protein/ml) was obtained from Genencor, Inc. (now DuPont Industrial Biosciences, Palo Alto, Calif.) and diluted similarly. Ax1A was prepared by expression in *Pichia pastoris* as described herein and stored in aliquots at −80° C. in 50 mM sodium acetate+20% glycerol, pH 5 (see also, Scott-Craig et al., *J Biol Chem* 2011, 286:42848-42854). The other pure enzymes, all derived from *T. reesei*, were obtained commercially or prepared by expression in *P. pastoris* as described by Banerjee et al. (*Biotechnol Bioengineer* 2010, 106:707-720) and Banerjee et al. (*Bioresour Technol* 2010, 101:9097-9105).

Enzyme Assays

Unless other specified, enzyme hydrolysis reactions were performed in 96-well deep-well plates in a reaction volume of 0.5 ml, as described by Banerjee et al. (*Biotechnol Bioengineer* 2010, 106:707-720). Glucan concentration was typically 2 mg/ml. The buffer was 50 mM sodium citrate, pH 4.8, containing 25 µg/ml each of tetracycline and cycloheximide. Assays were run in duplicate, sampled twice, and the glucose and xylose levels measured twice. Therefore, each data point represents the mean of eight values. All error bars represent ±one standard deviation of the mean.

Glucose and xylose were measured using enzyme-linked colorimetric assays (Megazyme kits K-GLUC and K-XYLOSE, respectively). These assays detect only free glucose and xylose and not cellobiose or oligomeric sugars.

Results

Commercial Cellulases do not Degrade Xyloglucan Because they Lack α-Xylosidase

In mixtures of pure enzymes (i.e., β-glucosidase, β-galactosidase, and xyloglucanase), Ax1A was required for release of free glucose and xylose from isolated pea xyloglucan fragments and from tamarind xyloglucan (Scott-Craig et al. *J Biol Chem* 286:42848-42854 (2011)). Similarly, supplementation with Ax1A was required for the release of free glucose from intact pea xyloglucan in response to the commercial cellulase cocktails CTec2 and HTec2 (FIG. 14). Addition of Ax1A enhanced glucose yield by 18-fold in 30 hours compared to CTec2:HTec2 alone. These results are consistent with the earlier results showing the absence of α-xylosidase activity in CTec2 or HTec2 against the model substrate pNPαX and against the disaccharide isoprimeverose (Scott-Craig et al., *J Biol Chem* 286:42848-42854 (2011)). These results furthermore indicate that a combination of CTec2 and HTec2 has all of the necessary enzymes to degrade pea xyloglucan except α-xylosidase. In this regard CTec2 and HTec2 are similar to the commercial product Driselase from the basidiomycetous fungus *Irpex lacteus*, which degrades xyloglucan only to isoprimeverose (Zeng et al. *Plant Physiol* 2008, 147:78-91). Ax1A supplementation was also necessary for complete depolymerization of tamarind xyloglucan by CTec2:HTec2 (FIG. 15). Tamarind xyloglucan is less fucosylated but more heavily galactosylated than pea xyloglucan, but both contain α-linked xylose. In the absence of Ax1A, CTec2:HTec2 released almost no glucose, even in 48 hr (FIG. 15). An Ax1A to CTec2:HTec2 ratio of 1 to 3 (on a protein mass basis) was near saturating for release of glucose in 48 hr (FIG. 15).

Although addition of Ax1A to CTec2:HTec2 greatly stimulated release of free glucose from tamarind xyloglucan, yields of glucose were still only about half of the maximal possible (FIG. 15). Tamarind xyloglucan is partially substituted with galactose (Gal) on some of the xylose side chains (Paper et al., 2012, Appl Microbiol Biotechnol 2012 Sep. 26, in press. [PMID: 23011349]. A possible explanation for the approximate half-possible yield is that β-galactosidase activity was limiting in these reactions, and therefore any glucose moiety substituted with galactose as well as xylose would not be released. In fact, addition of both β-galactosidase and Ax1A to CTec2:HTec2 strongly stimulated glucose release compared to reactions without β-galactosidase (FIG. 16). This experiment indicates that CTec2:HTec2 is sub-optimal in regard to β-galactosidase as well as α-xylosidase for the digestion of tamarind xyloglucan. Supplementation of commercial cellulases such as CTec2 and HTec2 with α-xylosidase might improve the usefulness of these cellulases for releasing of fermentable sugars from biomasses rich in xyloglucan.

Ax1A Supplementation Improves Glucose Yields from Real Biomass Substrates

The effect of Ax1A supplementation of CTec2:HTec2 on digestion of a biofuels-relevant biomass substrate, AHP-pretreated corn stover, is shown in FIG. 17. Because cellulose is the major form of glucose in corn stover and CTec2:HTec2 has strong cellulase activity, as expected glucose yields even without Ax1A supplementation were high (FIG. 17). At lower CTec/HTec2 loadings (i.e., 0.4 and 1.0 mg/g glucan), there was no apparent enhancement of glucose release by addition of Ax1A (FIG. 17). At the highest CTec2:HTec2 loading tested (2.5 mg/g glucan), however, there was a statistically significant increase in glucose yield after hydrolysis for 24 hr (data not shown) and 48 hr (FIG. 17). At 48 hours, glucose yields increased from ~82% to ~88% of the maximum possible glucose content at Ax1A loadings above 8 mg/g glucan. FIG. 18A shows the results from FIG. 17 in expanded scale to accentuate the enhancement effect. Xylose yields were also increased by Ax1A supplementation, as shown in expanded scale in FIG. 18B. The Ax1A effect on xylose yield (about 5% absolute increase) was statistically significant only at the highest CTec2:HTec2 (2.5 mg/g glucan) and Ax1A loadings (16 mg/g glucan) tested.

Ax1A also enhanced yields of glucose and xylose from pretreated corn stover in response to another commercial cellulase, Accellerase 1000 (FIG. 19). In 48 hr, Ax1A increased glucose yields by 9% (from 76% to 85% of maximum possible yield) and xylose yields by 1.8% (FIG. 19).

Time Course of Glucose Release

The release of glucose was monitored over 95 hours at two CTec2:HTec2 (75:25) loadings, with and without Ax1A. As expected, the higher CTec2:HTec2 loading released more glucose more quickly (FIG. 8). At the lower CTec2:HTec2 loading, Ax1A caused a small enhancement of glucose yield only at the highest Ax1A loading, and this was not statistically significant (FIG. 8). At the higher CTec2:HTec2 loading, a stimulatory effect of Ax1A was seen at 95 hour that was statistically significant. Under these conditions, Ax1A supplementation resulted in an 8.3% absolute increase in glucose yield, from 84% to 92.3% (FIG. 8).

The Enhancement by Ax1A is not a General Protein Effect

Addition of nonenzymatic proteins, such as bovine serum albumin (BSA), enhances apparent hydrolysis activity, probably by reducing nonspecific and/or nonproductive binding of cellulases and other enzymes to lignin (Yang & Wyman, Biotechnol Bioeng 2006, 94:611-617). To test whether the enhancement by Ax1A might be due to a nonspecific protective effect on cellulases as opposed to its intrinsic enzymatic activity, we compared the effect on hydrolysis enhancement of Ax1A against BSA and bovine gamma-globulin. As shown in FIG. 20, neither BSA nor IgG stimulated glucose yields in response to CTec2:HTec2, nor did either protein affect the enhancement by Ax1A (FIG. 20). Furthermore, Ax1A that had been boiled to destroy its activity did not stimulate glucose or xylose release from corn stover (data not shown). These data indicated that the Ax1A enhancement is due to the α-xylosidase activity of Ax1A and is not a general nonspecific protein effect.

Response of Herbaceous Dicotyledons to Ax1A Supplementation

Corn, like other plants in the Poaceae family, is generally considered to have lower levels of xyloglucan than dicotyledons and non-graminaceous monocotyledons (Vogel, Curr Opin Plant Biol 2008, 11:301-307). To test whether herbaceous dicotyledons might therefore respond differently to Ax1A supplementation, we tested dark-grown (etiolated) peas, light-grown (green) peas, and wild lamb's quarters. Peas were chosen because their primary wall xyloglucan has been well-characterized (Talbott & Ray, Curr Opin Plant Biol 2008, 11:301-307). Lamb's quarters was chosen because, as a soft annual, it should have a high primary wall content. This is consistent with its glucose/xylose ratio of about 5.7, which is very close to etiolated and green peas (ratios of 5.4 and 5.6, respectively) and much higher than corn stover (ratio 2.0) (Table 3).

Yields of glucose from etiolated or green (light brown) pea were generally lower than 50% of available glucose content (FIG. 21). Under no conditions tested did Ax1A increase glucose yields from either kind of pea (FIG. 21). However, Ax1A supplementation did have a strong positive effect on glucose yields from lamb's quarters (Chenopodium album) (FIG. 22), although higher loadings of CTec2:HTec2 were useful to obtain optimal glucose yields (e.g., glucose yields like those obtained using corn stover as biomass). At 30 mg/g CTec2:HTec2, 8 µg Ax1A enhanced glucose yields from 82.2% to 96.5% (an absolute increase of 14.3%) and xylose yields by 65.9% to 75.5% (an absolute increase of 9.6%) (FIG. 22). Therefore, although Ax1A supplementation did not significantly affect glucose yields from pea biomass, Ax1A supplementation did enhance both glucose and xylose yields from another herbaceous dicotyledon.

Discussion

All plant cell walls contain significant levels of α-linked xylose, and commercial cellulase preparations derived from T. reesei lack α-xylosidase activity (Scott-Craig et al., J Biol Chem 2011, 286:42848-42854).

This Example describes tests to evaluate whether supplementation of commercial cellulase mixtures with the secreted α-xylosidase of A. niger (known as Ax1A) would improve glucose and xylose yields under otherwise identical hydrolysis conditions. The data provided herein show that supplementation of two commercial cellulase cocktails with Ax1A resulted in higher yields of glucose and xylose from corn stover and lamb's quarters. The results also indicate that in some conditions β-galactosidase activity in current commercial cellulases might also be limiting. By supplementing lignocellulosic digestion mixtures with the right types of enzymes in optimal amounts, higher ethanol yields can be obtained from a given mass of lignocellulosic material.

These experiments indicate that the stimulatory effect of Ax1A supplementation was more apparent when higher CTec2:HTec2 levels were employed (FIGS. 15, 17, 22), longer hydrolysis times were employed (FIGS. 8, 14), or lower biomass recalcitrance was present (compare FIG. 21 with FIGS. 17, 19 and 22). The complex carbon sources in many biomass sources can more effectively be digested when several enzymes are present in an enzymatic digestion mixture, including other xyloglucan-active enzymes such as xyloglucanase and β-galactosidase. Such enzymes can work in concert to increasingly digest the biomass and make the substrate for all enzymes (including Ax1A) more available. Access to xyloglucan may also be occluded by other wall polymers (e.g., including cellulose). In a recently proposed model of the structure of the primary wall, most of the xyloglucan polymers are hypothesized to be appressed between or embedded within cellulose microfibrils rather than spanning cellulose microfibrils as in the original "tethered network" model (Park & Cosgrove, Plant Physiol 22012, 158:1933-1943). If so, then the cellulases (i.e., cellobiohydrolases and endo-β1,4-glucanases) would have to act before enzymes active on xyloglucan could gain access. Hence, Ax1A may most optimally increase glucose and xylose yields at the terminal stages of wall deconstruction. This could also explain the lack of an effect of Ax1A supplementation on glucose yields from pea cell walls, postulating that insufficient hydrolysis of cellulose by cellulases (manifested by relatively low yields of glucose) blocks access by the xyloglucan-active enzymes, including Ax1A, to the xyloglucan.

These studies also illuminate the levels of Ax1A protein relative to the levels of commercial enzymes that are more effective to achieve increased release of sugars. The ratio of Ax1A to commercial enzyme (on a protein mass basis) varied from 0.3 to 6.4 in different experiments. Depending upon the time for enzymatic digestion, enzymes mixtures containing at least about 2 mg Ax1A/g glucan, or at least about 3 mg Ax1A/g glucan, or at least about 4 mg Ax1A/g glucan, or at least about 5 mg Ax1A/g glucan were useful. Some biomasses were more optimally treated using at least about 6 mg Ax1A/g glucan, or at least about 7 mg Ax1A/g glucan, or at least about 8 mg Ax1A/g glucan.

Even though grasses are alleged to contain smaller amounts of xyloglucan compared to dicotyledonous plants, Ax1A supplementation was as effective on corn stover as it was on lamb's quarters. Pea biomass was somewhat recalcitrant to enzymatic digestion.

In conclusion, the data described herein shows that addition of α-xylosidase to enzymatic mixtures such as those currently available for commercial use (e.g., various cellulase preparations) can significantly increase glucose and xylose yields from biomass, thereby improving the overall efficiency of biofuels production from lignocellulosic materials.

REFERENCES

1. Banerjee G, Scott-Craig J S, Walton J D: Improving enzymes for biomass conversion: a basic research perspective. *Bioenerg Res* 2010a, 3:82-92.
2. Hayashi T: Xyloglucans in the primary cell wall. *Annu Rev Plant Physiol Plant Mol Biol* 1989, 40:139-168.
3. Hayashi T, Kaida R: Functions of xyloglucan in plant cells. *Mol Plant* 2011, 4:17-24.
4. Lerouxel O, Cavalier D M, Liepman A H, Keegstra K: Biosynthesis of plant cell wall polysaccharides—a complex process. *Curr Opin Plant Biol* 2006, 9:621-630.
5. Scott-Craig J S, Borrusch M S, Banerjee G, Harvey C M, Walton J D (2011) Biochemical and molecular characterization of secreted α-xylosidase from *Aspergillus niger. J Biol Chem* 2011, 286:42848-42854.
6. Banerjee G, Car S, Scott-Craig J S, Hodge D B, Walton J D: Alkaline peroxide pretreatment of corn stover: effects of biomass, peroxide, and enzyme loading and composition on yields of glucose and xylose. *Biotechnol Biofuels* 2011, 4:16.
7. Paper J M, Scott-Craig J S, Cavalier D, Faik A, Wiemels R E, Borrusch M S, Bongers M, Walton J D: α-Fucosidases with different substrate specificities from two species of *Fusarium. Appl Microbiol Biotechnol* 2012, in press.
8. Zablackis E, Huang J, Muller B, Darvill A G, Albersheim P: Characterization of the cell-wall polysaccharides of *Arabidopsis thaliana* leaves. *Plant Physiol* 1995, 107: 1129-1138.
9. Foster C E, Martin T M, Pauly M: Comprehensive compositional analysis of plant cell walls (lignocellulosic biomass) part II: carbohydrates. *J Vis Exp* 2010, doi:10.3791/1837.
10. Sluiter A, Hames B, Ruiz R, Scarlata C, Sluiter J, Templeton D, Crocker D: Determination of structural carbohydrates and lignin in biomass (Version Jul. 8, 2011). U.S. Department of Energy National Renewable Energy Laboratory, 2011.
11. Bradford M M: A rapid and sensitive method for the quantitation of microgram quantities of protein utilizing the principle of protein-dye binding. *Anal Biochem* 1976, 72:248-254.
12. Banerjee G, Car S, Scott-Craig J S, Borrusch M S, Aslam N, Walton J D: Synthetic enzyme mixtures for biomass deconstruction: production and optimization of a core set. *Biotechnol Bioengineer* 2010, 106:707-720.
13. Banerjee G, Car S, Scott-Craig J S, Borrusch M S, Bongers M, Walton J D: Synthetic multi-component enzyme mixtures for deconstruction of lignocellulosic biomass. *Bioresour Technol* 2010, 101:9097-9105.
14. Zeng W, Chatterjee M, Faik A: UDP-xylose-stimulated glucuronyltransferase activity in wheat microsomal membranes: characterization and role in glucurono(arabino) xylan biosynthesis. *Plant Physiol* 2008, 147:78-91.
15. Yang B, Wyman C E: BSA treatment to enhance enzymatic hydrolysis of cellulose in lignin containing substrates. *Biotechnol Bioeng* 2006, 94:611-617.
16. Vogel J: Unique aspects of the grass cell wall. *Curr Opin Plant Biol* 2008, 11:301-307.
17. Talbott L D, Ray P M: Molecular size and separability features of pea cell wall polysaccharides: implications for models of primary wall structure. *Plant Physiol* 1992, 98:357-368.
18. Chaillou S, Lokman B C, Leer R J, Posthuma C, Postma P W, Pouwels P H: Cloning, sequence analysis, and characterization of the genes involved in isoprimeverose metabolism in *Lactobacillus pentosus. J Bacteriol* 1998, 180:2312-2320.
19. Park Y B, Cosgrove D J: A revised architecture of primary cell walls based on biomechanical changes induced by substrate-specific endoglucanases. *Plant Physiol* 22012, 158:1933-1943.
20. Yokoyama R, Rose J K C, Nishitani K: A surprising diversity and abundance of xyloglucan endotransglucosylase/hydrolases in rice. Classification and expression analysis. *Plant Physiol* 2004, 134:10808-1099.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to describe and summarize various aspects of the invention according to the foregoing description in the specification.

Statements:

1. A composition comprising an enzyme mixture comprising an isolated α-xylosidase and at least 5% cellulase.
2. The composition of statement 1, wherein the isolated α-xylosidase is a secreted α-xylosidase.
3. The composition of statement 1 and 2, wherein the isolated α-xylosidase is a purified α-xylosidase.
4. The composition of any of statements 1-3, wherein the isolated α-xylosidase is about 50%, about 60%, about 70%, about 80%, about 90%, about 95%, about 97%, about 98%, or about 99% pure.
5. The composition of any of statements 1-4, wherein the isolated α-xylosidase lacks a quaternary structure.
6. The composition of any of statements 1-5, wherein the isolated α-xylosidase has a pH optimum of approximately 4.0 and/or has a temperature optimum of approximately 50° C.-60° C.
7. The composition of any of statements 1-6, wherein the isolated α-xylosidase has an amino acid sequence with at least about 55%, at least about 60%, at least about 70%, at least about 80%, at least about 90% or at least about 95% sequence identity with any of SEQ ID NO:1, 3, 5, 7-19, or 22.
8. The composition of any of statements 1-7, wherein the isolated α-xylosidase is derived from a fungal extracellular extract.
9. The composition of any of statements 1-8, wherein the isolated α-xylosidase is an *Aspergillus niger* extracellular extract.
10. The composition of any of statements 1-9, wherein the isolated α-xylosidase is identified by Aspni5|43342 or accession number GenBank DAA35002.1.
11. The composition of any of statement 1-10, further comprising at least 5%, or at least 10%, or at least 15% cellulase or at least 20%, or at least 25% cellulase, or at least 30% cellulase, or at least 40% cellulase, or at least 50% cellulase.
12. The composition of any of statements 1-11, further comprising a cellulase, wherein said cellulase is at least one enzyme selected from the group consisting of cellobiohydrolase, endoxylanase, β-glucosidase, β-1,4-glucanase, β-galactosidase, α-fucosidase, β-galactosidase, β-xylosidase, α-arabinosidase, α-glucuronidase, polysaccharide monooxygenase, esterase and combinations thereof
13. A kit comprising a container comprising the composition of any of statements 1-12, and instructions for incubating a plant biomass with the composition for a time and under conditions sufficient to create a degraded hemicellulose material from the plant biomass.
14. A method, comprising:
  a) providing;
    i) a plant biomass comprising a hemicellulose material; and
    ii) an enzyme mixture comprising an isolated α-xylosidase and at least 5% cellulase; and
  b) incubating said biomass with said enzyme mixture for a time and under conditions sufficient to create a depolymerized hemicellulose material;
    wherein said depolymerized hemicellulose material comprises a plurality of free fermentable xylose and glucose residues.
15. The method of statement 14, further comprising a pretreatment step performed before step (a).
16. The method of statement 14 or 15, further comprising a pretreatment step performed before step (a), wherein the pretreatment step decreases noncovalent interactions between polysaccharides and/or between cell wall polymers of the plant biomass.
17. The method of any of statements 14-16, wherein the method further comprises pretreating said plant biomass with alkaline hydrogen peroxide, acid, ammonia, ionic liquids, steam or a combination thereof.
18. The method of any of statements 14-17, wherein said degraded hemicellulose material is at least 50%, or at least 60%, or at least 70%, or at least 80%, or at least 90%, or at least 95%, or at least 98% degraded into the plurality of free fermentable xylose and glucose residues.
19. The method of any of statements 14-18, wherein the isolated α-xylosidase is a secreted α-xylosidase.
20. The method of any of statements 14-19, wherein the isolated α-xylosidase is a purified α-xylosidase.
21. The method of any of statements 14-20, wherein the isolated α-xylosidase is about 50%, about 60%, about 70%, about 80%, about 90%, about 95%, about 97%, about 98%, or about 99% pure.
22. The method of any of statements 14-21, wherein the isolated α-xylosidase lacks a quaternary structure.
23. The method of any of statements 14-22, wherein the isolated α-xylosidase has a pH optimum of approximately 4.0 and/or has a temperature optimum of approximately 50° C.-60° C.
24. The method of any of statements 14-23, wherein the isolated α-xylosidase has an amino acid sequence with at least about 55%, at least about 60%, at least about 70%, at least about 80%, at least about 90% or at least about 95% sequence identity with any of SEQ ID NO:1, 3, 5, 7-19, or 22.

25. The method of any of statements 14-24, wherein the isolated α-xylosidase is derived from a fungal extracellular extract.
26. The method of any of statements 14-25, wherein the isolated α-xylosidase is an *Aspergillus niger* extracellular extract.
27. The method of any of statements 14-26, wherein the isolated α-xylosidase is identified by Aspni5|43342 or accession number GenBank DAA35002.1.
28. The method of any of statements 14-27, further comprising at least 5%, or at least 10%, or at least 15% cellulase or at least 20%, or at least 25% cellulase, or at least 30% cellulase, or at least 40% cellulase, or at least 50% cellulase.
29. The method of any of statements 14-28, further comprising a cellulase, wherein said cellulase is at least one enzyme selected from the group consisting of cellobiohydrolase, endoxylanase, β-glucosidase, β-1,4-glucanase, β-galactosidase, α-fucosidase, β-galactosidase, β-xylosidase, α-arabinosidase, α-glucuronidase, polysaccharide mono-oxygenase, esterase and combinations thereof
30. The method of any of statements 14-29, wherein said plant biomass comprises a dicot xyloglucan.
31. The method of any of statements 14-30, wherein said plant biomass comprises a monocot xyloglucan.
32. The method of any of statements 14-31, wherein said plant biomass comprises grass xyloglucan or corn stover.
33. The method of any of statements 14-32, wherein said incubating is performed at a temperature ranging of approximately 40°-50° C.
34. The method of any of statements 14-33, wherein said incubating is performed at a pH of approximately 4-5.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Other embodiments are described within the following claims.

What is claimed:

1. A method, comprising:
   a) providing;
      i) a plant biomass comprising a hemicellulose material; and
      ii) an enzyme mixture comprising at least about 5% by weight of isolated Aspni5|43342 α-xylosidase, or an α-xylosidase with at least 95% sequence identity to SEQ ID NO:1, and at least 50% by weight of a cellulase mixture comprising cellobiohydrolase, endoglucanase, β-1,4-glucanase, β-glucosidase, endoxylanase, and β-xylosidase; and
   b) incubating said biomass with said enzyme mixture using at least about 2 mg of an isolated α-xylosidase per gram biomass for a time and under conditions sufficient to create a depolymerized hemicellulose material;
   wherein said depolymerized hemicellulose material comprises a plurality of free fermentable xylose and glucose residues.

2. The method of claim 1, wherein the α-xylosidase with at least 95% sequence identity to SEQ ID NO:1 has one or more conservative amino acid substitutions.

3. The method of claim 1, wherein said method further comprises pretreating said plant biomass with alkaline hydrogen peroxide, acid, ammonia, ionic liquids, steam or a combination thereof.

4. The method of claim 1, wherein said depolymerized hemicellulose material is at least 50% depolymerized into the plurality of free fermentable xylose and glucose residues.

5. The method of claim 1, wherein said cellulase mixture further comprises at least one enzyme selected from the group of α-fucosidase, β-galactosidase, α-arabinosidase, α-glucuronidase polysaccharide mono-oxygenase, esterase and combinations thereof.

6. The method of claim 1, wherein said isolated α-xylosidase lacks a quaternary structure.

7. The method of claim 1, wherein said isolated α-xylosidase is a secreted α-xylosidase.

8. The method of claim 1, wherein said isolated α-xylosidase has a pH optimum of approximately 4.0.

9. The method of claim 1, wherein said isolated α-xylosidase comprises or is derived from a fungal extracellular extract.

10. The method of claim 9, wherein said fungal extracellular extract is an *Aspergillus niger* extracellular extract.

11. The method of claim 1, wherein said plant biomass comprises a dicot xyloglucan.

12. The method of claim 1, wherein said plant biomass comprises a monocot xyloglucan.

13. The method of claim 1, wherein said plant biomass comprises grass xyloglucan or corn stover.

14. The method of claim 1, wherein said incubating is performed at a temperature ranging from approximately 40° C. to 50° C.

15. The method of claim 1, wherein said incubating is performed at a pH of approximately 4-5.

* * * * *

SEQUENCE LISTING

```
<160> NUMBER OF SEQ ID NOS: 22

<210> SEQ ID NO 1
<211> LENGTH: 736
<212> TYPE: PRT
<213> ORGANISM: Aspergillus niger

<400> SEQUENCE: 1

Met Tyr Phe Ser Ser Phe Leu Ala Leu Gly Ala Leu Val Gln Ala Ala
1               5                  10                  15

Ala Ala Thr Tyr Phe Ala Pro Asn Ser Thr Gly Leu Arg Ile Gln His
            20                  25                  30

Gly Phe Glu Thr Ile Leu Ile Gln Pro Phe Gly Tyr Asp Gly Phe Arg
        35                  40                  45

Val Arg Ala Trp Pro Phe Arg Pro Pro Ser Gly Asn Glu Ile Ser Phe
    50                  55                  60

Ile Tyr Asp Pro Pro Ile Glu Gly Tyr Glu Asp Thr Ala His Gly Met
65                  70                  75                  80

Ser Tyr Asp Thr Ala Thr Thr Gly Thr Glu Pro Arg Thr Leu Arg Asn
                85                  90                  95

Gly Asn Ile Ile Leu Arg Thr Thr Gly Trp Gly Thr Thr Ala Gly
            100                 105                 110

Tyr Arg Leu Ser Phe Tyr Arg Val Asn Asp Asp Gly Ser Glu Thr Leu
        115                 120                 125

Leu Thr Asn Glu Tyr Ala Pro Leu Lys Ser Leu Asn Pro Arg Tyr Tyr
    130                 135                 140

Tyr Trp Pro Gly Pro Gly Ala Glu Phe Ser Ala Glu Phe Ser Phe Ser
145                 150                 155                 160

Ala Thr Pro Asp Glu Gln Ile Tyr Gly Thr Gly Thr Gln Gln Asp His
                165                 170                 175

Met Ile Asn Lys Lys Gly Ser Val Ile Asp Met Val Asn Phe Asn Ser
            180                 185                 190

Tyr Ile Pro Thr Pro Val Phe Met Ser Asn Lys Gly Tyr Ala Phe Ile
        195                 200                 205

Trp Asn Met Pro Ala Glu Gly Arg Met Glu Phe Gly Thr Leu Arg Thr
    210                 215                 220
```

```
Arg Phe Thr Ala Ala Ser Thr Thr Leu Val Asp Tyr Val Ile Val Ala
225                 230                 235                 240

Ala Gln Pro Gly Asp Tyr Asp Thr Leu Gln Gln Arg Ile Ser Ala Leu
            245                 250                 255

Thr Gly Arg Ala Pro Ala Pro Pro Asp Phe Ser Leu Gly Tyr Ile Gln
        260                 265                 270

Ser Lys Leu Arg Tyr Glu Asn Gln Thr Glu Val Glu Leu Leu Ala Gln
    275                 280                 285

Asn Phe His Asp Arg Asn Ile Pro Val Ser Met Ile Val Ile Asp Tyr
290                 295                 300

Gln Ser Trp Ala His Gln Gly Asp Trp Ala Leu Asp Pro Arg Leu Trp
305                 310                 315                 320

Pro Asn Val Ala Gln Met Ser Ala Arg Val Lys Asn Leu Thr Gly Ala
                325                 330                 335

Glu Met Met Ala Ser Leu Trp Pro Ser Val Ala Asp Ser Val Asn
            340                 345                 350

Tyr Ala Ala Leu Gln Ala Asn Gly Leu Leu Ser Ala Thr Arg Asp Gly
        355                 360                 365

Pro Gly Thr Thr Asp Ser Trp Asn Gly Ser Tyr Ile Arg Asn Tyr Asp
370                 375                 380

Ser Thr Asn Pro Ser Ala Arg Lys Phe Leu Trp Ser Met Leu Lys Lys
385                 390                 395                 400

Asn Tyr Tyr Asp Lys Gly Ile Lys Asn Phe Trp Ile Asp Gln Ala Asp
                405                 410                 415

Gly Gly Ala Leu Gly Glu Ala Tyr Glu Asn Asn Gly Gln Ser Thr Tyr
            420                 425                 430

Ile Glu Ser Ile Pro Phe Thr Leu Pro Asn Val Asn Tyr Ala Ala Gly
        435                 440                 445

Thr Gln Leu Ser Val Gly Lys Leu Tyr Pro Trp Ala His Gln Gln Ala
450                 455                 460

Ile Glu Glu Gly Phe Arg Asn Ala Thr Asp Thr Lys Glu Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
            500                 505                 510

Leu Ala Val Gln Val Ala Ser Gly Leu Ser Ala Ala Thr Gly Trp
        515                 520                 525

Gly Trp Trp Thr Val Asp Ala Gly Gly Phe Glu Val Asp Ser Thr Val
530                 535                 540

Trp Trp Ser Gly Asn Ile Asp Thr Pro Glu Tyr Arg Glu Leu Tyr Val
545                 550                 555                 560

Arg Trp Leu Ala Trp Thr Thr Phe Leu Pro Phe Met Arg Thr His Gly
                565                 570                 575

Ser Arg Thr Cys Tyr Phe Gln Asp Ala Tyr Thr Cys Ala Asn Glu Pro
            580                 585                 590

Trp Ser Tyr Gly Ala Ser Asn Thr Pro Ile Ile Val Ser Tyr Ile His
        595                 600                 605

Leu Arg Tyr Gln Leu Gly Ala Tyr Leu Lys Ser Ile Phe Asn Gln Phe
610                 615                 620

His Leu Thr Gly Arg Ser Ile Met Arg Pro Leu Tyr Met Asp Phe Glu
625                 630                 635                 640
```

```
Lys Thr Asp Pro Lys Ile Ser Gln Leu Val Ser Ser Asn Ser Asn Tyr
                645                 650                 655

Thr Thr Gln Gln Tyr Met Phe Gly Pro Arg Leu Leu Val Ser Pro Val
            660                 665                 670

Thr Leu Pro Asn Val Thr Glu Trp Pro Val Tyr Leu Pro Gln Thr Gly
        675                 680                 685

Gln Asn Asn Thr Lys Pro Trp Thr Tyr Trp Trp Thr Asn Glu Thr Tyr
    690                 695                 700

Ala Gly Gly Gln Val Val Lys Val Pro Ala Pro Leu Gln His Ile Pro
705                 710                 715                 720

Val Phe His Leu Gly Ser Arg Glu Glu Leu Leu Ser Gly Asn Val Phe
                725                 730                 735

<210> SEQ ID NO 2
<211> LENGTH: 2211
<212> TYPE: DNA
<213> ORGANISM: Aspergillus niger

<400> SEQUENCE: 2
atgtacttct cttccttctt ggccctaggg gccttggttc aggctgcagc agcaacctat      60
tttgccccca actctaccgg tcttcgtatc cagcatggtt ttgagacgat tcttatccag     120
ccgtttgggt acgacggatt ccgtgtgcgc gcatggccct ccgtccgcc ttcgggtaac      180 gagatcagct tcatctacga tcccccgatc gaaggctatg aggacactgc gcatggcatg     240
agctatgaca ccgcaaccac cggcacggag cctcgcacct tgcgcaacgg caatatcatc     300
ctgcgcacca ccggctgggg tggtaccaca gccggatacc gactgtcctt ttatcgcgtc     360
aatgacgatg aagtgagac ccttctcaca acgaatatg ctccgctgaa gtctctcaac      420
ccccggtact attactggcc gggacctggg gccgaattct cagctgagtt ctctttcagt     480
gcgactccgg atgagcagat ctatggtacg ggcacgcaac aggatcatat gatcaacaag     540
aagggctccg taattgacat ggtcaacttc aactcctaca tccctacccc ggtcttcatg     600
agcaataaag gctatgcctt catctggaac atgccagctg aggggcgtat ggaatttggc     660
accctccgga ccagattcac cgccgcgtcc acgacgcttg ttgactatgt aatcgtcgcc     720
gcgcagccgg gcgactacga caccttgcag cagcggattt cggccctcac aggacgggcc     780
ccggccccgc ctgacttctc gcttggatac atccagtcca agctacgata tgaaaaccaa     840
acggaggtgg agctgctggc tcaaaacttc catgaccgaa catcccggt gtccatgatc      900 gttattgact accagtcctg ggctcaccag ggtgattggg cgctcgatcc tcgcctgtgg     960
cccaatgttg cgcagatgtc ggcgcgggtc aagaacctca ccggcgccga atgatggca     1020 tcgctatggc ccagtgttgc cgacgacagc gtcaattacg cagccctgca ggcgaacggc    1080
cttctctcgg ccacgcgcga tggacctggt accactgact cctggaacgg atcatacatc    1140
cggaactatg actccaccaa cccctcggcg cggaagttcc tctggagcat gctgaagaag    1200
aactactacg acaagggtat caaaaactt tggattgacc aagccgatgg cggagcgctg    1260
ggtgaggcgt atgagaacaa cggacagagc acgtatattg agtccatccc gttcaccctg    1320
ccaaacgtga actatgccgc tggtacgcag ctcagcgtgg gtaagctgta ccctggggcg    1380
catcagcagg caattgagga ggggttccgc aatgcaacag ataccaagga agggagcgca    1440
tgcgatcatg tctccctgag tcggtctgga tacatcggat cccagcggtt ctgcagcatg    1500
atctggtcgg gagacactac atccgttggg gacaccctgg cagtgcaagt agccagtgga    1560
ctgtccgccg cagcaacagg ctggggttgg tggacggtcg atgccggtgg cttcgaagtc    1620
```

```
gactcgactg tttggtggag tggaaacatt gacacgcctg aataccggga gttgtatgtg    1680
cgctggctgg cttggacgac tttcctgcca ttcatgcgca ctcacggtag ccggacctgc    1740
tatttccagg acgcctacac ctgtgccaat gagccgtggt cctatggtgc aagcaacaca    1800
cccatcattg tctcgtacat tcatctgcgc taccagctgg gtgcttacct gaagtccatc    1860
ttcaaccagt tccacctcac aggccggagc atcatgcgcc cattgtatat ggatttcgag    1920
aagacagacc cgaagatctc ccagctggtg tcgtcgaaca gcaactacac gacgcaacag    1980
tacatgtttg cccacgtct cctggtctcg ccagtgacct tgccgaacgt gactgagtgg    2040
cccgtgtatc tgccgcagac gggacagaac aacaccaagc cttggacata ctggtggacg    2100
aatgaaacgt atgccggagg acaggtcgtc aaggtgcctg ccccccttgca acatatcccc    2160 gtgtttcatc tgggatcgcg cgaagagctt ctctcgggta atgttttcta g            2211
```

<210> SEQ ID NO 3
<211> LENGTH: 720
<212> TYPE: PRT
<213> ORGANISM: Schizophyllum commune

<400> SEQUENCE: 3

```
Met Leu Leu Arg Ser Leu Ala Ala Leu Cys Ala Ala Leu Ala Cys Ala
1               5                   10                  15

Asn Leu Ala Leu Ala Gln Gly Ser Glu Thr Asn Ser Thr Gly Ile Lys
            20                  25                  30

Leu Gln Asn Gly Phe Glu Arg Val Phe Ile Gln Pro Phe Gly Glu Asn
        35                  40                  45

Gly Phe Arg Val Arg Thr Ser Leu Met Arg Asp Pro Thr Gly Asn Glu
    50                  55                  60

Trp Ser Gly Leu Ile Asp Pro Pro Leu Glu Gly Pro Gly Gly Asn Ala
65                  70                  75                  80

Gly Leu Thr Tyr Asp Thr Leu Leu Pro Tyr His Gly Asn Ala Thr Ile
                85                  90                  95

Gln Asn Gly Asn Ile Leu Ala Thr Val Asp Leu Gly Val Leu Ser Phe
            100                 105                 110

Phe Arg Leu Glu Pro Asn Gly Ser Thr Thr Leu Leu Thr Gly Glu Phe
        115                 120                 125

Thr Asp Glu Lys Ala Ile Pro Ala Arg Tyr Tyr Thr Arg Asn Phe Leu
    130                 135                 140

Ser Asp Ser Phe Ala Val Asp Leu Ala Phe Ser Ala Glu Lys Asp Glu
145                 150                 155                 160

Gln Phe Tyr Gly Thr Gly Gln Gln Ala Cys Cys Lys Asp His Ser Val
                165                 170                 175

Asn Lys Lys Gly Gln Val Val Asp Leu Phe Asn Phe Asn Ser Asn Val
            180                 185                 190

Ala Leu Pro Val Tyr Met Ser Ser Lys Gly Tyr Leu Gln Phe Phe Asn
        195                 200                 205

Met Pro Ser Gln Gly Arg Ile Glu Phe Ser Pro Leu Arg Thr Arg Phe
    210                 215                 220

His Ala Thr Glu Thr Thr Val Val Asp Tyr Tyr Ile Thr Thr Ala Gln
225                 230                 235                 240

Pro Gly Asp Tyr Asp Thr Leu Gln Lys Gln Phe Thr Ser Val Thr Gly
                245                 250                 255

Arg Gln Pro Thr Pro Pro Asp Phe Leu Leu Gly Tyr Gln His Ser Lys
            260                 265                 270
```

```
Leu Arg Tyr Phe Glu Gln Gln Val Leu Asp Val Ala Gln Arg Phe
        275                 280                 285

His Asp Glu Gln Ile Asn Val Ser Leu Leu Val Asp Phe Phe Ala
    290                 295                 300

Trp Lys Tyr Gln Gly Asp Trp Ser Phe Asn Pro Glu Tyr Trp Pro Asp
305                 310                 315                 320

Pro Glu Gly Met Ala Ala Lys Val Lys Glu Leu Thr Gly Ala Glu Met
                325                 330                 335

Met Ala Ser Leu Trp Pro Ser Val Glu Asp Asn Ser Glu Asn Tyr Ala
                340                 345                 350

Ala Leu Gln Glu Gln Gly Leu Leu Ala Thr Thr Arg Asp Gly Thr Gly
                355                 360                 365

Val Thr Asp Ser Phe Ala Gly Ala Tyr Thr Arg Leu Ile Asp Ser Thr
    370                 375                 380

Asn Pro Ala Ala Arg Glu Phe Leu Trp Lys Arg Leu Asn Asp Ser Tyr
385                 390                 395                 400

Phe Ser Lys Gly Ile Tyr Asn Phe Trp Ile Asp Gln Ala Asp Gly Gly
                405                 410                 415

Thr Leu Gly Glu Ala Phe Glu Asn Asn Gly Gln Thr Ile Gln Asn Ile
                420                 425                 430

Pro Tyr Ser Arg Ala Phe Thr Gln Tyr Tyr Ile Gly Thr Gln Glu Gly
                435                 440                 445

Ala Gly Lys Met Tyr Pro Trp Phe His Glu Gln Ala Val Asp Glu Gly
                450                 455                 460

His Arg Asn Leu Thr Asn Thr Ala Arg Asp Asp Pro Ala Cys Pro Tyr
465                 470                 475                 480

Met Ser Leu Thr Arg Ser Thr Trp Val Gly Gly Gln Arg Phe Cys Thr
                485                 490                 495

Tyr Leu Trp Ser Gly Asp Thr Arg Ser Glu Trp Ala Thr Leu Ser Gln
                500                 505                 510

Gln Val Thr Ala Gly Ala Ser Val Ala Ala Ser Gly Ile Ser Ser Trp
                515                 520                 525

Thr Leu Asp Ile Gly Gly Phe Ala Gly Leu Asn Val Asp Gln Glu Glu
                530                 535                 540

Asp Arg Glu Leu Phe Val Arg Trp Phe Gly Phe Gly Thr Phe Leu Pro
545                 550                 555                 560

Tyr Val Ser Thr Tyr Thr Val Ala Gly Glu Arg Glu Pro Trp Ser Phe
                565                 570                 575

Gly Asp Asp Asn Phe Val Val Leu Lys Lys Tyr Ile Ser Leu Arg Tyr
                580                 585                 590

Gln Leu Val Pro Tyr Val Lys Lys Leu Phe Val Asp Leu Gln Ala Ser
                595                 600                 605

Gly Lys Thr Ile Met Arg Ala Leu Tyr Tyr Asp Phe Ser Leu Ser Asp
                610                 615                 620

Pro Ala Val Val Glu Gly Thr Arg Thr Asn Asp Pro Ser Ile Val His
625                 630                 635                 640

Glu Tyr Met Leu Gly Pro Arg Leu Leu Val Ala Pro Val Trp Ala Thr
                645                 650                 655

Asn Val Thr Ser Trp Glu Val Tyr Leu Pro Lys Leu Pro Glu Ala Tyr
                660                 665                 670

Val Asp Glu Gly Trp Glu Trp Thr His Trp Trp Thr Asp Glu Ala Tyr
                675                 680                 685
```

Gly Ala Gly Gly Glu Lys Val Asn Val Ser Ala Gln Leu Asp Glu Ile
    690             695                 700

Pro Val Phe Tyr Leu Gly Ser Lys Asp Asp Ile Phe Ser Gly Asn Val
705                 710                 715                 720

<210> SEQ ID NO 4
<211> LENGTH: 2163
<212> TYPE: DNA
<213> ORGANISM: Schizophyllum commune

<400> SEQUENCE: 4

| | | | | | |
|---|---|---|---|---|---|
| atgctactaa | gatcacttgc | cgccctatgt | gcggcgcttg | cttgcgcgaa | ccttgccctc | 60 |
| gcgcaaggtt | ccgagaccaa | ctccacgggc | atcaaacttc | agaacggctt | cgaacgcgtc | 120 |
| ttcattcaac | cctttggcga | gaatggcttc | cgcgtccgga | ccagcctcat | gcgcgatccc | 180 |
| accgggaacg | aatggagcgg | ccttatcgac | ccgcccctcg | aaggcccccgg | aggcaatgcg | 240 |
| ggactcacct | acgacaccct | cctccccctac | acggcaacg | cgactatcca | gaacggcaac | 300 |
| attctcgcca | ccgtagacct | cggcgttctc | tccttcttcc | gcctcgagcc | taacggtagc | 360 |
| accacgcttc | tcaccggcga | gtttaccgac | gagaaggcga | tcccggcgcg | atactacacg | 420 |
| cgcaacttcc | tctccgatag | ctttgccgtc | gatctcgcgt | tctcggcgga | gaaggacgag | 480 |
| cagttctatg | gcacggggca | gcaggcgtgt | tgcaaggacc | actcggtcaa | taagaagggg | 540 |
| caggtggtgg | acttgttcaa | cttcaatagc | aatgtgcac | ttccggtgta | tatgtcgagc | 600 |
| aaggggtacc | tgcagttctt | caatatgcct | agtcaaggga | ggatagagtt | cagcccattg | 660 |
| aggactcgtt | tccatgccac | ggaaacgacc | gtcgtggatt | actatatcac | gaccgcacaa | 720 |
| cccggcgact | atgataccct | gcagaaacag | ttcacctccg | tcaccgggcg | tcagcctacg | 780 |
| ccgcccgact | tccttctcgg | ctaccagcac | tccaaactgc | ggtactttga | gcagcaacaa | 840 |
| gtcctcgacg | tcgcgcagcg | cttccatgat | gaacagatca | acgtctcgct | gctggtcgta | 900 |
| gacttctttg | cttggaagta | ccagggtgac | tggtctttca | acccagagta | ttggcccgac | 960 |
| cccgagggca | tggccgcgaa | agtcaaggag | ctcactggcg | ccgagatgat | ggcctcgctc | 1020 |
| tggcccagcg | tcgaagataa | ctccgagaac | tacgcagcgc | tgcaggagca | gggtctgttg | 1080 |
| gcgacgacgc | gtgatggcac | gggcgtgacg | gactcatttg | cggggcgta | tacgaggttg | 1140 |
| atcgactcga | cgaatccggc | agcgcgcgag | ttttgtgga | agcggctgaa | tgatagttac | 1200 |
| ttctctaagg | gtatatacaa | cttctggatc | gatcaggcag | acggtggaac | cctcggagag | 1260 |
| gctttcgaga | caacggtca | aaccatccaa | aacatcccct | acagccgcgc | cttcacccaa | 1320 |
| tactacatcg | gcacgcagga | aggcgccggc | aagatgtacc | cctggttcca | cgaacaagcc | 1380 |
| gtcgacgagg | gccaccgcaa | cctcaccaac | accgcgcgcg | acgacccccgc | gtgcccctac | 1440 |
| atgtccctca | cgcgcagcac | gtgggtcggc | gggcagcgct | tctgcacgta | cctctggtcg | 1500 |
| ggcgacacgc | gctcggagtg | ggcgacgctg | tcgcagcagg | tgacggcggg | cgcgagcgtc | 1560 |
| gcggcatcgg | gcatctcgtc | gtggacgctc | gatattggcg | ggtttgcggg | gttgaatgtc | 1620 |
| gatcaggagg | aggataggga | gttgtttgtg | cggtggtttg | ggtttgggac | gttttttgccg | 1680 |
| tatgtgagta | catacacggt | ggcggggagag | agggagcccct | ggtccttcgg | agatgacaac | 1740 |
| ttcgttgttt | tgaagaagta | catctctctg | cgctaccagc | tcgtcccctta | cgtcaagaag | 1800 |
| ctcttcgtcg | acctccaggc | ctcgggcaag | acgatcatgc | gcgcgcttta | ctacgacttc | 1860 |
| tcgctctcgg | acccagcagt | agtcgagggc | acgcgcacca | acgatccgtc | gatcgtccac | 1920 |
| gagtacatgc | tgggcccgcg | gctgcttgtt | gcgccggtgt | gggcgacaaa | cgtgacgagc | 1980 |

```
tgggaggtgt atcttccgaa gttgccggag gcttatgtgg atgagggttg ggagtggacg      2040
cattggtgga cggacgaggc ttacggcgcc gggggcgaga aggtgaacgt aagcgcgcag      2100
ctggacgaga ttcctgtgtt ctatctcggg tccaaggacg atatcttctc aggcaatgtt      2160
tga                                                                    2163
```

<210> SEQ ID NO 5
<211> LENGTH: 967
<212> TYPE: PRT
<213> ORGANISM: A. flavus

<400> SEQUENCE: 5

```
Met Leu Ile Leu Ala Leu Gly Ala Val Lys Phe Ala Gly Val Gly His
1               5                   10                  15

His Ile Pro Trp Leu Met Val Lys Asp Pro Ala Ser Leu Arg Ile Trp
            20                  25                  30

Ala Lys Tyr Leu Leu Ala Leu Ser Phe Leu Tyr Leu Gly Ser Val Asn
        35                  40                  45

Leu Pro Lys Phe Ser Ile Leu Leu Tyr His Arg Leu Phe Pro Thr
    50                  55                  60

Lys Lys Met Gly Ala Ile Ile Lys Leu Met Met Val Val Leu Cys Val
65                  70                  75                  80

Ile Thr Ile Ser Thr Ile Val Gly Ala Ser Leu Val Cys Arg Pro Phe
                85                  90                  95

Ser Ala Asn Trp Asp Gly Pro Ile Pro Gly Asn Cys Gly Asn Lys Lys
            100                 105                 110

Val Leu Tyr Ile Trp Ala Ser Phe Pro Asn Ile Val Thr Asp Val Ile
        115                 120                 125

Leu Leu Leu Leu Pro Met Pro Val Leu Trp Ser Leu Asn Val Ser Pro
    130                 135                 140

Arg Leu Lys Val Gly Leu Thr Ile Thr Phe Ala Val Gly Ser Ile Gly
145                 150                 155                 160

Leu Val Thr Ser Val Met Arg Phe Gln Ile Phe Phe Arg Asn Asn Ala
                165                 170                 175

Phe Leu Asp Gly Thr Trp Val Ala Val Glu Leu Ile Ile Trp Thr Gln
            180                 185                 190

Val Glu Thr Gly Val Tyr Leu Ile Ser Ala Cys Leu Pro Thr Tyr Arg
        195                 200                 205

Pro Leu Ile Glu His Gly Phe Asn Pro Lys Met Leu Ser Lys Met Tyr
    210                 215                 220

Arg Trp Leu Val Ala Leu Thr Val Cys Ala Thr Gln Leu Val Gln Ala
225                 230                 235                 240

Thr Pro Ile Gln Thr Arg Glu Ser Asp Tyr Phe Leu Pro Asn Ser Thr
                245                 250                 255

Gly Phe Arg Met Gln His Gly Phe Glu Thr Ile Leu Val Gln Pro Phe
            260                 265                 270

Gly Phe Asp Gly Phe Arg Val Arg Ala Trp Pro Phe Arg Pro Pro Thr
        275                 280                 285

Gly His Glu Ile Ser Phe Ile Tyr Asp Pro Pro Leu Glu Gly Phe Glu
    290                 295                 300

Asn Gly Gln Ala His Gly Leu Thr Phe Asp Thr Ala Phe Asn Gly Asn
305                 310                 315                 320

His Thr Val Ala Ile Arg Asn Gly Asn Thr Ile Val Arg Thr Ser Gly
                325                 330                 335
```

```
Trp Gly Gly Asn Pro Gly Gly Tyr Arg Leu Ala Phe Tyr Arg Ile Glu
            340                 345                 350

Gln Asp Gly Ser Glu Ser Leu Leu Thr Asn Glu Tyr Ala Pro Leu Lys
            355                 360                 365

Ser Ile Asn Pro Arg Tyr Tyr Ser Trp Asn Gly Pro Gly Ser Glu Phe
370                 375                 380

Ser Ala Glu Phe Ser Phe Ser Thr Asp Pro Asp Glu Gln Phe Tyr Gly
385                 390                 395                 400

Thr Gly Thr Gln Gln Asp His Leu Val Asn Lys Lys Gly Thr Val Ile
            405                 410                 415

Asp Leu Ile Asn Phe Asn Thr His Ile Pro Thr Pro Val Phe Met Ser
            420                 425                 430

Asn Lys Gly Tyr Ala Phe Ile Trp Asn Met Pro Ala Gln Gly Arg Met
            435                 440                 445

Glu Phe Gly Gln Leu Arg Thr Lys Leu Thr Ala Glu Ser Thr Thr Val
            450                 455                 460

Val Asp Tyr Val Ile Val Ala Thr Thr Pro Gly Asp Tyr Asp Thr Leu
465                 470                 475                 480

Gln Lys Arg Leu Ser Ala Leu Thr Gly Arg Ala Pro Thr Pro Pro Asp
            485                 490                 495

Phe Ser Leu Gly Tyr Ile Gln Ser Lys Leu Arg Tyr Glu Asn Gln Thr
            500                 505                 510

Glu Leu Glu Leu Leu Ala Gln Lys Phe Lys Asp Asn Asn Val Pro Val
            515                 520                 525

Gly Met Phe Val Ile Asp Tyr Gln Ser Trp Arg Asn Gly Asp Trp
            530                 535                 540

Gly Leu Asp Pro Ala Leu Trp Pro Asp Val Ala Ala Met Ala Lys Lys
545                 550                 555                 560

Val Lys Asp Leu Thr Gly Ala Glu Ile Met Ala Ser Leu Trp Pro Ser
            565                 570                 575

Val Ser Asp Ala Ser Asp Asn Tyr Leu Glu Leu Gln Ala Asn Gly Tyr
            580                 585                 590

Leu Ser Ala Thr Arg Asp Gly Pro Gly Thr Thr Asp Ser Trp Asn Gly
            595                 600                 605

Ser Tyr Ile Arg Asn Val Asp Ser Thr Asn Pro Gly Ala Arg Lys Phe
            610                 615                 620

Ile Trp Ser Thr Leu Lys Arg Asn Tyr Tyr Asp Lys Gly Ile Lys Asn
625                 630                 635                 640

Phe Trp Ile Asp Gln Ala Asp Gly Gly Ala Leu Gly Glu Ala Tyr Glu
            645                 650                 655

Asn Asn Gly Gln Ser Thr Tyr Ile Gln Ser Val Pro Phe Ala Leu Pro
            660                 665                 670

Asn Val Leu Tyr Ala Ala Gly Thr Gln Gln Ser Ala Gly Lys Tyr Tyr
            675                 680                 685

Pro Trp Ala His Gln Leu Ala Ile Glu Glu Gly Phe Arg Asn Val Thr
            690                 695                 700

Asp Ser Lys Glu Gly Glu Ala Cys Glu His Ile Ser Leu Ser Arg Ser
705                 710                 715                 720

Gly Tyr Ile Gly Ser Gln Arg Phe Cys Ser Met Ile Trp Ser Gly Asp
            725                 730                 735

Thr Thr Ser Ala Trp Glu Thr Leu Gly Leu Gln Val Ala Ser Gly Leu
            740                 745                 750
```

| | | | | | | | | | | | | |
|---|---|---|---|---|---|---|---|---|---|---|---|---|
|Ser|Ala|Ala|Ala|Thr|Gly|Trp|Gly|Trp|Trp|Thr|Met|Asp|Ala|Gly|Gly|
| | |755| | | |760| | | |765| | | | | |

Ser Ala Ala Ala Thr Gly Trp Gly Trp Trp Thr Met Asp Ala Gly Gly
           755                 760                765

Phe Gln Pro Asp Pro Thr Val Pro Trp Ser Ser Asn Ile Asp Thr Pro
    770             775                 780

Glu Tyr Arg Glu Leu Tyr Val Arg Trp Leu Gln Trp Ala Thr Phe Val
785             790                 795                     800

Pro Phe Met Arg Thr His Gly Gln Arg Val Cys Asp Asn Gln Asp Ala
            805                 810                 815

Tyr Thr Cys Asn Asn Glu Pro Trp Ser Tyr Gly Lys Asn Thr Pro
        820                 825                 830

Ile Ile Leu Ser Tyr Ile His Leu Arg Tyr Gln Leu Ala Ser Tyr Leu
            835                 840                 845

Arg Ala Leu Phe Asp Gln Phe His Lys Thr Gly Arg Met Ile Met Arg
850                 855                 860

Pro Leu Tyr Met Asp Phe Glu Lys Thr Asp Pro Lys Val Ser Gln Trp
865             870                 875                     880

Thr Gln Ala Asn Asn Val Thr Thr Gln Tyr Met Phe Gly Pro
                885                 890                 895

Arg Leu Leu Val Ser Pro Ile Thr Thr Pro Asn Val Thr Glu Trp Ser
            900                 905                 910

Val Tyr Leu Pro Gln Thr Gly Gln Asn Gly Thr Lys Pro Trp Thr Tyr
            915                 920                 925

Trp Trp Thr Asn Gln Thr Tyr Ala Gly Gly Gln Thr Val Thr Val Pro
            930                 935                 940

Ala Pro Val Glu His Ile Pro Val Phe His Leu Gly Lys Arg Glu Asp
945                 950                 955                 960

Ile Leu Ser Gly Asn Val Phe
                965

<210> SEQ ID NO 6
<211> LENGTH: 2904
<212> TYPE: DNA
<213> ORGANISM: A. flavus

<400> SEQUENCE: 6

```
atgctaattc ttgctttagg tgctgtaaag ttcgctggcg tgggacacca catcccatgg    60
ttaatggtga agaccctgc cagtctaaga atttgggcga atatctcct ggctttgtca    120
tttctctatt tgggaagtgt taatcttcca agttctcta tcctattact gtaccatagg    180
ctcttcccca caaagaaaat gggcgcgatc atcaaattga tgatggtggt cctgtgtgtc    240
atcacgatat ctacgatcgt tggcgcgagt ctcgtctgcc gaccgttctc cgctaactgg    300
gacggtccta tccctggcaa ctgtggtaac aagaaagttc tttacatctg gccagtttt    360
cctaacattg tgaccgatgt aattctactg ctccttccaa tgccagtgct gtggtcactt    420
aatgtcagtc cacgactgaa ggtaggactg acaatcacat cgcagtagg gagcataggc    480
ttagtcactt ccgttatgcg cttccagatc ttttttcgaa caacgcctt cctcgatggg    540
acctgggtag cggttgagct gattatatgg acccaagtcg agaccggggt ttacctgata    600
tctgcctgcc tgcccacata tagaccactt atcgaacacg gcttcaatcc aagatgttg    660
agcaaaatgt atcgctggct ggtggcccta acagtctgcg ccacacagct ggtgcaggcg    720
accccaatcc agacgcggga gtcggactac ttcctgccca actcgactgg atttcgcatg    780
cagcatggct tcgagactat tctggtacag ccctttggct tcgatgggtt ccgtgtgcgc    840
gcctggccct tccggccgcc tacgggccat gagatcagct tcatctacga tccaccattg    900
```

```
gaaggattcg agaatggaca agcgcatgga ctaacctttg acacggcatt taatggcaat    960
cacactgttg ctatccgcaa tggaaacact atcgtgcgca cctctggctg gggtggaaat   1020
cccggaggat atcggctggc attctaccgc atcgagcaag atggttctga gtcactgtta   1080
acaaacgagt atgcgccact caaatcgatc aatccacgat actactcgtg aacggcccg    1140
ggaagcgaat tttctgccga gttttcattc agtacggacc ccgacgagca gttctatggc   1200
acgggtacgc aacaggacca tcttgtcaac aagaaaggaa cggtcattga cttgatcaac   1260
ttcaataccc acatccccac acctgtgttc atgagcaaca agggctacgc cttcatctgg   1320
aatatgccag ctcagggtcg catggaattt ggacagctac gcaccaagct caccgcggag   1380
tccaccacgg tcgtcgacta tgtcattgtg ccacgacac caggcgacta cgacacattg    1440
cagaaacgtc tatccgccct gacgggtaga gcacccactc cgcctgactt ctcactcgga   1500
tacatccagt ctaagctccg ctatgagaac cagactgaac tagaactcct ggctcagaag   1560
ttcaaggaca caacgtccc cgttggaatg ttcgtcatcg actaccaatc ctggcggaat    1620
caaggcgact ggggtcttga cccagcgcta tggccggacg tagcagcaat ggcgaagaag   1680
gtaaaggatc tcaccggagc agagatcatg gcatctctct ggcccagtgt atcggatgcg   1740
agcgacaact acttggagct tcaagccaac ggatacctat ctgcgactcg cgacggaccc   1800
ggaaccaccg attcatggaa cggctcgtac atccgcaacg tggactctac gaacccaggc   1860
gcacggaaat tcatctggtc gaccttgaag cgcaactact acgacaaggg aatcaagaac   1920
ttctggatcg accaagctga cggtggtgcc ctgggcgaag cctacgaaaa caacggtcaa   1980
agcacctaca ttcagtctgt ccccttcgcc ctacccaacg tcctctacgc agctggcacc   2040
caacagagcg ccggaaaata ttaccctgg gcccaccagc tggcaatcga agagggcttc    2100
cgcaacgtca ccgacagcaa ggaaggcgaa gcctgcgagc acatctcgct cagtcggtct   2160
ggctacatcg gatctcaacg attctgcagc atgatctggt caggagacac cacctccgcc   2220
tgggaaacac taggcctcca agttgctagt ggactatccg ccgccgcaac aggatggggc   2280
tggtggacta tggacgcagg cggttttccaa cctgacccga cagtaccatg gagctctaac   2340
atcgacacac cggagtaccg cgagttgtac gtgcgctggc tgcagtgggc tacattcgtc   2400
cccttcatgc gtacacacgg tcagcgagtc tgcgacaacc aggacgcata cacatgtaac   2460
aacgagccgt ggtcgtatgg cgagaagaac accccacatta tcctctcgta cattcacctc   2520
cgataccaat tggcctcgta tctgcgtgcc ctcttcgacc agttccacaa gaccggtcgc   2580
atgatcatgc gtcccttgta tatggatttc gagaagactg atccgaaagt ttcacagtgg   2640
acgcaggcca acaacaatgt gacaacgcag cagtacatgt tcggccgcag attgctggta   2700
tcacctatta ccacgccgaa tgtcaccgaa tggtcggtat atctgccgca gacgggccag   2760
aatgggacga agccttggac gtactggtgg actaatcaga catatgctgg tggtcagacg   2820
gttactgtgc cggcgcctgt ggagcatatt cctgtgttcc atcttgggaa gagagaggat   2880
attctcagtg gtaatgtctt ctag                                         2904
```

<210> SEQ ID NO 7
<211> LENGTH: 736
<212> TYPE: PRT
<213> ORGANISM: Aspergillus kawachii

<400> SEQUENCE: 7

Met Tyr Phe Ser Ser Phe Leu Ala Leu Gly Ala Leu Ile Gln Ala Ala
 1               5                  10                  15

```
Ala Ala Thr Tyr Leu Ala Pro Asn Ser Thr Gly Leu Arg Ile Gln His
             20                  25                  30
Gly Phe Glu Thr Ile Leu Ile Gln Pro Phe Gly Tyr Asp Gly Phe Arg
         35                  40                  45
Val Arg Ala Trp Pro Phe Arg Pro Pro Ser Gly Asn Glu Ile Ser Phe
 50                  55                  60
Ile Tyr Asp Pro Pro Ile Glu Gly Tyr Glu Thr Ala His Gly Met
 65                  70                  75                  80
Ser Tyr Asp Thr Ala Thr Thr Gly Thr Glu Pro Arg Thr Leu Arg Asn
             85                  90                  95
Gly Asn Ile Ile Leu Arg Thr Thr Gly Trp Gly Gly Thr Ala Gly
            100                 105                 110
Tyr Arg Leu Ser Phe Tyr Arg Val Asn Asp Asp Gly Ser Glu Thr Leu
            115                 120                 125
Leu Thr Asn Glu Tyr Ala Pro Leu Lys Ser Leu Asn Pro Arg Tyr Tyr
130                 135                 140
Ser Trp Pro Gly Pro Gly Ala Glu Phe Ser Ala Glu Phe Ser Phe Ser
145                 150                 155                 160
Ala Thr Pro Asp Glu Gln Ile Tyr Gly Thr Gly Thr Gln Gln Asp His
                165                 170                 175
Met Ile Asn Lys Lys Gly Ser Val Ile Asp Leu Val Asn Phe Asn Thr
            180                 185                 190
His Ile Pro Thr Pro Val Phe Met Ser Asn Lys Gly Tyr Ala Phe Ile
            195                 200                 205
Trp Asn Met Pro Ala Glu Gly Arg Met Glu Phe Gly Ser Leu Arg Thr
210                 215                 220
Arg Phe Thr Ala Ala Ser Thr Thr Leu Val Asp Tyr Val Ile Val Ala
225                 230                 235                 240
Ala Gln Pro Gly Asp Tyr Asp Thr Leu Gln Gln Arg Ile Ser Ala Leu
                245                 250                 255
Thr Gly Arg Ala Pro Thr Pro Pro Asp Phe Ser Leu Gly Tyr Ile Gln
            260                 265                 270
Ser Lys Leu Arg Tyr Glu Asn Gln Thr Glu Val Glu Leu Leu Ala Gln
            275                 280                 285
Asn Phe His Asp Arg Asp Ile Pro Val Ser Met Ile Val Ile Asp Tyr
            290                 295                 300
Gln Ser Trp Ala His Gln Gly Asp Trp Ala Leu Asp Pro Arg Leu Trp
305                 310                 315                 320
Pro Asn Val Ala Gln Met Ser Ala Thr Val Lys Asn Leu Thr Gly Ala
                325                 330                 335
Glu Met Met Ala Ser Leu Trp Pro Ser Val Ala Asp Asp Ser Val Asn
            340                 345                 350
Tyr Ala Ala Leu Gln Ala Asn Gly Leu Leu Ser Ala Thr Arg Asp Gly
            355                 360                 365
Pro Gly Thr Thr Asp Ser Trp Asn Gly Ser Tyr Ile Arg Asn Tyr Asp
            370                 375                 380
Ser Thr Asn Pro Ser Ala Arg Lys Phe Leu Trp Ser Met Leu Lys Lys
385                 390                 395                 400
Asn Tyr Tyr Asp Lys Gly Ile Lys Asn Phe Trp Ile Asp Gln Ala Asp
                405                 410                 415
Gly Gly Ala Leu Gly Glu Ala Tyr Glu Asn Asn Gly Gln Ser Thr Tyr
            420                 425                 430
```

Ile Gln Ser Ile Pro Tyr Thr Leu Pro Asn Val Asn Tyr Ala Ala Gly
            435                 440                 445

Thr Gln Leu Gly Val Gly Lys Leu Tyr Pro Trp Ala His Gln Gln Ala
450                 455                 460

Ile Glu Glu Gly Phe Arg Asn Ala Thr Asp Thr Lys Glu Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
            500                 505                 510

Leu Ala Val Gln Val Ala Ser Gly Leu Ser Ala Ala Thr Gly Trp
            515                 520                 525

Gly Trp Trp Thr Val Asp Ala Gly Gly Phe Glu Val Asp Ser Thr Val
530                 535                 540

Trp Trp Ser Gly Asn Ile Asp Thr Pro Glu Phe Arg Glu Leu Tyr Val
545                 550                 555                 560

Arg Trp Leu Ala Cys Thr Thr Phe Leu Pro Phe Met Arg Thr His Gly
                565                 570                 575

Ser Arg Ala Cys Tyr Tyr Gln Asp Ala Tyr Thr Cys Ala Asn Glu Pro
            580                 585                 590

Trp Ser Tyr Gly Ala Ser Asn Thr Pro Ile Ile Val Ser Tyr Ile His
            595                 600                 605

Leu Arg Tyr Gln Leu Gly Ala Tyr Leu Lys Ser Ile Phe Asn Gln Phe
            610                 615                 620

His Leu Thr Gly Arg Ser Ile Met Arg Pro Leu Tyr Met Asp Phe Glu
625                 630                 635                 640

Lys Thr Asp Pro Lys Ile Ser Gln Leu Val Ser Ser Asn Ser Asn Tyr
                645                 650                 655

Thr Thr Gln Gln Tyr Met Phe Gly Pro Arg Leu Leu Val Ser Pro Val
            660                 665                 670

Thr Leu Pro Asn Val Thr Glu Trp Pro Val Tyr Leu Pro Gln Thr Gly
            675                 680                 685

Asp Asn Ser Thr Lys Pro Trp Thr Tyr Trp Trp Thr Asn Glu Thr Tyr
690                 695                 700

Ala Gly Gly Gln Val Val Lys Val Pro Ala Pro Val Gln His Ile Pro
705                 710                 715                 720

Val Phe His Leu Gly Ser Arg Glu Glu Leu Leu Ser Gly Asp Val Phe
                725                 730                 735

<210> SEQ ID NO 8
<211> LENGTH: 745
<212> TYPE: PRT
<213> ORGANISM: Aspergillus terreus

<400> SEQUENCE: 8

Met Tyr Arg Trp Leu Val Ala Leu Ala Ala Cys Ala Gly Gln Leu Ala
1               5                  10                  15

Leu Ala Asn Pro Val His Pro Arg Asp Thr Asp Tyr Phe Lys Pro Asn
            20                  25                  30

Ser Thr Gly Phe Arg Met Arg His Gly Phe Glu Thr Val Leu Val Gln
        35                  40                  45

Pro Phe Gly Tyr Asp Gly Phe Arg Val Arg Ala Trp Pro Phe Arg Pro
    50                  55                  60

Pro Thr Gly Gln Glu Leu Ser Phe Val Tyr Asp Pro Pro Leu Glu Gly
65                  70                  75                  80

```
Phe Glu Asp Gly Gln Ala His Gly Met Asp Tyr Asp Thr Ala Phe Thr
                85                  90                  95
Gly Asn Glu Ser Leu Ala Ile Arg Asn Gly Asn Met Ile Val Arg Thr
            100                 105                 110
Thr Gly Trp Gly Gly Asn Pro Gly Gly Tyr Arg Leu Ala Phe Tyr Arg
        115                 120                 125
Val Glu Glu Asp Gly Ser Glu Thr Leu Leu Thr Asn Glu Tyr Ala Pro
130                 135                 140
Leu Lys Ser Val Asn Pro Arg Tyr Tyr Ser Trp Asn Gly Pro Gly Ala
145                 150                 155                 160
Glu Phe Ser Ala Glu Phe Thr Phe Ser Thr Thr Pro Glu Gln Phe
                165                 170                 175
Tyr Gly Thr Gly Thr Gln Gln Asp His Leu Val Asn Lys Lys Gly Thr
                180                 185                 190
Val Ile Asp Leu Ile Asn Phe Asn Thr His Ile Pro Thr Pro Val Phe
            195                 200                 205
Met Ser Asn Lys Gly Tyr Gly Phe Val Trp Asn Met Ala Ser Glu Gly
        210                 215                 220
Arg Met Glu Phe Gly Gln Leu Arg Asn Lys Phe Thr Ala Ala Ser Ala
225                 230                 235                 240
Thr Leu Val Asp Tyr Val Ile Val Ala Ser Pro Ala Gly Asp Tyr Asp
                245                 250                 255
Thr Leu Gln Gln Arg Leu Ser Ala Leu Thr Gly Arg Ala Pro Thr Pro
                260                 265                 270
Pro Asp Phe Ala Leu Gly Tyr Ile Gln Ser Lys Leu Arg Tyr Glu Asn
                275                 280                 285
Gln Thr Glu Val Glu Leu Leu Ala Gln Asn Phe Lys Asp His Asn Ile
            290                 295                 300
Pro Val Gly Met Ile Val Ile Asp Tyr Gln Ser Trp Ala Asp Gln Gly
305                 310                 315                 320
Asp Trp Ala Leu Asp Pro Arg Leu Trp Pro Asp Val Ala Ala Met Ala
                325                 330                 335
Arg Lys Val Lys Glu Leu Thr Gly Ala Glu Met Met Ala Ser Leu Trp
            340                 345                 350
Pro Ser Val Ser Asp Asp Ser Val Asn Tyr Glu Ala Leu Gln Met Asn
        355                 360                 365
Gly Trp Leu Thr Ala Thr Arg Asp Gly Pro Gly Thr Thr Asp Ser Trp
    370                 375                 380
Asn Gly Ser Tyr Ile Arg Asn Ile Asp Ser Thr Asn Pro Asp Ala Arg
385                 390                 395                 400
Arg Phe Leu Trp Asp Thr Leu Lys Arg Asn Tyr Tyr Lys Gly Ile
                405                 410                 415
Arg Asn Phe Trp Ile Asp Gln Ala Asp Gly Gly Ala Leu Gly Glu Ala
                420                 425                 430
Tyr Glu Asn Asn Gly Gln Ser Leu Tyr Ile Gln Ser Ile Pro Tyr Ala
            435                 440                 445
Leu Pro Asn Val Leu Tyr Ala Ala Gly Thr Gln Leu Gly Val Gly Lys
        450                 455                 460
Met Tyr Pro Trp Thr His Gln Met Ala Ile Asp Glu Gly Phe Arg Asn
465                 470                 475                 480
Ala Thr Asp Ser Lys Pro Gly Ser Ala Cys Glu His Ile Ser Leu Ser
                485                 490                 495
```

```
Arg Ser Gly Tyr Ile Gly Ser Gln Arg Phe Cys Ser Met Ile Trp Ser
            500                 505                 510

Gly Asp Ile Thr Ser Val Trp Glu Thr Leu Gly Leu Gln Val Ala Ser
        515                 520                 525

Gly Leu Ser Ala Ala Ala Thr Gly Trp Gly Trp Trp Thr Val Asp Ala
    530                 535                 540

Gly Gly Phe Gln Pro Asp Pro Thr Val Pro Trp Ser Ala Asn Ile Asp
545                 550                 555                 560

Thr Pro Glu Tyr Arg Glu Leu Tyr Val Arg Trp Leu Gln Trp Thr Thr
                565                 570                 575

Phe Leu Pro Phe Met Arg Thr His Gly Ser Arg Glu Cys Asp Ser Gln
            580                 585                 590

Asn Ala Tyr Thr Cys Asn Asn Glu Pro Trp Ser Tyr Gly Glu Glu Asn
        595                 600                 605

Thr Pro Val Ile Val Ser Tyr Ile His Leu Arg Tyr Gln Leu Gly Ala
    610                 615                 620

Tyr Leu Arg Ala Ile Phe Lys Lys Phe His Glu Thr Gly Arg Ser Ile
625                 630                 635                 640

Met Arg Pro Leu Tyr Met Asp Phe Glu Lys Thr Asp Pro Arg Ile Arg
                645                 650                 655

Thr Met Thr Gln Ala Asn Thr Asn Val Thr Thr Gln Gln Tyr Met Phe
            660                 665                 670

Gly Pro Arg Leu Leu Val Ser Pro Val Thr Thr Pro Asn Thr Thr Glu
        675                 680                 685

Trp Pro Val Tyr Leu Pro Gln Thr Gly Gln Asn Gly Thr Lys Pro Trp
    690                 695                 700

Thr Tyr Trp Trp Thr Asn Glu Thr Tyr Ala Gly Gly Gln Thr Val Lys
705                 710                 715                 720

Val Pro Ala Pro Val Glu His Ile Pro Val Phe His Leu Gly Thr Arg
                725                 730                 735

Glu Glu Ile Leu Ser Gly Asp Val Phe
            740                 745

<210> SEQ ID NO 9
<211> LENGTH: 746
<212> TYPE: PRT
<213> ORGANISM: Neosartorya fischeri

<400> SEQUENCE: 9

Met Val Ser Ile Lys Arg Trp Leu Leu Gly Leu Cys Ala Val Ser Thr
1               5                   10                  15

Val Trp Ala Asn Pro Ile Gln Thr Arg Glu Ala Asp Tyr Val Met Pro
            20                  25                  30

Asn Ser Thr Gly Phe Arg Met Gln His Gly Phe Glu Thr Val Leu Val
        35                  40                  45

Gln Pro Phe Gly Tyr Asp Gly Phe Arg Val Arg Ala Trp Pro Tyr Arg
    50                  55                  60

Pro Pro Thr Gly Asn Glu Val Ser Phe Ile Tyr Asp Pro Pro Leu Glu
65                  70                  75                  80

Gly Phe Glu Asp Gly Met Ala His Gly Leu Gly Phe Asp Thr Ala Phe
                85                  90                  95

Asn Gly Asn Arg Thr Val Ala Ile Arg Asn Gly Lys Ile Val Val Arg
            100                 105                 110

Thr Ser Gly Trp Gly Gly Asn Pro Gly Gly Tyr Arg Leu Ala Phe Tyr
        115                 120                 125
```

-continued

Arg Val Glu Lys Asp Gly Ser Glu Thr Leu Leu Thr Asn Glu Tyr Ala
    130                 135                 140

Pro Leu Lys Ser Val Asn Pro Arg Tyr Tyr Phe Trp Arg Gly Pro Gly
145                 150                 155                 160

Ser Glu Phe Ser Ala Glu Phe Ser Phe Ser Thr Pro Asp Glu Gln
                165                 170                 175

Ile Tyr Gly Thr Gly Thr Gln Gln Asp His Met Val Asn Lys Lys Gly
            180                 185                 190

Ser Val Ile Asp Leu Ile Asn Phe Asn Thr His Ile Pro Thr Pro Val
        195                 200                 205

Ile Val Ser Asn Lys Gly Tyr Gly Phe Val Trp Asn Met Ala Ser Glu
    210                 215                 220

Gly Arg Met Glu Leu Gly Ala Leu Arg Thr Lys Phe Thr Ala Glu Ser
225                 230                 235                 240

Ala Thr Val Val Asp Tyr Ala Ile Val Ala Ala Glu Gln Gly Asp Tyr
                245                 250                 255

Asp Thr Leu Gln Arg Arg Leu Ser Ala Leu Thr Gly Arg Ala Pro Thr
            260                 265                 270

Pro Pro Glu Ala Ser Leu Gly Tyr Ile Gln Ser Lys Leu Arg Tyr Glu
        275                 280                 285

Asn Gln Thr Glu Val Glu Leu Leu Ala Gln Gln Phe Lys Asp His Asn
    290                 295                 300

Ile Pro Val Ser Met Ile Val Ile Asp Tyr Gln Ser Trp Ala His Gln
305                 310                 315                 320

Gly Asp Trp Ala Leu Asp Pro Arg Leu Trp Pro Asp Val Ala Ser Met
                325                 330                 335

Ala Lys Lys Val Lys Asp Leu Thr Gly Ala Glu Met Met Ala Ser Leu
            340                 345                 350

Trp Pro Ser Val Ala Asp Asn Ser Glu Asn Tyr Leu Glu Leu Ile Ala
        355                 360                 365

Asn Gly Leu Leu Ser Ala Thr Arg Ser Gly Pro Gly Thr Thr Asp Ser
    370                 375                 380

Trp Asn Gly Ser Tyr Ile Arg Asn Ile Asp Ser Thr Asn Pro Ala Ala
385                 390                 395                 400

Arg Ala Phe Leu Trp Lys Thr Leu Lys Arg Asn Tyr Tyr Asp Lys Gly
                405                 410                 415

Ile Lys Asn Phe Trp Ile Asp Gln Ala Asp Gly Gly Ala Leu Gly Glu
            420                 425                 430

Ala Tyr Glu Asn Asn Gly Gln Ser Tyr Ile Glu Ser Ile Pro Phe
        435                 440                 445

Ser Leu Pro Asn Val Leu Tyr Ala Ala Gly Thr Gln Leu Ser Ala Gly
    450                 455                 460

Lys Leu Tyr Pro Trp Ala His Gln Gln Ala Ile Glu Glu Gly Tyr Arg
465                 470                 475                 480

Asn Ala Thr Gly Thr Lys Met Gly Glu Ala Cys Asp His Ile Ser Leu
                485                 490                 495

Ser Arg Ser Gly Tyr Ile Gly Ser Gln Arg Phe Cys Ser Met Ile Trp
            500                 505                 510

Ser Gly Asp Thr Thr Ser Val Trp Asp Thr Leu Ala Val Gln Val Ala
        515                 520                 525

Ser Gly Leu Ser Ala Ala Ala Thr Gly Trp Gly Trp Trp Thr Met Asp
    530                 535                 540

```
Ala Gly Gly Phe Gln Ala Asp Pro Thr Val Pro Trp Ser Ser Asn Ile
545                 550                 555                 560

Asp Thr Pro Glu Tyr Arg Glu Leu Tyr Val Arg Trp Phe Gln Trp Ala
                565                 570                 575

Ala Phe Leu Pro Phe Met Arg Thr His Gly Ser Arg Lys Cys Asn Val
            580                 585                 590

Gln Asn Ala Tyr Thr Cys Asn Asn Glu Pro Trp Ser Tyr Gly Glu Glu
        595                 600                 605

Asn Thr Pro Ile Ile Val Ser Tyr Ile Gln Leu Arg Tyr Gln Leu Lys
    610                 615                 620

Ala Tyr Leu Gln Ala Val Phe Glu Gln Phe His His Thr Gly Arg Ala
625                 630                 635                 640

Leu Met Arg Pro Leu Tyr Met Asp Phe Glu Arg Thr Asp Pro Gln Ile
                645                 650                 655

Ala Lys Met Thr Arg Glu Asn Val Asn Ala Thr Thr Gln Gln Tyr Met
            660                 665                 670

Leu Gly Pro Arg Leu Leu Val Thr Pro Val Thr Leu Pro Asn Ala Thr
        675                 680                 685

Glu Trp Glu Val Tyr Leu Pro Leu Thr Ala Gln Asn Glu Thr Lys Pro
    690                 695                 700

Trp Thr Tyr Trp Trp Thr Asn Glu Thr Tyr Ala Gly Gly Gln Thr Val
705                 710                 715                 720

Thr Val Pro Ala Pro Ile Glu His Ile Pro Leu Phe Tyr Leu Gly Lys
                725                 730                 735

Arg Glu Asp Ile Leu Ser Gly Ser Val Phe
            740                 745

<210> SEQ ID NO 10
<211> LENGTH: 967
<212> TYPE: PRT
<213> ORGANISM: Aspergillus flavus

<400> SEQUENCE: 10

Met Leu Ile Leu Ala Leu Gly Ala Val Lys Phe Ala Gly Val Gly His
1               5                   10                  15

His Ile Pro Trp Leu Met Val Lys Asp Pro Ala Ser Leu Arg Ile Trp
            20                  25                  30

Ala Lys Tyr Leu Leu Ala Leu Ser Phe Leu Tyr Leu Gly Ser Val Asn
        35                  40                  45

Leu Pro Lys Phe Ser Ile Leu Leu Tyr His Arg Leu Phe Pro Thr
    50                  55                  60

Lys Lys Met Gly Ala Ile Ile Lys Leu Met Met Val Val Leu Cys Val
65                  70                  75                  80

Ile Thr Ile Ser Thr Ile Val Gly Ala Ser Leu Val Cys Arg Pro Phe
                85                  90                  95

Ser Ala Asn Trp Asp Gly Pro Ile Pro Gly Asn Cys Gly Asn Lys Lys
            100                 105                 110

Val Leu Tyr Ile Trp Ala Ser Phe Pro Asn Ile Val Thr Asp Val Ile
        115                 120                 125

Leu Leu Leu Leu Pro Met Pro Val Leu Trp Ser Leu Asn Val Ser Pro
    130                 135                 140

Arg Leu Lys Val Gly Leu Thr Ile Thr Phe Ala Val Gly Ser Ile Gly
145                 150                 155                 160

Leu Val Thr Ser Val Met Arg Phe Gln Ile Phe Phe Arg Asn Asn Ala
                165                 170                 175
```

```
Phe Leu Asp Gly Thr Trp Val Ala Val Glu Leu Ile Ile Trp Thr Gln
            180                 185                 190
Val Glu Thr Gly Val Tyr Leu Ile Ser Ala Cys Leu Pro Thr Tyr Arg
            195                 200                 205
Pro Leu Ile Glu His Gly Phe Asn Pro Lys Met Leu Ser Lys Met Tyr
            210                 215                 220
Arg Trp Leu Val Ala Leu Thr Val Cys Ala Thr Gln Leu Val Gln Ala
225                 230                 235                 240
Thr Pro Ile Gln Thr Arg Glu Ser Asp Tyr Phe Leu Pro Asn Ser Thr
            245                 250                 255
Gly Phe Arg Met Gln His Gly Phe Glu Thr Ile Leu Val Gln Pro Phe
            260                 265                 270
Gly Phe Asp Gly Phe Arg Val Arg Ala Trp Pro Phe Arg Pro Pro Thr
            275                 280                 285
Gly His Glu Ile Ser Phe Ile Tyr Asp Pro Pro Leu Glu Gly Phe Glu
            290                 295                 300
Asn Gly Gln Ala His Gly Leu Thr Phe Asp Thr Ala Phe Asn Gly Asn
305                 310                 315                 320
His Thr Val Ala Ile Arg Asn Gly Asn Thr Ile Val Arg Thr Ser Gly
            325                 330                 335
Trp Gly Gly Asn Pro Gly Gly Tyr Arg Leu Ala Phe Tyr Arg Ile Glu
            340                 345                 350
Gln Asp Gly Ser Glu Ser Leu Leu Thr Asn Glu Tyr Ala Pro Leu Lys
            355                 360                 365
Ser Ile Asn Pro Arg Tyr Tyr Ser Trp Asn Gly Pro Gly Ser Glu Phe
370                 375                 380
Ser Ala Glu Phe Ser Phe Ser Thr Asp Pro Asp Glu Gln Phe Tyr Gly
385                 390                 395                 400
Thr Gly Thr Gln Gln Asp His Leu Val Asn Lys Lys Gly Thr Val Ile
            405                 410                 415
Asp Leu Ile Asn Phe Asn Thr His Ile Pro Thr Pro Val Phe Met Ser
            420                 425                 430
Asn Lys Gly Tyr Ala Phe Ile Trp Asn Met Pro Ala Gln Gly Arg Met
            435                 440                 445
Glu Phe Gly Gln Leu Arg Thr Lys Leu Thr Ala Glu Ser Thr Thr Val
            450                 455                 460
Val Asp Tyr Val Ile Val Ala Thr Thr Pro Gly Asp Tyr Asp Thr Leu
465                 470                 475                 480
Gln Lys Arg Leu Ser Ala Leu Thr Gly Arg Ala Pro Thr Pro Pro Asp
            485                 490                 495
Phe Ser Leu Gly Tyr Ile Gln Ser Lys Leu Arg Tyr Glu Asn Gln Thr
            500                 505                 510
Glu Leu Glu Leu Leu Ala Gln Lys Phe Lys Asp Asn Asn Val Pro Val
            515                 520                 525
Gly Met Phe Val Ile Asp Tyr Gln Ser Trp Arg Asn Gln Gly Asp Trp
            530                 535                 540
Gly Leu Asp Pro Ala Leu Trp Pro Asp Val Ala Ala Met Ala Lys Lys
545                 550                 555                 560
Val Lys Asp Leu Thr Gly Ala Glu Ile Met Ala Ser Leu Trp Pro Ser
            565                 570                 575
Val Ser Asp Ala Ser Asp Asn Tyr Leu Glu Leu Gln Ala Asn Gly Tyr
            580                 585                 590
```

```
Leu Ser Ala Thr Arg Asp Gly Pro Gly Thr Thr Asp Ser Trp Asn Gly
            595                 600                 605

Ser Tyr Ile Arg Asn Val Asp Ser Thr Asn Pro Gly Ala Arg Lys Phe
610                 615                 620

Ile Trp Ser Thr Leu Lys Arg Asn Tyr Tyr Asp Lys Gly Ile Lys Asn
625                 630                 635                 640

Phe Trp Ile Asp Gln Ala Asp Gly Gly Ala Leu Gly Glu Ala Tyr Glu
                645                 650                 655

Asn Asn Gly Gln Ser Thr Tyr Ile Gln Ser Val Pro Phe Ala Leu Pro
            660                 665                 670

Asn Val Leu Tyr Ala Ala Gly Thr Gln Gln Ser Ala Gly Lys Tyr Tyr
            675                 680                 685

Pro Trp Ala His Gln Leu Ala Ile Glu Glu Gly Phe Arg Asn Val Thr
690                 695                 700

Asp Ser Lys Glu Gly Glu Ala Cys Glu His Ile Ser Leu Ser Arg Ser
705                 710                 715                 720

Gly Tyr Ile Gly Ser Gln Arg Phe Cys Ser Met Ile Trp Ser Gly Asp
                725                 730                 735

Thr Thr Ser Ala Trp Glu Thr Leu Gly Leu Gln Val Ala Ser Gly Leu
            740                 745                 750

Ser Ala Ala Ala Thr Gly Trp Gly Trp Trp Thr Met Asp Ala Gly Gly
            755                 760                 765

Phe Gln Pro Asp Pro Thr Val Pro Trp Ser Ser Asn Ile Asp Thr Pro
770                 775                 780

Glu Tyr Arg Glu Leu Tyr Val Arg Trp Leu Gln Trp Ala Thr Phe Val
785                 790                 795                 800

Pro Phe Met Arg Thr His Gly Gln Arg Val Cys Asp Asn Gln Asp Ala
                805                 810                 815

Tyr Thr Cys Asn Asn Glu Pro Trp Ser Tyr Gly Glu Lys Asn Thr Pro
            820                 825                 830

Ile Ile Leu Ser Tyr Ile His Leu Arg Tyr Gln Leu Ala Ser Tyr Leu
            835                 840                 845

Arg Ala Leu Phe Asp Gln Phe His Lys Thr Gly Arg Met Ile Met Arg
850                 855                 860

Pro Leu Tyr Met Asp Phe Glu Lys Thr Asp Pro Lys Val Ser Gln Trp
865                 870                 875                 880

Thr Gln Ala Asn Asn Asn Val Thr Thr Gln Gln Tyr Met Phe Gly Pro
                885                 890                 895

Arg Leu Leu Val Ser Pro Ile Thr Thr Pro Asn Val Thr Glu Trp Ser
            900                 905                 910

Val Tyr Leu Pro Gln Thr Gly Gln Asn Gly Thr Lys Pro Trp Thr Tyr
            915                 920                 925

Trp Trp Thr Asn Gln Thr Tyr Ala Gly Gly Gln Thr Val Thr Val Pro
930                 935                 940

Ala Pro Val Glu His Ile Pro Val Phe His Leu Gly Lys Arg Glu Asp
945                 950                 955                 960

Ile Leu Ser Gly Asn Val Phe
                965
```

<210> SEQ ID NO 11
<211> LENGTH: 749
<212> TYPE: PRT
<213> ORGANISM: Aspergillus oryzae

<400> SEQUENCE: 11

-continued

```
Met Leu Ser Lys Met Tyr Arg Trp Leu Val Ala Leu Thr Val Cys Ala
 1               5                  10                  15

Thr Gln Leu Val Gln Ala Thr Pro Ile Gln Thr Arg Glu Ser Asp Tyr
                20                  25                  30

Phe Leu Pro Asn Ser Thr Gly Phe Arg Met Gln His Gly Phe Glu Thr
             35                  40                  45

Ile Leu Val Gln Pro Phe Gly Phe Asp Gly Phe Arg Val Arg Ala Trp
 50                  55                  60

Pro Phe Arg Pro Pro Thr Gly His Glu Ile Ser Phe Ile Tyr Asp Pro
 65                  70                  75                  80

Pro Leu Glu Gly Phe Glu Asn Gly Gln Ala His Gly Leu Thr Phe Asp
                 85                  90                  95

Thr Ala Phe Asn Gly Asn His Thr Val Ala Ile Arg Asn Gly Asn Thr
                100                 105                 110

Ile Val Arg Thr Ser Gly Trp Gly Gly Asn Pro Gly Gly Tyr Arg Leu
            115                 120                 125

Ala Phe Tyr Arg Ile Glu Gln Asp Gly Ser Glu Ser Leu Leu Thr Asn
130                 135                 140

Glu Tyr Ala Pro Leu Lys Ser Ile Asn Pro Arg Tyr Tyr Ser Trp Asn
145                 150                 155                 160

Gly Pro Gly Ser Glu Phe Ser Ala Glu Phe Ser Phe Ser Thr Thr Pro
                165                 170                 175

Asp Glu Gln Phe Tyr Gly Thr Gly Thr Gln Gln Asp His Leu Val Asn
                180                 185                 190

Lys Lys Gly Thr Val Ile Asp Leu Ile Asn Phe Asn Thr His Ile Pro
            195                 200                 205

Thr Pro Val Phe Met Ser Asn Lys Gly Tyr Ala Phe Ile Trp Asn Met
210                 215                 220

Pro Ala Gln Gly Arg Met Glu Phe Gly Gln Leu Arg Thr Lys Leu Thr
225                 230                 235                 240

Ala Glu Ser Thr Thr Val Val Asp Tyr Val Ile Val Ala Thr Thr Pro
                245                 250                 255

Gly Asp Tyr Asp Thr Leu Gln Lys Arg Leu Ser Ala Leu Thr Gly Arg
                260                 265                 270

Ala Pro Thr Pro Pro Asp Phe Ser Leu Gly Tyr Ile Gln Ser Lys Leu
            275                 280                 285

Arg Tyr Glu Asn Gln Thr Glu Leu Glu Leu Ala Gln Lys Phe Lys
290                 295                 300

Asp Asn Asn Val Pro Val Gly Met Ile Val Ile Asp Tyr Gln Ser Trp
305                 310                 315                 320

Arg Asn Gln Gly Asp Trp Gly Leu Asp Pro Ala Leu Trp Pro Asp Val
                325                 330                 335

Ala Ala Met Ala Lys Lys Val Lys Asp Leu Thr Gly Ala Glu Ile Met
                340                 345                 350

Ala Ser Leu Trp Pro Ser Val Ser Asp Ala Ser Asp Asn Tyr Leu Glu
            355                 360                 365

Leu Gln Ala Asn Gly Tyr Leu Ser Ala Thr Arg Asp Gly Pro Gly Thr
370                 375                 380

Thr Asp Ser Trp Asn Gly Ser Tyr Ile Arg Asn Val Asp Ser Thr Asn
385                 390                 395                 400

Pro Gly Ala Arg Lys Phe Ile Trp Ser Thr Leu Lys Arg Asn Tyr Tyr
                405                 410                 415
```

```
Glu Lys Gly Ile Lys Asn Phe Trp Ile Asp Gln Ala Asp Gly Ala
            420                 425                 430

Leu Gly Glu Ala Tyr Glu Asn Asn Gly Gln Ser Thr Tyr Ile Gln Ser
        435                 440                 445

Val Pro Phe Ala Leu Pro Asn Val Leu Tyr Ala Ala Gly Thr Gln Gln
450                 455                 460

Ser Ala Gly Lys Tyr Tyr Pro Trp Ala His Gln Leu Ala Ile Glu Glu
465                 470                 475                 480

Gly Phe Arg Asn Val Thr Asp Ser Lys Glu Gly Glu Ala Cys Glu His
                485                 490                 495

Ile Ser Leu Ser Arg Ser Gly Tyr Ile Gly Ser Gln Arg Phe Cys Ser
            500                 505                 510

Met Ile Trp Ser Gly Asp Thr Thr Ser Ala Trp Glu Thr Leu Gly Leu
        515                 520                 525

Gln Ile Ala Ser Arg Leu Ser Ala Ala Thr Gly Trp Gly Trp Trp
530                 535                 540

Thr Met Asp Ala Gly Gly Phe Gln Pro Asp Pro Thr Val Pro Trp Ser
545                 550                 555                 560

Ser Asn Ile Asp Thr Pro Glu Tyr Arg Glu Leu Tyr Val Arg Trp Leu
                565                 570                 575

Gln Trp Ala Thr Phe Val Pro Phe Met Arg Thr His Gly Gln Arg Val
            580                 585                 590

Cys Asp Asn Gln Asp Ala Tyr Thr Cys Asn Asn Glu Pro Trp Ser Tyr
        595                 600                 605

Gly Glu Lys Asn Thr Pro Ile Ile Leu Ser Tyr Ile His Leu Arg Tyr
610                 615                 620

Gln Leu Ala Ser Tyr Leu Arg Ala Leu Phe Asp Gln Phe His Lys Thr
625                 630                 635                 640

Gly Arg Met Ile Met Arg Pro Leu Tyr Met Asp Phe Glu Lys Thr Asp
                645                 650                 655

Pro Lys Val Ser Gln Trp Thr Gln Ala Asn Asn Val Thr Thr Gln
            660                 665                 670

Gln Tyr Met Phe Gly Pro Arg Leu Leu Val Ser Pro Ile Thr Thr Pro
        675                 680                 685

Asn Val Thr Glu Trp Ser Val Tyr Leu Pro Gln Thr Gly Gln Asn Gly
690                 695                 700

Thr Lys Pro Trp Thr Tyr Trp Trp Thr Asn Gln Thr Tyr Ala Gly Gly
705                 710                 715                 720

Gln Thr Val Thr Val Pro Ala Pro Val Glu His Ile Pro Val Phe His
                725                 730                 735

Leu Gly Lys Arg Glu Asp Ile Leu Ser Gly Asn Val Phe
            740                 745

<210> SEQ ID NO 12
<211> LENGTH: 741
<212> TYPE: PRT
<213> ORGANISM: Macrophomina phaseolina

<400> SEQUENCE: 12

Met His Leu Leu Tyr Ser Leu Val Ser Leu Pro Leu Leu Thr Val Ser
 1               5                  10                  15

Ala Gln Asn Ile Thr Ser Glu Tyr Phe Ala Pro Asn Ser Thr Gly Phe
                20                  25                  30

Arg Met Thr His Gly Phe Glu Thr Ile Leu Val Gln Pro Tyr Gly Tyr
            35                  40                  45
```

```
Asp Gly Phe Arg Val Arg Ala Trp Pro Phe Arg Pro Pro Asn Gly Asn
 50                  55                  60

Glu Ile Ser Phe Leu Tyr Asp Pro Pro Leu Glu Gly Pro Glu Asn Gly
 65                  70                  75                  80

Glu Ala Arg Ala Met Ser Tyr Asp Phe Thr Thr Asn Gly Asn Gln Ser
                 85                  90                  95

Ala Ile Ile Arg Asn Gly Asn Thr Val Val Lys Thr Tyr Gly Leu Glu
                100                 105                 110

Gly Ala His Tyr Arg Leu Ala Phe Tyr Arg Ile Glu Pro Asp Gly Thr
                115                 120                 125

Glu Thr Leu Leu Thr Asn Glu Phe Asn Pro Val Lys Ala Leu Asn Pro
130                 135                 140

Arg Tyr Tyr Ser Trp Thr Ser Thr Gly Tyr Glu Phe Ser Ala Ser Phe
145                 150                 155                 160

Ser Phe Thr Thr Thr Pro Asp Glu Gln Ile Phe Gly Thr Gly Thr Gln
                165                 170                 175

Gln Asp Phe Leu Leu Asn Lys Lys Gly Ser Val Ile Asp Met Ile Asn
                180                 185                 190

Phe Asn Ser Tyr Ile Pro Thr Pro Val Phe Met Ser Ser Lys Gly Tyr
                195                 200                 205

Gly Phe Val Trp Asn Ser Ala Ala Gln Gly Arg Met Glu Phe Gly Pro
210                 215                 220

Arg Arg Asn Lys Phe Thr Ser Asp Ser Thr Thr Leu Val Asp Tyr Ala
225                 230                 235                 240

Ile Val Ser Ala Pro Glu Gly Asp Tyr Asp Ser Leu Gln Gln Lys Leu
                245                 250                 255

Thr Ala Ile Thr Gly Arg Ala Pro Thr Pro Pro Asp Phe Ser Leu Gly
                260                 265                 270

Tyr Leu His Ser Lys Leu Arg Tyr Glu Asn Gln Thr Glu Val Val Leu
                275                 280                 285

Leu Ala Gln Gly Phe Arg Asp Arg Asn Ile Pro Val Ser Met Ile Val
290                 295                 300

Ile Asp Tyr Glu Ser Trp Ala Gln Asn Gly Asp Trp Gly Leu Asp Pro
305                 310                 315                 320

Ala Leu Trp Pro Asp Val Ala Ser Met Ala Ala Gln Val Lys Asn Leu
                325                 330                 335

Thr Gly Ala Glu Met Met Ala Ser Leu Trp Pro Ala Val Glu Asp Asp
                340                 345                 350

Ser Leu Asn Tyr Ala Glu Met Gln Gln Leu Gly Leu Leu Ala Ala Thr
                355                 360                 365

Met Ser Gly Pro Gly Thr Thr Asp Ser Trp Asn Gly Ser Tyr Ile Arg
370                 375                 380

Asn Tyr Asp Ser Thr Asn Pro Arg Ala Arg Glu Phe Leu Trp Asn Thr
385                 390                 395                 400

Leu Lys Arg Asn Tyr Tyr Asp Lys Gly Ile Lys Asn Phe Trp Ile Asp
                405                 410                 415

Gln Ala Asp Gly Gly Ala Leu Gly Glu Ala Trp Glu Asn Asn Gly Gln
                420                 425                 430

Thr Ala Tyr Val Gln Ser Ile Pro Tyr Pro Leu Pro Gln Val Leu Tyr
                435                 440                 445

His Ala Gly Thr Gln Ala Ser Val Gly Lys Leu Tyr Pro Trp Ala His
450                 455                 460
```

```
Gln Gln Ala Ile Glu Glu Gly Thr Arg Asn Ala Thr Gly Thr Glu Gln
465                 470                 475                 480

Gly Thr Ala Cys Asp Tyr Ile Ser Leu Ser Arg Ser Gly Tyr Ile Gly
                485                 490                 495

Ser Gln Arg Phe Cys Ser Met Ile Trp Ser Gly Asp Thr Glu Ala Ser
            500                 505                 510

Trp Glu Val Leu Gly Asn Gln Ile Pro Asn Ala Leu Ser Ala Ala Ala
        515                 520                 525

Thr Gly Trp Ser Trp Tyr Thr Val Asp Ala Gly Phe Gln Pro Asp
    530                 535                 540

Pro Ala Ile Glu Trp Ser Asn Asn Ile Asp Arg Pro Glu Tyr Arg Glu
545                 550                 555                 560

Leu Tyr Val Arg Trp Leu Gln Trp Thr Thr Phe Leu Pro Phe Met Arg
                565                 570                 575

Asn His Gly Ser Arg Ala Cys Asp Val Gln His Ala Phe Thr Cys Asp
            580                 585                 590

Asn Glu Pro Trp Thr Tyr Gly Ala Gln Asn Thr Pro Thr Ile Val Ser
        595                 600                 605

Tyr Ile Asn Leu Arg Tyr Arg Leu Ala Pro Tyr Val Arg Ala Leu Phe
    610                 615                 620

Glu Gln Leu Ser Arg Thr Gly Arg Gln Ile Leu Arg Pro Leu Phe Met
625                 630                 635                 640

Asp Phe Gly Lys Ser Asp Ala Asn Val Val Ala Trp Thr Arg Glu Asn
                645                 650                 655

Lys Asn Ile Thr Thr Gln Gln Tyr Met Phe Gly Pro Arg Leu Leu Val
            660                 665                 670

Ala Pro Val Val Leu Pro Asn Val Thr Thr Trp Pro Val Tyr Leu Pro
        675                 680                 685

Lys Thr Ala Gly Glu Gly Ser Gly Gln Arg Pro Trp Thr Tyr Trp Trp
    690                 695                 700

Thr Asn Glu Thr Phe Ala Gly Gly Gln Thr Val Asn Val Ser Ala Pro
705                 710                 715                 720

Val Glu His Ile Pro Leu Phe Tyr Leu Gly Asp Arg Asp Ile Phe
                725                 730                 735

Ser Gly Asn Val Phe
            740

<210> SEQ ID NO 13
<211> LENGTH: 751
<212> TYPE: PRT
<213> ORGANISM: Serpula lacrymans

<400> SEQUENCE: 13

Met Pro Tyr Lys Pro Ser Arg Asn Ile Val Arg Leu Cys Val Pro Ser
 1               5                  10                  15

Arg Thr Cys Lys Met Leu Gly Ile Leu Ser Ile Val Ala Val Ile Thr
                20                  25                  30

Thr Ala Tyr Ala Ala Asn Thr Ser Ile Pro Ser Ser Thr Gly Ile Lys
            35                  40                  45

Leu Gln Asn Gly Phe Glu Arg Val Tyr Ile Gln Pro Phe Gly Asn Asn
        50                  55                  60

Gly Ile Arg Val Arg Ala Ser Leu Leu Arg Asp Pro Thr Gly Asn Glu
65                  70                  75                  80

Leu Ser Ala Leu Leu Asp Pro Pro Leu Glu Gly Pro Gly Gly Asn Gln
                85                  90                  95
```

```
Gly Leu Ala Tyr Asp Gln Leu Val Gly Phe Gln Gly Asn Ala Asn Leu
                100                 105                 110

Thr Asn Gly Asn Ile Ala Ala Glu Ile Ala Thr Gly Tyr Leu Ser Phe
            115                 120                 125

Tyr Arg Ile Glu Ser Asn Gly Ser Arg Thr Leu Leu Thr Ser Glu Phe
130                 135                 140

Thr Asp Asp Lys Ala Leu Tyr Pro Arg Tyr Tyr Ile Gln Glu Tyr Lys
145                 150                 155                 160

Ser Pro Ser Phe Ser Ala Glu Phe Ser Phe Thr Ala Glu Pro Asp Glu
                165                 170                 175

Gln Ile Tyr Gly Val Gly Gln Gln Ala Cys Cys Lys Asp Asn Ser Val
            180                 185                 190

Asn Lys Lys Gly Gln Ser Ile Asp Leu Ile Asn Phe Asn Ser Phe Val
        195                 200                 205

Pro Leu Pro Val Tyr Met Ser Asn Lys Gly Tyr Leu Gln Phe Phe Asn
    210                 215                 220

Met Pro Ser Gln Gly Arg Met Glu Phe Ser Pro Ile Arg Thr Arg Phe
225                 230                 235                 240

Val Ser Ser Glu Ala Thr Val Val Asp Tyr Trp Ile Thr Thr Ala Glu
                245                 250                 255

Pro Gly Asp Tyr Asp Thr Leu Gln Glu Gln Tyr Thr Ala Val Thr Gly
            260                 265                 270

Arg Gln Pro Thr Pro Pro Thr Phe Thr His Gly Tyr Gln Gln Ser Lys
        275                 280                 285

Leu Arg Tyr Phe Asn Gln Thr Gln Val Glu Asp Leu Ala Gln Glu Phe
    290                 295                 300

His Asp Arg Gln Ile Asn Val Ser Leu Ile Val Ile Asp Phe Phe Asn
305                 310                 315                 320

Trp Lys Tyr Gln Gly Asp Trp Ser Phe Asp Pro Glu Tyr Trp Pro Asp
                325                 330                 335

Pro Ala Ala Met Thr Ala Lys Val Lys Glu Leu Thr Gly Ala Glu Met
            340                 345                 350

Met Val Ser Leu Trp Pro Ser Val Glu Asp Leu Ser Val Asn Tyr Leu
        355                 360                 365

Thr Leu Gln Glu Gln Gly Leu Leu Ala Thr Thr Arg Asp Gly Thr Gly
    370                 375                 380

Ile Ser Asp Ser Phe Ala Gly Val Tyr Thr Arg Leu Ile Asp Ser Thr
385                 390                 395                 400

Asn Pro Ala Ser Arg Glu Phe Leu Trp Lys Arg Leu Asn Glu Ser Tyr
                405                 410                 415

Phe Ser Asn Gly Ile His Asn Phe Trp Ile Asp Gln Ala Asp Gly Gly
            420                 425                 430

Thr Leu Gly Glu Ala Phe Glu Asn Asn Gly Gln Thr Ile Glu Thr Ile
        435                 440                 445

Pro Tyr Ala Arg Ala Phe Ser Gln Tyr Phe Ile Gly Thr Gln Glu Gly
    450                 455                 460

Ala Gly Lys Met Tyr Pro Trp Leu His Gln Gln Ala Ile Asn Glu Gly
465                 470                 475                 480

Leu His Asn Leu Thr Asp Thr Pro Ala Thr Ala Thr Ser Cys Glu Tyr
                485                 490                 495

Met Ser Leu Thr Arg Ser Thr Phe Ala Gly Gly Gln Arg Tyr Cys Ser
            500                 505                 510
```

```
Tyr Leu Trp Ser Gly Asp Thr Met Ala Glu Phe Pro Val Leu Leu Gln
            515                 520                 525

Gln Ile Thr Ser Ala Val Ser Ala Ala Ser Gly Ile Ser Ser Trp
        530                 535                 540

Thr Leu Asp Leu Gly Gly Phe Thr Gly Leu Asp Ile Asp Thr Ala Tyr
545                 550                 555                 560

Gly Lys Glu Leu Tyr Val Arg Trp Phe Ala Met Gly Val Phe Leu Pro
                565                 570                 575

Tyr Met Arg Thr His Gly Asp Arg Ile Cys Asp Ile Pro Pro Thr
            580                 585                 590

Thr Pro Ser Asn Ala Asn Tyr Cys Pro Asn Glu Pro Trp Ser Tyr Gly
            595                 600                 605

Glu Glu Asn Tyr Pro Ile Leu Lys Met Tyr Ile Glu Leu Arg Tyr Lys
610                 615                 620

Leu Val Pro Tyr Val Thr Gln Leu Phe Ala Met Leu Gln Asn Asn Gly
625                 630                 635                 640

Arg Thr Ile Met Arg Ala Leu Tyr Phe Asp Phe Ser Leu Ser Asp Pro
                645                 650                 655

Phe Val Ala Ser Ala Thr Ala Ala Asn Asp Pro Leu Val Ser His Gln
                660                 665                 670

Phe Met Phe Gly Pro Arg Ile Leu Val Ser Pro Val Gly Val Gln Asn
            675                 680                 685

Ala Thr Ser Lys Glu Val Tyr Leu Pro Arg Leu Thr Gln Ala Met Leu
            690                 695                 700

Asp Gln Asn Tyr Thr Trp Thr His Trp Trp Thr Asn Thr Ser Tyr Gly
705                 710                 715                 720

Gln Gly Gly Ala Ser Val Asn Val Ser Ala Pro Leu Asp Gln Ile Pro
                725                 730                 735

Val Phe Tyr Leu Gly Ser Met Ala Asp Ile Leu Ser Gly Asn Ile
            740                 745                 750

<210> SEQ ID NO 14
<211> LENGTH: 737
<212> TYPE: PRT
<213> ORGANISM: Agaricus bisporus

<400> SEQUENCE: 14

Met Val Leu Gln Ser Leu Ile Leu Cys Tyr Leu Val Leu Pro Ile Ser
 1               5                  10                  15

Leu Ser Leu Ala Ala Asp Tyr Phe Asn Pro Asn Ala Thr Gly Ile Lys
            20                  25                  30

Leu Gln Asn Gly Phe Glu Arg Ile His Ile Gln Pro Phe Gly Asn His
        35                  40                  45

Gly Phe Arg Val Arg Ala Ser Leu Leu Arg Asp Pro Thr Gly Arg Glu
    50                  55                  60

Pro Ser Ala Leu Ile Asp Pro Leu Glu Gly Pro Ser Ser Lys Gly
65                  70                  75                  80

Leu Glu His Ser Ile Thr Ile Pro Phe Arg Gly Asn Ala Thr Val Arg
                85                  90                  95

Asn Gly Asn Leu Val Val Asp Val Ser Phe Gly Val Thr Ser Phe Ser
            100                 105                 110

Arg Val Glu Pro Asn Gly Thr Leu Thr Leu Leu Thr Ser Glu Tyr Ala
        115                 120                 125

Asp Thr Lys Val Leu Pro Ala Arg Tyr Tyr Val Gln Asp Ile His Gly
    130                 135                 140
```

```
Gln Ser Phe Gln Ala Gln Phe Gly Phe Ser Ala Asp Pro Asp Glu Met
145                 150                 155                 160

Phe Phe Gly Thr Gly Gln His Ala Cys Cys Lys Asp His Thr Val Asn
            165                 170                 175

Lys Lys Gly Gln Ile Val Asp Leu Ile Asn Tyr Asn Ser His Val Thr
            180                 185                 190

Leu Pro Ile Trp Met Ser Asn Lys Gly Tyr Leu Met Phe Phe Asn Tyr
            195                 200                 205

Pro Gly Gln Gly Arg Ile Glu Phe Asp Arg Leu Arg Thr Arg Phe Val
            210                 215                 220

Ala Asp Glu Ala Thr Val Val Asp Tyr Trp Ile Thr Thr Ala Pro Pro
225                 230                 235                 240

Glu Asp Tyr Asp Ala Leu Gln Gln Phe Thr Gly Val Thr Gly Arg
                245                 250                 255

Gln Pro Thr Pro Pro Asp Phe Ser Leu Gly Phe Gln Gln Ser Lys Leu
            260                 265                 270

Arg Tyr Tyr Asn Gln Thr Gln Ile Ile Asp Leu Ala Gln Arg Phe His
            275                 280                 285

Asp Glu Gln Val Pro Ile Ser Leu Ile Val Ile Asp Phe Phe Ala Trp
290                 295                 300

Lys Phe Gln Gly Asp Trp Ser Leu Asp Val Asp Val Trp Pro Asp Pro
305                 310                 315                 320

Thr Ala Met Ala Ala Glu Val Lys Arg Leu Thr Gly Ala Glu Leu Met
                325                 330                 335

Val Ser Leu Trp Pro Ser Val Glu Asp Leu Ser Glu Asn Tyr Leu Thr
            340                 345                 350

Leu Gln Glu Glu Gly Leu Leu Ala Ile Thr Arg Asp Gly Thr Gly Ile
            355                 360                 365

Gln Asp Ser Phe Glu Gly Val Tyr Thr Arg Leu Ile Asp Ser Thr Asn
370                 375                 380

Pro Asp Ala Arg Glu Phe Leu Trp Lys Arg Leu Asn Asp Ser Tyr Phe
385                 390                 395                 400

Ser Lys Gly Ile His Asn Phe Trp Ile Asp Gln Ala Asp Gly Gly Thr
                405                 410                 415

Leu Gly Glu Pro Phe Glu Asn Asn Gly Gln Ser Ile Ser Ser Ile Pro
            420                 425                 430

Tyr Ser Arg Ser Phe Thr Gln Tyr Phe Leu Gly Ser Gln Glu Gly Phe
            435                 440                 445

Gly Lys Met Tyr Pro Trp Leu His Gln Gln Ala Ile Gln Glu Gly Phe
            450                 455                 460

Gln Asn Leu Thr Gly Thr Asp Ser Ser Gln Glu Ser Cys Glu Tyr Met
465                 470                 475                 480

Ser Leu Thr Arg Ser Thr Phe Ile Gly Gly Gln Arg Phe Cys Ser Tyr
                485                 490                 495

Leu Trp Ser Gly Asp Thr Asp Ser Lys Phe Asp Val Leu Leu Gln Gln
            500                 505                 510

Ile Thr Ala Gly Val Ser Val Ala Ala Ser Gly Ile Ser Ser Trp Thr
            515                 520                 525

Leu Asp Ile Gly Gly Phe Ala Gly Leu Asp Ile Asp Thr Asp Glu Gly
            530                 535                 540

Lys Glu Leu Phe Val Arg Trp Phe Ser Met Gly Val Phe Leu Pro Tyr
545                 550                 555                 560
```

```
Thr Arg Val His Gly Thr Arg Ser Cys Asn Ile Pro Arg Thr Ser Thr
                565                 570                 575
Leu Pro His Ala Asn Pro Cys Pro Asn Glu Pro Trp Ser Tyr Gly Glu
            580                 585                 590
Asp Asn Phe Val Ile Leu Lys Lys Tyr Ile Ala Leu Arg Tyr Gln Leu
        595                 600                 605
Ile Pro Tyr Val Lys Thr Leu Phe Gln Met Leu His Thr Ser Gly Lys
    610                 615                 620
Val Ile Leu Arg Pro Leu Tyr Phe Asp Phe Ser Lys Ser Asp Glu Phe
625                 630                 635                 640
Val Arg Lys Gly Thr Lys Thr Asn Asp Pro Val Val His Gln Phe
                645                 650                 655
Met Phe Gly Pro Arg Leu Leu Val Ala Pro Val Gly Glu Phe Gly Val
                660                 665                 670
Lys Thr Trp Asp Val Tyr Leu Pro Lys Leu Asp Thr Gln Thr Trp Lys
                675                 680                 685
His Trp Gln Val Thr Thr Asn Gln Ile Pro Arg Trp Thr Asp His Asp
                690                 695                 700
Phe Gly Lys Gly Gly Met Ser Ile Thr Ile Asp Ala Pro Leu Asp Gln
705                 710                 715                 720
Ile Pro Val Phe Tyr Leu Gly Asp Lys Asp Asp Ile Leu Asn Gly Asn
                725                 730                 735
Ile

<210> SEQ ID NO 15
<211> LENGTH: 655
<212> TYPE: PRT
<213> ORGANISM: Penicillium chrysogenum

<400> SEQUENCE: 15

Met Leu Tyr Ala Glu Asp Asp Lys Leu Val Phe Arg Phe Asp His
  1               5                  10                  15
Ile Leu Trp Val Gln Pro Trp Gly Glu Asn Ala Phe Arg Val Arg Ala
                 20                  25                  30
Thr Lys Gln Ala Ser Ile Pro Thr Glu Asp Trp Ala Leu Pro Ser Lys
             35                  40                  45
Pro Ser Ser Pro Ser Pro Ser Ile Glu Ile Ser Ala Asp Gln Glu Ala
         50                  55                  60
Thr Ile Thr Asn Gly Lys Ile Lys Ala Thr Val Ser Arg Arg Gly Lys
 65                  70                  75                  80
Ile Ile Ile Tyr Asp Ser Lys Gly Asn Lys Leu Leu Glu Glu Tyr Ala
                 85                  90                  95
Arg His Arg Gln Asp Pro Met Asp Pro Lys Cys Ser Ala Leu Thr Val
                100                 105                 110
Glu Ala Arg Glu Leu Arg Pro Ile Leu Gly Gly Asp Tyr His Leu Thr
            115                 120                 125
Met Arg Phe Glu Ser Leu Asp His Lys Glu Lys Ile Phe Gly Met Gly
        130                 135                 140
Gln Tyr Gln Gln Pro Tyr Leu Asn Leu Lys Gly Ala Asp Leu Glu Leu
145                 150                 155                 160
Ala His Arg Asn Ser Gln Ala Ser Val Pro Phe Ala Val Ser Ser Leu
                165                 170                 175
Gly Tyr Gly Phe Leu Trp Asn Asn Pro Gly Ile Gly Arg Ala Val Leu
            180                 185                 190
```

-continued

```
Gly Thr Asn Val Met Ser Phe Glu Ala Tyr Ser Thr Lys Ala Leu Asp
            195                 200                 205

Tyr Trp Val Val Ala Gly Asp Thr Pro Ala Glu Ile Glu Glu Ala Tyr
210                 215                 220

Ala Lys Val Thr Gly Tyr Val Pro Met Met Pro Glu Tyr Gly Leu Gly
225                 230                 235                 240

Phe Trp Gln Cys Lys Leu Arg Tyr Thr Asn Gln Glu Gln Leu Leu Asn
                245                 250                 255

Ile Ala Arg Glu Tyr Arg Arg Glu Val Pro Leu Asp Leu Ile Val
            260                 265                 270

Ile Asp Phe Phe His Trp Lys His Gln Gly Glu Trp Ser Phe Asp Pro
        275                 280                 285

Glu Phe Trp Pro Asp Pro Glu Ala Met Val Lys Glu Leu Lys Glu Leu
    290                 295                 300

Lys Val Glu Leu Met Val Ser Ile Trp Pro Thr Val Glu Asn Ala Ser
305                 310                 315                 320

Glu Asn Phe Pro Glu Met Leu Glu Gln Gly Leu Leu Ile Arg His Asp
                325                 330                 335

Arg Gly Met Arg Val Ala Met Gln Cys Asp Gly Asp Ile Thr His Phe
            340                 345                 350

Asp Ala Thr Asn Pro Ala Ala Arg Lys Phe Ile Trp Ser Lys Ala Lys
        355                 360                 365

Gln Asn Tyr Tyr Asp Ile Gly Ile Lys Thr Phe Trp Leu Asp Glu Ala
    370                 375                 380

Glu Pro Glu Tyr Ser Ile Tyr Asp Phe Asp Ile Tyr Arg Tyr His Ala
385                 390                 395                 400

Gly Ser Asn Leu Gln Ile Gly Asn Thr Tyr Pro Lys Glu Tyr Ala Arg
                405                 410                 415

Gly Phe Tyr Glu Gly Met Thr Ala Glu Gly Gln Thr Asn Ile Val Asn
            420                 425                 430

Leu Leu Arg Cys Ala Trp Ala Gly Ser Gln Lys Tyr Gly Ala Leu Val
        435                 440                 445

Trp Ser Gly Asp Ile Ala Ser Ser Trp Ser Ser Phe Arg Asn Gln Leu
450                 455                 460

Ala Ala Gly Leu Asn Met Gly Leu Ala Gly Ile Pro Trp Trp Thr Thr
465                 470                 475                 480

Asp Ile Gly Gly Phe His Gly Gly Asn Pro Asp Asp Pro Leu Phe Arg
                485                 490                 495

Glu Leu Phe Thr Arg Trp Phe Gln Trp Gly Thr Phe Cys Pro Val Met
            500                 505                 510

Arg Leu His Gly Asp Arg Glu Pro Lys Pro Glu Gly Gln Pro Thr Ala
        515                 520                 525

Ser Gly Ala Asp Asn Glu Ile Trp Ser Tyr Gly Asp Glu Val Tyr Glu
    530                 535                 540

Ile Cys Lys Arg Tyr Ile Gly Ile Arg Glu Lys Leu Arg Glu Tyr Thr
545                 550                 555                 560

Arg Gly Leu Met Arg Glu Ala His Glu Lys Gly Thr Pro Val Met Arg
                565                 570                 575

Thr Leu Phe Tyr Glu Phe Pro Ser Asp Glu Arg Ala Trp Glu Val Glu
            580                 585                 590

Thr Gln Tyr Met Phe Gly Ser Lys Tyr Leu Val Val Pro Val Leu Glu
        595                 600                 605

Pro Gly Gln Arg Thr Val Lys Val Tyr Leu Pro Ala Gly Ala Ser Trp
```

```
                  610                 615                 620
Lys Leu Trp Asp Glu Lys Asp Val Leu His Glu Gly Arg Asn Val
625                 630                 635                 640

Glu Ile Glu Cys Pro Ile Glu Asn Met Pro Val Phe Cys Arg Gln
                    645                 650                 655

<210> SEQ ID NO 16
<211> LENGTH: 744
<212> TYPE: PRT
<213> ORGANISM: Penicillium chrysogenum

<400> SEQUENCE: 16

Met Arg Leu Ala Leu Ile Ala Leu Gly Ala Ile Trp Ala Ser Ser Ser
  1               5                  10                  15

Val Ala Ser Pro Val Gln Gln Thr Thr Tyr His Lys Pro Thr Ser Lys
             20                  25                  30

Gly Phe Arg Met Gln His Gly Phe Glu Thr Val Leu Val Gln Pro Phe
         35                  40                  45

Gly Tyr Asp Gly Phe Arg Val Arg Ala Trp Pro Phe Arg Ala Pro Thr
 50                  55                  60

Gly His Glu Ile Gly Phe Val Tyr Asp Pro Pro Leu Glu Gly Pro Glu
 65                  70                  75                  80

Asn Gly Glu Ala His Gly Met Thr Phe Asp Thr Ala Phe Asn Gly Asn
                 85                  90                  95

Arg Ser Glu Glu Leu Arg Asn Gly Asn Met Ile Val Arg Thr Ser Gly
            100                 105                 110

Trp Gly Gly Ser Pro Gly Gly Tyr Arg Leu Ala Phe Tyr Arg Val Glu
        115                 120                 125

Ala Asn Gly Ser Glu Thr Leu Leu Thr Asn Glu Tyr Ala Pro Leu Lys
130                 135                 140

Ser Leu Asn Pro Arg Tyr Tyr Ser Trp Thr Gly Pro Gly Ser Glu Phe
145                 150                 155                 160

Ala Ala Glu Phe Ser Phe Ser Thr Thr Pro Glu Glu Gln Ile Tyr Gly
                165                 170                 175

Thr Gly Thr Gln Gln Asp His Leu Val Asn Lys Lys Gly Leu Thr Ile
            180                 185                 190

Asp Leu Ile Asn Phe Asn Thr His Ile Pro Thr Pro Val Phe Met Ser
        195                 200                 205

Asn Lys Gly Tyr Gly Phe Ile Trp Asn Met Ala Ser Thr Gly Arg Met
210                 215                 220

Glu Phe Gly Pro Leu Arg Asn Arg Phe Thr Ala Asp Ala Ala Ser Val
225                 230                 235                 240

Val Asp Tyr Val Ile Val Ser Ser Asp Pro Ser Asp Tyr Asp Thr Leu
                245                 250                 255

Gln Gln Arg Leu Ser Ala Leu Val Gly Arg Ala Pro Thr Pro Pro Asp
            260                 265                 270

Trp Ser Leu Gly Tyr Leu Gln Ser Lys Leu Arg Tyr Glu Asn Gln Ser
        275                 280                 285

Glu Val Ile Gln Leu Ala Gln Gln Phe His Asp Arg Lys Ile Pro Val
290                 295                 300

Ser Met Ile Val Ile Asp Tyr Gln Ser Trp Ala His Gln Gly Asp Trp
305                 310                 315                 320

Gly Leu Asp Pro Ala Leu Trp Pro Asp Val Ala Glu Met Ala Arg Gln
                325                 330                 335
```

-continued

Val Lys Asp Leu Thr Asn Ala Glu Met Met Ala Ser Leu Trp Pro Ser
            340                 345                 350

Val Ala Asp Asp Ser Val Asn Tyr Leu Glu Met Met Ala Gln Gly Phe
            355                 360                 365

Leu Ser Ala Thr Arg Ser Gly Pro Gly Thr Thr Asp Ser Trp Asn Gly
            370                 375                 380

Ser Tyr Ile Arg Asn Tyr Asp Ser Thr Asn Pro Gly Ala Arg Arg Phe
385                 390                 395                 400

Leu Trp Asn Thr Leu Lys Arg Asn Tyr Phe Asp Lys Gly Ile Lys Asn
            405                 410                 415

Phe Trp Ile Asp Gln Ala Asp Gly Gly Ser Leu Gly Glu Ala Tyr Glu
            420                 425                 430

Asn Asn Gly Gln Ser Asp Tyr Ile Gln Ser Leu Pro Phe Pro Met Pro
            435                 440                 445

Asp Val Leu Tyr Ala Ala Gly Thr Gln Arg Asn Val Gly Lys Leu Tyr
            450                 455                 460

Pro Trp Ala His Gln Gln Ala Ile Glu Glu Gly Phe Arg Asn Ala Thr
465                 470                 475                 480

Ser Thr Asp Met Gly Ser Pro Cys Asn Tyr Leu Ser Leu Ser Arg Ser
            485                 490                 495

Gly Tyr Ile Gly Ser Gln Arg Phe Cys Ser Met Ile Trp Ser Gly Asp
            500                 505                 510

Ile Thr Ser Val Trp Glu Thr Leu Ser Ala Gln Val Ala Ser Gly Leu
            515                 520                 525

Ser Ala Ala Ala Thr Gly Trp Gly Trp Trp Thr Leu Asp Ala Gly Gly
530                 535                 540

Phe Gln Ala Asp Pro Thr Val Pro Trp Ser Gly Asn Ile Asp Ser Pro
545                 550                 555                 560

Glu Tyr Arg Glu Leu Tyr Val Arg Trp Phe Gln Trp Ser Thr Phe Leu
            565                 570                 575

Pro Phe Met Arg Thr His Gly Ser Arg Thr Cys Asp Phe Gln Asp Ala
            580                 585                 590

Tyr Thr Cys Ala Asn Glu Pro Trp Ser Tyr Gly Ser Glu Asn Thr Pro
            595                 600                 605

Ile Leu Val Ser Tyr Ile Asn Leu Arg Tyr Gln Leu Ser Ala Tyr Leu
            610                 615                 620

Arg Ala Val Phe Ala Gln Leu His Lys Ser Gly Arg Met Ile Met Arg
625                 630                 635                 640

Pro Leu Tyr Met Asp Phe Glu Lys Ser Asp Pro His Val Ala Arg Trp
            645                 650                 655

Thr Ser Ala Asn Thr Asn Ile Thr Thr Gln Gln Tyr Met Phe Gly Pro
            660                 665                 670

Arg Leu Leu Val Ser Pro Val Thr Ile Pro Asn Val Thr Glu Trp Ser
            675                 680                 685

Val Tyr Leu Pro Gln Thr Ala Gly Asp Ser Lys Pro Trp Thr Tyr
            690                 695                 700

Trp Trp Ser Asn Gln Thr Tyr Ser Gly Gly Gln Thr Val Thr Val Pro
705                 710                 715                 720

Ala Pro Lys Glu His Ile Pro Leu Phe His Leu Gly Thr Arg Ala Asp
            725                 730                 735

Ile Val Asp Gly Arg Val Phe Ala
            740

<210> SEQ ID NO 17
<211> LENGTH: 736
<212> TYPE: PRT
<213> ORGANISM: Aspergillus carbonarius

<400> SEQUENCE: 17

Met Tyr Phe Pro Ser Leu Leu Ala Leu Gly Ala Leu Val Gln Ala Ala
1               5                   10                  15

Ala Ala Thr Tyr Ile Ala Pro Asn Ser Thr Gly Leu Arg Leu Gln His
            20                  25                  30

Gly Phe Glu Thr Ile Leu Ile Gln Pro Phe Gly Tyr Asp Gly Phe Arg
        35                  40                  45

Val Arg Ala Trp Pro Phe Arg Pro Pro Ser Gly Asn Glu Ile Ser Phe
50                  55                  60

Ile Tyr Asp Pro Pro Leu Glu Gly Phe Glu Asp Ser Ala His Gly Met
65                  70                  75                  80

Ser Tyr Asp Thr Ala Thr Thr Gly Ser Glu Pro Arg Thr Leu Arg Asn
                85                  90                  95

Gly Asn Met Ile Leu Arg Thr Thr Gly Trp Gly Glu Thr Gly Gly
            100                 105                 110

Tyr Arg Leu Ser Phe Ser Arg Val Asn Glu Asp Gly Ser Glu Thr Leu
        115                 120                 125

Leu Thr Asn Glu Tyr Ala Pro Leu Lys Ser Leu Asn Pro Arg Tyr Tyr
130                 135                 140

His Trp Pro Gly Pro Gly Pro Glu Phe Ser Ala Glu Phe Ser Phe Ser
145                 150                 155                 160

Ala Thr Pro Asp Glu Gln Ile Tyr Gly Thr Gly Thr Gln Gln Asp His
                165                 170                 175

Met Ile Asn Lys Lys Gly Gln Val Ile Asp Met Val Asn Phe Asn Thr
            180                 185                 190

His Ile Pro Thr Pro Val Phe Met Ser Asn Lys Gly Tyr Ala Phe Ile
        195                 200                 205

Trp Asn Met Pro Ala Glu Gly Arg Met Glu Phe Gly Pro Leu Arg Thr
210                 215                 220

Arg Phe Thr Ala Ala Thr Thr Thr Leu Val Asp Tyr Val Ile Val Ala
225                 230                 235                 240

Ser Ala Pro Gly Asp Tyr Asp Thr Leu Gln Arg Arg Ile Ser Ala Leu
                245                 250                 255

Thr Gly Arg Ala Pro Val Pro Pro Asp Phe Ala Leu Gly Tyr Ile Gln
            260                 265                 270

Ser Lys Leu Arg Tyr Glu Asn Glu Thr Glu Val Glu Leu Leu Ala Gln
        275                 280                 285

Asn Phe His Asp Arg Gly Ile Pro Val Ala Met Ile Val Ile Asp Tyr
290                 295                 300

Gln Ser Trp Ala His Gln Gly Asp Trp Ala Leu Asp Pro Arg Leu Trp
305                 310                 315                 320

Pro Asn Val Gly Gln Met Ser Ala Arg Val Lys Asn Leu Thr Gly Ala
                325                 330                 335

Glu Met Met Ala Ser Leu Trp Pro Ser Val Ala Asp Asn Ser Val Asn
            340                 345                 350

Tyr Ala Ala Leu Gln Ala Asn Gly Leu Leu Ser Ala Thr Arg Asp Gly
        355                 360                 365

Pro Gly Thr Thr Asp Ser Trp Asn Gly Ser Tyr Ile Arg Asn Tyr Asp
370                 375                 380

-continued

```
Ser Thr Asn Pro Ser Ala Arg Gln Phe Leu Trp Ser Met Leu Lys Lys
385                 390                 395                 400

Asn Tyr Tyr Asp Lys Gly Ile Lys Asn Phe Trp Ile Asp Gln Ala Asp
            405                 410                 415

Gly Gly Ala Leu Gly Glu Ala Tyr Glu Asn Asn Gly Gln Ser Thr Tyr
                420                 425                 430

Ile Glu Ser Ile Pro Phe Ala Leu Pro Asn Val Leu Tyr Ala Ala Gly
            435                 440                 445

Thr Gln Leu Ser Val Gly Lys Leu Tyr Pro Trp Ala His Gln Gln Ala
        450                 455                 460

Ile Asp Glu Gly Phe Arg Asn Ala Thr Asp Thr Glu Glu Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
            500                 505                 510

Leu Ala Val Gln Val Ala Ser Gly Leu Ser Ala Ala Thr Gly Trp
        515                 520                 525

Gly Trp Trp Thr Val Asp Ala Gly Gly Phe Gln Ala Asp Pro Thr Val
    530                 535                 540

Trp Trp Ser Gly Asn Ile Asp Thr Pro Glu Phe Arg Glu Leu Tyr Val
545                 550                 555                 560

Arg Trp Leu Ser Trp Thr Thr Phe Leu Pro Phe Met Arg Thr His Gly
                565                 570                 575

Ser Arg Ala Cys Tyr Phe Gln Asp Ala Tyr Thr Cys Ala Asn Glu Pro
            580                 585                 590

Trp Ser Tyr Gly Glu Ala Asn Thr Pro Ile Ile Val Ser Tyr Ile His
        595                 600                 605

Leu Arg Tyr Gln Leu Gly Ala Tyr Leu Arg Ser Ile Phe Lys Gln Phe
    610                 615                 620

His Leu Thr Gly Arg Ser Ile Met Arg Pro Leu Tyr Met Asp Phe Glu
625                 630                 635                 640

Lys Thr Asp Pro Lys Ile Ser Thr Leu Thr Ala Ser Asn Ser Asn Tyr
                645                 650                 655

Thr Thr Gln Gln Tyr Met Phe Gly Pro Arg Leu Leu Val Ser Pro Val
            660                 665                 670

Thr Leu Pro Asn Val Thr Glu Trp Pro Val Tyr Leu Pro Gln Thr Gly
        675                 680                 685

Gly Asn Ser Thr Lys Pro Trp Thr Tyr Trp Trp Thr Asn Glu Thr Tyr
    690                 695                 700

Ala Gly Gly Gln Val Val Thr Val Ser Ala Pro Val Gln His Ile Pro
705                 710                 715                 720

Val Phe His Leu Gly Ser Arg Glu Glu Leu Thr Gly Asn Val Phe
                725                 730                 735
```

<210> SEQ ID NO 18
<211> LENGTH: 736
<212> TYPE: PRT
<213> ORGANISM: Aspergillus brasiliensis

<400> SEQUENCE: 18

```
Met Tyr Phe Ser Ser Phe Phe Ala Leu Gly Ala Leu Val Gln Ala Ala
1               5                   10                  15

Ala Ala Thr Tyr Phe Ala Pro Asn Ser Thr Gly Leu Arg Ile Gln His
            20                  25                  30
```

-continued

```
Gly Phe Glu Thr Ile Leu Val Gln Pro Phe Gly Tyr Asp Gly Phe Arg
         35                  40                  45

Val Arg Ala Trp Pro Phe Arg Pro Pro Ser Gly Asn Glu Ile Ser Phe
 50                  55                  60

Ile Tyr Asp Pro Pro Ile Glu Gly Tyr Glu Asp Thr Ala His Gly Met
 65                  70                  75                  80

Ser Tyr Asp Thr Ala Thr Thr Gly Ala Glu Pro Arg Thr Leu Arg Asn
                 85                  90                  95

Gly Asn Ile Ile Leu Arg Thr Thr Gly Trp Gly Gly Asp Thr Ala Gly
                100                 105                 110

Tyr Arg Leu Ser Phe Tyr Arg Val Asn Glu Asp Gly Ser Glu Thr Leu
                115                 120                 125

Leu Thr Asn Glu Tyr Ala Pro Leu Lys Ser Leu Asn Pro Arg Tyr Tyr
        130                 135                 140

Ser Trp Pro Gly Pro Gly Ala Glu Phe Ser Ala Glu Phe Ser Phe Ser
145                 150                 155                 160

Ala Thr Pro Asp Glu Gln Ile Tyr Gly Thr Gly Gln Gln Asp His
                165                 170                 175

Met Ile Asn Lys Lys Gly Ser Val Ile Asp Met Val Asn Phe Asn Thr
                180                 185                 190

His Ile Pro Thr Pro Val Phe Met Ser Asn Lys Gly Tyr Ala Phe Ile
        195                 200                 205

Trp Asn Met Pro Ala Glu Gly Arg Met Glu Phe Gly Thr Leu Arg Thr
        210                 215                 220

Arg Phe Thr Ala Ala Ser Thr Thr Leu Val Asp Tyr Val Ile Val Ala
225                 230                 235                 240

Ala Gln Pro Gly Asp Tyr Asp Thr Leu Gln Gln Arg Ile Ser Ala Leu
                245                 250                 255

Thr Gly Arg Ala Pro Thr Pro Asp Phe Ser Leu Gly Tyr Ile Gln
                260                 265                 270

Ser Lys Leu Arg Tyr Glu Asn Gln Thr Glu Val Glu Leu Leu Ala Gln
        275                 280                 285

Asn Phe His Asp Arg Asn Ile Pro Val Ser Met Ile Val Ile Asp Tyr
        290                 295                 300

Gln Ser Trp Ala His Gln Gly Asp Trp Ala Leu Asp Pro Arg Leu Trp
305                 310                 315                 320

Pro Asn Val Ala Gln Met Ser Ala Arg Val Lys Asn Leu Thr Gly Ala
                325                 330                 335

Glu Met Met Ala Ser Leu Trp Pro Ser Val Glu Asp Asn Ser Val Asn
                340                 345                 350

Tyr Ala Thr Leu Gln Ala Asn Gly Leu Leu Ser Ala Thr Arg Asp Gly
        355                 360                 365

Pro Gly Thr Thr Asp Ser Trp Asn Gly Ser Tyr Ile Arg Asn Ile Asp
        370                 375                 380

Ser Thr Asn Pro Ala Ala Arg Lys Phe Leu Trp Ser Thr Leu Lys Lys
385                 390                 395                 400

Asn Tyr Tyr Asp Lys Gly Ile Lys Asn Phe Trp Ile Asp Gln Ala Asp
                405                 410                 415

Gly Gly Ala Leu Gly Glu Ala Tyr Glu Asn Asn Gly Gln Ser Thr Tyr
                420                 425                 430

Ile Gln Ser Ile Pro Tyr Thr Leu Pro Asn Val Asn Tyr Ala Ala Gly
        435                 440                 445
```

```
Thr Gln Leu Gly Val Gly Lys Leu Tyr Pro Trp Ala His Gln Gln Ala
    450                 455                 460

Ile Glu Glu Gly Phe Arg Asn Ala Thr Asp Thr Lys Glu Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
                500                 505                 510

Leu Ala Val Gln Val Ala Ser Gly Leu Ser Ala Ala Thr Gly Trp
                515                 520                 525

Gly Trp Trp Thr Val Asp Ala Gly Gly Phe Glu Val Asp Ser Thr Val
530                 535                 540

Trp Trp Ser Gly Asn Ile Asp Thr Pro Glu Phe Arg Glu Leu Tyr Val
545                 550                 555                 560

Arg Trp Leu Ala Trp Thr Thr Phe Leu Pro Phe Met Arg Thr His Gly
                565                 570                 575

Ser Arg Thr Cys Tyr Tyr Gln Asp Ala Tyr Thr Cys Ala Asn Glu Pro
                580                 585                 590

Trp Ser Tyr Gly Ala Ser Asn Thr Pro Ile Ile Val Ser Tyr Ile His
                595                 600                 605

Leu Arg Tyr Gln Leu Gly Ala Tyr Leu Lys Ser Ile Phe Asn Gln Phe
                610                 615                 620

His Leu Thr Gly Arg Ser Ile Met Arg Pro Leu Tyr Met Asp Phe Glu
625                 630                 635                 640

Lys Thr Asp Pro Lys Ile Ser Gln Leu Val Ser Ser Asn Ser Asn Tyr
                645                 650                 655

Thr Thr Gln Gln Tyr Met Phe Gly Pro Arg Leu Leu Val Ser Pro Val
                660                 665                 670

Thr Leu Pro Asn Val Thr Glu Trp Pro Val Tyr Leu Pro Gln Thr Gly
                675                 680                 685

Glu Asn Asn Thr Lys Pro Trp Thr Tyr Trp Trp Thr Asn Glu Thr Tyr
                690                 695                 700

Ala Gly Gly Gln Val Val Lys Val Pro Ala Pro Val Gln His Ile Pro
705                 710                 715                 720

Val Phe His Leu Gly Ser Arg Glu Glu Leu Leu Ser Gly Asp Val Phe
                725                 730                 735

<210> SEQ ID NO 19
<211> LENGTH: 736
<212> TYPE: PRT
<213> ORGANISM: Aspergillus acidus

<400> SEQUENCE: 19

Met Tyr Phe Ser Ser Phe Leu Ala Leu Gly Ala Leu Ile Gln Ala Ala
 1               5                  10                  15

Ala Ala Thr Tyr Leu Ala Pro Asn Ser Thr Gly Leu Arg Ile Gln His
                20                  25                  30

Gly Phe Glu Thr Ile Leu Ile Gln Pro Phe Gly Tyr Asp Gly Phe Arg
                35                  40                  45

Val Arg Ala Trp Pro Phe Arg Pro Pro Ser Gly Asn Glu Ile Ser Phe
50                  55                  60

Ile Tyr Asp Pro Pro Ile Glu Gly Tyr Glu Asp Thr Ala His Gly Met
65                  70                  75                  80

Ser Tyr Asp Thr Ala Thr Thr Gly Thr Glu Pro Arg Thr Leu Arg Asn
                85                  90                  95
```

```
Gly Asn Ile Ile Leu Arg Thr Thr Gly Trp Gly Thr Thr Ala Gly
            100                 105                 110

Tyr Arg Leu Ser Phe Tyr Arg Val Asn Asp Asp Gly Ser Glu Thr Leu
            115                 120                 125

Leu Thr Asn Glu Tyr Ala Pro Leu Lys Ser Leu Asn Pro Arg Tyr Phe
            130                 135                 140

Ser Trp Pro Gly Pro Gly Ala Glu Phe Ser Ala Glu Phe Ser Phe Ser
145                 150                 155                 160

Ala Thr Pro Asp Glu Gln Ile Tyr Gly Thr Gly Thr Gln Gln Asp His
                165                 170                 175

Met Ile Asn Lys Lys Gly Ser Val Ile Asp Leu Val Asn Phe Asn Thr
            180                 185                 190

His Ile Pro Thr Pro Val Phe Met Ser Asn Lys Gly Tyr Ala Phe Ile
            195                 200                 205

Trp Asn Met Pro Ala Glu Gly Arg Met Glu Phe Gly Ser Leu Arg Thr
            210                 215                 220

Arg Phe Thr Ala Ala Ser Thr Thr Leu Val Asp Tyr Val Ile Val Ala
225                 230                 235                 240

Ala Gln Pro Gly Asp Tyr Asp Thr Leu Gln Gln Arg Ile Ser Ala Leu
                245                 250                 255

Thr Gly Arg Ala Pro Thr Pro Pro Asp Phe Ser Leu Gly Tyr Ile Gln
            260                 265                 270

Ser Lys Leu Arg Tyr Glu Asn Gln Thr Glu Val Glu Leu Leu Ala Gln
            275                 280                 285

Asn Phe His Asp Arg Asp Ile Pro Val Ser Met Ile Val Ile Asp Tyr
            290                 295                 300

Gln Ser Trp Ala His Gln Gly Asp Trp Ala Leu Asp Pro Arg Leu Trp
305                 310                 315                 320

Pro Asn Val Ala Gln Met Ser Ala Thr Val Lys Asn Leu Thr Gly Ala
                325                 330                 335

Glu Met Met Ala Ser Leu Trp Pro Ser Val Ala Asp Asp Ser Val Asn
            340                 345                 350

Tyr Ala Ala Leu Gln Ala Asn Gly Leu Leu Ser Ala Thr Arg Asp Gly
            355                 360                 365

Pro Gly Thr Thr Asp Ser Trp Asn Gly Ser Tyr Ile Arg Asn Tyr Asp
            370                 375                 380

Ser Thr Asn Pro Ser Ala Arg Lys Phe Leu Trp Ser Met Leu Lys Lys
385                 390                 395                 400

Asn Tyr Tyr Asp Lys Gly Ile Lys Asn Phe Trp Ile Asp Gln Ala Asp
                405                 410                 415

Gly Gly Ala Leu Gly Glu Ala Tyr Glu Asn Asn Gly Gln Ser Thr Tyr
            420                 425                 430

Ile Gln Ser Ile Pro Tyr Thr Leu Pro Asn Val Asn Tyr Ala Ala Gly
            435                 440                 445

Thr Gln Leu Gly Val Gly Lys Leu Tyr Pro Trp Ala His Gln Gln Ala
            450                 455                 460

Ile Glu Glu Gly Phe Arg Asn Ala Thr Asp Thr Lys Glu Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
            500                 505                 510
```

```
Leu Ala Val Gln Val Ala Ser Gly Leu Ser Ala Ala Ala Thr Gly Trp
            515                 520                 525

Gly Trp Trp Thr Val Asp Ala Gly Gly Phe Glu Val Asp Ser Thr Val
530                 535                 540

Trp Trp Ser Gly Asn Ile Asp Thr Pro Glu Phe Arg Glu Leu Tyr Val
545                 550                 555                 560

Arg Trp Leu Ala Trp Thr Thr Phe Leu Pro Phe Met Arg Thr His Gly
                565                 570                 575

Ser Arg Ala Cys Tyr Tyr Gln Asp Ala Tyr Thr Cys Ala Asn Glu Pro
            580                 585                 590

Trp Ser Tyr Gly Ala Ser Asn Thr Pro Ile Ile Val Ser Tyr Ile His
            595                 600                 605

Leu Arg Tyr Gln Leu Gly Ala Tyr Leu Lys Ser Ile Phe Asn Gln Phe
            610                 615                 620

His Leu Thr Gly Arg Ser Ile Met Arg Pro Leu Tyr Met Asp Phe Glu
625                 630                 635                 640

Lys Thr Asp Pro Lys Ile Ser Gln Leu Val Ser Ser Asn Ser Asn Tyr
                645                 650                 655

Thr Thr Gln Gln Tyr Met Phe Gly Pro Arg Leu Leu Val Ser Pro Val
            660                 665                 670

Thr Leu Pro Asn Val Thr Glu Trp Pro Val Tyr Leu Pro Gln Thr Gly
            675                 680                 685

Asp Asn Ser Thr Lys Pro Trp Thr Tyr Trp Trp Thr Asn Glu Thr Tyr
            690                 695                 700

Ala Gly Gly Gln Val Val Lys Val Pro Ala Pro Val Gln His Ile Pro
705                 710                 715                 720

Val Phe His Leu Gly Ser Arg Glu Glu Leu Leu Ser Gly Asp Val Phe
                725                 730                 735

<210> SEQ ID NO 20
<211> LENGTH: 2211
<212> TYPE: DNA
<213> ORGANISM: Aspergillus acidus

<400> SEQUENCE: 20
atgtattttt cttccttttt ggccctaggg gccctgattc aggcagcagc agcaacctat      60
ctcgccccca actctaccgg tctccgtatc cagcatggct cgagaccat cctcatccag      120 ccgtttggt acgacggatt ccgcgtgcgc gcatggccct tccgtccgcc ttcgggcaac      180
gagattagct tcatctatga tccccgatt gaaggttatg aggacaccgc acatggcatg      240
agctatgaca ccgcaacaac cggcacggag cctcgcacct tgcgcaacgg caatatcatc      300
ctgcgcacca ctggctgggg tggcaccacc gccggatacc gcctgtcctt ctaccgcgtc      360
aatgatgatg ggagtgagac cctgctcaca acgaatatg ctccgctgaa gtctctcaac      420
ccccgatact tttcctggcc gggacctggg gccgaattct ctgccgagtt ctccttcagt      480
gcgactccgg atgagcagat ttatggcacg ggcacgcaac aagaccatat gatcaacaag      540
aagggttccg ttatcgactt ggtcaacttc aacaccccaca tccctacccc agtcttcatg      600
agcaacaaag gctatgcctt atctggaac atgccggccg aggggcgtat ggagtttggc      660
agcctgcgca ccaggttcac cgcggcgtcc acgacgcttg tcgactatgt aatcgtcgcc      720
gctcagccag gtgattacga caccctccag cagcggatt cggccctgac aggacgggca      780
ccgaccccgc ccgactttc tctcgggtac atccagtcca agctacgata tgagaaccaa      840
acggaggtgg agctgctggc tcagaacttc catgatagag acatcccggt gtccatgatc      900
```

```
gttattgact accagtcgtg ggctcatcag ggtgactggg cgctcgatcc gcgcctgtgg    960
cccaatgtcg cgcagatgtc ggcgacagtc aagaatctga ccggagccga aatgatggcg   1020
tctctatggc ccagtgttgc cgatgacagt gtcaactacg cagccctgca ggcgaacggt   1080
ctgctctcag ccaccgcga cggccctggt accactgact cctggaacgg atcatacatc   1140
cggaactatg actccaccaa cccctcggcg cggaaattcc tctggagcat gctgaagaaa   1200
aactactacg acaagggtat taagaacttt tggattgatc aggccgatgg cggagcattg   1260
ggcgaggctt atgagaacaa cggccagagc acatacattc agtccattcc gtatacCctg   1320
ccgaacgtga actacgccgc tggcacgcag ctcggcgtgg gtaagttgta ccctgggcg    1380
catcagcagg caatcgaaga aggcttccgc aatgcgacag acaccaagga aggaagcgct   1440
tgcgatcact ctccctgag tcggtccgga tacatcggat ctcagcggtt ctgcagcatg    1500
atctggtctg agacaccac ctctgtttgg gacacactgg cagtgcaggt cgccagtggt    1560
ctgtccgccg cagcaacagg ctggggttgg tggaccgtcg atgctggcgg cttcgaagtc   1620
gactcgacag tttggtggag tggaaacatt gacacgcccg aattccggga gttgtatgtg   1680
cgctggctgg cctggacgac cttcctgcca ttcatgcgca ctcatggtag tcgggcctgc   1740
tactaccagg acgcctacac ttgtgccaat gagccatggt cctatggtgc aagcaacacc   1800
cccattattg tctcgtatat ccacctgcgt taccaattgg gtgcttatct gaagtcgatt   1860
ttcaaccagt tccacctcac gggtcgcagt atcatgcgcc cgttgtacat ggatttcgag   1920
aagaccgacc cgaagatctc tcagctggtg tcgtcgaaca gcaactacac aactcaacag   1980
tacatgtttg gtccacgtct cctagtctct ccagtgacct tgccaaacgt cactgagtgg   2040
cctgtgtatc ttccgcagac gggagataat agcactaagc cttggacgta ctggtggacg   2100
aatgagacgt atgcgggagg acaggtcgtc aaggttcctg cgcccgtgca gcatatcccg   2160
gtattccatc tgggatcgcg cgaggagctt ctgtcgggtg atgtattcta g            2211
```

<210> SEQ ID NO 21
<211> LENGTH: 736
<212> TYPE: PRT
<213> ORGANISM: Aspergillus tubingensis

<400> SEQUENCE: 21

```
Met Tyr Phe Ser Ser Leu Leu Ala Leu Gly Ala Leu Val Gln Ala Ala
1               5                   10                  15

Ala Ala Thr Tyr Phe Ala Pro Asn Ser Thr Gly Leu Arg Ile Gln His
            20                  25                  30

Gly Phe Glu Thr Ile Leu Ile Gln Pro Phe Gly Tyr Asp Gly Phe Arg
        35                  40                  45

Val Arg Ala Trp Pro Phe Arg Pro Pro Ser Gly Asn Glu Ile Ser Phe
    50                  55                  60

Ile Tyr Asp Pro Pro Ile Glu Gly Tyr Glu Asp Thr Ala His Gly Met
65                  70                  75                  80

Ser Tyr Asp Thr Ala Thr Thr Gly Thr Glu Pro Arg Thr Leu Arg Asn
                85                  90                  95

Gly Asn Ile Ile Leu Arg Thr Gly Trp Gly Thr Thr Ala Gly
            100                 105                 110

Tyr Arg Leu Ser Phe Tyr Arg Val Asn Asp Asp Gly Ser Glu Thr Leu
        115                 120                 125

Leu Thr Asn Glu Tyr Ala Pro Leu Lys Ser Leu Asn Pro Arg Tyr Tyr
    130                 135                 140
```

```
Tyr Trp Pro Gly Pro Gly Ala Glu Phe Ser Ala Glu Phe Ser Phe Ser
145                 150                 155                 160

Ala Thr Pro Asp Glu Gln Ile Tyr Gly Thr Gly Gln Gln Asp His
        165                 170                 175

Met Ile Asn Lys Lys Gly Ser Val Ile Asp Leu Val Asn Phe Asn Thr
            180                 185                 190

His Ile Pro Thr Pro Val Phe Met Ser Asn Lys Gly Tyr Ala Phe Ile
        195                 200                 205

Trp Asn Met Pro Ala Glu Gly Arg Met Glu Phe Gly Ser Leu Arg Thr
            210                 215                 220

Arg Phe Thr Ala Ala Ser Thr Thr Leu Val Asp Tyr Val Ile Val Ala
225                 230                 235                 240

Ala Gln Pro Gly Asp Tyr Asp Thr Leu Gln Gln Arg Ile Ser Ala Leu
                245                 250                 255

Thr Gly Arg Ala Pro Thr Pro Pro Asp Phe Ser Leu Gly Tyr Ile Gln
                260                 265                 270

Ser Lys Leu Arg Tyr Glu Asn Gln Thr Glu Val Glu Leu Leu Ala Gln
            275                 280                 285

Asn Phe His Asp Arg Asp Ile Pro Val Ser Met Ile Val Ile Asp Tyr
            290                 295                 300

Gln Ser Trp Ala His Gln Gly Asp Trp Ala Leu Asp Pro Arg Leu Trp
305                 310                 315                 320

Pro Asn Val Ala Gln Met Ser Ala Thr Val Lys Asn Leu Thr Gly Ala
                325                 330                 335

Glu Met Met Ala Ser Leu Trp Pro Ser Val Ala Asp Asp Ser Val Asn
                340                 345                 350

Tyr Ala Ala Leu Gln Ala Asn Gly Leu Leu Ser Ala Thr Arg Asp Gly
            355                 360                 365

Pro Gly Thr Thr Asp Ser Trp Asn Gly Ser Tyr Ile Arg Asn Tyr Asp
        370                 375                 380

Ser Thr Asn Pro Ser Ala Arg Lys Phe Leu Trp Ser Met Leu Lys Lys
385                 390                 395                 400

Asn Tyr Tyr Asp Lys Gly Ile Lys Asn Phe Trp Ile Asp Gln Ala Asp
                405                 410                 415

Gly Gly Ala Leu Gly Glu Ala Tyr Glu Asn Asn Gly Gln Ser Thr Tyr
            420                 425                 430

Ile Gln Ser Ile Pro Tyr Thr Leu Pro Asn Val Asn Tyr Ala Ala Gly
        435                 440                 445

Thr Gln Leu Gly Val Gly Lys Leu Tyr Pro Trp Ala His Gln Gln Ala
        450                 455                 460

Ile Glu Glu Gly Phe Arg Asn Ala Thr Asp Thr Lys Lys Gly Ser Ala
465                 470                 475                 480

Cys Asp His Val Ser Leu Ser Arg Ser Gly Tyr Ile Gly Ser Gln Arg
                485                 490                 495

Phe Cys Ser Met Ile Trp Ser Gly Asp Thr Thr Ser Val Trp Asp Thr
            500                 505                 510

Leu Ala Val Gln Val Ala Ser Gly Leu Ser Ala Ala Thr Gly Trp
            515                 520                 525

Gly Trp Trp Thr Val Asp Ala Gly Gly Phe Glu Val Asp Ser Thr Val
        530                 535                 540

Trp Trp Ser Gly Asn Ile Asp Thr Pro Glu Phe Arg Glu Leu Tyr Val
545                 550                 555                 560
```

```
Arg Trp Leu Ala Trp Thr Thr Phe Leu Pro Phe Met Arg Thr His Gly
                565                 570                 575
Ser Arg Thr Cys Tyr Tyr Gln Asp Ala Tyr Thr Cys Ala Asn Glu Pro
            580                 585                 590
Trp Ser Tyr Gly Ala Ser Asn Thr Pro Ile Ile Val Ser Tyr Ile His
        595                 600                 605
Leu Arg Tyr Gln Leu Gly Ala Tyr Leu Lys Ser Ile Phe Asn Gln Phe
    610                 615                 620
His Leu Thr Gly Arg Ser Ile Met Arg Pro Leu Tyr Met Asp Phe Glu
625                 630                 635                 640
Lys Thr Asp Pro Lys Ile Ser Gln Leu Val Ser Ser Asn Ser Asn Tyr
                645                 650                 655
Thr Thr Gln Gln Tyr Met Phe Gly Pro Arg Leu Leu Val Ser Pro Val
            660                 665                 670
Thr Leu Pro Asn Val Thr Glu Trp Pro Val Tyr Leu Pro Gln Thr Gly
        675                 680                 685
Asp Asn Ser Thr Lys Pro Trp Thr Tyr Trp Thr Asn Glu Thr Tyr
    690                 695                 700
Ala Gly Gly Gln Val Val Lys Val Pro Ala Pro Val Gln His Ile Pro
705                 710                 715                 720
Val Phe His Leu Gly Ser Arg Glu Glu Leu Leu Ser Gly Asp Val Phe
                725                 730                 735

<210> SEQ ID NO 22
<211> LENGTH: 780
<212> TYPE: PRT
<213> ORGANISM: Aspergillus nidulans

<400> SEQUENCE: 22

Met Lys Phe Thr Glu Gly Met Trp Leu Leu Arg Glu Gly Ile Arg Ile
1               5                   10                  15
Asp Trp Met Ser Asn Val Glu Arg Leu Asn Val Asp Lys Asp Thr Val
                20                  25                  30
Asn Leu Leu Leu Asn Lys Phe Gln Arg His Arg Gly Asp Thr Leu Asn
            35                  40                  45
Ser Ser Thr Val Ser Ala Arg Val Thr Ser Pro Leu Glu Gly Ile Ile
        50                  55                  60
Gly Val Lys Leu Val His Trp Ala Gly Leu Asp Asn Gly Pro His
65                  70                  75                  80
Tyr Glu Leu Asn Thr Ser Ala Gly His Thr Glu Ile Thr His Glu Lys
                85                  90                  95
Gly Lys Asn Leu Lys Tyr Thr Ser Gly Arg Leu Glu Leu Asp Ile Asn
            100                 105                 110
Ile Ala Pro Asn Glu Leu Ala Phe Thr Phe Thr Gly Ala Asp Gly
        115                 120                 125
Gln Asp Lys Arg Lys Leu Thr Gly His Ser Phe Arg Ser Ile Gly
    130                 135                 140
Tyr Val Gly Asp Ser Thr Thr Pro Lys Ser Gln Leu Ser Asp Gly Ile
145                 150                 155                 160
Phe Tyr Glu Arg Gln Gly Tyr Thr Leu Ala Leu Asp Leu Ser Val
                165                 170                 175
Gly Glu Lys Leu Tyr Gly Leu Gly Glu Arg Phe Gly Pro Phe Val Lys
            180                 185                 190
Asn Gly Gln Ser Val Asn Ile Trp Asn Glu Asp Gly Gly Thr Ser Ser
        195                 200                 205
```

```
Glu Leu Ala Tyr Lys Asn Ile Pro Phe Tyr Ile Ser Ser Asn Gly Tyr
    210                 215                 220

Gly Val Phe Val Asn His Pro Gly Lys Val Ser Leu Glu Leu Gln Ser
225                 230                 235                 240

Glu Arg Thr Thr Arg Val Asn Val Ser Val Glu Gly Glu Glu Leu Glu
                245                 250                 255

Tyr Phe Val Ile Glu Gly Lys Asn Pro Lys Glu Ile Leu Lys Arg Trp
                260                 265                 270

Thr Asp Leu Thr Gly Lys Pro Ala Leu Val Pro Ala Trp Ser Tyr Gly
            275                 280                 285

Leu Trp Leu Thr Thr Ser Phe Thr Thr Asn Tyr Ser Glu Arg Thr Val
    290                 295                 300

Thr Gly Phe Leu Asp Gly Phe Lys Asp Arg Asn Leu Pro Leu Ser Val
305                 310                 315                 320

Phe His Phe Asp Cys Phe Trp Met Lys Ser Tyr Gln Trp Cys Asp Phe
                325                 330                 335

Glu Phe Asp Ala Asp Met Phe Pro Asp Ala Ala Gly Tyr Leu Ala Arg
                340                 345                 350

Leu Lys Glu Arg Gly Leu Lys Leu Ser Ile Trp Ile Asn Pro Tyr Val
            355                 360                 365

Gly Gln Ala Ser Pro Leu Phe Glu Ile Gly Lys Arg Glu Gly Tyr Phe
    370                 375                 380

Ile Lys Arg Ile Asp Gly Ser Val Trp Gln Trp Asp Leu Trp Gln Ala
385                 390                 395                 400

Gly Met Ala Val Val Asp Phe Thr Asn Pro Ala Ala Cys Ser Trp Tyr
                405                 410                 415

Thr Gly His Leu Lys Arg Leu Met Asp Leu Gly Ile Asp Thr Phe Lys
            420                 425                 430

Thr Asp Phe Ala Glu Arg Ile Pro Phe Lys Asn Ile Thr Tyr His Asp
            435                 440                 445

Gly Ser Asp Pro Ala Arg Met His Asn Tyr Tyr Ala Leu Leu Tyr Asn
    450                 455                 460

Lys Val Val Tyr Glu Thr Met Thr Ser Ile Ser Gly Lys Ser Asn Ser
465                 470                 475                 480

Leu Leu Phe Ala Arg Ser Thr Ser Val Gly Gly Gln Lys Tyr Pro Val
                485                 490                 495

His Trp Gly Gly Asp Cys Glu Ser Thr Tyr Glu Ala Met Ala Glu Ser
            500                 505                 510

Leu Arg Gly Gly Leu Ser Leu Gly Leu Ala Gly Tyr Ile Phe Trp Ala
            515                 520                 525

Ser Asp Ile Gly Gly Phe Glu Gly Thr Pro Pro Ala Leu Tyr Lys
    530                 535                 540

Arg Trp Val Gln Phe Gly Leu Leu Ser Ser His Ser Arg Leu His Gly
545                 550                 555                 560

Ser Ser Ser Phe Arg Val Pro Trp Ile Tyr Gly Glu Asp Cys Ser Asp
                565                 570                 575

Val Leu Arg Asp Cys Val Lys Arg Lys Ile Ser Leu Thr Pro Tyr Leu
            580                 585                 590

Leu Ala Glu Ala Leu Asn Gly His Arg Ser Gly Thr Pro Leu Met Arg
    595                 600                 605

Pro Met Phe Met Glu Phe Pro Glu Asp Leu Asn Thr Tyr Pro Leu Asp
    610                 615                 620
```

```
Thr Gln Tyr Met Phe Gly Ser Asn Leu Leu Val Ala Pro Val Phe Ser
625                 630                 635                 640

Asp Glu Gly Ile Val Thr Phe Tyr Val Pro Arg Thr Pro Glu Glu Glu
            645                 650                 655

Gly Arg Lys Gln Trp Ile Ser Trp Phe Asp His Gly Lys Lys Tyr Glu
            660                 665                 670

Gly Gly Arg Trp Tyr Thr Glu Thr His Gly Phe Asp Thr Leu Pro Ile
        675                 680                 685

Leu Ile Arg Pro Gly Ser Val Thr Pro Ile Asn Tyr Lys Leu Glu Lys
        690                 695                 700

Pro Glu Gly Asn Pro Leu Asp Gly Leu Glu Ile Leu Val Asn Gly Ser
705                 710                 715                 720

Ile Asp Lys Glu Val Glu Ile Glu Ile Val Asp Pro Glu Thr Thr His
            725                 730                 735

Lys Val Leu Lys Val Met Thr Val Ser Glu Arg Glu Thr Glu Asn Gly
            740                 745                 750

Val Glu Val Ile Ala Arg Leu Asp Gly Val Asp Gly Asn Glu Asn Ser
        755                 760                 765

Val Lys Val Asn Trp Val Gly His Gly Val Thr Lys
770                 775                 780
```